(12) United States Patent
Bishai et al.

(10) Patent No.: US 12,359,209 B2
(45) Date of Patent: Jul. 15, 2025

(54) RECOMBINANT THERAPEUTIC INTERVENTIONS FOR CANCER

(71) Applicant: The Johns Hopkins University, Baltimore, MD (US)

(72) Inventors: William R. Bishai, Baltimore, MD (US); Trinity J. Bivalacqua, Baltimore, MD (US); Alok Singh, Baltimore, MD (US); Monali Praharaj, Baltimore, MD (US); Takahiro Yoshida, Baltimore, MD (US)

(73) Assignee: THE JOHNS HOPKINS UNVERSITY, Baltimore, MD (US)

( * ) Notice: Subject to any disclaimer, the term of this patent is extended or adjusted under 35 U.S.C. 154(b) by 80 days.

(21) Appl. No.: 17/797,055

(22) PCT Filed: Feb. 12, 2021

(86) PCT No.: PCT/US2021/018007
§ 371 (c)(1),
(2) Date: Aug. 2, 2022

(87) PCT Pub. No.: WO2021/163602
PCT Pub. Date: Aug. 19, 2021

(65) Prior Publication Data
US 2023/0092817 A1    Mar. 23, 2023

Related U.S. Application Data

(63) Continuation of application No. 16/638,943, filed as application No. PCT/US2019/022341 on Mar. 14, 2019, application No. 17/797,055 is a continuation of application No. 16/790,161, filed on Feb. 13, 2020, now abandoned.

(60) Provisional application No. 62/658,661, filed on Apr. 17, 2018.

(51) Int. Cl.
| | |
|---|---|
| C12N 15/74 | (2006.01) |
| A61K 9/00 | (2006.01) |
| A61K 38/17 | (2006.01) |
| A61K 38/45 | (2006.01) |
| A61K 39/395 | (2006.01) |
| A61K 48/00 | (2006.01) |
| A61P 35/00 | (2006.01) |
| C07K 14/47 | (2006.01) |
| C12N 9/12 | (2006.01) |

(52) U.S. Cl.
CPC ............ *C12N 15/74* (2013.01); *A61K 9/0019* (2013.01); *A61K 38/1709* (2013.01); *A61K 38/45* (2013.01); *A61K 39/3955* (2013.01); *A61P 35/00* (2018.01); *C07K 14/4703* (2013.01); *C07K 14/4705* (2013.01); *C12N 9/1241* (2013.01); *C12Y 207/07* (2013.01); *A61K 48/00* (2013.01)

(58) Field of Classification Search
None
See application file for complete search history.

(56) References Cited

U.S. PATENT DOCUMENTS

| | | |
|---|---|---|
| 9,926,346 B2 | 3/2018 | Fulkerson et al. |
| 2010/0183547 A1 | 7/2010 | Horwitz et al. |
| 2015/0071873 A1 | 3/2015 | Biot et al. |
| 2017/0254808 A1 | 9/2017 | Prokunina et al. |
| 2018/0028577 A1* | 2/2018 | Bishai ............... A61P 35/00 |
| 2019/0008841 A1 | 1/2019 | Cohen et al. |
| 2019/0030091 A1 | 1/2019 | Bishai et al. |
| 2019/0336544 A1* | 11/2019 | Falb ................. A61K 31/506 |
| 2020/0253562 A1 | 8/2020 | Newberry et al. |

FOREIGN PATENT DOCUMENTS

| | | |
|---|---|---|
| CN | 106479946 A | 3/2017 |
| CN | 107217026 A | 9/2017 |
| MX | 2015015918 A | 5/2017 |
| WO | WO 2008/140598 A2 | 11/2008 |
| WO | WO 2016/130616 A1 | 8/2016 |
| WO | WO 2017/011444 A1 | 1/2017 |
| WO | WO 2017/049127 A1 | 3/2017 |
| WO | WO 2018/112360 A1 | 6/2018 |
| WO | WO 2019/014391 A1 | 1/2019 |
| WO | WO 2019/203965 A1 | 10/2019 |
| WO | WO 2020/002905 A1 | 1/2020 |
| WO | WO2021163602 A1 | 8/2021 |

OTHER PUBLICATIONS

Ryan et al., (Indian Journal of Urology, vol. 34, No. 1, pp. 11-19, Jan.-Mar. 2018 (Year: 2018).*
Ablasser et al., "Cell intrinsic immunity spreads to bystander cells via the intercellular transfer to cGAMP", Nature, Nov. 2013, 503(7477):530-534.
Agarwal et al., "Cyclic AMP intoxication of macrophages by a Mycobacterium tuberculosis adenylate cyclase", Nature Letters, Jun. 2009, 460: 98-102.
Ahmed et al., "Role of cellular metabolism in regulating type I interferon responses: Implications for tumor immunology and treatment", Cancer Lett. Nov. 28, 2017; 409:20-29.

(Continued)

*Primary Examiner* — Jana A Hines
*Assistant Examiner* — Khatol S Shahnan Shah
(74) *Attorney, Agent, or Firm* — DLA PIPER LLP (US)

(57) ABSTRACT

Described are methods of suppressing the expression of myeloid-derived suppressor cells (MDSCs), M2 macrophages, and Treg cells in a tumor and inducing the expression of macrophages, dendritic cells (DCs), and T effector cells in a tumor in a subject. A pharmaceutical composition comprising a strain of *Mycobacteria* including an expression vector of the present invention is administered to a subject.

17 Claims, 25 Drawing Sheets
Specification includes a Sequence Listing.

(56) References Cited

OTHER PUBLICATIONS

Askeland et al., "Bladder Cancer Immunotherapy: BCG and Beyond", Adv Ural. May 2012; 2012:181987.
Bai et al., "Mycobacterium tuberculosis Rv3586 (DacA) Is a Diadenylate Cyclase That Converts ATP or ADP into c-di-AMP", PLoS One, 2012, 7(4):1-10.
Bai et al., "Two DHH subfamily 1 proteins in *Streptococcus pneumoniae* possess cyclic di-AMP phosphodiesterase activity and affect bacterial growth and virulence", J Bacterial. Nov. 2013; 195(22):5123-32.
Barker et al., "STING-Dependent Recognition of Cylic di-AMP Mediates Type I Interferon Responses during Chlamydia trachomatis Infection", MBIO ASM, May-Jun. 2013, 4(3), 11 pages.
Bharati et al., "A full-length bifunctional protein involved in c-di-GMP turnover is required for long-term survival under nnutrient starvation in Mycobacterium smegmatis", Microbiology. Jun. 2012; 158(Pt6):1415-27.
Bowie, "Innate sensing of bacterial cyclic dinucleotides: more than just STING" Nat Immunol. Dec. 2012; 13(12):1137-9.
Cai et al., "The cGAS-cGAMP-STING Pathway of Cytosolic DNA Sensing and Signaling" Molecular Cell, Apr. 2014, 54: 289-296.
Burdette et al., "STING is a direct innate immune sensor of cyclic di-GMP", Nature. Sep. 25, 2011; 478(7370):515-8.
Cho et al., "*Streptococcus pyogenes* c-di-AMP Phosphodiesterase, GdpP, Influences SpeB Processing and Virulence", PLoS One. 2013; 8(7): e69425.
Collins et al., "Cyclic GMP-AMP Synthase Is an Innate Immune DNA Sensor for Mycobacterium tuberculosis", Cell Hlost Microbe. Jun. 10, 2015; 17(6):820-8.
Corrigan et al., "Cyclic di-AMP: another second messenger enters the fray", Nat Rev Microbiol. Aug. 2013; 11(8):513-24.
Corrigan et al., "c-di-AMP Is a New Second Messenger in *Staphylococcus aureus* with a Role in Controlling Cell Size and Envelope Stress", PLos Pathogens, Sep. 2011, 7(9), 16 pages.
Dey et al., "A bacterial cyclic dinucleotide activates the cytosolic surveillance pathway and mediates innate resistance to tuberculosis", Nat Med. Apr. 2015; 21(4):401-6.
Dey et al., "Crosstalk between Mycobacterium tuberculosis and the host cell", Semin Immunol. Dec. 2014; 26(6):486-96.
Dey et al., "Inhibition of innate immune cytosolic surveillance by an M. tuberculosis phosphodiesterase", Nat Chem Biol. Feb. 2017; 13(2):210-217.
Diner et al., "The innate immune DNA sensor cGAS produces a noncanonical cyclic dinucleotide that activates human STING", Cell Rep. May 30, 2013; 3(5):1355-61.
Du et al., "Functional analysis of c-di-AMP phosphodiesterase, GdpP, in *Streptococcus* suis serotype 2", Microbiol Res. Sep.-Oct. 2014; 169(9-10):749-58.
EP Extended European Search Report in European Application No. 198788935, dated Jan. 19, 2022, 9 pages.
Fitzgerald et al., "IKKepsilon and TBK1 are essential components of the IRF3 signaling pathway", Nat Immunol. May 2003; 4(5):491-6.
Francica et al., "TNFα and Radioresistant Stromal Cells Are Essential for Therapeutic Efficacy of Cyclic Dinucleotide STING Agonists in Nonimmunogenic Tumors", Cancer Immunol Res. Apr. 2018; 6(4):422-433.
Gao et al., "Cyclic GMP-AMP synthase is an innate immune sensor of HIV and other retroviruses", Science. Aug. 23, 2013; 341(6148):903-6.
Gupta et al., "Identification, activity and disulfide connectivity of C-di-GMP regulating proteins in Mycobacterium Tuberculosis", PLoS One. Nov. 30, 2010; 5(11):e15072.
Hansen et al., "Listeria monocytogenes induces IFNI3 expression through an IFI16-, cGAS- and STING-dependent pathway", EMBO J. Aug. 1, 2014; 33(15):1654-66.
Hornung et al., "PAS proteins and cGAS: unifying concepts in sensing and responding to cytosolic nucleic acids", Nature Reviews, August 20147, 14:521-528.

Hwang et al., "Derivation of class II force fields. VI. Carbohydrate compounds and anomeric effects", Biopolymers. May 1998; 45(6):435-68.
Hwang et al., "Gastric retentive drug-delivery systems". Crit Rev Ther Drug Carrier Syst. 1998; 15(3):243-84.
Hwang et al., "Synthesis of sulfonylurea conjugated copolymer via PEO spacer and its in vitro short-term bioactivity in insulin secretion from islets of Langerhans", Biomaterials. Jul. 1998; 19(13):1189-95.
Kalia et al., "Nucleotide, c-di-GMP, c-di-AMP, cGMP, cAMP, (p)ppGpp signaling in bacteria and implications in pathogenesis", Chem Soc Rev. Jan. 7, 2013; 42(1):305-41.
Kates et al., "Intravesical BCG Induces CD4+ T-Cell Expansion in an Immune Competent Model of Bladder Cancer", Cancer Immunol Res. Jul. 2017; 5(7):594-603.
Kim et al., "Caseation of human tuberculosis granulomas correlates with elevated host lipid metabolism", EMBO Molecular Medicine, May 2010, 2:258-274.
Kranzusch et al., "Structure of human cGAS reveals a conserved family of second-messenger enzymes in innate immunity", Cell Rep. May 30, 2013; 3(5): 1362-1368.
Konno et al., "Cyclic Di Nucleotides Trigger ULK1 (ATG1) Phosphorylation of STING to Prevent Sustained Innate Immune Signaling", Cell, Oct. 2013, 155(3), 24 pages.
Kubota et al., "Identification of 2'-Phosphodiesterase, Which Plays a Role in the 2-5A Systems Regulated by Interferon", The Journal of Biological Chemistry, Sep. 2004, 279(36):37832-37841.
Lahaye et al., "The capsids of HIV-1 and HIV-2 determine immune detection of the viral cDNA by the innate sensor cGAS in dendritic cells", Immunity, Dec. 12, 2013; 39(6):1132-42.
Lamichhane et al., "A postgenomic method for predicting essential genes at subsaturation levels of mutagenesis: Application to Mycobacterium tuberculosis", PNAS, Jun. 2003, 100(12):7212-7218.
Lau et al., "DNA tumor virus oncogenes antagonize the cGAS-STING DNA-sensing pathway" Science, Oct. 30, 2015; 350(6260):568-71.
Li et al., "Human cytomegalovirus tegument protein pUL83 inhibits IFI16-mediated DNA sensing for immune evasion", Cell Host Microbe. Nov. 13, 2013;14(5):591-9.
Li et al., "Hydrolysis of 2'3'-cGAMP by ENPP1 and design of non-hydrolyzable analogs", Nat Chem Biol., Dec. 2014, 10(12): 1043-1048.
Li et al., "Pivotal roles of cGAS-cGAMP signaling in antiviral defense and immune adjuvant effects", Science, Sep. 20, 2013; 341(6152):1390-4.
Liang et al., "Crosstalk between cGAS DNA sensor and Beclin-1 autophagy protein shapes innate anti-microbial immune responses", Cell Host Microbe, Feb. 2014, 15(2): 228-238.
Manikandan et al., "Two-step synthesis and hydrolysis of cyclic di-AMP in Mycobacterium tuberculosis", PLoS One, Jan. 23, 2014; 9(1):e86096.
Malen et al., "Definition of novel cell envelope associated proteins in Triton X-114 extracts of Mycobacterium tuberculosis H37Rv", BMC Microbiology, 2010 10:132, 11 pages.
Manzanillo et al., "Mycobacterium tuberculosis activates the DNA-dependent cytosolic surveillance pathway within macrophages", Cell Host Microbe., May 2012, 11(5): 469-480.
Mathiowitz et al., Biologically erodible microspheres as potential oral drug delivery systems. Nature. Mar. 1997; 386:410-414.
Morales, "BCG: A throwback from the stone age of vaccines opened the path for bladder cancer immunotherapy", San J Urol. Jun. 2017; 24(3):8788-8793.
Orzalli et al, "Nuclear IFI16 induction of IRF-3 signaling during herpesviral infection and degradation of IFI16 by the viral ICP0 protein", Proc Natl Arad Sci U S A. Oct. 30, 2012; 109(44):E3008-17.
Parvatiyar et al., "The helicase DDX41 recognizes the bacterial secondary messengers cyclic di-GMP and cyclic di-AMP to activate a type I interferon immune response", Nat Immunol. Dec. 2012; 13(12):1155-61.

(56) References Cited

OTHER PUBLICATIONS

PCT International Search Report and Written Opinion in International Application No. PCT/US2021/018007, dated Apr. 29, 2021, 10 pages.
PCT International Search Report and Written Opinion in International Application No. PCT/US2019/022341, dated Jul. 4, 2019, 10 pages.
PCT International Search Report and Written Opinion in International Application No. PCT/US2021/053234, dated Mar. 3, 2022, 12 pages.
Postic et al., "Characterization of NmA homologs from Mycobacterium tuberculosis and Mycoplasma pneumoniae", RNA. Jan. 2012; 18(1): 155-165.
Powels et al., "MPDL3280A (anti-PD-L1) treatment leads to clinical activity in metastatic bladder cancer", Nature, 2014, 515: 558-562.
Rachman et al., "Unique Transcriptome Signature of Mycobacterium tuberculosis in Pulmonary Tuberculosis", Infection and Immunity, Feb. 2006, pp. 1233-1242.
Rao et al., "YybT is a signaling protein that contains a cyclic dinucleotide phosphodiesterase domain and a GGDEF domain with ATPase activity", J Biol Chem, Jan. 1, 2010; 285(1):473-82.
Rederlman-Sidi et al., The mechanism of action of BCG therapy for bladder cancer—a current perspective. Nat Rev Urol. Mar. 2014; 11(3):153-62.
Romling. "Great times for small molecules: c-di-AMP, a second messenger candidate in Bacteria and Archaea", Sci Signal. Aug. 19, 2008;1(33):pe39.
Rorbach et al., "PDE12 removes mitocondrial RNA poly(a) tails and controls translation in human mitochondria", Nucleic Acids Research, Jun. 2011, 39(17): 7750-7763.
Rayn et al., "New therapies in nonmuscle invasive bladder cancer treatment.", Indian journal of Urology, Jan.-Mar. 2018, 34(1):11-19.
Sambandmurthy et al., "Mycobacterium tuberculosis DeltaRD1 Del-tapanCD: a safe and limited replicating mutant strain that protects immunocompetent and immunocompromised mice against experimental tuberculosis." Vaccine. 2006, 24(37-39): 6309-6320.
Schirmer et al., "Structural and mechanistic determinants of c-di-GMP signalling", Nat Rev Microbial. Oct. 2009; 7(10):724-35.
Siddiqui et al., "Current clinical trials in non-muscle invasive bladder cancer", Urologic Oncology, 2017, 35(8): 516-527.
Srivastav et al., "Unique subunit packing in mycobacterial nanoRNase leads to alternate substrate recognitions in DHH phosphodiesterases", Nucleic Acids Res, Jul. 2014; 42(12):7894-910.
Sun et al., "Cyclic GMP-AMP synthase is a cytosolic DNA sensor that activates the type I interferon pathway", Science, Feb. 15, 2013; 339(6121):786-91.
Takenaga et al., "Microparticle resins as a potential nasal drug delivery system for insulin", J Control Release. Mar. 2, 1998; 52(1-2):81-7.
Wassermann et al., "Mycobacterium tuberculosis Differentially Activates cGAS- and Inflammasome-Dependent Intracellular Immune Responses through ESX-1", Cell Host Microbe. Jun. 10, 2015; 17(6):799-810.
Woodward et al., "c-di-AMP secreted by intracellular Listeria monocytogenes activates a host type I interferon response", Science. Jun. 25, 2010; 328(5986):1703-5.
Wu et al., "Cyclic GMP-AMP is an endogenous second messenger in innate immune signaling by cytosolic DNA", Science, Feb. 15, 2013; 339(6121):826-30.
Wu et al., "Inhibition of cGAS DNA Sensing by a Herpesvirus Virion Protein", Cell Host Microbe. Sep. 9, 2015;18 (3):333-44.
Yang et al., "Deletion of the cyclic di-AMP phosphodiesterase gene (cnpB) in Mycobacterium tuberculosis leads to reduced virulence in a mouse model of infection", Mol Microbial, Jul. 2014; 93(1):65-79.
Yang et al., "Regulating STING in health and disease", Journal of Inflammation, Jun. 2017, 14(11):1-21.
Zhang et al., "The DNA sensor, cyclic GMP-AMP synthase, is essential for induction of IFN-13 during Chlamydia trachomatis infection", J Immunol. Sep. 1, 2014; 193(5):2394-404.
Zhao et al., "Interferon regulatory factors: at the crossroads of immunity, metabolism, and disease", Biochim Biophys Acta. Feb. 2015; 1852(2):365-78.
Zhu et al., "Structural Biochemistry of a Vibrio Cholerae Dinucleotide Cyclase Reveals Cyclase Activity Reguloation by Folates", Molecular Cell, Sep. 2014, 55(6): 931-937.
Zitzvogel et al., "Type I interferons in anticancer immunity", Nat Rev Immunol. Jul. 2015; 15(7):405-14.
CN Office Action in Chinese Application No. 2019800405920, dated Dec. 6, 2023, 15 pages (with English translation).
Fang et al., "Physiological Function of Second Messenger Cyclic Diguanylate Signaling in Mycobacterium tuberculosis", China Doctoral Dissertation Full-text Database, Jul. 2015, E059-41, 115 pages (with English abstract).
Evans et al., "Squamous cell carcinoma secondary to Buruli ulcer", Transactions of the Royal Society of Tropical Medicine and Hygiene, 1999, 93: 63-64.
JP Office Action in Japanese Application No. 2020-557965, dated Feb. 1, 2023, 12 pages (with English translation).
JP Office Action in Japanese Application No. 2020-557965, dated Aug. 2, 2024, 7 pages (with English translation).
Zaczek et al., "Genetic evaluation of relationship between mutations in rpoB and resistance of Mycobacterium tuberculosis to rifampin", BMC Microbiology, Jan. 2009, 9:10, 8 pages.
CN Office Action in Chinese Application No. 202180028637, dated Feb. 24, 2024, 15 pages (with English translation).
EP Search Report in European Application No. 21754580.5, dated Apr. 10, 2024, 7 pages.
Zhang et al., "STING signaling remodels the tumor microenvironment by antagonizing myeloid-derived suppressor cell expansion", Cell Death & Differentiation, Feb. 2019, 26:2314-2328.
Canadian Examination Report for Canadian Patent Application No. 3,097,569 issued Jan. 21, 2025, 5 pages.
Extended European Search Report for European Patent Application No. 21876626.9 issued Feb. 11, 2025, 8 pages.
Rotcheewaphan, S., "Characterization of Mycobacterium leprae diguanylate cyclases", Ph.D. Dissertation, Colorado State University, Fort Collins, Colorado, Summer 2016, 237pp., downloaded from the internet on Jan. 19, 2025 (Jan. 19, 2025): https://api.mountainscholar.org/server/api/core/bitstreams/7272eddf-631f-420a-b828-ccadd5be4dc6/content.
Sambandamurthy et al., "A pantothenate auxotroph of Mycobacterium tuberculosis is highly attenuated and protects mice against tuberculosis," Nature Medicine, vol. 8, No. 10, Oct. 2022, 1171-1174.

\* cited by examiner

Figure 10
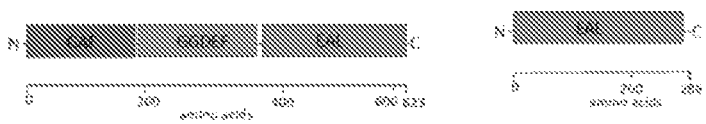
Figure 11
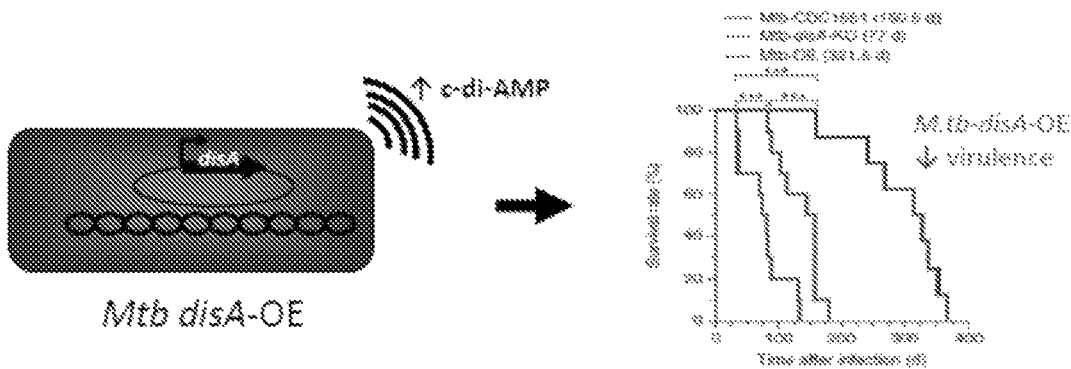
Figure 12

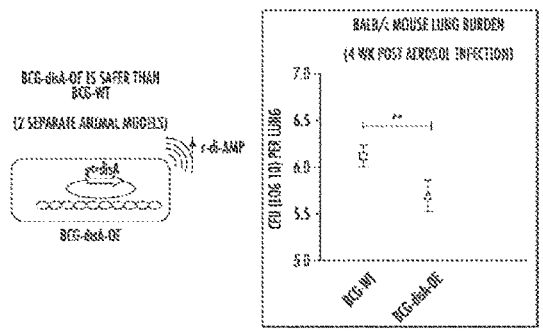
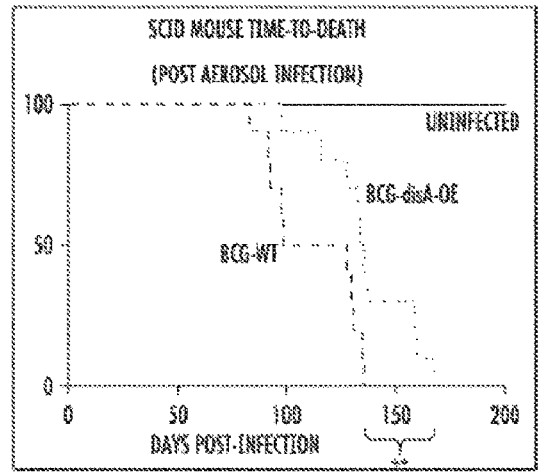
Figure 17A
Figure 17B
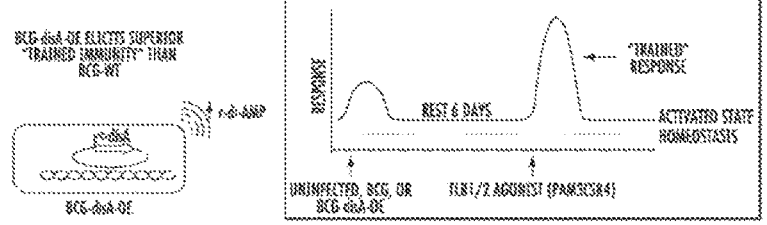
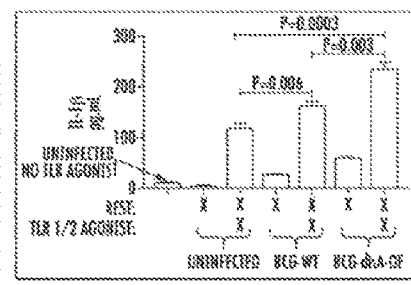
Figure 18
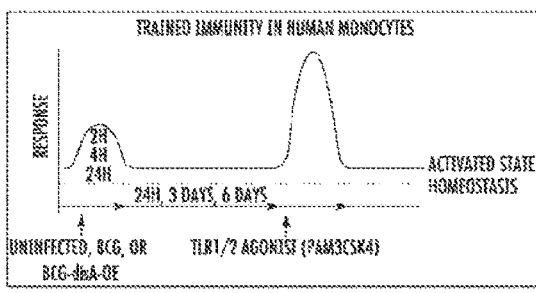
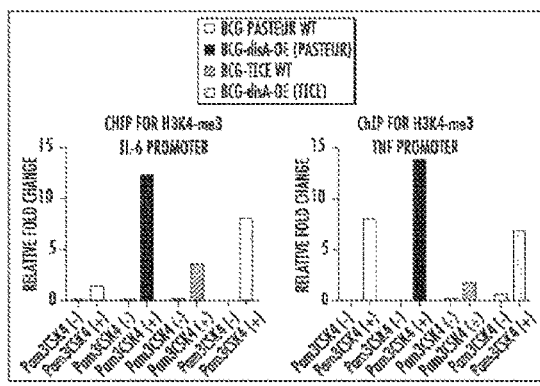
Figure 19

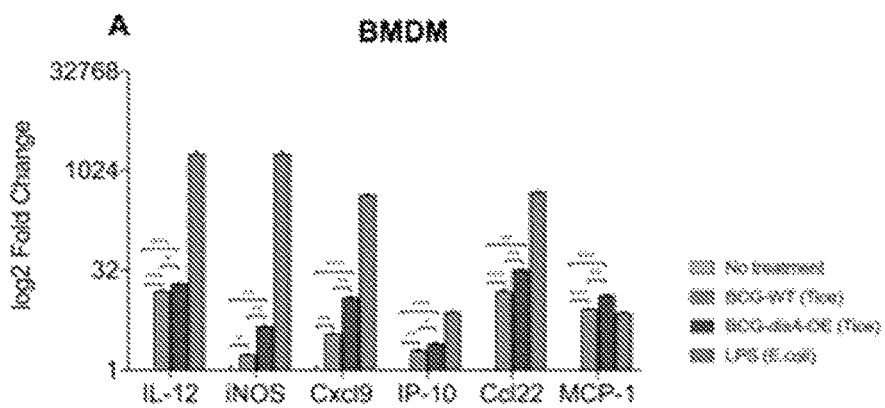
Figure 43A
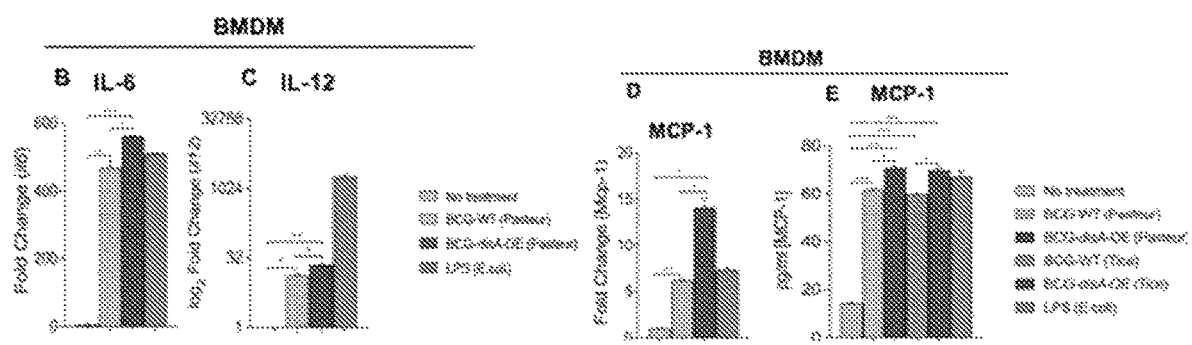
Figure 43B  Figure 43C  Figure 43D  Figure 43E
Figure 44A
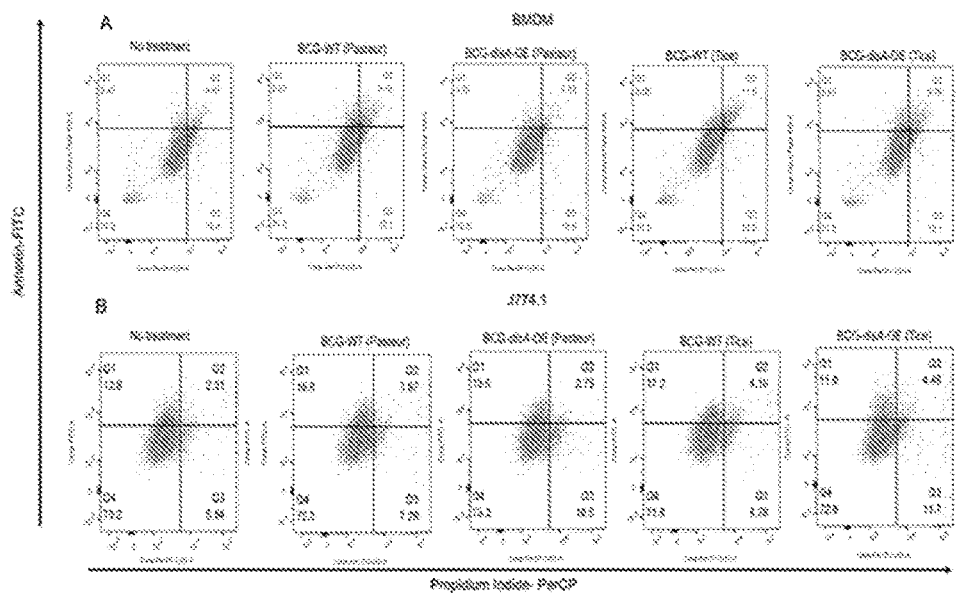
Figure 44B

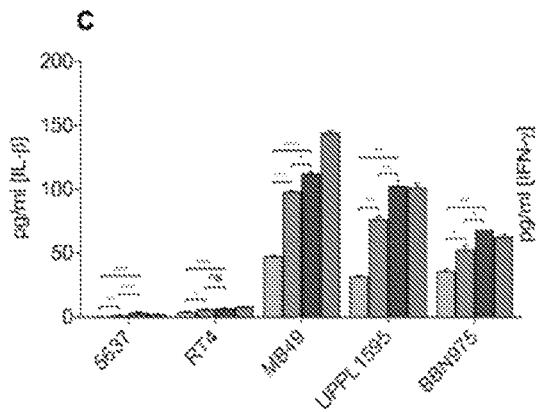
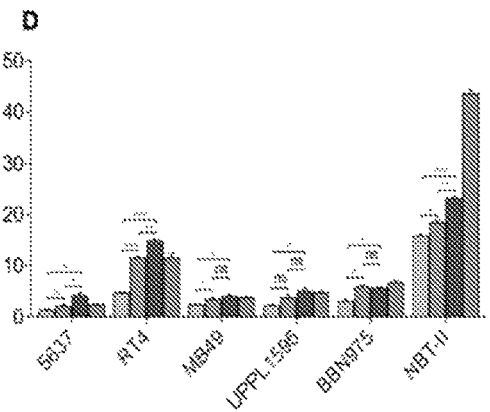
Figure 46C   Figure 46D
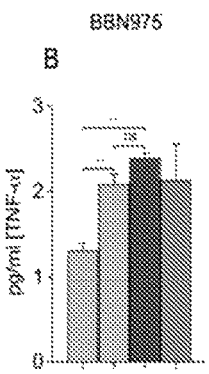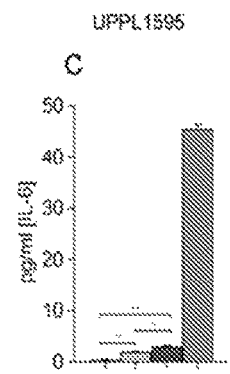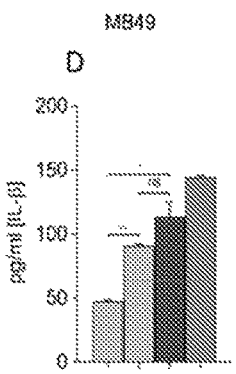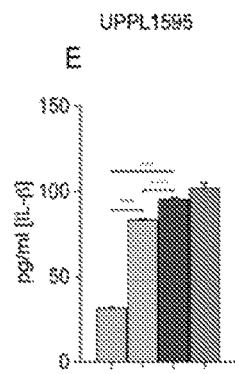
Figure 47A   Figure 47B   Figure 47C   Figure 47D   Figure 47E
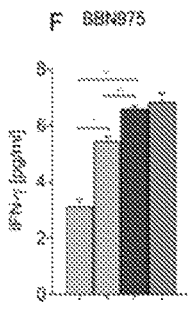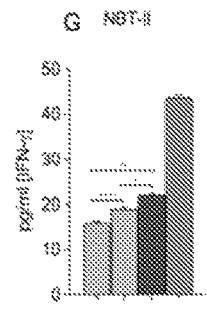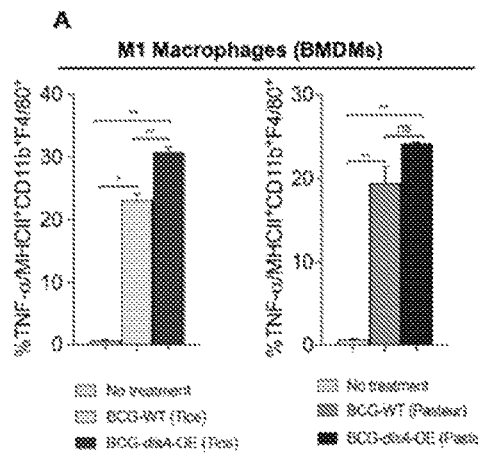
Figure 47F   Figure 47G   Figure 48A

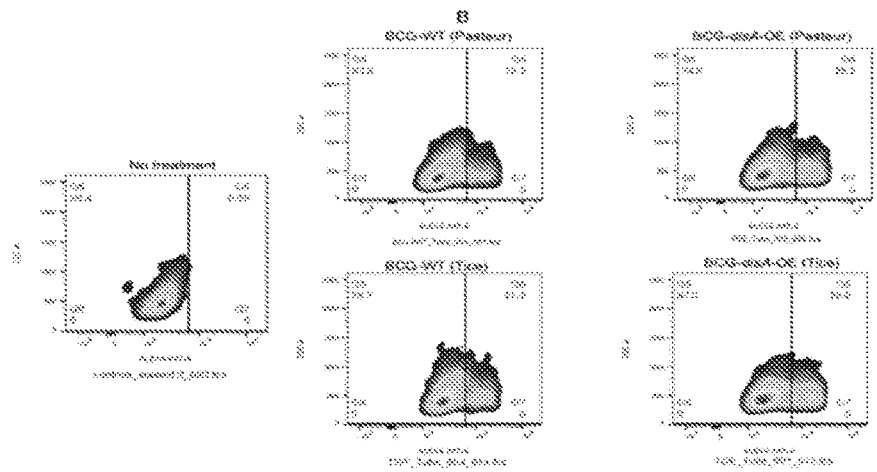
Figure 48B
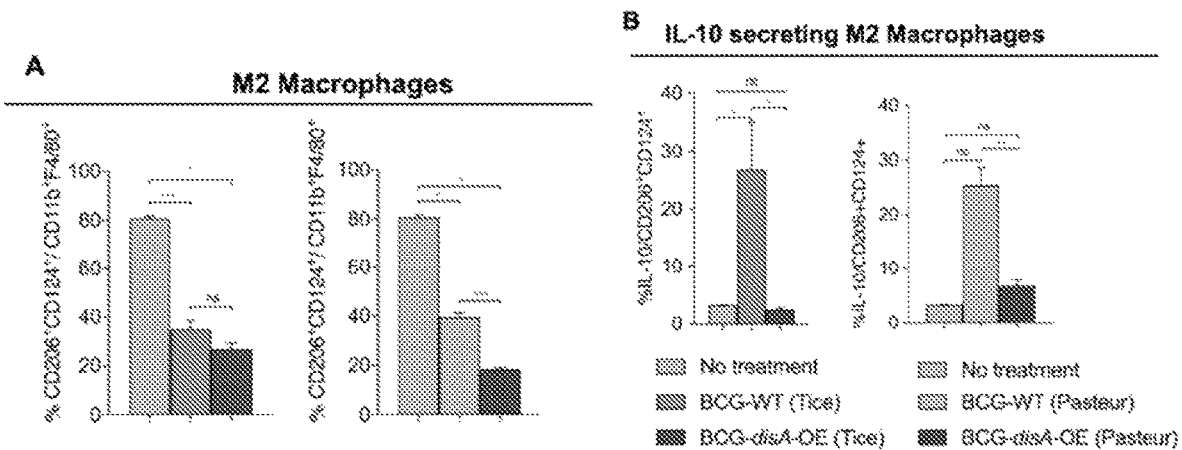
Figure 49A
Figure 49B
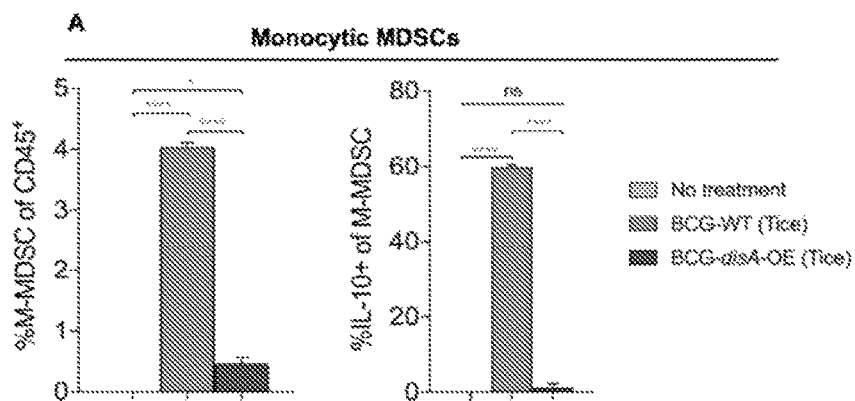
Figure 50A

SEQUENCE LISTING

```
<160> NUMBER OF SEQ ID NOS: 107

<210> SEQ ID NO 1
<211> LENGTH: 358
<212> TYPE: PRT
<213> ORGANISM: Unknown
<220> FEATURE:
<223> OTHER INFORMATION: Description of Unknown:
      Diadenylate cyclase sequence

<400> SEQUENCE: 1

Met His Ala Val Thr Arg Pro Thr Leu Arg Glu Ala Val Ala Arg Leu
1               5                   10                  15

Ala Pro Gly Thr Gly Leu Arg Asp Gly Leu Glu Arg Ile Leu Arg Gly
```

```
            20                  25                  30
Arg Thr Gly Ala Leu Ile Val Leu Gly His Asp Glu Asn Val Glu Ala
        35                  40                  45

Ile Cys Asp Gly Gly Phe Ser Leu Asp Val Arg Tyr Ala Ala Thr Arg
    50                  55                  60

Leu Arg Glu Leu Cys Lys Met Asp Gly Ala Val Val Leu Ser Thr Asp
65                  70                  75                  80

Gly Ser Arg Ile Val Arg Ala Asn Val Gln Leu Val Pro Asp Pro Ser
                85                  90                  95

Ile Pro Thr Asp Glu Ser Gly Thr Arg His Arg Ser Ala Glu Arg Ala
            100                 105                 110

Ala Ile Gln Thr Gly Tyr Pro Val Ile Ser Val Ser His Ser Met Asn
        115                 120                 125

Ile Val Thr Val Tyr Val Arg Gly Glu Arg His Val Leu Thr Asp Ser
    130                 135                 140

Ala Thr Ile Leu Ser Arg Ala Asn Gln Ala Ile Ala Thr Leu Glu Arg
145                 150                 155                 160

Tyr Lys Thr Arg Leu Asp Glu Val Ser Arg Gln Leu Ser Arg Ala Glu
                165                 170                 175

Ile Glu Asp Phe Val Thr Leu Arg Asp Val Met Thr Val Val Gln Arg
            180                 185                 190

Leu Glu Leu Val Arg Arg Ile Gly Leu Val Ile Asp Tyr Asp Val Val
        195                 200                 205

Glu Leu Gly Thr Asp Gly Arg Gln Leu Arg Leu Gln Leu Asp Glu Leu
    210                 215                 220

Leu Gly Gly Asn Asp Thr Ala Arg Glu Leu Ile Val Arg Asp Tyr His
225                 230                 235                 240

Ala Asn Pro Glu Pro Pro Ser Thr Gly Gln Ile Asn Ala Thr Leu Asp
                245                 250                 255

Glu Leu Asp Ala Leu Ser Asp Gly Asp Leu Leu Asp Phe Thr Ala Leu
            260                 265                 270

Ala Lys Val Phe Gly Tyr Pro Thr Thr Thr Glu Ala Gln Asp Ser Thr
        275                 280                 285

Leu Ser Pro Arg Gly Tyr Arg Ala Met Ala Gly Ile Pro Arg Leu Gln
    290                 295                 300

Phe Ala His Ala Asp Leu Leu Val Arg Ala Phe Gly Thr Leu Gln Gly
305                 310                 315                 320

Leu Leu Ala Ala Ser Ala Gly Asp Leu Gln Ser Val Asp Gly Ile Gly
                325                 330                 335

Ala Met Trp Ala Arg His Val Arg Glu Gly Leu Ser Gln Leu Ala Glu
            340                 345                 350

Ser Thr Ile Ser Asp Gln
        355

<210> SEQ ID NO 2
<211> LENGTH: 1077
<212> TYPE: DNA
<213> ORGANISM: Unknown
<220> FEATURE:
<223> OTHER INFORMATION: Description of Unknown:
      Diadenylate cyclase sequence

<400> SEQUENCE: 2
atgcacgctg tgactcgtcc gaccctgcgt gaggctgtcg cccgcctagc cccgggcact      60
gggctgcggg acggcctgga gcgtatcctg cgcggccgca ctggtgccct gatcgtgctg     120
```

```
ggccatgacg agaatgtcga ggccatctgc gatggtggct tctccctcga tgtccgctat    180
gcagcaaccc ggctacgcga gctgtgcaag atggacggcg ccgtggtgct gtccaccgac    240
ggcagccgca tcgtgcgggc caacgtgcaa ctggtaccgg atccgtcgat ccccaccgac    300
gaatcgggga cccggcaccg ctcggccgag cgggccgcga tccagaccgg ttacccggtg    360
atctcagtga gccactcgat gaacatcgtg accgtctacg tccgcgggga acgtcacgta    420
ttgaccgact cggcaaccat cctgtcgcgg gccaaccagg ccatcgcaac cctggagcgg    480
tacaaaacca ggctcgacga ggtcagccgg caactgtcca gggcagaaat cgaggacttc    540
gtcacgctgc gcgatgtgat gacggtggtg caacgcctcg agctggtccg gcgaatcggg    600
ctggtgatcg actacgacgt ggtcgaactc ggcactgatg gtcgtcagct gcggctgcag    660
ctcgacgagt tgctcggcgg caacgacacc gcccgggaat tgatcgtgcg cgattaccac    720
gccaacccgg aaccaccgtc cacggggcaa atcaatgcca ccctggacga actggacgcc    780
ctgtcggacg gcgacctcct cgatttcacc gcgctggcaa aggttttcgg atatccgacg    840
accacggaag cgcaggattc ggcgctgagc ccgcgtggct accgcgcgat ggccggtatc    900
ccccggctcc agttcgccca tgccgacctg ctggtccggg cgttcggaac gttgcagggt    960
ctgctggcgg ccagcgccgg cgatctgcaa tcagtggacg gcatcggcgc catgtgggcc   1020
cgtcatgtgc gcgatgggtt gtcacagctg gcggaatcga ccatcagcga tcaataa     1077
```

<210> SEQ ID NO 3
<211> LENGTH: 7742
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
ggatccttct agaattccgg aattgcactc gccttagggg agtgctaaaa atgatcctgg     60
cactcgcgat cagcgagtgc caggtcggga cggtgagacc cagccagcaa gctgtggtcg    120
tccgtcgcgg gcactgcacc cggccagcgt aagtaatggg ggttgtcggc acccggtgac    180
ctagacacat gcatgcatgc ttaattaatt aagcgatatc cggaggaatc acttccatat    240
gatgcacgct gtgactcgtc cgaccctgcg tgaggctgtc gcccgcctag ccccgggcac    300
tgggctgcgg gacggcctgg agcgtatcct gcgcggccgc actggtgccc tgatcgtgct    360
gggccatgac gagaatgtcg aggccatctg cgatggtggc ttctccctcg atgtccgcta    420
tgcagcaacc cggctacgcg agctgtgcaa gatggacggc gccgtggtgc tgtccaccga    480
cggcagccgc atcgtgcggg ccaacgtgca actggtaccg gatccgtcga tccccaccga    540
cgaatcgggg acccggcacc gctcggccga gcgggccgcg atccagaccg gttacccggt    600
gatctcagtg agccactcga tgaacatcgt gaccgtctac gtccgcgggg aacgtcacgt    660
attgaccgac tcggcaacca tcctgtcgcg ggccaaccag gccatcgcaa ccctggagcg    720
gtacaaaacc aggctcgacg aggtcagccg gcaactgtcc agggcagaaa tcgaggactt    780
cgtcacgctg cgcgatgtga tgacggtggt gcaacgcctc gagctggtcc ggcgaatcgg    840
gctggtgatc gactacgacg tggtcgaact cggcactgat ggtcgtcagc tgcggctgca    900
gctcgacgag ttgctcggcg gcaacgacac cgcccgggaa ttgatcgtgc gcgattacca    960
cgccaacccg gaaccaccgt ccacggggca aatcaatgcc accctggacg aactggacgc   1020
cctgtcggac ggcgacctcc tcgatttcac cgcgctggca aaggttttcg gatatccgac   1080
```

```
gaccacggaa gcgcaggatt cgacgctgag cccgcgtggc taccgcgcga tggccggtat   1140 ccccggctc cagttcgccc atgccgacct gctggtccgg gcgttcggaa cgttgcaggg    1200
tctgctggcg gccagcgccg gcgatctgca atcagtggac ggcatcggcg ccatgtgggc   1260
ccgtcatgtg cgcgaggggt tgtcacagct ggcggaatcg accatcagcg atcaataaac   1320
gcgttctggc gtaatagcga agaggcccgc accgatcgcc cttcccaaca gttgcgcagc   1380
ctgaatggcg aatggcgctt tgcctggttt ccggtcgaag cttggccgga tctaaagttt   1440
tgtcgtcttt ccagacgtta gtaaatgaat tttctgtatg aggttttgct aaacaacttt   1500
caacagtttc agcggagtga aatagaaag gaacaactaa aggaattgcg aataataatt    1560
ttttcacgtt gaaaatctcc aaaaaaaag ctccaaaag gagcctttaa ttgtatcggt      1620
ttatcagctt gctttcgagg tgaatttctt aaacagcttg ataccgatag ttgcgccgac   1680
aatgacaaca accatcgccc acgcataacc gatatattcg gtcgctgagg cttgcaggga   1740
gtcaaaggcc gcttttgcgg ggatccgctc ggaggcgcgg tcgcggcgcg gctgtggcat   1800
gtcggggcgt gccgctcccc cggcgccgcc catcggcccg cccattggca ttccgcccat   1860
gccgcccatc attcctgtgg agccagaact gatccagcct gtgccacagc cgacaggatg   1920
gtgaccacca tttgccccat atcaccgtcg gtactgatcc cgtcgtcaat aaaccgaacc   1980
gctacaccct gagcatcaaa ctcttttatc agttggatca tgtcggcggt gtcgcggcca   2040
agacggtcga gcttcttcac cagaatgaca tcaccttcct ccaccttcat cctcagcaaa   2100
tccagcccct tcccgatctgt tgaactgccg gatgccttgt cggtaaagat gcggttagct   2160 tttaccctg catctttgag cgctgaggtc tgcctcgtga agaaggtgtt gctgactcat    2220
accaggcctg aatcgcccca tcatccagcc agaaagtgag ggagccacgg ttgatgagag   2280
ctttgttgta ggtggaccag ttggtgattt tgaactttg ctttgccacg gaacggtctg    2340
cgttgtcggg aagatgcgtg atctgatcct tcaactcagc aaaagttcga tttattcaac   2400
aaagccgccg tcccgtcaag tcagcgtaat gctctgccag tgttacaacc aattaaccaa   2460
ttctgattag aaaaactcat cgagcatcaa atgaaactgc aattattca tatcaggatt    2520 atcaatacca tattttgaa aaagccgttt ctgtaatgaa ggagaaaact caccgaggca    2580
gttccatagg atggcaagat cctggtatcg gtctgcgatt ccgactcgtc caacatcaat   2640
acaacctatt aatttccct cgtcaaaaat aaggttatca agtgagaaat caccatgagt    2700
gacgactgaa tccggtgaga atggcaaaag cttatgcatt tctttccaga cttgttcaac   2760
aggccagcca ttacgctcgt catcaaaatc actcgcatca accaaaccgt tattcattcg   2820
tgattgcgcc tgagcgagac gaaatacgcg atcgctgtta aaaggacaat tacaaacagg   2880
aatcgaatgc aaccggcgca ggaacactgc cagcgcatca acaatatttt cacctgaatc   2940
aggatattct tctaatacct ggaatgctgt ttccccgggg atcgcagtgg tgagtaacca   3000
tgcatcatca ggagtacgga taaaatgctt gatggtcgga agaggcataa attccgtcag   3060
ccagtttagt ctgaccatct catctgtaac atcattggca acgctacctt tgccatgttt   3120
cagaaacaac tctggcgcat cgggcttccc atacaatcga tagattgtcg cacctgattg   3180
cccgacatta tcgcgagccc atttataccc atataaatca gcatccatgt tggaatttaa   3240
tcgcggcctc gagcaagacg tttcccgttg aatatggctc ataacacccc ttgtattact   3300
gtttatgtaa gcagacagtt ttattgttca tgatgatata ttttatctt gtgcaatgta    3360 acatcagaga ttttgagaca caacgtggct ttgttgaata aatcgaactt tgctgagtt    3420
```

-continued

```
gaaggatcag atcacgcatc ttcccgacaa cgcagaccgt tccgtggcaa agcaaaagtt    3480
caaaatcacc aactggtcca cctacaacaa agctctcatc aaccgtggct ccctcacttt    3540
ctggctggat gatggggcga ttcaggcctg gtatgagtca gcaacacctt cttcacgagg    3600
cagacctcag cgctagcgga gtgtatactg gcttactatg ttggcactga tgagggtgtc    3660
agtgaagtgc ttcatgtggc aggagaaaaa aggctgcacc ggtgcgtcag cagaatatgt    3720
gatacaggat atattccgct tcctcgctca ctgactcgct acgctcggtc gttcgactgc    3780
ggcgagcgga atggcttac gaacggggcg gagatttcct ggaagatgcc aggaagatac     3840
ttaacaggga agtgagaggg ccgcggcaaa gccgttttc cataggctcc gccccctga     3900 caagcatcac gaaatctgac gctcaaatca gtggtggcga aacccgacag gactataaag    3960
ataccaggcg tttccccctg gcggctccct cgtgcgctct cctgttcctg cctttcggtt    4020
taccggtgtc attccgctgt tatggccgcg tttgtctcat tccacgcctg acactcagtt    4080
ccgggtaggc agttcgctcc aagctggact gtatgcacga accccccgtt cagtccgacc    4140
gctgcgcctt atccggtaac tatcgtcttg agtccaaccc ggaaagacat gcaaaagcac    4200
cactggcagc agccactggt aattgattta gaggagttag tcttgaagtc atgcgccggt    4260
taaggctaaa ctgaaaggac aagttttggt gactgcgctc ctccaagcca gttacctcgg    4320
ttcaaagagt tggtagctca gagaaccttc gaaaaccgc cctgcaaggc ggttttttcg     4380
ttttcagagc aagagattac gcgcagacca aaacgatctc aagaagatca tcttattaag    4440
gggtctgacg ctcagtggaa cgaaaactca cgttaaggga ttttggtcat gagattatca    4500
aaaaggatct tcacctagat ccttttaaaa gtgctcatca ttggaaaacg ttcttcgggg    4560
cgaaaactct caaggatctt accgctgttg agatccagtt cgatgtaacc cactcgtgca    4620
cccaactgat cttcagcatc ttttactttc accagcgttt ctgggtgagc aaaaacagga    4680
aggcaaaatg ccgcaaaaaa gggaataagg gcgacacgga aatgttgaat actcatactc    4740
ttcctttttc aatattattg aagcatttat cagggttatt gtctcatgag cggatacata    4800
tttgaatgta tttagaaaaa taaacaaata ggggttccgc gcacatttcc ccgaaaagtg    4860
ccacctgacg tctaagaaac cattattatc atgacattaa cctataaaaa taggcgtatc    4920
acgaggccct ttcgtcttca agaattccca ggcatcaaat aaaacgaaag gctcagtcga    4980
aagactgggc ctttcgtttt atctgttgtt tgtcggtgaa cgctctcctg agtaggacaa    5040
atccgccggg agcggatttg aacgttgcga agcaacggcc cggagggtgg cgggcaggac    5100
gcccgccata aactgccagg gaattccat cgagccgaga acgttatcga agttggtcat      5160
gtgtaatccc ctcgtttgaa cttttggatta agcgtagata caccccttgga caagccagtt    5220 ggattcggag acaagcaaat tcagccttaa aaagggcgag ccctgcggt ggtgaacac       5280 cgcagggcct ctaaccgctc gacgcgctgc accaaccagc ccgcgaacgg ctggcagcca    5340
gcgtaaggcg cggctcatcg ggcggcgttc gccacgatgt cctgcacttc gagccaagcc    5400
tcgaacacct gctggtgtgc acgactcacc cggttgttga caccgcgcgc ggccgtgcgg    5460
gctcggtggg gcggctctgt cgcccttgcc agcgtgagta gcgcgtacct cacctcgccc    5520
aacaggtcgc acacagccga ttcgtacgcc ataaagccag gtgagcccac cagctccgta    5580
agttcgggcg ctgtgtggct cgtacccgcg cattcaggcg gcaggggtc taacgggtct     5640 aaggcggcgt gtacgcggcc acagcggctc tcagcggccc ggaaacgtcc tcgaaacgac    5700
gcatgtgttc ctcctggttg gtacaggtgg ttggggtgc tcggctgtcg cggttgttcc    5760
accaccaggg ctcgacggga gagcgggga gtgtgcagtt gtggggtggc ccctcagcga    5820
```

```
aatatctgac ttggagctcg tgtcggacca tacaccggtg attaatcgtg gtctactacc    5880
aagcgtgagc cacgtcgccg acgaatttga gcagctctgg ctgccgtact ggccgctggc    5940
aagcgacgat ctgctcgagg ggatctaccg ccaaagccgc gcgtcggccc taggccgccg    6000
gtacatcgag gcgaacccaa cagcgctggc aaacctgctg gtcgtggacg tagaccatcc    6060
agacgcagcg ctccgagcgc tcagcgcccg ggggtcccat ccgctgccca cgcgatcgt    6120
gggcaatcgc gccaacggcc acgcacacgc agtgtgggca ctcaacgccc ctgttccacg    6180
caccgaatac gcgcggcgta agccgctcgc atacatggcg gcgtgcgccg aaggccttcg    6240
gcggccgtcg acgcgaccg cagttactca ggcctcatga ccaaaaaccc cggccacatc    6300
gcctgggaaa cggaatggct ccactcagat ctctacacac tcagccacat cgaggccgag    6360
ctcggcgcga acatgccacc gccgcgctgg cgtcagcaga ccacgtacaa agcggctccg    6420
acgccgctag gcggaattg cgcactgttc gattccgtca ggttgtgggc ctatcgtccc    6480
gccctcatgc ggatctacct gccgacccgg aacgtggacg gactcggccg cgcgatctat    6540
gccgagtgcc acgcgcgaaa cgccgaattc ccgtgcaacg acgtgtgtcc cggaccgcta    6600
ccggacagcg aggtccgcgc catcgccaac agcatttggc gttggatcac aaccaagtcg    6660
cgcatttggg cggacgggat cgtggtctac gaggccacac tcagtgcgcg ccagtcggcc    6720
atctcgcgga agggcgcagc agcgcgcacg cggcgagca cagttgcgcg cgcgcaaag    6780
tccgcgtcag ccatggaggc attgctatga gcgacggcta cagcgacggc tacagcgacg    6840
gctacaaccg gcagccgact gtccgcaaaa agccgtgacg cgccgaaggc gctcgaatca    6900
ccggactatc cgaacgccac gtcgtccggc tcgtggcgca ggaacgcagc gagtggctcg    6960
ccgagcaggc tgcacgcgcg cgaagcatcc gcgcctatca cgacgacgag gccactctt    7020
ggccgcaaac ggccaaacat ttcgggctgc atctggacac cgttaagcga ctcggctatc    7080
gggcgaggaa agagcgtgcg gcagaacagg aagcggctca aaaggcccac aacgaagccg    7140
acaatccacc gctgttctaa cgcaattggg gacgggtgtc gcggggttc cgtgggggt    7200
tccgttgcaa cgggtcggac aggtaaaagt cctggtagac gctagttttc tggtttgggc    7260
catgcctgtc tcgttgcgtg tttcgttgcg ccgttttgaa taccagccag acgagacggg    7320
gttctacgaa tcttggtcga taccaagcca tttccgctga atatcgggga gctcaccgcc    7380
agaatcggtg gttgtggtga tgtacgtggc gaactccgtt gtagtgcctg tggtggcatc    7440
cgtggccact ctcgttgcac ggttcgttgt gccgttacag gccccgttga cagctcaccg    7500
aacgtagtta aaacatgctg gtcaaactag gtttaccaac gatacgagtc agctcatcta    7560
gggccagttc taggcgttgt tcgttgcgcg gttcgttgcg catgtttcgt gtggttgcta    7620
gatggctccg caaccacacg cttcgaggtt gagtgcttcc agcacgggcg cgatccagaa    7680
gaacttcgtc gtgcgactgt cctcgttggg atctagcccg cctaatgagc gggcttttt    7740
tt                                                                  7742
```

<210> SEQ ID NO 4
<211> LENGTH: 623
<212> TYPE: PRT
<213> ORGANISM: Unknown
<220> FEATURE:
<223> OTHER INFORMATION: Description of Unknown:
      Bifunctional diguanylate cyclase/phosphodiesterase sequence

<400> SEQUENCE: 4

Met Cys Asn Asp Thr Ala Thr Pro Gln Leu Glu Glu Leu Val Thr Thr

-continued

```
1               5                   10                  15
Val Ala Asn Gln Leu Met Thr Val Asp Ala Ala Thr Ser Ala Glu Val
                20                  25                  30

Ser Gln Arg Val Leu Ala Tyr Leu Val Glu Gln Leu Gly Val Asp Val
                35                  40                  45

Ser Phe Leu Arg His Asn Asp Arg Asp Arg Ala Thr Arg Leu Val
 50                      55                  60

Ala Glu Trp Pro Pro Arg Leu Asn Ile Pro Asp Pro Asp Pro Leu Arg
 65                  70                  75                  80

Leu Ile Tyr Phe Ala Asp Ala Asp Pro Val Phe Ala Leu Cys Glu His
                 85                  90                  95

Ala Lys Glu Pro Leu Val Phe Arg Pro Glu Pro Ala Thr Glu Asp Tyr
                100                 105                 110

Gln Arg Leu Ile Glu Glu Ala Arg Gly Val Pro Val Thr Ser Ala Ala
                115                 120                 125

Ala Val Pro Leu Val Ser Gly Glu Ile Thr Thr Gly Leu Leu Gly Phe
                130                 135                 140

Ile Lys Phe Gly Asp Arg Lys Trp His Glu Ala Glu Leu Asn Ala Leu
145                 150                 155                 160

Met Thr Ile Ala Thr Leu Phe Ala Gln Val Gln Ala Arg Val Ala Ala
                165                 170                 175

Glu Ala Arg Leu Arg Tyr Leu Ala Asp His Asp Asp Leu Thr Gly Leu
                180                 185                 190

His Asn Arg Arg Ala Leu Leu Gln His Leu Asp Gln Arg Leu Ala Pro
                195                 200                 205

Gly Gln Pro Gly Pro Val Ala Ala Leu Phe Leu Asp Leu Asp Arg Leu
                210                 215                 220

Lys Ala Ile Asn Asp Tyr Leu Gly His Ala Ala Gly Asp Gln Phe Ile
225                 230                 235                 240

His Val Phe Ala Gln Arg Ile Gly Asp Ala Leu Val Gly Glu Ser Leu
                245                 250                 255

Ile Ala Arg Leu Gly Gly Asp Glu Phe Val Leu Ile Pro Ala Ser Pro
                260                 265                 270

Met Ser Ala Asp Ala Ala Gln Pro Leu Ala Glu Arg Leu Arg Asp Gln
                275                 280                 285

Leu Lys Asp His Val Ala Ile Gly Gly Glu Val Leu Thr Arg Thr Val
                290                 295                 300

Ser Ile Gly Val Ala Ser Gly Thr Pro Gly Gln His Thr Pro Ser Asp
305                 310                 315                 320

Leu Leu Arg Arg Ala Asp Gln Ala Ala Leu Ala Ala Lys His Ala Gly
                325                 330                 335

Gly Asp Ser Val Ala Ile Phe Thr Ala Asp Met Ser Val Ser Gly Glu
                340                 345                 350

Leu Arg Asn Asp Ile Glu Leu His Leu Arg Arg Gly Ile Glu Ser Asp
                355                 360                 365

Ala Leu Arg Leu Val Tyr Leu Pro Glu Val Asp Leu Arg Thr Gly Asp
                370                 375                 380

Ile Val Gly Thr Glu Ala Leu Val Arg Trp Gln His Pro Thr Arg Gly
385                 390                 395                 400

Leu Leu Ala Pro Gly Cys Phe Ile Pro Val Ala Glu Ser Ile Asn Leu
                405                 410                 415

Ala Gly Glu Leu Asp Arg Trp Val Leu Arg Arg Ala Cys Asn Glu Phe
                420                 425                 430
```

Ser Glu Trp Gln Ser Ala Gly Leu Gly His Asp Ala Leu Leu Arg Ile
              435                 440                 445

Asn Val Ser Ala Gly Gln Leu Val Thr Gly Gly Phe Val Asp Phe Val
        450                 455                 460

Ala Asp Thr Ile Gly Gln His Gly Leu Asp Ala Ser Ser Val Cys Leu
465                 470                 475                 480

Glu Ile Thr Glu Asn Val Val Val Gln Asp Leu His Thr Ala Arg Ala
                485                 490                 495

Thr Leu Ala Arg Leu Lys Glu Val Gly Val His Ile Ala Ile Asp Asp
            500                 505                 510

Phe Gly Thr Gly Tyr Ser Ala Ile Ser Leu Leu Gln Thr Leu Pro Ile
        515                 520                 525

Asp Thr Leu Lys Ile Asp Lys Thr Phe Val Arg Gln Leu Gly Thr Asn
530                 535                 540

Thr Ser Asp Leu Val Ile Val Arg Gly Ile Met Thr Leu Ala Glu Gly
545                 550                 555                 560

Phe Gln Leu Asp Val Val Ala Glu Gly Val Glu Thr Glu Ala Ala Ala
                565                 570                 575

Arg Ile Leu Leu Asp Gln Arg Cys Tyr Arg Ala Gln Gly Phe Leu Phe
            580                 585                 590

Ser Arg Pro Val Pro Gly Glu Ala Met Arg His Met Leu Ser Ala Arg
        595                 600                 605

Arg Leu Pro Pro Thr Cys Ile Pro Ala Thr Asp Pro Ala Leu Ser
610                 615                 620

<210> SEQ ID NO 5
<211> LENGTH: 1872
<212> TYPE: DNA
<213> ORGANISM: Unknown
<220> FEATURE:
<223> OTHER INFORMATION: Description of Unknown:
      Bifunctional diguanylate cyclase/phosphodiesterase sequence

<400> SEQUENCE: 5
atgtgcaacg acaccgcgac gccgcagctt gaggagctcg tcaccaccgt agccaaccag      60
ctcatgacag tcgacgctgc cacgtcagcc gaagtcagtc agcgcgtttt ggcctatcta     120
gtggaacagc tgggcgtaga tgtcagcttt ttgcgtcata cgatcgcga caggcgcgcg     180 acgaggctgg tggccgaatg gccacctcgc ctcaacatac cggaccccga tccgctcagg     240
ctgatctact cgctgatgc cgacccggtg tttgcgctat gcaacacgc caaagagcct     300 ctcgtgttcc ggcccgagcc ggccaccgag gactatcaac gcctcatcga agaagcccgc     360
ggggttccgg taacgtcggc tgccgccgtg ccgctggtat ctggcgagat caccactgga     420
ctgctggggt tcatcaagtt cggtgatcgg aaatggcacg aggccgagct taacgccctc     480
atgaccatcg ctacactctt cgcccaggtg caggctcgcg tcgccgccga ggcgcggctt     540
cgctatctgg ccgaccatga cgatctgacc ggactgcata accgtcgcgc gttgctgcag     600
cacctggacc aaagactggc ccccggacaa cctggcccgg tcgcggcgct atttctcgac     660
ttggaccgcc tcaaggccat caacgactac ctgggccacg ccgccggtga ccagttcatc     720
catgtgttcg cccaacggat cggtgacgca ctcgttggcg agagcctgat cgcccgactc     780
ggcggcgacg aattcgtcct catacccgca tctccaatga gtgccgatgc cgctcaaccg     840
ctcgccgaac gtcttcgcga ccagctcaag gaccacgtcg ctatcggcgg tgaggtgctc     900
acccgcaccg tcagtatcgg tgtcgcctca gggactcccg gacagcacac accgtcggac     960

-continued

```
ctcctgcgcc gagccgacca agccgctctg gcagccaaac acgccggcgg agatagcgtc    1020
gcgattttca ccgcggacat gtcggtcagc ggcgaactgc gcaacgatat tgaactcac     1080 cttcgacgtg gtatcgaatc cgacgccctt cgcctggtct acctacccga ggtcgaccta    1140
cggaccggcg acattgtcgg gaccgaggca ttggtccggt ggcagcaccc cacccgtggg    1200
ctgctggcac cgggctgctt catccctgtg gccgaatcca tcaaccttgc aggcgaattg    1260
gatagatggg tgctgcggag ggcctgcaat gaattctccg agtggcagtc agccggtttg    1320
ggccacgacg cgctgctgcg tatcaacgtc tcagctggac agctggtgac gggcgggttt    1380
gttgacttcg tcgcagacac gatcggccag cacggtctgg acgcctcgtc cgtgtgtttg    1440
gaaatcaccg aaaacgttgt ggtgcaagac ctacataccg ccagagccac cctggctcga    1500
ctcaaagaag tcggcgttca catcgctatc gacgatttcg gcaccggcta tagcgccata    1560
tcactgttgc agacgctacc gatcgacacg ctcaagatcg acaaaacatt cgtgcggcaa    1620
ctcggaacca acactagcga tctggtcatt gtgcgcggca tcatgacact cgccgaaggc    1680
ttccaactcg atgtagtagc cgaaggcgtc gagaccgagg ctgccgccag aattctattg    1740
gatcagcgct gttaccgtgc gcaaggcttc ttgttctccc ggcctgtccc cggggaggcc    1800
atgcggcaca tgttgtccgc acgacgacta ccgccgacct gcatacctgc aactgacccg    1860
gcgttatctt ga                                                       1872
```

<210> SEQ ID NO 6
<211> LENGTH: 353
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Cys Asn Asp Thr Ala Thr Pro Gln Leu Glu Glu Leu Val Thr Thr
1               5                   10                  15

Val Ala Asn Gln Leu Met Thr Val Asp Ala Ala Thr Ser Ala Glu Val
                20                  25                  30

Ser Gln Arg Val Leu Ala Tyr Leu Val Glu Gln Leu Gly Val Asp Val
            35                  40                  45

Ser Phe Leu Arg His Asn Asp Arg Asp Arg Ala Thr Arg Leu Val
        50                  55                  60

Ala Glu Trp Pro Pro Arg Leu Asn Ile Pro Asp Pro Asp Pro Leu Arg
65                  70                  75                  80

Leu Ile Tyr Phe Ala Asp Ala Asp Pro Val Phe Ala Leu Cys Glu His
                85                  90                  95

Ala Lys Glu Pro Leu Val Phe Arg Pro Glu Pro Ala Thr Glu Asp Tyr
                100                 105                 110

Gln Arg Leu Ile Glu Glu Ala Arg Gly Val Pro Val Thr Ser Ala Ala
            115                 120                 125

Ala Val Pro Leu Val Ser Gly Glu Ile Thr Thr Gly Leu Leu Gly Phe
        130                 135                 140

Ile Lys Phe Gly Asp Arg Lys Trp His Glu Ala Glu Leu Asn Ala Leu
145                 150                 155                 160

Met Thr Ile Ala Thr Leu Phe Ala Gln Val Gln Ala Arg Val Ala Ala
                165                 170                 175

Glu Ala Arg Leu Arg Tyr Leu Ala Asp His Asp Asp Leu Thr Gly Leu
            180                 185                 190

His Asn Arg Arg Ala Leu Leu Gln His Leu Asp Gln Arg Leu Ala Pro
            195                 200                 205

Gly Gln Pro Gly Pro Val Ala Ala Leu Phe Leu Leu Asp Arg Leu
    210                 215                 220

Lys Ala Ile Asn Asp Tyr Leu Gly His Ala Ala Gly Asp Gln Phe Ile
225                 230                 235                 240

His Val Phe Ala Gln Arg Ile Gly Asp Ala Leu Val Gly Glu Ser Leu
                245                 250                 255

Ile Ala Arg Leu Gly Gly Asp Glu Phe Val Leu Ile Pro Ala Ser Pro
            260                 265                 270

Met Ser Ala Asp Ala Ala Gln Pro Leu Ala Glu Arg Leu Arg Asp Gln
            275                 280                 285

Leu Lys Asp His Val Ala Ile Gly Gly Glu Val Leu Thr Arg Thr Val
        290                 295                 300

Ser Ile Gly Val Ala Ser Gly Thr Pro Gly Gln His Thr Pro Ser Asp
305                 310                 315                 320

Leu Leu Arg Arg Ala Asp Gln Ala Leu Ala Ala Lys His Ala Gly
                325                 330                 335

Gly Asp Ser Val Ala Ile Phe Thr Ala Asp Met Ser Val Ser Gly Glu
            340                 345                 350

Leu

<210> SEQ ID NO 7
<211> LENGTH: 1059
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

```
atgtgcaacg acaccgcgac gccgcagctt gaggagctcg tcaccaccgt agccaaccag      60
ctcatgacag tcgacgctgc cacgtcagcc gaagtcagtc agcgcgtttt ggcctatcta     120
gtggaacagc tgggcgtaga tgtcagcttt ttgcgtcata cgatcgcga caggcgcgcg     180
acgaggctgg tggccgaatg gccacctcgc ctcaacatac cggaccccga tccgctcagg     240
ctgatctact cgctgatgc cgacccggtg tttgcgctat gcaacacgc caaagagcct     300
ctcgtgttcc ggcccgagcc ggccaccgag gactatcaac gcctcatcga agaagcccgc     360
ggggttccgg taacgtcggc tgccgccgtg ccgctggtat ctggcgagat caccactgga     420
ctgctggggt tcatcaagtt cggtgatcgg aaatggcacg aggccgagct taacgccctc     480
atgaccatcg ctacactctt cgcccaggtg caggctcgcg tcgccgccga ggcgcggctt     540
cgctatctgg ccgaccatga cgatctgacc ggactgcata accgtcgcgc gttgctgcag     600
cacctggacc aaagactggc ccccggacaa cctgggccgg tcgcggcgct atttctcgac     660
ttggaccgcc tcaaggccat caacgactac ctggccacg ccgccggtga ccagttcatc     720
catgtgttcg cccaacggat cggtgacgca ctcgttggcg agagcctgat cgcccgactc     780
ggcggcgacg aattcgtcct catacccgca tctccaatga gtgccgatgc cgctcaaccg     840
ctcgccgaac gtcttcgcga ccagctcaag gaccacgtcg ctatcggcgg tgaggtgctc     900
acccgcaccg tcagtatcgg tgtcgcctca gggactcccg acagcacac accgtcggac     960
ctcctgcgcc gagccgacca agccgctctg gcagccaaac acgccggcgg agatagcgtc    1020
gcgattttca ccgcggacat gtcggtcagc ggcgaactg                           1059
```

<210> SEQ ID NO 8
<211> LENGTH: 436
<212> TYPE: PRT
<213> ORGANISM: Vibrio cholera

<400> SEQUENCE: 8

```
Met Arg Met Thr Trp Asn Phe His Gln Tyr Tyr Thr Asn Arg Asn Asp
1               5                   10                  15

Gly Leu Met Gly Lys Leu Val Leu Thr Asp Glu Glu Lys Asn Asn Leu
            20                  25                  30

Lys Ala Leu Arg Lys Ile Ile Arg Leu Arg Thr Arg Asp Val Phe Glu
        35                  40                  45

Glu Ala Lys Gly Ile Ala Lys Ala Val Lys Lys Ser Ala Leu Thr Phe
    50                  55                  60

Glu Ile Ile Gln Glu Lys Val Ser Thr Thr Gln Ile Lys His Leu Ser
65                  70                  75                  80

Asp Ser Glu Gln Arg Glu Val Ala Lys Leu Ile Tyr Glu Met Asp Asp
                85                  90                  95

Asp Ala Arg Asp Glu Phe Leu Gly Leu Thr Pro Arg Phe Trp Thr Gln
            100                 105                 110

Gly Ser Phe Gln Tyr Asp Thr Leu Asn Arg Pro Phe Gln Pro Gly Gln
        115                 120                 125

Glu Met Asp Ile Asp Asp Gly Thr Tyr Met Pro Met Pro Ile Phe Glu
    130                 135                 140

Ser Glu Pro Lys Ile Gly His Ser Leu Leu Ile Leu Leu Val Asp Ala
145                 150                 155                 160

Ser Leu Lys Ser Leu Val Ala Glu Asn His Gly Trp Lys Phe Glu Ala
                165                 170                 175

Lys Gln Thr Cys Gly Arg Ile Lys Ile Glu Ala Lys Thr His Ile
            180                 185                 190

Asp Val Pro Met Tyr Ala Ile Pro Lys Asp Glu Phe Gln Lys Lys Gln
        195                 200                 205

Ile Ala Leu Glu Ala Asn Arg Ser Phe Val Lys Gly Ala Ile Phe Glu
    210                 215                 220

Ser Tyr Val Ala Asp Ser Ile Thr Asp Ser Glu Thr Tyr Glu Leu
225                 230                 235                 240

Asp Ser Glu Asn Val Asn Leu Ala Leu Arg Glu Gly Asp Arg Lys Trp
                245                 250                 255

Ile Asn Ser Asp Pro Lys Ile Val Glu Asp Trp Phe Asn Asp Ser Cys
            260                 265                 270

Ile Arg Ile Gly Lys His Leu Arg Lys Val Cys Arg Phe Met Lys Ala
        275                 280                 285

Trp Arg Asp Ala Gln Trp Asp Val Gly Gly Pro Ser Ser Ile Ser Leu
    290                 295                 300

Met Ala Ala Thr Val Asn Ile Leu Asp Ser Val Ala His Asp Ala Ser
305                 310                 315                 320

Asp Leu Gly Glu Thr Met Lys Ile Ile Ala Lys His Leu Pro Ser Glu
                325                 330                 335

Phe Ala Arg Gly Val Glu Ser Pro Asp Ser Thr Asp Glu Lys Pro Leu
            340                 345                 350

Phe Pro Pro Ser Tyr Lys His Gly Pro Arg Glu Met Asp Ile Met Ser
        355                 360                 365

Lys Leu Glu Arg Leu Pro Glu Ile Leu Ser Ser Ala Glu Ser Ala Asp
```

```
                370                 375                 380
Ser Lys Ser Glu Ala Leu Lys Lys Ile Asn Met Ala Phe Gly Asn Arg
385                 390                 395                 400

Val Thr Asn Ser Glu Leu Ile Val Leu Ala Lys Ala Leu Pro Ala Phe
                405                 410                 415

Ala Gln Glu Pro Ser Ser Ala Ser Lys Pro Glu Lys Ile Ser Ser Thr
            420                 425                 430

Met Val Ser Gly
        435

<210> SEQ ID NO 9
<211> LENGTH: 1311
<212> TYPE: DNA
<213> ORGANISM: Vibrio cholera

<400> SEQUENCE: 9
gtgagaatga cttggaactt tcaccagtac tacacaaacc gaaatgatgg cttgatgggc      60
aagctagttc ttcagacga ggagaagaac aatctaaagg cattgcgtaa gatcatccgc     120
ttaagaacac gagatgtatt tgaagaagct aagggtattg ccaaggctgt gaaaaaaagt     180
gctcttacgt ttgaaattat tcaggaaaag gtgtcaacga cccaaattaa gcacctttct     240
gacagcgaac aacgagaagt ggctaagctt atttacgaga tggatgatga tgctcgtgat     300 gagttttttgg gattgacacc tcgcttttgg actcagggaa gctttcagta tgacacgctg     360
aatcgcccgt ttcagcctgg tcaagaaatg gatattgatg atggaaccta tatgccaatg     420
cctatttttg agtcagagcc taagattggt cattctttac taattcttct tgttgacgcg     480
tcacttaagt cacttgtagc tgaaaatcat ggctggaaat ttgaagctaa gcagacttgt     540
gggaggatta agattgaggc agagaaaaca catattgatg taccaatgta tgcaatccct     600
aaagatgagt tccagaaaaa gcaaatagct ttagaagcaa atagatcatt tgttaaaggt     660
gccatttttg aatcatatgt tgcagattca attactgacg atagtgaaac ttatgaatta     720
gattcagaaa acgtaaacct tgctcttcgt gaaggtgatc ggaagtggat caatagcgac     780
cccaaaatag ttgaagattg gttcaacgat agttgtatac gtattggtaa acatcttcgt     840
aaggtttgtc gctttatgaa agcgtggaga gatgcgcagt gggatgttgg aggtccgtca     900
tcgattagtc ttatggctgc aacggtaaat attcttgata gcgttgctca tgatgctagt     960
gatctcggag aaacaatgaa gataattgct aagcatttac ctagtgagtt tgctagggga    1020
gtagagagcc ctgacagtac cgatgaaaag ccactcttcc caccctctta taagcatggc    1080
cctcgggaga tggacattat gagcaaacta gagcgtttgc cagagattct gtcatctgct    1140
gagtcagctg actctaagtc agaggccttg aaaaagatta tatgcgcgtt tgggaatcgt    1200
gttactaata gcgagcttat tgttttggca aaggctttac cggctttcgc tcaagaacct    1260
agttcagcct cgaaacctga aaaaatcagc agcacaatgg taagtggctg a             1311

<210> SEQ ID NO 10
<211> LENGTH: 522
<212> TYPE: PRT
<213> ORGANISM: Homo sapiens

<400> SEQUENCE: 10

Met Gln Pro Trp His Gly Lys Ala Met Gln Arg Ala Ser Glu Ala Gly
1               5                   10                  15

Ala Thr Ala Pro Lys Ala Ser Ala Arg Asn Ala Arg Gly Ala Pro Met
            20                  25                  30
```

-continued

Asp Pro Thr Glu Ser Pro Ala Ala Pro Glu Ala Ala Leu Pro Lys Ala
        35                  40                  45

Gly Lys Phe Gly Pro Ala Arg Lys Ser Gly Ser Arg Gln Lys Lys Ser
 50                  55                  60

Ala Pro Asp Thr Gln Glu Arg Pro Pro Val Arg Ala Thr Gly Ala Arg
 65                  70                  75                  80

Ala Lys Lys Ala Pro Gln Arg Ala Gln Asp Thr Gln Pro Ser Asp Ala
                 85                  90                  95

Thr Ser Ala Pro Gly Ala Glu Gly Leu Glu Pro Pro Ala Ala Arg Glu
                100                 105                 110

Pro Ala Leu Ser Arg Ala Gly Ser Cys Arg Gln Arg Gly Ala Arg Cys
            115                 120                 125

Ser Thr Lys Pro Arg Pro Pro Gly Pro Trp Asp Val Pro Ser Pro
        130                 135                 140

Gly Leu Pro Val Ser Ala Pro Ile Leu Val Arg Arg Asp Ala Ala Pro
145                 150                 155                 160

Gly Ala Ser Lys Leu Arg Ala Val Leu Glu Lys Leu Lys Leu Ser Arg
                165                 170                 175

Asp Asp Ile Ser Thr Ala Ala Gly Met Val Lys Gly Val Val Asp His
            180                 185                 190

Leu Leu Leu Arg Leu Lys Cys Asp Ser Ala Phe Arg Gly Val Gly Leu
        195                 200                 205

Leu Asn Thr Gly Ser Tyr Tyr Glu His Val Lys Ile Ser Ala Pro Asn
210                 215                 220

Glu Phe Asp Val Met Phe Lys Leu Glu Val Pro Arg Ile Gln Leu Glu
225                 230                 235                 240

Glu Tyr Ser Asn Thr Arg Ala Tyr Tyr Phe Val Lys Phe Lys Arg Asn
                245                 250                 255

Pro Lys Glu Asn Pro Leu Ser Gln Phe Leu Glu Gly Glu Ile Leu Ser
            260                 265                 270

Ala Ser Lys Met Leu Ser Lys Phe Arg Lys Ile Ile Lys Glu Glu Ile
        275                 280                 285

Asn Asp Ile Lys Asp Thr Asp Val Ile Met Lys Arg Lys Arg Gly Gly
290                 295                 300

Ser Pro Ala Val Thr Leu Leu Ile Ser Glu Lys Ile Ser Val Asp Ile
305                 310                 315                 320

Thr Leu Ala Leu Glu Ser Lys Ser Ser Trp Pro Ala Ser Thr Gln Glu
                325                 330                 335

Gly Leu Arg Ile Gln Asn Trp Leu Ser Ala Lys Val Arg Lys Gln Leu
            340                 345                 350

Arg Leu Lys Pro Phe Tyr Leu Val Pro Lys His Ala Lys Glu Gly Asn
        355                 360                 365

Gly Phe Gln Glu Glu Thr Trp Arg Leu Ser Phe Ser His Ile Glu Lys
370                 375                 380

Glu Ile Leu Asn Asn His Gly Lys Ser Lys Thr Cys Cys Glu Asn Lys
385                 390                 395                 400

Glu Glu Lys Cys Cys Arg Lys Asp Cys Leu Lys Leu Met Lys Tyr Leu
                405                 410                 415

Leu Glu Gln Leu Lys Glu Arg Phe Lys Asp Lys Lys His Leu Asp Lys
            420                 425                 430

Phe Ser Ser Tyr His Val Lys Thr Ala Phe Phe His Val Cys Thr Gln
        435                 440                 445

```
Asn Pro Gln Asp Ser Gln Trp Asp Arg Lys Asp Leu Gly Leu Cys Phe
    450                 455                 460
Asp Asn Cys Val Thr Tyr Phe Leu Gln Cys Leu Arg Thr Glu Lys Leu
465                 470                 475                 480
Glu Asn Tyr Phe Ile Pro Glu Phe Asn Leu Phe Ser Ser Asn Leu Ile
                485                 490                 495
Asp Lys Arg Ser Lys Glu Phe Leu Thr Lys Gln Ile Glu Tyr Glu Arg
            500                 505                 510
Asn Asn Glu Phe Pro Val Phe Asp Glu Phe
            515                 520

<210> SEQ ID NO 11
<211> LENGTH: 1802
<212> TYPE: DNA
<213> ORGANISM: Homo sapiens

<400> SEQUENCE: 11
```

| | | | |
|---|---|---|---|
| agcctggggt tccccttcgg gtcgcagact cttgtgtgcc cgccagtagt gcttggtttc | 60 |
| caacagctgc tgctggctct tcctcttgcg gccttttcct gaaacggatt cttctttcgg | 120 |
| ggaacagaaa gcgccagcca tgcagccttg gcacggaaag gccatgcaga gagcttccga | 180 |
| ggccggagcc actgccccca aggcttccgc acggaatgcc aggggcgccc cgatggatcc | 240 |
| caccgagtct ccggctgccc ccgaggccgc cctgcctaag gcgggaaagt tcggccccgc | 300 |
| caggaagtcg ggatcccggc agaaaaagag cgccccggac acccaggaga ggccgcccgt | 360 |
| ccgcgcaact ggggcccgcg ccaaaaaggc ccctcagcgc gcccaggaca cgcagccgtc | 420 |
| tgacgccacc agcgcccctg ggcagagggg ctggagcct cctgcggctc gggagccggc | 480 |
| tctttccagg gctggttctt gccgccagag gggcgcgcgc tgctccacga agccaagacc | 540 |
| tccgcccggg ccctgggacg tgcccagccc cggcctgccg gtctcggccc ccattctcgt | 600 |
| acggagggat gcggcgcctg gggcctcgaa gctccgggcg ttttggaga agttgaagct | 660 |
| cagccgcgat gatatctcca cggcggcggg gatggtgaaa ggggttgtgg accacctgct | 720 |
| gctcagactg aagtgcgact ccgcgttcag aggcgtcggg ctgctgaaca ccggagcta | 780 |
| ctatgagcac gtgaagattt ctgcacctaa tgaatttgat gtcatgttta aactggaagt | 840 |
| ccccagaatt caactagaag aatattccaa cactcgtgca tattactttg tgaaatttaa | 900 |
| aagaaatccg aaagaaaatc ctctgagtca gtttttagaa ggtgaaatat tatcagcttc | 960 |
| taagatgctg tcaaagttta ggaaaatcat taggaagaa attaacgaca ttaaagatac | 1020 |
| agatgtcatc atgaagagga aaagaggagg gagccctgct gtaacacttc ttattagtga | 1080 |
| aaaaatatct gtggatataa ccctggcttt ggaatcaaaa agtagctggc ctgctagcac | 1140 |
| ccaagaaggc ctgcgcattc aaaactggct ttcagcaaaa gttaggaagc aactacgact | 1200 |
| aaagccattt taccttgtac ccaagcatgc aaaggaagga atggtttcc aagaagaaac | 1260 |
| atggcggcta tccttctctc acatcgaaaa ggaaattttg aacaatcatg gaaaatctaa | 1320 |
| aacgtgctgt gaaaacaaag aagagaaatg ttgcaggaaa gattgtttaa aactaatgaa | 1380 |
| ataccttta gaacagctga agaaaggtt taaagacaaa aaacatctgg ataaattctc | 1440 |
| ttcttatcat gtgaaaactg ccttctttca cgtatgtacc cagaaccctc aagacagtca | 1500 |
| gtgggaccgc aaagacctgg gcctctgctt tgataactgc gtgacatact tcttcagtg | 1560 |
| cctcaggaca gaaaaacttg agaattattt tattcctgaa ttcaatctat tctctagcaa | 1620 |
| cttaattgac aaaagaagta aggaatttct gacaaagcaa attgaatatg aaagaaacaa | 1680 | tgagtttcca gttttttgatg aattttgaga ttgtattttt agaaagatct aagaactaga   1740 gtcaccctaa atcctggaga atacaagaaa aatttgaaaa ggggccagac gctgtggctc   1800 ac   1802

<210> SEQ ID NO 12
<211> LENGTH: 1569
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
atgcaaccat ggcacgggaa agccatgcag cgtgcgagcg aagccggggc gacggccccc    60
aaggcgtcgg cgcgtaacgc gcggggtgcg cccatggacc cgacggagtc ccccgcggcg   120
ccggaggcgg ccctgccgaa agcgggtaag ttcggtccag cgcggaaaag cgggagccgc   180
caaaagaagt ccgcgcccga cacccaggag cgtcccccgg tccgggccac cggcgcgcgt   240
gccaaaaaag ccccgcaacg ggcgcaagat acgcagccaa gcgatgcgac ctccgccccc   300
ggggcggagg gtctggagcc cccggccgcc cgggagccag cgctctcgcg cgcgggttcc   360
tgccgtcagc ggggcgcgcg gtgttccacg aaaccccgtc ccccaccagg tccctgggac   420
gtgccgtcgc cggtttttgcc ggtgagcgcg ccaatcctgg tccggcgcga cgcggccccg   480
ggggcgtcga aattgcgtgc ggtgctcgag aaattgaagt tgtcgcgcga cgacatctcc   540
acggccgcgg gtatggtcaa gggcgtggtc gatcatttgt tgttgcggct caagtgtgat   600
tcggcgttcc gcggggtggg cttgctgaac acggggtcct actatgagca tgtcaaaatc   660
agcgccccca acgaatttga cgtgatgttt aagctggaag tgccacgtat ccaattggaa   720
gagtattcca ataccccgtgc gtattatttc gtcaaattta agcgcaatcc gaaggaaaat   780
ccactcagcc aattcttgga gggcgaaatt ctgtcggcct cgaaaatgct ctccaaattt   840
cgtaagatta tcaaggagga gatcaacgac attaaggaca cggatgtgat catgaaacgt   900
aaacgtggcg gttccccccgc ggtgacgctc ctcatttcgg aaaaaatttc ggtggacatt   960
accctggcgt tggaatcgaa gtccagctgg ccggcgtcga cccaggaggg cctgcggatt  1020
caaaactggt tgagcgccaa agtgcggaag cagctgcgtc tcaaaccctt ttatttggtc  1080
ccgaaacatg ccaaagaggg taacggttttt caagaggaaa cctggcgttt gagcttctcc  1140
cacattgaga aggagatttt gaacaaccat ggtaagtcca aaacgtgctg cgagaataag  1200
gaagaaaaat gttgtcgcaa agattgtctc aaattgatga aatatttgct ggaacaactc  1260
aaagagcgtt ttaaggacaa gaagcatctc gacaagttct cctcgtatca cgtcaagacc  1320
gccttctttc atgtctgtac gcagaacccg caagatagcc agtgggatcg caaggacttg  1380
gggttgtgtt ttgacaattg cgtcacctat ttcttgcaat gtttgcggac cgagaaattg  1440
gagaactact ttattccaga attcaacttg ttttcctcga atctgattga caaacgctcc  1500
aaagagtttc tgacgaagca gattgaatac gagcgtaaca atgagtttcc ggtctttgac  1560
gagttttga   1569

<210> SEQ ID NO 13
<211> LENGTH: 10841
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accaaaattg taaacgttaa tattttgtta aaattcgcgt taaattttg ttaaatcagc      240
tcatttttta accaataggc cgaaatcggc aaaatcccctt ataaatcaaa agaatagccc    300
gagatagggt tgagtgttgt tccagtttgg aacaagagtc cactattaaa gaacgtggac     360
tccaacgtca aagggcgaaa aaccgtctat cagggcgatg gcccactacg tgaaccatca     420
cccaaatcaa gttttttggg gtcgaggtgc cgtaaagcac taaatcggaa ccctaaaggg     480
agcccccgat ttagagcttg acggggaaag ccggcgaacg tggcgagaaa ggaagggaag     540
aaagcgaaag gagcgggcgc tagggcgctg gcaagtgtag cggtcacgct gcgcgtaacc     600
accacacccg ccgcgcttaa tgcgccgcta cagggcgcgt actatggttg ctttgacgtg     660
cggtgtgaaa taccgcacag atgcgtaagg agaaaatacc gcatcaggcg ccattcgcca     720
ttcaggctgc gcaactgttg ggaagggcga tcggtgcggg cctcttcgct attacgccag     780
ctggcgaaag ggggatgtgc tgcaaggcga ttaagttggg taacgccagg ttttcccag     840
tcacgacgtt gtaaaacgac ggccagtgaa ttcgagctcg gtaccggggg atcctctaga     900
aattccggaa ttgcactcgc cttaggggag tgctaaaaat gatcctggca ctcgcgatca     960
gcgagtgcca ggtcgggacg tgagaccca gccagcaagc tgtggtcgtc cgtcgcgggc     1020
actgcacccg gccagcgtaa gtaatggggg ttgtcggcac ccggtgacat gcacgctgtg     1080
actcgtccga ccctgcgtga ggctgtcgcc cgcctagccc cgggcactgg gctgcgggac     1140
ggcctggagc gtatcctgcg cggccgcact ggtgccctga tcgtgctggg ccatgacgag     1200
aatgtcgagg ccatctgcga tggtggcttc tccctcgatg tccgctatgc agcaacccgg     1260
ctacgcgagc tgtgcaagat ggacggcgcc gtggtgctgt ccaccgacgg cagccgcatc     1320
gtgcgggcca acgtgcaact ggtaccggat ccgtcgatcc ccaccgacga atcggggacc     1380
cggcaccgct cggccgagcg ggccgcgatc cagaccggtt accccggtgat ctcagtgagc    1440
cactcgatga acatcgtgac cgtctacgtc cgcggggaac gtcacgtatt gaccgactcg     1500
gcaaccatcc tgtcgcgggc caaccaggcc atcgcaaccc tggagcggta caaaaccagg    1560
ctcgacgagg tcagccggca actgtccagg gcagaaatcg aggacttcgt cacgctgcgc    1620
gatgtgatga cggtggtgca acgcctcgag ctggtccggc gaatcgggct ggtgatcgac    1680
tacgacgtgg tcgaactcgg cactgatggt cgtcagctgc ggctgcagct cgacgagttg    1740
ctcggcggca acgacaccgc ccgggaattg atcgtgcgcg attaccacgc caacccggaa    1800
ccaccgtcca cggggcaaat caatgccacc ctggacgaac tggacgccct gtcggacggc    1860
gacctcctcg atttcaccgc gctggcaaag gttttcggat atccgacgac cacggaagcg    1920
caggattcga cgctgagccc gcgtggctac cgcgcgatgg ccggtatccc ccggctccag    1980
ttcgcccatg ccgacctgct ggtccgggcg ttcggaacgt tgcagggtct gctggcggcc    2040
agcgccggcg atctgcaatc agtggacggc atcggcgcca tgtgggcccg tcatgtgcgc    2100
gaggggttgt cacagctggc ggaatcgacc atcagcgatc aataagagca catcgatatg    2160
caaccatggc acgggaaagc catgcagcgt gcgagcgaag ccggggcgac ggcccccaag    2220
gcgtcggcgc gtaacgcgcg gggtgcgccc atggacccga cggagtcccc cgcggcgccg    2280
```

-continued

| | |
|---|---|
| gaggcggccc tgccgaaagc gggtaagttc ggtccagcgc ggaaaagcgg gagccgccaa | 2340 |
| aagaagtccg cgcccgacac ccaggagcgt cccccggtcc gggccaccgg cgcgcgtgcc | 2400 |
| aaaaaagccc cgcaacgggc gcaagatacg cagccaagcg atgcgacctc cgcccccggg | 2460 |
| gcggagggtc tggagccccc ggccgccggg gagccagcgc tctcgcgcgc gggttcctgc | 2520 |
| cgtcagcggg gcgcgcggtg ttccacgaaa ccccgtcccc caccaggtcc ctgggacgtg | 2580 |
| ccgtcgccgg gtttgccggt gagcgcgcca atcctggtcc ggcgcgacgc ggccccgggg | 2640 |
| gcgtcgaaat tgcgtgcggt gctcgagaaa ttgaagttgt cgcgcgacga catctccacg | 2700 |
| gccgcgggta tggtcaaggg cgtggtcgat catttgttgt tgcggctcaa gtgtgattcg | 2760 |
| gcgttccgcg gggtgggctt gctgaacacg gggtcctact atgagcatgt caaaatcagc | 2820 |
| gccccccaacg aatttgacgt gatgtttaag ctggaagtgc cacgtatcca attggaagag | 2880 |
| tattccaata cccgtgcgta ttatttcgtc aaatttaagc gcaatccgaa ggaaaatcca | 2940 |
| ctcagccaat tcttggaggg cgaaattctg tcggcctcga aaatgctctc caaatttcgt | 3000 |
| aagattatca aggaggagat caacgacatt aaggacacgg atgtgatcat gaaacgtaaa | 3060 |
| cgtggcggtt cccccgcggt gacgctcctc atttcggaaa aaatttcggt ggacattacc | 3120 |
| ctggcgttgg aatcgaagtc cagctggccg gcgtcgaccc aggagggcct gcggattcaa | 3180 |
| aactggttga gcgccaaagt gcggaagcag ctgcgtctca aacccttta tttggtcccg | 3240 |
| aaacatgcca aagagggtaa cggttttcaa gaggaaacct ggcgtttgag cttctcccac | 3300 |
| attgagaagg agattttgaa caaccatggt aagtccaaaa cgtgctgcga gaataaggaa | 3360 |
| gaaaaatgtt gtcgcaaaga ttgtctcaaa ttgatgaaat atttgctgga acaactcaaa | 3420 |
| gagcgtttta aggacaagaa gcatctcgac aagttctcct cgtatcacgt caagaccgcc | 3480 |
| ttctttcatg tctgtacgca gaacccgcaa gatagccagt gggatcgcaa ggacttgggg | 3540 |
| ttgtgttttg acaattgcgt cacctatttc ttgcaatgtt tgcggaccga gaaattggag | 3600 |
| aactacttta ttccagaatt caacttgttt tcctcgaatc tgattgacaa acgctccaaa | 3660 |
| gagtttctga cgaagcagat tgaatacgag cgtaacaatg agtttccggt ctttgacgag | 3720 |
| ttttgaaagc ttgagatggt gagcaagggc gaggaggata acatgccat catcaaggag | 3780 |
| ttcatgcgct tcaaggtgca catggagggc tccgtgaacg gccacgagtt cgagatcgag | 3840 |
| ggcgagggcg agggccgccc ctacgagggc acccagaccg ccaagctgaa ggtgaccaag | 3900 |
| ggtggccccc tgcccttcgc ctgggacatc ctgtcccctc agttcatgta cggctccaag | 3960 |
| gcctacgtga agcaccccgc cgacatcccc gactacttga agctgtcctt ccccgagggc | 4020 |
| ttcaagtggg agcgcgtgat gaacttcgag gacggcggcg tggtgaccgt gacccaggac | 4080 |
| tcctcctgc aggacggcga gttcatctac aaggtgaagc tgcgcggcac caacttcccc | 4140 |
| tccgacggcc ccgtaatgca gaagaagacc atgggctggg aggcctcctc cgagcggatg | 4200 |
| taccccgagg acggcgccct gaagggcgag atcaagcaga ggctgaagct gaaggacggc | 4260 |
| ggccactacg acgctgaggt caagaccacc tacaaggcca agaagcccgt gcagctgccc | 4320 |
| ggcgcctaca acgtcaacat caagttggac atcacctccc acaacgagga ctacaccatc | 4380 |
| gtggaacagt acgaacgcgc cgagggccgc cactccaccg gcgcatgga cgagctgtac | 4440 |
| aagtagacta gttgcctggc ggcagtagcg cggtggtccc acctgacccc atgccgaact | 4500 |
| cagaagtgaa acgccgtagc gccgatggta gtgtggggtc tccccatgcg agagtaggga | 4560 |
| actgccaggc atcaaataaa acgaaaggct cagtcgaaag actgggcctt tcgttttatc | 4620 |
| tgttgtttgt cggtgaacgc tctcctgagt aggacaaatc cgccgggagc ggatttgaac | 4680 |

```
gttgcgaagc aacggcccgg aagggtggcg ggcaggacgc ccgccataaa ctgccaggca    4740
tcaaattaag cagaaggcca tcctgacgga tggcctttt  tctagagtcg accaccaagg    4800
gcaccatctc tgcttgggcc accccgttgg ccgcagccag ctcgctgaga gccgtgaacg    4860
acagggcgaa cgccagcccg ccgacggcga gggttccgac cgctgcaact cccggtgcaa    4920
ccttgtcccg gtctattctc ttcactgcac cagctccaat ctggtgtgaa tgcccctcgt    4980
ctgttcgcgc aggcggggg  ctctattcgt ttgtcagcat cgaaagtagc cagatcaggg    5040
atgcgttgca accgcgtatg cccaggtcag aagagtcgca caagagttgc agacccctgg    5100
aaagaaaaat ggccagaggg cgaaaacacc ctctgaccag cggagcgggc gacgggaatc    5160
gaacccgcgt agctagtttg aagaatgggt tgtctgccga ccacatatgg gccggtcaag    5220
ataggttttt accccctctc ggctgcatcc tctaagtgga aagaaattgc aggtcgtaga    5280
agcgcgttga agcctgagag ttgcacagga gttgcaaccc ggtagccttg ttcacgacga    5340
gaggagacct agttggcacg tcgcggatgg ggatcgctga agactcagcg cagcgggagg    5400
atccaagcct catacgtcaa cccgcaggac ggtgtgaggt actacgcgct gcagacctac    5460
gacaacaaga tggacgccga agcctggctc gcgggcgaga agcggctcat cgagatggag    5520
acctggaccc ctccacagga ccgggcgaag aaggcagccg ccagcgccat cacgctggag    5580
gagtacaccc ggaagtggct cgtggagcgc gacctgcag  acggcaccag ggatctgtac    5640
agcgggcacg cggagcgccg catctacccg gtgctaggtg aagtggcggt cacagagatg    5700
acgccagctc tggtgcgtgc gtggtgggcc gggatgggta ggaagcaccc gactgcccgc    5760
cggcatgcct acaacgtcct ccgggcggtg atgaacacag cggtcgagga caagctgatc    5820
gcagagaacc cgtgccggat cgagcagaag gcagccgatg agcgcgacgt agaggcgctg    5880
acgcctgagg agctggacat cgtcgccgct gagatcttcg agcactaccg gatcgcggca    5940
tacatcctgg cgtggacgag cctccggttc ggagagctga tcgagcttcg ccgcaaggac    6000
atcgtggacg acggcatgac gatgaagctc cgggtgcgcc gtggcgcttc ccgcgtgggg    6060
aacaagatcg tcgttggcaa cgccaagacc gtccggtcga agcgtcctgt gacggttccg    6120
cctcacgtcg cggagatgat ccgagcgcac atgaaggacc gtacgaagat gaacaagggc    6180
cccgaggcat tcctggtgac cacgacgcag ggcaaccggc tgtcgaagtc cgcgttcacc    6240
aagtcgctga agcgtggcta cgccaagatc ggtcggccgg aactccgcat ccacgacctc    6300
cgcgctgtcg gcgctacgtt cgccgctcag gcaggtgcga cgaccaagga gctgatggcc    6360
cgtctcggtc acacgactcc taggatgcg  atgaagtacc agatggcgtc tgaggcccgc    6420
gacgaggcta cgctgaggc  gatgtccaag ctggccaaga cctcctgaaa cgcaaaaagc    6480
cccctccca aggacactga gtcctaaaga gggggttttc ttgtcagtac gcgaagaacc    6540
acgcctggcc gcgagcgcca gcaccgccgc tctgtgcgga gacctgggca ccagccccgc    6600
cgccgccagg agcattgccg ttcccgccag ctgagttctg ttgtgcgccg cctatgtaga    6660
gctggtcgtt gtaggtccga tctccaggcg actttccggc gacgctgagg atgtcgatca    6720
cagagcctcc gggaccgccg gttgcggtca aacctgacca tccgacagcg gacgccgtgg    6780
tgtttcctcc agggcctccg gccttgcctg agaatacaga gccagctccc gctgcgcctc    6840
cagctccgac gagcccggtg atcgtcttgg tcgacctgca ggcatgcaaa agctgatcct    6900
tgccgagctg ggatggaagc ccggccgacc caccctggag gagatgatcg aggatgccag    6960
ggcctttcac gcccgccgct gctgagcgtc cgccgccggg cccgcaccgc cgtcggccgg    7020
```

```
cccgctccgg gctcgcagca gcgggcttcg gcgcgggccc ggggctcccg ggccgccggg    7080
cggggctccg cccggcggcc gccggggcc ggggcggcg ccgggcggcc cggggcgtca      7140
ggcgccgggg gcggtgtccg gcggcccca gaggaactgc gccagttcct ccggatcggt    7200
gaagccggag agatccagcg gggtctcctc gaacacctcg aagtcgtgca ggaaggtgaa    7260
ggcgagcagt tcgcgggcga agtcctcggt ccgcttccac tgcgcccgt cgagcagcgc    7320 ggccaggatc tcgcggtcgc cccggaaggc gttgagatgc agttgcacca ggctgtagcg    7380
ggagtctccc gcatagacgt cggtgaagtc gacgatcccg gtgacctcgg tcgcggccag    7440
gtccacgaag atgttggtcc cgtgcaggtc gccgtggacg aaccggggtt cgcggccggc    7500
cagcagcgtg tccacgtccg gcagccagtc ctccaggcgg tccagcagcc ggggcgagag    7560
gtagccccac ccgcgtggt cctcgacggt cgccgcgcgg cgttcccgca gcagttccgg      7620
gaagacctcg gaatgggggg tgagcacggt gttcccggtc agcggcaccc tgtgcagccg    7680
gccgagcacc cggccgagtt cgcgggccag ggcgagcagc gcgttccggt cggtcgtgcc    7740
gtccatcgcg gaccgccagg tggtgccggt catccggctc atcaccaggt agggccacgg    7800
ccaggctccg gtgccgggcc gcagctcgcc gcggccgagg aggcggggca ccggcaccgg    7860
ggcgtccgcc aggaccgcgt acgcctccga ctccgacgcg aggctctccg gaccgccacca   7920 gtgctcgccg aacagcttga tcaccgggcc gggctcgccg accagtacgg ggttggtgct    7980
ctcgccgggc acccgcagca ccggcggcac cggcagcccg agctcctcca gggctcggcg    8040
ggccagcggc tcccagaatt cctggtcgtt ccgcaggctc gcgtaggaat catccgaatc    8100
aatacggtcg agaagtaaca gggattcttg tgtcacagcg gacctctatt cacagggtac    8160
gggccggctt aattccgcac ggccggtcgc gacacggcct gtccgcaccg cggatcaggc    8220
gttgacgatg acgggctggt cggccacgtc ggggacgttc tcggtggtgc tgcggtcggg    8280
atcgccaatc tctacgggcc gaccgaggcg acggtgtacg ccaccgcctg gttctgcgac    8340
ggcgaggcgc cgtcccaggc cccgccgatc ccgtccccc gcgtcgtcga gcgcggtgcc     8400
gacgacaccg ccgcgtggct cgtcacggag gccgtcccg gcgtcgcggc ggccgaggag    8460
tggcccgagc accagcggtt cgccgtggtc gaggcgatgg cggagctggc ccgcgccctc    8520
cacgagctgc ccgtggagga ctgccccttc gaccggcgcc tcgacgcggc ggtcgccgag    8580
gcccggcgga acgtcgccga gggctgtgg acctcgacga cctgcaggca tgcaagctag    8640
cttttgttat ccgctcacaa ttccacacaa catacgagcc ggaagcataa agtgtaaagc    8700
ctggggtgcc taatgagtga gctaactcac attaattgcg ttgcgctcac tgcccgcttt    8760
ccagtcggga aacctgtcgt gccagctgca ttaatgaatc ggccaacgcg cggggagagg    8820
cggtttgcgt attgggcgct cttccgcttc ctcgctcact gactcgctgc gctcggtcgt    8880
tcggctgcgg cgagcggtat cagctcactc aaaggcggta atacggttat ccacagaatc    8940
aggggataac gcaggaaaga acatgtgagc aaaaggccag caaaaggcca ggaaccgtaa    9000
aaaggccgcg ttgctggcgt ttttccatag gctccgcccc cctgacgagc atcacaaaaa    9060
tcgacgctca agtcagaggt ggcgaaaccc gacaggacta taaagatacc aggcgtttcc    9120
ccctggaagc tccctcgtgc gctctcctgt tccgaccctg ccgcttaccg gatacctgtc    9180
cgcctttctc ccttcgggaa gcgtggcgct ttctcaatgc tcacgctgta ggtatctcag    9240
ttcggtgtag gtcgttcgct ccaagctggg ctgtgtgcac gaaccccccg ttcagcccga    9300
ccgctgcgcc ttatccggta actatcgtct tgagtccaac ccggtaagac acgacttatc    9360
gccactggca gcagccactg gtaacaggat tagcagagcg aggtatgtag gcggtgctac    9420
```

```
agagttcttg aagtggtggc ctaactacgg ctacactaga aggacagtat ttggtatctg   9480
cgctctgctg aagccagtta ccttcggaaa aagagttggt agctcttgat ccggcaaaca   9540
aaccaccgct ggtagcggtg gtttttttgt ttgcaagcag cagattacgc gcagaaaaaa   9600
aggatctcaa gaagatcctt tgatcttttc tacggggtct gacgctcagt ggaacgaaaa   9660
ctcacgttaa gggattttgg tcatgagatt atcaaaaagg atcttcacct agatcctttt   9720
aaattaaaaa tgaagtttta aatcaatcta aagtatatat gagtaaactt ggtctgacag   9780
ttaccaatgc ttaatcagtg aggcacctat ctcagcgatc tgtctatttc gttcatccat   9840
agttgcctga ctccccgtcg tgtagataac tacgatacgg gagggcttac catctggccc   9900
cagtgctgca atgataccgc gagacccacg ctcaccggct ccagatttat cagcaataaa   9960
ccagccagcc ggaagggccg agcgcagaag tggtcctgca actttatccg cctccatcca  10020
gtctattaat tgttgccggg aagctagagt aagtagttcg ccagttaata gtttgcgcaa  10080
cgttgttgcc attgctacag gcatcgtggt gtcacgctcg tcgtttggta tggcttcatt  10140
cagctccggt tcccaacgat caaggcgagt tacatgatcc cccatgttgt gcaaaaaagc  10200
ggttagctcc ttcggtcctc cgatcgttgt cagaagtaag ttggccgcag tgttatcact  10260
catggttatg gcagcactgc ataattctct tactgtcatg ccatccgtaa gatgcttttc  10320
tgtgactggt gagtactcaa ccaagtcatt ctgagaatag tgtatgcggc gaccgagttg  10380
ctcttgcccg gcgtcaatac gggataatac cgcgccacat agcagaactt taaaagtgct  10440
catcattgga aaacgttctt cggggcgaaa actctcaagg atcttaccgc tgttgagatc  10500
cagttcgatg taacccactc gtgcacccaa ctgatcttca gcatctttta ctttcaccag  10560
cgtttctggg tgagcaaaaa caggaaggca aaatgccgca aaaaagggaa taagggcgac  10620
acggaaatgt tgaatactca tactcttcct ttttcaatat tattgaagca tttatcaggg  10680
ttattgtctc atgagcggat acatatttga atgtatttag aaaaataaac aaataggggt  10740
tccgcgcaca tttccccgaa aagtgccacc tgacgtctaa gaaaccatta ttatcatgac  10800
attaacctat aaaaataggc gtatcacgag gccctttcgt c                      10841

<210> SEQ ID NO 14
<211> LENGTH: 316
<212> TYPE: PRT
<213> ORGANISM: Mycobacterium bovis

<400> SEQUENCE: 14

Met Asp Ala Val Gly Ala Ala Ala Leu Leu Ser Ala Ala Ala Arg Val
1               5                   10                  15

Gly Val Val Cys His Val His Pro Asp Ala Asp Thr Ile Gly Ala Gly
            20                  25                  30

Leu Ala Leu Ala Leu Val Leu Asp Gly Cys Gly Lys Arg Val Glu Val
        35                  40                  45

Ser Phe Ala Ala Pro Ala Thr Leu Pro Glu Ser Leu Arg Ser Leu Pro
    50                  55                  60

Gly Cys His Leu Leu Val Arg Pro Glu Val Met Arg Arg Asp Val Asp
65                  70                  75                  80

Leu Val Val Thr Val Asp Ile Pro Ser Val Asp Arg Leu Gly Ala Leu
                85                  90                  95

Gly Asp Leu Thr Asp Ser Gly Arg Glu Leu Leu Val Ile Asp His His
            100                 105                 110

Ala Ser Asn Asp Leu Phe Gly Thr Ala Asn Phe Ile Asp Pro Ser Ala
```

```
        115                 120                 125

Asp Ser Thr Thr Thr Met Val Ala Glu Ile Leu Asp Ala Trp Gly Lys
    130                 135                 140

Pro Ile Asp Pro Arg Val Ala His Cys Ile Tyr Ala Gly Leu Ala Thr
145                 150                 155                 160

Asp Thr Gly Ser Phe Arg Trp Ala Ser Val Arg Gly Tyr Arg Leu Ala
                165                 170                 175

Ala Arg Leu Val Glu Ile Gly Val Asp Asn Ala Thr Val Ser Arg Thr
            180                 185                 190

Leu Met Asp Ser His Pro Phe Thr Trp Leu Pro Leu Leu Ser Arg Val
        195                 200                 205

Leu Gly Ser Ala Gln Leu Val Ser Glu Ala Val Gly Gly Arg Gly Leu
    210                 215                 220

Val Tyr Val Val Val Asp Asn Arg Glu Trp Val Ala Ala Arg Ser Glu
225                 230                 235                 240

Glu Val Glu Ser Ile Val Asp Ile Val Arg Thr Thr Gln Gln Ala Glu
                245                 250                 255

Val Ala Ala Val Phe Lys Glu Val Glu Pro His Arg Trp Ser Val Ser
            260                 265                 270

Met Arg Ala Lys Thr Val Asn Leu Ala Ala Val Ala Ser Gly Phe Gly
        275                 280                 285

Gly Gly Gly His Arg Leu Ala Ala Gly Tyr Thr Thr Thr Gly Ser Ile
    290                 295                 300

Asp Asp Ala Val Ala Ser Leu Arg Ala Ala Leu Gly
305                 310                 315

<210> SEQ ID NO 15
<211> LENGTH: 951
<212> TYPE: DNA
<213> ORGANISM: Mycobacterium bovis

<400> SEQUENCE: 15
gtggacgccg tcggtgccgc tgcgctgttg tcggccgctg ccagggtcgg ggtagtctgc      60
cacgtccacc ccgatgccga caccatcggc gccggattgg cattggcatt ggtgttggac     120
gggtgcggca agcgggtaga ggtcagcttt gccgcgccgg cgacactgcc cgagtcgctg     180
cgttcgctgc cgggctgcca tctgctggtc cgccctgagg tgatgcgccg cgatgtcgat     240
ttggttgtga ctgttgacat tccgagtgtt gatcggctcg gtgctctggg cgatctaact     300
gattccgggc gggagctcct ggtaatcgac catcacgcct ccaacgacct gttcggcacc     360
gcgaatttca ttgacccgtc ggcggattcc accacgacga tggttgccga gatcctcgac     420
gcgtggggga aaccgataga cccgcgcgtc gcgcactgca tctacgccgg gttggcgacc     480
gacacggggt cgtttcgctg ggccagtgtg cgggggtatc ggctggcggc gcggctggta     540
gagatcggtg tggacaacgc caccgtcagc aggaccttga tggacagcca tcccttcacc     600
tggttgccgt tgctatcgcg ggtgttgggt tcggcgcagc tggtgtccga ggcggtcggt     660
ggccgcgggc tggtttacgt cgtcgtcgac aaccgggagt gggtcgctgc gcgctcggag     720
gaagtggaaa gcatcgtcga catcgtccgc accacgcaac aagccgaggt cgcggcggtg     780
ttcaaggagg tcgaaccgca tcggtggtcg gtgtcgatgc gggctaagac cgtgaatttg     840
gccgcggttg cctctgggtt cggtggcggt ggtcaccggc tggccgcggg gtatacgacc     900
accggctcga tcgacgacgc tgtggcgtcg ttgcgcgcgg cgcttggtta g              951
```

<210> SEQ ID NO 16
<211> LENGTH: 336
<212> TYPE: PRT
<213> ORGANISM: Mycobacterium tuberculosis

<400> SEQUENCE: 16

```
Met Thr Thr Ile Asp Pro Arg Ser Glu Leu Val Asp Gly Arg Arg
1               5                   10                  15

Ala Gly Ala Arg Val Asp Ala Val Gly Ala Ala Leu Leu Ser Ala
                20                  25                  30

Ala Ala Arg Val Gly Val Val Cys His Val His Pro Asp Ala Asp Thr
                35                  40                  45

Ile Gly Ala Gly Leu Ala Leu Ala Leu Val Leu Asp Gly Cys Gly Lys
50                  55                  60

Arg Val Glu Val Ser Phe Ala Ala Pro Ala Thr Leu Pro Glu Ser Leu
65                  70                  75                  80

Arg Ser Leu Pro Gly Cys His Leu Leu Val Arg Pro Glu Val Met Arg
                85                  90                  95

Arg Asp Val Asp Leu Val Val Thr Val Asp Ile Pro Ser Val Asp Arg
                100                 105                 110

Leu Gly Ala Leu Gly Asp Leu Thr Asp Ser Gly Arg Glu Leu Leu Val
                115                 120                 125

Ile Asp His His Ala Ser Asn Asp Leu Phe Gly Thr Ala Asn Phe Ile
130                 135                 140

Asp Pro Ser Ala Asp Ser Thr Thr Thr Met Val Ala Glu Ile Leu Asp
145                 150                 155                 160

Ala Trp Gly Lys Pro Ile Asp Pro Arg Val Ala His Cys Ile Tyr Ala
                165                 170                 175

Gly Leu Ala Thr Asp Thr Gly Ser Phe Arg Trp Ala Ser Val Arg Gly
                180                 185                 190

Tyr Arg Leu Ala Ala Arg Leu Val Glu Ile Gly Val Asp Asn Ala Thr
                195                 200                 205

Val Ser Arg Thr Leu Met Asp Ser His Pro Phe Thr Trp Leu Pro Leu
210                 215                 220

Leu Ser Arg Val Leu Gly Ser Ala Gln Leu Val Ser Glu Ala Val Gly
225                 230                 235                 240

Gly Arg Gly Leu Val Tyr Val Val Val Asp Asn Arg Glu Trp Val Ala
                245                 250                 255

Ala Arg Ser Glu Glu Val Glu Ser Ile Val Asp Ile Val Arg Thr Thr
                260                 265                 270

Gln Gln Ala Glu Val Ala Ala Val Phe Lys Glu Val Glu Pro His Arg
                275                 280                 285

Trp Ser Val Ser Met Arg Ala Lys Thr Val Asn Leu Ala Ala Val Ala
                290                 295                 300

Ser Gly Phe Gly Gly Gly Gly His Arg Leu Ala Ala Gly Tyr Thr Thr
305                 310                 315                 320

Thr Gly Ser Ile Asp Asp Ala Val Ala Ser Leu Arg Ala Ala Leu Gly
                325                 330                 335
```

<210> SEQ ID NO 17
<211> LENGTH: 288
<212> TYPE: PRT
<213> ORGANISM: Unknown
<220> FEATURE:
<223> OTHER INFORMATION: Description of Unknown:
      Diguanylate phosphodiesterase sequence

<400> SEQUENCE: 17

```
Met Ile Asp Tyr Glu Glu Met Phe Arg Gly Ala Met Gln Ala Arg Ala
1               5                   10                  15

Met Val Ala Asn Pro Asp Gln Trp Ala Asp Ser Asp Arg Asp Gln Val
            20                  25                  30

Asn Thr Arg His Tyr Leu Ser Thr Ser Met Arg Val Ala Leu Asp Arg
        35                  40                  45

Gly Glu Phe Phe Leu Val Tyr Gln Pro Ile Ile Arg Leu Ala Asp Asn
    50                  55                  60

Arg Ile Ile Gly Ala Glu Ala Leu Leu Arg Trp Glu His Pro Thr Leu
65                  70                  75                  80

Gly Thr Leu Leu Pro Gly Arg Phe Ile Asp Arg Ala Glu Asn Asn Gly
                85                  90                  95

Leu Met Val Pro Leu Thr Ala Phe Val Leu Glu Gln Ala Cys Arg His
            100                 105                 110

Val Arg Ser Trp Arg Asp His Ser Thr Asp Pro Gln Pro Phe Val Ser
        115                 120                 125

Val Asn Val Ser Ala Ser Thr Ile Cys Asp Pro Gly Phe Leu Val Leu
    130                 135                 140

Val Glu Gly Val Leu Gly Glu Thr Gly Leu Pro Ala His Ala Leu Gln
145                 150                 155                 160

Leu Glu Leu Ala Glu Asp Ala Arg Leu Ser Arg Asp Glu Lys Ala Val
                165                 170                 175

Thr Arg Leu Gln Glu Leu Ser Ala Leu Gly Val Gly Ile Ala Ile Asp
            180                 185                 190

Asp Phe Gly Ile Gly Phe Ser Ser Leu Ala Tyr Leu Pro Arg Leu Pro
        195                 200                 205

Val Asp Val Val Lys Leu Gly Gly Lys Phe Ile Glu Cys Leu Asp Gly
    210                 215                 220

Asp Ile Gln Ala Arg Leu Ala Asn Glu Gln Ile Thr Arg Ala Met Ile
225                 230                 235                 240

Asp Leu Gly Asp Lys Leu Gly Ile Thr Val Thr Ala Lys Leu Val Glu
                245                 250                 255

Ser Pro Ser Gln Ala Ala Arg Leu Arg Ala Phe Gly Cys Lys Ala Ala
            260                 265                 270

Gln Gly Trp His Phe Ala Lys Ala Leu Pro Val Asp Phe Phe Arg Glu
        275                 280                 285
```

<210> SEQ ID NO 18
<211> LENGTH: 867
<212> TYPE: DNA
<213> ORGANISM: Unknown
<220> FEATURE:
<223> OTHER INFORMATION: Description of Unknown:
    Diguanylate phosphodiesterase sequence

<400> SEQUENCE: 18

```
ttgatcgact acgaagagat gtttaggggc gcgatgcaag cgcgagcgat ggtagccaat    60
cctgaccaat gggcggactc cgaccgcgac caggtcaaca ctcgccatta tctgtccact   120
tcgatgcgcg tggcactgga tcgcggtgaa ttcttcctcg tctaccagcc aatcatccgg   180
cttgccgaca accgcatcat cggcgccgag gccctgctgc gctgggaaca cccgacgttg   240
ggcacgctac tcccggggcg gttcatcgac cgtgccgaga caacggact gatggtgccg   300 ctcacggcct tcgtgctcga gcaggcctgc cgccacgtcc gcagttggcg tgaccacagc   360
```

-continued

```
accgacccgc aaccgtttgt cagcgtcaac gtctccgcca gcaccatctg cgatcccggc      420
ttcctggtgc tggtcgaagg tgtgctcggc gaaaccggcc tgcccgccca tgccctgcag      480
ctcgaactgg ccgaggacgc gcgccttagc agagacgaga aggcggtgac caggctacaa      540
gaattgtccg ctctcggcgt cggcatcgcc atcgacgact tcggcattgg attctccagc      600
ctcgcctacc ttccccgcct ccccgtcgac gtggtcaaac tcggggggaaa gttcatcgag      660 tgcctcgatg gcgacattca agctcggctg gccaacgaac agatcacccg gcaatgatc       720 gaccttggcg acaagctcgg tatcaccgtc actgcaaagc tagtcgaaag ccccagccaa      780 gccgccggt tgcgcgcctt cggctgtaaa gccgcacaag gctggcactt tgccaaggca       840
ctgccggtcg actttttcag agagtag                                          867
```

<210> SEQ ID NO 19
<211> LENGTH: 307
<212> TYPE: PRT
<213> ORGANISM: Mycobacterium tuberculosis

<400> SEQUENCE: 19

```
Met Asp Arg Cys Cys Gln Arg Ala Thr Ala Phe Ala Cys Ala Leu Arg
1               5                   10                  15

Pro Thr Lys Leu Ile Asp Tyr Glu Glu Met Phe Arg Gly Ala Met Gln
            20                  25                  30

Ala Arg Ala Met Val Ala Asn Pro Asp Gln Trp Ala Asp Ser Asp Arg
        35                  40                  45

Asp Gln Val Asn Thr Arg His Tyr Leu Ser Thr Ser Met Arg Val Ala
    50                  55                  60

Leu Asp Arg Gly Glu Phe Phe Leu Val Tyr Gln Pro Ile Ile Arg Leu
65                  70                  75                  80

Ala Asp Asn Arg Ile Ile Gly Ala Glu Ala Leu Leu Arg Trp Glu His
                85                  90                  95

Pro Thr Leu Gly Thr Leu Leu Pro Gly Arg Phe Ile Asp Arg Ala Glu
            100                 105                 110

Asn Asn Gly Leu Met Val Pro Leu Thr Ala Phe Val Leu Glu Gln Ala
        115                 120                 125

Cys Arg His Val Arg Ser Trp Arg Asp His Ser Thr Asp Pro Gln Pro
    130                 135                 140

Phe Val Ser Val Asn Val Ser Ala Ser Thr Ile Cys Asp Pro Gly Phe
145                 150                 155                 160

Leu Val Leu Val Glu Gly Val Leu Gly Glu Thr Gly Leu Pro Ala His
                165                 170                 175

Ala Leu Gln Leu Glu Leu Ala Glu Asp Ala Arg Leu Ser Arg Asp Glu
            180                 185                 190

Lys Ala Val Thr Arg Leu Gln Glu Leu Ser Ala Leu Gly Val Gly Ile
        195                 200                 205

Ala Ile Asp Asp Phe Gly Ile Gly Phe Ser Ser Leu Ala Tyr Leu Pro
    210                 215                 220

Arg Leu Pro Val Asp Val Lys Leu Gly Gly Lys Phe Ile Glu Cys
225                 230                 235                 240

Leu Asp Gly Asp Ile Gln Ala Arg Leu Ala Asn Glu Gln Ile Thr Arg
                245                 250                 255

Ala Met Ile Asp Leu Gly Asp Lys Leu Gly Ile Thr Val Thr Ala Lys
            260                 265                 270

Leu Val Glu Thr Pro Ser Gln Ala Ala Arg Leu Arg Ala Phe Gly Cys
        275                 280                 285
```

```
Lys Ala Ala Gln Gly Trp His Phe Ala Lys Ala Leu Pro Val Asp Phe
    290                 295                 300

Phe Arg Glu
305

<210> SEQ ID NO 20
<211> LENGTH: 1350
<212> TYPE: DNA
<213> ORGANISM: Mycobacterium bovis

<400> SEQUENCE: 20
atgacgattc ctgcgttcca tcccggtgaa ctcaatgtgt actcggcacc gggggatgtc      60
gccgatgtca gtcgcgcact gcgactcacc ggccggcgag tgatgttggt gcctactatg     120
ggtgcgctgc acgaaggcca cctcgcgttg gtgcgtgcgg ccaagcgggt gcccggatcg     180
gtcgtcgtcg tgtcgatctt cgtcaacccg atgcaattcg gtgccgggga agatctcgac     240
gcctatcccc gcaccccgga cgacgacctg gcgcaactgc gggccgaagg cgtggaaatc     300
gctttcacgc caactaccgc ggcgatgtat cccgacggcc tgcgcaccac cgtgcaaccc     360
ggtccgttgg ccgccgaact cgagggcggc ccgcggccaa cccatttcgc cggcgtgctg     420
acggtcgtgc taaagctgct gcagatcgtg cgcccggatc gggtgttctt cggtgagaag     480
gactaccagc agctggtgct gatccggcag ctggtcgcgg acttcaacct cgatgtcgcg     540
gtggtcggcg tgccgaccgt gcgcgaagcc gacgggctgg cgatgtcgtc gcgcaaccgc     600
tacctggacc cggcccagcg tgcggcggcc gtcgcgctct cggcggcgct aacggccgca     660
gcgcatgcgg caacggctgg cgcgcaggcc gcgctggatg ccgcccgtgc ggtgctcgac     720
gctgcacccg gcgtggcggt cgactacctg gagctgcgcg atatcgggct tggcccgatg     780
ccgctcaacg gttccggtcg gctgctggtt gctgcccggc ttggcaccac caggctgctg     840
gacaacattg cgattgaaat cggaactttc gccggcaccg accgcccgga cggataccgg     900
gcaatcctcg aatcacattg gagaaactga tgttacggac gatgctgaag tcgaagatcc     960
accgcgccac ggtgacctgc gccgacctgc actacgtcgg ctcggtgacc atcgatgccg    1020
acttgatgga cgccgccgac ctgctggaag gcgaacaggt aaccatcgtc gatatcgaca    1080
acggtgctcg actggtcacc tacgcgatca ccggcgaacg cggcagtggt gtgattggca    1140
tcaacggtgc cgccgcgcac ttggtgcatc cgggggatct ggtgattctg attgcgtacg    1200
cgacgatgga cgacgcccgg gcccgcacat accagccgcg gatcgtgttt gtcgacgctt    1260
acaacaaacc gatcgacatg ggccacgatc cggcatttgt gcccgaaaac gcgggcgagc    1320
tgctagaccc ccggctcggt gtgggatagc                                     1350

<210> SEQ ID NO 21
<211> LENGTH: 309
<212> TYPE: PRT
<213> ORGANISM: Mycobacterium bovis

<400> SEQUENCE: 21

Met Thr Ile Pro Ala Phe His Pro Gly Glu Leu Asn Val Tyr Ser Ala
1               5                   10                  15

Pro Gly Asp Val Ala Asp Val Ser Arg Ala Leu Arg Leu Thr Gly Arg
            20                  25                  30

Arg Val Met Leu Val Pro Thr Met Gly Ala Leu His Glu Gly His Leu
        35                  40                  45

Ala Leu Val Arg Ala Ala Lys Arg Val Pro Gly Ser Val Val Val Val
```

```
                      50                  55                  60
Ser Ile Phe Val Asn Pro Met Gln Phe Gly Ala Gly Glu Asp Leu Asp
 65                  70                  75                  80

Ala Tyr Pro Arg Thr Pro Asp Asp Leu Ala Gln Leu Arg Ala Glu
                 85                  90                  95

Gly Val Glu Ile Ala Phe Thr Pro Thr Ala Ala Met Tyr Pro Asp
                100                 105                 110

Gly Leu Arg Thr Thr Val Gln Pro Gly Pro Leu Ala Ala Glu Leu Glu
                115                 120                 125

Gly Gly Pro Arg Pro Thr His Phe Ala Gly Val Leu Thr Val Val Leu
            130                 135                 140

Lys Leu Leu Gln Ile Val Arg Pro Asp Arg Val Phe Phe Gly Glu Lys
145                 150                 155                 160

Asp Tyr Gln Gln Leu Val Leu Ile Arg Gln Leu Val Ala Asp Phe Asn
                    165                 170                 175

Leu Asp Val Ala Val Val Gly Val Pro Thr Val Arg Glu Ala Asp Gly
                180                 185                 190

Leu Ala Met Ser Ser Arg Asn Arg Tyr Leu Asp Pro Ala Gln Arg Ala
                195                 200                 205

Ala Ala Val Ala Leu Ser Ala Ala Leu Thr Ala Ala Ala His Ala Ala
            210                 215                 220

Thr Ala Gly Ala Gln Ala Ala Leu Asp Ala Ala Arg Ala Val Leu Asp
225                 230                 235                 240

Ala Ala Pro Gly Val Ala Val Asp Tyr Leu Glu Leu Arg Asp Ile Gly
                    245                 250                 255

Leu Gly Pro Met Pro Leu Asn Gly Ser Gly Arg Leu Leu Val Ala Ala
                260                 265                 270

Arg Leu Gly Thr Thr Arg Leu Leu Asp Asn Ile Ala Ile Glu Ile Gly
                275                 280                 285

Thr Phe Ala Gly Thr Asp Arg Pro Asp Gly Tyr Arg Ala Ile Leu Glu
            290                 295                 300

Ser His Trp Arg Asn
305

<210> SEQ ID NO 22
<211> LENGTH: 139
<212> TYPE: PRT
<213> ORGANISM: Mycobacterium bovis

<400> SEQUENCE: 22

Met Leu Arg Thr Met Leu Lys Ser Lys Ile His Arg Ala Thr Val Thr
 1               5                  10                  15

Cys Ala Asp Leu His Tyr Val Gly Ser Val Thr Ile Asp Ala Asp Leu
                20                  25                  30

Met Asp Ala Asp Leu Leu Glu Gly Glu Gln Val Thr Ile Val Asp
             35                  40                  45

Ile Asp Asn Gly Ala Arg Leu Val Thr Tyr Ala Ile Thr Gly Glu Arg
             50                  55                  60

Gly Ser Gly Val Ile Gly Ile Asn Gly Ala Ala His Leu Val His
 65                  70                  75                  80

Pro Gly Asp Leu Val Ile Leu Ile Ala Tyr Ala Thr Met Asp Asp Ala
                 85                  90                  95

Arg Ala Arg Thr Tyr Gln Pro Arg Ile Val Phe Val Asp Ala Tyr Asn
                100                 105                 110
```

-continued

```
Lys Pro Ile Asp Met Gly His Asp Pro Ala Phe Val Pro Glu Asn Ala
        115                 120                 125

Gly Glu Leu Leu Asp Pro Arg Leu Gly Val Gly
    130                 135

<210> SEQ ID NO 23
<211> LENGTH: 2501
<212> TYPE: DNA
<213> ORGANISM: Mycobacterium bovis

<400> SEQUENCE: 23
atgacgattc ctgcgttcca tcccggtgaa ctcaatgtgt actcggcacc gggggatgtc     60
gccgatgtca gtcgcgcact gcgactcacc ggccggcgag tgatgttggt gcctactatg    120
ggtgcgctgc acgaaggcca cctcgcgttg gtgcgtgcgg ccaagcgggt gcccggatcg    180
gtcgtcgtcg tgtcgatctt cgtcaacccg atgcaattcg gtgccgggga agatctcgac    240
gcctatcccc gcaccccgga cgacgacctg gcgcaactgc gggccgaagg cgtggaaatc    300
gctttcacgc caactaccgc ggcgatgtat cccgacggcc tgcgcaccac cgtgcaaccc    360
ggtccgttgg ccgccgaact cgagggcggc ccgcggccaa cccatttcgc cggcgtgctg    420
acggtcgtgc taaagctgct gcagatcgtg cgcccggatc gggtgttctt cggtgagaag    480
gactaccagc agctggtgct gatccggcag ctggtcgcgg acttcaacct cgatgtcgcg    540
gtggtcggcg tgccgaccgt gcgcgaagcc gacgggctgg cgatgtcgtc gcgcaaccgc    600
tacctggacc cggcccagcg tgcggcggcc gtcgcgctct cggcggcgct aacggccgca    660
gcgcatgcgg caacggctgg cgcgcaggcc gcgctggatg ccgcccgtgc ggtgctcgac    720
gctgcacccg gcgtggcgtg gcggtcgact acctggagct gcgcgatatc gggcttggcc    780
cgatgccgct caacggttcc ggtcggctgc tggttgctgc ccggcttggc accaccaggc    840
tgctggacaa cattgcgatt gaaatcggaa ctttcgccgg caccgaccgc ccggacggat    900
accgggcaat cctcgaatca cattggagaa actgatgtta cggacgatgc tgaagtcgaa    960
gatccaccgc gccacggtga cctgcgccga cctgcactac gtcggctcgg tgaccatcga   1020
tgccgacttg atggacgccg ccgacctgct ggaaggcgaa caggtaacca tcgtcgatat   1080
cgacaacggt gctcgactgg tcacctacgc gatcaccggc gaacgcggca gtggtgtgat   1140
tggcatcaac ggtgccgccg cgcacttggt gcatccgggg gatctggtga ttctgattgc   1200
gtacgcgacg atggacgacg cccgggcccg cacataccag ccgcggatcg tgtttgtcga   1260
cgcttacaac aaaccgatcg acatgggcca cgatccggca tttgtgcccg aaaacgcggg   1320
cgagctgcta gacccccggc tcggtgtggg atagccgtgc tgctggcgat tgacgtccgc   1380
aacacccaca ccgttgtggg cctgctgtcc ggaatgaaag agcacgcaaa ggtcgtgcag   1440
cagtggcgga tacgcaccga atccgaagtc accgccgacg aactggcact gacgatcgac   1500
gggctgatcg gcgaggattc cgagcggctc accggtaccg ccgccttgtc cacggtcccg   1560
tccgtgctgc acgaggtgcg gataatgctc gaccagtact ggccgtcggt gccgcacgtg   1620
ctgatcgagc ccggagtacg caccgggatc cctttgctcg tcgacaaccc gaaggaagtg   1680
ggcgcagacc gcatcgtgaa ctgtttggcc gcctatgacc ggttccggaa ggccgccatc   1740
gtcgttgact ttggatcctc gatctgtgtt gatgttgtat cggccaaggg tgaatttctt   1800
ggcggcgcca tcgcgcccgg ggtgcaggtg tcttccgatg ccgcggcggc ccgctcggcg   1860
gcattgcgcc gcgttgaact tgcccgccca cgttcggtgg ttggcaagaa caccgtcgaa   1920
tgcatgcaag ccggtgcggt gttcggcttc gccgggctgg tagacgggtt ggtaggccgc   1980
```

-continued

```
atccgcgagg acgtgtccgg tttctccgtc gaccacgatg tcgcgatcgt ggctaccggg    2040
cataccgcgc ccctgctgct gccggaattg cacaccgtcg accattacga ccagcacctg    2100
accttgcagg gtctgcggct ggtgttcgag cgtaacctcg aagtccagcg cggccggctc    2160
aagacggcgc gctgacgtcg atgccggcat cgagtctggg taccgggtcg cccgccgccg    2220
acaggctcga cgccacccac gagcgtcggc gtgaggtcat ttaagctggc acgtcgtgag    2280
tgccgctgac acagcagaag accttcctga gcagttccgg attcgccggg acaagcgcgc    2340
tcgcttgctg gcccaggggc gcgatcccta tcccgtcgcg gtgccgcgca ctcacacgtt    2400
ggccgaggtt cgcgccgccc accctgactt gccgatcgat accgcgaccg aagacatcgt    2460
cggcgtcgcg ggccgagtga tctttgcgcg caactcggga a                        2501
```

<210> SEQ ID NO 24
<211> LENGTH: 724
<212> TYPE: PRT
<213> ORGANISM: Mycobacterium bovis

<400> SEQUENCE: 24

```
Met Thr Ile Pro Ala Phe His P

```
            275                 280                 285
Ser Glu Leu Ser Pro Ala Pro Thr Ala Arg Thr Asp Thr Gly Gln Ser
290                 295                 300
Ser Asn His Ile Gly Glu Thr Asp Val Thr Asp Ala Glu Val Glu
305                 310                 315                 320
Asp Pro Pro Arg His Gly Asp Leu Arg Arg Pro Ala Leu Arg Arg Leu
                325                 330                 335
Gly Asp His Arg Cys Arg Leu Asp Gly Arg Arg Pro Ala Gly Arg
                340                 345                 350
Arg Thr Gly Asn His Arg Arg Tyr Arg Gln Arg Cys Ser Thr Gly His
                355                 360                 365
Leu Arg Asp His Arg Arg Thr Arg Gln Trp Cys Asp Trp His Gln Arg
        370                 375                 380
Cys Arg Arg Ala Leu Gly Ala Ser Gly Gly Ser Gly Asp Ser Asp Cys
385                 390                 395                 400
Val Arg Asp Asp Gly Arg Arg Pro Gly Pro His Ile Pro Ala Ala Asp
                405                 410                 415
Arg Val Cys Arg Arg Leu Gln Gln Thr Asp Arg His Gly Pro Arg Ser
                420                 425                 430
Gly Ile Cys Ala Arg Lys Arg Gly Arg Ala Ala Arg Pro Pro Ala Arg
                435                 440                 445
Cys Gly Ile Ala Val Leu Leu Ala Ile Asp Val Arg Asn Thr His Thr
        450                 455                 460
Val Val Gly Leu Leu Ser Gly Met Lys Glu His Ala Lys Val Val Gln
465                 470                 475                 480
Gln Trp Arg Ile Arg Thr Glu Ser Glu Val Thr Ala Asp Glu Leu Ala
                485                 490                 495
Leu Thr Ile Asp Gly Leu Ile Gly Glu Asp Ser Glu Arg Leu Thr Gly
                500                 505                 510
Thr Ala Ala Leu Ser Thr Val Pro Ser Val Leu His Glu Val Arg Ile
                515                 520                 525
Met Leu Asp Gln Tyr Trp Pro Ser Val Pro His Val Leu Ile Glu Pro
        530                 535                 540
Gly Val Arg Thr Gly Ile Pro Leu Leu Val Asp Asn Pro Lys Glu Val
545                 550                 555                 560
Gly Ala Asp Arg Ile Val Asn Cys Leu Ala Ala Tyr Asp Arg Phe Arg
                565                 570                 575
Lys Ala Ala Ile Val Val Asp Phe Gly Ser Ser Ile Cys Val Asp Val
                580                 585                 590
Val Ser Ala Lys Gly Glu Phe Leu Gly Gly Ile Ala Pro Gly Val
                595                 600                 605
Gln Val Ser Ser Asp Ala Ala Ala Arg Ser Ala Leu Arg Arg
        610                 615                 620
Val Glu Leu Ala Arg Pro Arg Ser Val Gly Lys Asn Thr Val Glu
625                 630                 635                 640
Cys Met Gln Ala Gly Ala Val Phe Gly Phe Ala Gly Leu Val Asp Gly
                645                 650                 655
Leu Val Gly Arg Ile Arg Glu Asp Val Ser Gly Phe Ser Val Asp His
                660                 665                 670
Asp Val Ala Ile Val Ala Thr Gly His Thr Ala Pro Leu Leu Leu Pro
                675                 680                 685
Glu Leu His Thr Val Asp His Tyr Asp Gln His Leu Thr Leu Gln Gly
        690                 695                 700
```

Leu Arg Leu Val Phe Glu Arg Asn Leu Glu Val Gln Arg Gly Arg Leu
705                 710                 715                 720

Lys Thr Ala Arg

<210> SEQ ID NO 25
<211> LENGTH: 139
<212> TYPE: PRT
<213> ORGANISM: Mycobacterium bovis

<400> SEQUENCE: 25

Met Leu Arg Thr Met Leu Lys Ser Lys Ile His Arg Ala Thr Val Thr
1               5                   10                  15

Cys Ala Asp Leu His Tyr Val Gly Ser Val Thr Ile Asp Ala Asp Leu
                20                  25                  30

Met

```
gcaatcctcg aatcacattg gagaaactga                                     930
```

<210> SEQ ID NO 27
<211> LENGTH: 420
<212> TYPE: DNA
<213> ORGANISM: Mycobacterium bovis

<400> SEQUENCE: 27

```
atgttacgga cgatgctgaa gtcgaagatc caccgcgcca cggtgacctg cgccgacctg    60
cactacgtcg gctcggtgac catcgatgcc gacttgatgg acgccgccga cctgctggaa   120
ggcgaacagg taaccatcgt cgatatcgac aacggtgctc gactggtcac ctacgcgatc   180
accggcgaac gcggcagtgg tgtgattggc atcaacggtg ccgccgcgca cttggtgcat   240
ccgggggatc tggtgattct gattgcgtac gcgacgatgg acgacgcccg ggcccgcaca   300
taccagccgc ggatcgtgtt tgtcgacgct acaacaaac cgatcgacat gggccacgat    360
ccggcatttg tgcccgaaaa cgcgggcgag ctgctagacc cccggctcgg tgtgggatag   420
```

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28

```
ggggatgacg attcctgcg                                                  19
```

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29

```
gggctatccc acaccgagc                                                  19
```

<210> SEQ ID NO 30
<211> LENGTH: 7738
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30

```
ggatccttct agaattccgg aattgcactc gccttagggg agtgctaaaa atgatcctgg    60
cactcgcgat cagcgagtgc caggtcggga cggtgagacc cagccagcaa gctgtggtcg   120
tccgtcgcgg gcactgcacc cggccagcgt aagtaatggg ggttgtcggc acccggtgac   180
ctagacacat gcatgcatgc ttaattaatt aagcgatatc cggaggaatc acttccatat   240
gcacgctgtg actcgtccga ccctgcgtga ggctgtcgcc cgcctagccc cgggcactgg   300
gctgcgggac ggcctggagc gtatcctgcg cggccgcact ggtgccctga tcgtgctggg   360
ccatgacgag aatgtcgagg ccatctgcga tggtggcttc tccctcgatg tccgctatgc   420
agcaaccccg g ctacgcgagc tgtgcaagat ggacggcgcc gtggtgctgt ccaccgacgg   480
cagccgcatc gtgcgggcca acgtgcaact ggtaccggat ccgtcgatcc ccaccgacga   540
```

```
atcggggacc cggcaccgct cggccgagcg ggccgcgatc cagaccggtt acccggtgat    600
ctcagtgagc cactcgatga acatcgtgac cgtctacgtc cgcggggaac gtcacgtatt    660
gaccgactcg gcaaccatcc tgtcgcgggc caaccaggcc atcgcaaccc tggagcggta    720
caaaaccagg ctcgacgagg tcagccggca actgtccagg cagaaatcg aggacttcgt     780
cacgctgcgc gatgtgatga cggtggtgca acgcctcgag ctggtccggc gaatcgggct    840
ggtgatcgac tacgcgtgg tcgaactcgg cactgatggt cgtcagctgc ggctgcagct     900
cgacgagttg ctcggcggca acgacaccgc ccgggaattg atcgtgcgcg attaccacgc    960
caacccggaa ccaccgtcca cggggcaaat caatgccacc ctggacgaac tggacgccct   1020
gtcggacggc gacctcctcg atttcaccgc gctggcaaag gtttcggat atccgacgac    1080
cacggaagcg caggattcga cgctgagccc cgtggctac cgcgcgatgg ccggtatccc    1140
ccggctccag ttcgcccatg ccgacctgct ggtccgggcg ttcggaacgt tgcagggtct   1200
gctggcggcc agcgccggcg atctgcaatc agtggacggc atcggcgcca tgtgggcccg   1260
tcatgtgcgc gaggggttgt cacagctggc ggaatcgacc atcagcgatc aataacgcgt   1320
tctggcgtaa tagcgaagag gcccgcaccg atcgccttc caacagttg cgcagcctga    1380
atggcgaatg gcgcttgcc tggttccgg tcgaagcttg gccggatcta aagttttgtc    1440
gtctttccag acgttagtaa atgaattttc tgtatgaggt tttgctaaac aactttcaac   1500
agtttcagcg gagtgagaat agaaaggaac aactaaagga attgcgaata ataatttttt    1560
cacgttgaaa atctccaaaa aaaaaggctc caaaggagc ctttaattgt atcggtttat    1620
cagcttgctt tcgaggtgaa tttcttaaac agcttgatac cgatagttgc gccgacaatg   1680
acaacaacca tcgcccacgc ataaccgata tattcggtcg ctgaggcttg cagggagtca   1740
aaggccgctt ttgcggggat ccgctcggag gcgcggtcgc ggcgcggctg tggcatgtcg   1800
gggcgtgccg ctcccccggc gccgcccatc ggcccgccca ttggcattcc gcccatgccg   1860
cccatcattc ctgtggagcc agaactgatc cagcctgtgc cacagccgac aggatggtga   1920
ccaccatttg ccccatatca ccgtcggtac tgatcccgtc gtcaataaac cgaaccgcta   1980
caccctgagc atcaaactct tttatcagtt ggatcatgtc ggcggtgtcg cggccaagac   2040
ggtcgagctt cttcaccaga atgacatcac cttcctccac cttcatcctc agcaaatcca   2100
gcccttcccg atctgttgaa ctgccggatg ccttgtcggt aaagatgcgg ttagcttta    2160
cccctgcatc tttgagcgct gaggtctgcc tcgtgaagaa ggtgttgctg actcatacca   2220
ggcctgaatc gccccatcat ccagccagaa agtgagggag ccacggttga tgagagcttt   2280
gttgtaggtg gaccagttgg tgattttgaa cttttgcttt gccacggaac ggtctgcgtt   2340
gtcgggaaga tgcgtgatct gatccttcaa ctcagcaaaa gttcgattta ttcaacaaag   2400
ccgccgtccc gtcaagtcag cgtaatgctc tgccagtgtt acaaccaatt aaccaattct   2460
gattagaaaa actcatcgag catcaaatga aactgcaatt tattcatatc aggattatca   2520
ataccatatt tttgaaaaag ccgtttctgt aatgaaggag aaaactcacc gaggcagttc   2580
cataggatgg caagatcctg gtatcggtct gcgattccga ctcgtccaac atcaatacaa   2640
cctattaatt tcccctcgtc aaaaataagg ttatcaagtg agaaatcacc atgagtgacg   2700
actgaatccg gtgagaatgg caaaagctta tgcatttctt tccagacttg ttcaacaggc   2760
cagccattac gctcgtcatc aaaatcactc gcatcaacca aaccgttatt cattcgtgat   2820
tgcgcctgag cgagacgaaa tacgcgatcg ctgttaaaag gacaattaca acaggaatc    2880
gaatgcaacc ggcgcaggaa cactgccagc gcatcaacaa tattttcacc tgaatcagga   2940
```

| | |
|---|---|
| tattcttcta ataccggaa tgctgttttc ccggggatcg cagtggtgag taaccatgca | 3000 |
| tcatcaggag tacggataaa atgcttgatg gtcggaagag gcataaattc cgtcagccag | 3060 |
| tttagtctga ccatctcatc tgtaacatca ttggcaacgc tacctttgcc atgtttcaga | 3120 |
| aacaactctg gcgcatcggg cttcccatac aatcgataga ttgtcgcacc tgattgcccg | 3180 |
| acattatcgc gagcccattt atacccatat aaatcagcat ccatgttgga atttaatcgc | 3240 |
| ggcctcgagc aagacgtttc ccgttgaata tggctcataa cacccctgt attactgttt | 3300 |
| atgtaagcag acagttttat tgttcatgat gatatatttt tatcttgtgc aatgtaacat | 3360 |
| cagagatttt gagacacaac gtggctttgt tgaataaatc gaacttttgc tgagttgaag | 3420 |
| gatcagatca cgcatcttcc cgacaacgca gaccgttccg tggcaaagca aaagttcaaa | 3480 |
| atcaccaact ggtccaccta caacaaagct ctcatcaacc gtggctccct cactttctgg | 3540 |
| ctggatgatg gggcgattca ggcctggtat gagtcagcaa ccttcttc acgaggcaga | 3600 |
| cctcagcgct agcggagtgt atactggctt actatgttgg cactgatgag ggtgtcagtg | 3660 |
| aagtgcttca tgtggcagga gaaaaaggc tgcaccggtg cgtcagcaga atatgtgata | 3720 |
| caggatatat tccgcttcct cgctcactga ctcgctacgc tcggtcgttc gactgcggcg | 3780 |
| agcggaaatg gcttacgaac ggggcggaga tttcctggaa gatgccagga agatacttaa | 3840 |
| cagggaagtg agagggccgc ggcaaagccg ttttccata ggctccgccc cctgacaag | 3900 |
| catcacgaaa tctgacgctc aaatcagtgg tggcgaaacc cgacaggact ataaagatac | 3960 |
| caggcgtttc cccctggcgg ctccctcgtg cgctctcctg ttcctgcctt tcggtttacc | 4020 |
| ggtgtcattc cgctgttatg gccgcgtttg tctcattcca cgcctgacac tcagttccgg | 4080 |
| gtaggcagtt cgctccaagc tggactgtat gcacgaaccc cccgttcagt ccgaccgctg | 4140 |
| cgccttatcc ggtaactatc gtcttgagtc aacccggaa agacatgcaa aagcaccact | 4200 |
| ggcagcagcc actggtaatt gatttagagg agttagtctt gaagtcatgc gccggttaag | 4260 |
| gctaaactga aaggacaagt tttggtgact gcgctcctcc aagccagtta cctcggttca | 4320 |
| aagagttggt agctcagaga accttcgaaa aaccgccctg caaggcggtt ttttcgtttt | 4380 |
| cagagcaaga gattacgcgc agaccaaaac gatctcaaga agatcatctt attaagggt | 4440 |
| ctgacgctca gtggaacgaa aactcacgtt aagggatttt ggtcatgaga ttatcaaaaa | 4500 |
| ggatcttcac ctagatcctt ttaaaagtgc tcatcattgg aaaacgttct cggggcgaa | 4560 |
| aactctcaag gatcttaccg ctgttgagat ccagttcgat gtaacccact cgtgcaccca | 4620 |
| actgatcttc agcatctttt actttcacca gcgtttctgg gtgagcaaaa acaggaaggc | 4680 |
| aaaatgccgc aaaaaggga ataagggcga cacggaaatg ttgaatactc atactcttcc | 4740 |
| tttttcaata ttattgaagc atttatcagg gttattgtct catgagcgga tacatatttg | 4800 |
| aatgtattta gaaaaataaa caaatagggg ttccgcgcac atttccccga aaagtgccac | 4860 |
| ctgacgtcta agaaaccatt attatcatga cattaaccta taaaaatagg cgtatcacga | 4920 |
| ggcccttcg tcttcaagaa ttcccaggca tcaaataaaa cgaaaggctc agtcgaaaga | 4980 |
| ctgggccttt cgttttatct gttgtttgtc ggtgaacgct ctcctgagta ggacaaatcc | 5040 |
| gccgggagcg gatttgaacg ttgcgaagca acggcccgga gggtggcggg caggacgccc | 5100 |
| gccataaact gccagggaat tcccatcgag ccgagaacgt tatcgaagtt ggtcatgtgt | 5160 |
| aatcccctcg tttgaacttt ggattaagcg tagatacacc cttggacaag ccagttggat | 5220 |
| tcggagacaa gcaaattcag ccttaaaaag ggcgaggccc tgcggtggtg gaacaccgca | 5280 |

```
gggcctctaa ccgctcgacg cgctgcacca accagcccgc gaacggctgg cagccagcgt    5340
aaggcgcggc tcatcgggcg gcgttcgcca cgatgtcctg cacttcgagc caagcctcga    5400
acacctgctg gtgtgcacga ctcacccggt tgttgacacc gcgcgcggcc gtgcgggctc    5460
ggtggggcgc tctgtcgcc cttgccagcg tgagtagcgc gtacctcacc tcgcccaaca    5520
ggtcgcacac agccgattcg tacgccataa agccaggtga gcccaccagc tccgtaagtt    5580
cgggcgctgt gtggctcgta cccgcgcatt caggcggcag ggggtctaac gggtctaagg    5640
cggcgtgtac gcggccacag cggctctcag cggcccggaa acgtcctcga aacgacgcat    5700
gtgttcctcc tggttggtac aggtggttgg gggtgctcgg ctgtcgcggt tgttccacca    5760
ccagggctcg acgggagagc gggggagtgt gcagttgtgg ggtggcccct cagcgaaata    5820
tctgacttgg agctcgtgtc ggaccataca ccggtgatta atcgtggtct actaccaagc    5880
gtgagccacg tcgccgacga atttgagcag ctctggctgc cgtactggcc gctggcaagc    5940
gacgatctgc tcgaggggat ctaccgccaa agccgcgcgt cggccctagg ccgccggtac    6000
atcgaggcga acccaacagc gctggcaaac ctgctggtcg tggacgtaga ccatccagac    6060
gcagcgctcc gagcgctcag cgcccggggg tcccatccgc tgcccaacgc gatcgtgggc    6120
aatcgcgcca acgccacgc acacgcagtg tgggcactca acgcccctgt tccacgcacc    6180
gaatacgcgc ggcgtaagcc gctcgcatac atggcggcgt gcgccgaagg ccttcggcgg    6240
ccgtcgacgc cgaccgcagt tactcaggcc tcatgaccaa aaaccccggc cacatcgcct    6300
gggaaacgga atggctccac tcagatctct acacactcag ccacatcgag gccgagctcg    6360
gcgcgaacat gccaccgccg cgctggcgtc agcagaccac gtacaaagcg gctccgacgc    6420
cgctagggcg gaattgcgca ctgttcgatt ccgtcaggtt gtgggcctat cgtcccgccc    6480
tcatgcggat ctacctgccg acccggaacg tggacggact cggccgcgcg atctatgccg    6540
agtgccacgc gcgaaacgcc gaattcccgt gcaacgacgt gtgtcccgga ccgctaccgg    6600
acagcgaggt ccgcgccatc gccaacagca tttggcgttg gatcacaacc aagtcgcgca    6660
tttgggcgga cgggatcgtg gtctacgagg ccacactcag tgcgcgccag tcggccatct    6720
cgcggaaggg cgcagcagcg cgcacggcgg cgagcacagt tgcgcggcgc gcaaagtccg    6780
cgtcagccat ggaggcattg ctatgagcga cggctacagc gacggctaca gcgacggcta    6840
caaccggcag ccgactgtcc gcaaaaagcc gtgacgcgcc gaaggcgctc gaatcaccgg    6900
actatccgaa cgccacgtcg tccggctcgt ggcgcaggaa cgcagcgagt ggctcgccga    6960
gcaggctgca cgcgcgcgaa gcatccgcgc ctatcacgac gacgagggcc actcttggcc    7020
gcaaacggcc aaacatttcg ggctgcatct ggacaccgtt aagcgactcg gctatcgggc    7080
gaggaaagag cgtgcggcag aacaggaagc ggctcaaaag gccacaacg aagccgacaa    7140 tccaccgctg ttctaacgca attggggacg ggtgtcgcgg gggtccgtg ggggttccg    7200 ttgcaacggg tcggacaggt aaaagtcctg gtagacgcta gttttctggt ttgggccatg    7260
cctgtctcgt tgcgtgtttc gttgcgccgt tttgaatacc agccagacga gacggggttc    7320
tacgaatctt ggtcgatacc aagccatttc cgctgaatat cggggagctc accgccagaa    7380
tcggtggttg tggtgatgta cgtggcgaac tccttgtag tgcctgtggt ggcatccgtg    7440
gccactctcg ttgcacggtt cgttgtgccg ttacaggccc cgttgacagc tcaccgaacg    7500
tagttaaaac atgctggtca aactaggttt accaacgata cgagtcagct catctagggc    7560
cagttctagg cgttgttcgt tgcgcggttc gttgcgcatg tttcgtgtgg ttgctagatg    7620
gctccgcaac cacacgcttc gaggttgagt gcttccagca cgggcgcgat ccagaagaac    7680
```

```
ttcgtcgtgc gactgtcctc gttgggatct agcccgccta atgagcgggc ttttttttt    7738
```

<210> SEQ ID NO 31
<211> LENGTH: 8534
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31

```
cttctagaat tccggaattg cactcgcctt aggggagtgc taaaaatgat cctggcactc      60
gcgatcagcg agtgccaggt cgggacggtg agacccagcc agcaagctgt ggtcgtccgt     120
cgcgggcact gcacccggcc agcgtaagta atgggggttg tcggcacccg gtgacctaga     180
cacatgcatg catgcttaat taattaagcg atatccggag gaatcacttc catatgcacg     240
ctgtgactcg tccgaccctg cgtgaggctg tcgcccgcct agcccggggc actgggctgc     300
gggacggcct ggagcgtatc ctgcgcggcc gcactggtgc cctgatcgtg ctgggccatg     360
acgagaatgt cgaggccatc tgcgatggtg gcttctccct cgatgtccgc tatgcagcaa     420
cccggctacg cgagctgtgc aagatggacg gcgccgtggt gctgtccacc gacggcagcc     480
gcatcgtgcg ggccaacgtg caactggtac cggatccgtc gatccccacc gacgaatcgg     540
ggacccggca ccgctcggcc gagcgggccg cgatccagac cggttacccg gtgatctcag     600
tgagccactc gatgaacatc gtgaccgtct acgtccgcgg gaacgtcac gtattgaccg      660
actcggcaac catcctgtcg cgggccaacc aggccatcgc aaccctggag cggtacaaaa     720
ccaggctcga cgaggtcagc cggcaactgt ccagggcaga aatcgaggac ttcgtcacgc     780
tgcgcgatgt gatgacggtg gtgcaacgcc tcgagctggt ccggcgaatc gggctggtga     840
tcgactacga cgtggtcgaa ctcggcactg atggtcgtca gctgcggctg cagctcgacg     900
agttgctcgg cggcaacgac accgcccggg aattgatcgt gcgcgattac cacgccaacc     960
cggaaccacc gtccacgggg caaatcaatg ccaccctgga cgaactggac gccctgtcgg    1020
acggcgacct cctcgatttc accgcgctgg caaaggtttt cggatatccg acgaccacgg    1080
aagcgcagga ttcgacgctg agccgcgtg gctaccgcgc gatggccggt atccccggc      1140
tccagttcgc ccatgccgac ctgctggtcc gggcgttcgg aacgttgcag ggtctgctgg    1200
cggccagcgc cggcgatctg caatcagtgg acggcatcgg cgccatgtgg gcccgtcatg    1260
tgcgcgaggg gttgtcacag ctggcggaat cgaccatcag cgatcaataa cgcgttctgg    1320
cgtaatagcg aagaggcccg caccgatcgc ccttcccaac agttgcgcag cctgaatggc    1380
gaatggcgct ttgcctggtt tccggtcgaa gcttggccgg atctaaagtt ttgtcgtctt    1440
tccagacgtt agtaaatgaa ttttctgtat gaggttttgc taaacaactt tcaacagttt    1500
cagcggagtg agaatagaaa ggaacaacta aaggaattgc gaataataat ttttttcacgt    1560
tgaaaatctc caaaaaaaaa ggctccaaaa ggagccttta attgtatcgg tttatcagct    1620
tgctttcgag gtgaatttct aaacagcttg ataccgata gttgcgccga caatgacaac     1680
aaccatcgcc cacgcataac cgatatattc ggtcgctgag gcttgcaggg agtcaaaggc    1740
cgcttttgcg gggatccgct cggaggcgcg gtcgcggcgc ggctgtggca tgtcggggcg    1800
tgccgctccc ccggcgccgc ccatcggccc gcccattggc attccgccca tgccgcccat    1860
cattcctgtg gagccagaac tgatccagcc tgtgccacag ccgacaggat ggtgaccacc    1920
atttgcccca tatcaccgtc ggtactgatc ccgtcgtcaa taaaccgaac cgctacaccc    1980
```

```
tgagcatcaa actcttttat cagttggatc atgtcggcgg tgtcgcggcc aagacggtcg    2040
agcttcttca ccagaatgac atcaccttcc tccaccttca tcctcagcaa atccagccct    2100
tcccgatctg ttgaactgcc ggatgccttg tcggtaaaga tgcggttagc ttttacccct    2160
gcatctttga gcgctgaggt ctgcctcgtg aagaaggtgt tgctgactca taccaggcct    2220
gaatcgcccc atcatccagc cagaaagtga gggagccacg gttgatgaga gctttgttgt    2280
aggtggacca gttggtgatt ttgaactttt gctttgccac ggaacggtct gcgttgtcgg    2340
gaagatgcgt gatctgatcc ttcaactcag caaaagttcg atttattcaa caaagccgcc    2400
gtcccgtcaa gtcagcgtaa tgctctgcca gtgttacaac caattaacca attctgatga    2460
tcagctatcc cacaccgagc cgggggtcta gcagctcgcc cgcgttttcg ggcacaaatg    2520
ccggatcgtg gccatgtcg atcggtttgt tgtaagcgtc gacaaacacg atccgcggct    2580
ggtatgtgcg ggcccgggcg tcgtccatcg tcgcgtacgc aatcagaatc accagatccc    2640
ccggatgcac caagtgcgcg gcggcaccgt tgatgccaat cacaccactg ccgcgttcgc    2700
cggtgatcgc gtaggtgacc agtcgagcac cgttgtcgat atcgacgatg gttacctgtt    2760
cgccttccag caggtcggcg gcgtccatca agtcggcatc gatggtcacc gagccgacgt    2820
agtgcaggtc ggcgcaggtc accgtggcgc ggtggatctt cgacttcagc atcgtccgta    2880
acatcagttt ctccaatgtg attcgaggat tgcccggtat ccgtccgggc ggtcggtgcc    2940
ggcgaaagtt ccgatttcaa tcgcaatgtt gtccagcagc ctggtggtgc caagccgggc    3000
agcaaccagc agccgaccgg aaccgttgag cggcatcggg ccaagcccga tatcgcgcag    3060
ctccaggtag tcgaccgcca cgccgggtgc agcgtcgagc accgcacggg cggcatccag    3120
cgcggcctgc gcgccagccg ttgccgcatg cgctgcggcc gttagcgccg ccgagagcgc    3180
gacggccgcc gcacgctggg ccgggtccag gtagcggttg cgcgacgaca tcgccagccc    3240
gtcggcttcg cgcacggtcg gcacgccgac caccgcgaca tcgaggttga agtccgcgac    3300
cagctgccgg atcagcacca gctgctggta gtccttctca ccgaagaaca cccgatccgg    3360
gcgcacgatc tgcagcagct ttagcacgac cgtcagcacg ccggcgaaat gggttggccg    3420
cgggccgccc tcgagttcgg cggccaacgg accgggttgc acggtggtgc gcaggccgtc    3480
gggatacatc gccgcggtag ttggcgtgaa agcgatttcc acgccttcgg cccgcagttg    3540
cgccaggtcg tcgtccgggg tgcggggata ggcgtcgaga tcttccccgg caccgaattg    3600
catcgggttg acgaagatcg acacgacgac gaccgatccg ggcacccgct tggccgcacg    3660
caccaacgcg aggtggccctt cgtgcagcgc acccatagta ggcaccaaca tcactcgccg    3720
gccggtgagt cgcagtgcgc gactgacatc ggcgacatcc cccggtgccg agtacacatt    3780
gagttcaccg gatggaacg caggaatcgt catgccgtca aaacctcgac gacatccgcg    3840
ggggcgtgtg cgcgctgcgc ggtccgcagc gcgtttatcc ggtatgcctg gccagcgct    3900 gcgtcgacgt ccgcgagggc cgccagatga tccgcgaccg ctgccgcatc gccgcgggcg    3960
accggtccgg tgagcgcggc ctgtccccgc tgcagcgtgt tctccagcgc cgctctggcc    4020
agcggcccga cgatgcgctc cacgatcccg cccggctggt cgtactagta acacccttg    4080 tattactgtt tatgtaagca gacagttttta ttgttcatga tgatatattt ttatcttgtg    4140
caatgtaaca tcagagattt tgagacacaa cgtggctttg ttgaataaat cgaacttttg    4200
ctgagttgaa ggatcagatc acgcatcttc ccgacaacgc agaccgttcc gtggcaaagc    4260
aaaagttcaa aatcaccaac tggtccacct acaacaaagc tctcatcaac cgtggctccc    4320
```

| | |
|---|---|
| tcactttctg gctggatgat ggggcgattc aggcctggta tgagtcagca acaccttctt | 4380 |
| cacgaggcag acctcagcgc tagcggagtg tatactggct tactatgttg gcactgatga | 4440 |
| gggtgtcagt gaagtgcttc atgtggcagg agaaaaaagg ctgcaccggt gcgtcagcag | 4500 |
| aatatgtgat acaggatata ttccgcttcc tcgctcactg actcgctacg ctcggtcgtt | 4560 |
| cgactgcggc gagcggaaat ggcttacgaa cggggcggag atttcctgga agatgccagg | 4620 |
| aagatactta acagggaagt gagagggccg cggcaaagcc gttttccat aggctccgcc | 4680 |
| cccctgacaa gcatcacgaa atctgacgct caaatcagtg gtggcgaaac ccgacaggac | 4740 |
| tataaagata ccaggcgttt ccccctggcg gctccctcgt gcgctctcct gttcctgcct | 4800 |
| ttcggtttac cggtgtcatt ccgctgttat ggccgcgttt gtctcattcc acgcctgaca | 4860 |
| ctcagttccg ggtaggcagt tcgctccaag ctggactgta tgcacgaacc ccccgttcag | 4920 |
| tccgaccgct gcgccttatc cggtaactat cgtcttgagt ccaacccgga agacatgca | 4980 |
| aaagcaccac tggcagcagc cactggtaat tgatttagag gagttagtct tgaagtcatg | 5040 |
| cgccggttaa ggctaaactg aaaggacaag ttttggtgac tgcgctcctc caagccagtt | 5100 |
| acctcggttc aaagagttgg tagctcagag aaccttcgaa aaaccgccct gcaaggcggt | 5160 |
| tttttcgttt tcagagcaag agattacgcg cagaccaaaa cgatctcaag aagatcatct | 5220 |
| tattaagggg tctgacgctc agtggaacga aaactcacgt taagggattt tggtcatgag | 5280 |
| attatcaaaa aggatcttca cctagatcct tttaaaagtg ctcatcattg gaaaacgttc | 5340 |
| ttcggggcga aaactctcaa ggatcttacc gctgttgaga tccagttcga tgtaacccac | 5400 |
| tcgtgcaccc aactgatctt cagcatcttt tactttcacc agcgtttctg ggtgagcaaa | 5460 |
| aacaggaagg caaaatgccg caaaaaaggg aataagggcg acacggaaat gttgaatact | 5520 |
| catactcttc cttttcaat attattgaag catttatcag ggttattgtc tcatgagcgg | 5580 |
| atacatattt gaatgtattt agaaaaataa acaaataggg gttccgcgca catttccccg | 5640 |
| aaaagtgcca cctgacgtct aagaaaccat tattatcatg acattaacct ataaaaatag | 5700 |
| gcgtatcacg aggccctttc gtcttcaaga attcccaggc atcaaataaa acgaaaggct | 5760 |
| cagtcgaaag actgggcctt tcgttttatc tgttgtttgt cggtgaacgc tctcctgagt | 5820 |
| aggacaaatc cgccgggagc ggatttgaac gttgcgaagc aacggcccgg agggtggcgg | 5880 |
| gcaggacgcc cgccataaac tgccagggaa ttcccatcga gccgagaacg ttatcgaagt | 5940 |
| tggtcatgtg taatcccctc gtttgaactt tggattaagc gtagatacac ccttggacaa | 6000 |
| gccagttgga ttcggagaca agcaaattca gccttaaaaa gggcgaggcc ctgcggtggt | 6060 |
| ggaacaccgc agggcctcta accgctcgac gcgctgcacc aaccagcccg cgaacggctg | 6120 |
| gcagccagcg taaggcgcgg ctcatcgggc ggcgttcgcc acgatgtcct gcacttcgag | 6180 |
| ccaagcctcg aacacctgct ggtgtgcacg actcacccgg ttgttgacac cgcgcgcggc | 6240 |
| cgtgcgggct cggtggggcg gctctgtcgc ccttgccagc gtgagtagcg cgtacctcac | 6300 |
| ctcgcccaac aggtcgcaca cagccgattc gtacgccata aagccaggtg agcccaccag | 6360 |
| ctccgtaagt tcgggcgctg tgtggctcgt acccgcgcat tcaggcggca ggggtctaa | 6420 |
| cgggtctaag gcgcgtgta cgcggccaca gcggctctca gcgcccgga aacgtcctcg | 6480 |
| aaacgacgca tgtgttcctc ctggttggta caggtggttg ggggtgctcg gctgtcgcgg | 6540 |
| ttgttccacc accagggctc gacgggagag cggggagtg tgcagttgtg ggtggcccc | 6600 |
| tcagcgaaat atctgacttg gagctcgtgt cggaccatac accggtgatt aatcgtggtc | 6660 |
| tactaccaag cgtgagccac gtcgccgacg aatttgagca gctctggctg ccgtactggc | 6720 |

```
cgctggcaag cgacgatctg ctcgagggga tctaccgcca aagccgcgcg tcggccctag    6780
gccgccggta catcgaggcg aacccaacag cgctggcaaa cctgctggtc gtggacgtag    6840
accatccaga cgcagcgctc cgagcgctca gcgcccgggg gtcccatccg ctgcccaacg    6900
cgatcgtggg caatcgcgcc aacggccacg cacacgcagt gtgggcactc aacgccctg    6960 ttccacgcac cgaatacgcg cggcgtaagc cgctcgcata catggcggcg tgcgccgaag    7020
gccttcggcg gccgtcgacg gcgaccgcag ttactcaggc ctcatgacca aaaccccgg    7080 ccacatcgcc tgggaaacgg aatggctcca ctcagatctc tacacactca gccacatcga    7140
ggccgagctc ggcgcgaaca tgccaccgcc gcgctggcgt cagcagacca cgtacaaagc    7200
ggctccgacg ccgctagggc ggaattgcgc actgttcgat tccgtcaggt tgtgggccta    7260
tcgtcccgcc ctcatgcgga tctacctgcc gacccggaac gtggacggac tcggccgcgc    7320
gatctatgcc gagtgccacg cgcgaaacgc cgaattcccg tgcaacgacg tgtgtcccgg    7380
accgctaccg gacagcgagg tccgcgccat cgccaacagc atttggcgtt ggatcacaac    7440
caagtcgcgc atttgggcgg acgggatcgt ggtctacgag gccacactca gtgcgcgcca    7500
gtcggccatc tcgcggaagg gcgcagcagc gcgcacggcg gcgagcacag ttgcgcggcg    7560
cgcaaagtcc gcgtcagcca tggaggcatt gctatgagcg acggctacag cgacggctac    7620
agcgacggct acaaccggca gccgactgtc cgcaaaaagc cgtgacgcgc cgaaggcgct    7680
cgaatcaccg gactatccga cgccacgtc gtccggctcg tggcgcagga acgcagcgag    7740
tggctcgccg agcaggctgc acgcgcgcga agcatccgcg cctatcacga cgacgagggc    7800
cactcttggc cgcaaacggc caaacatttc gggctgcatc tggacaccgt taagcgactc    7860
ggctatcggg cgaggaaaga gcgtgcggca gaacaggaag cggctcaaaa ggcccacaac    7920
gaagccgaca atccaccgct gttctaacgc aattggggac gggtgtcgcg ggggttccgt    7980 gggggggttcc gttgcaacgg gtcggacagg taaaagtcct ggtagacgct agttttctgg    8040
tttgggccat gcctgtctcg ttgcgtgttt cgttgcgccg ttttgaatac cagccagacg    8100
agacggggtt ctacgaatct tggtcgatac caagccattt ccgctgaata tcggggagct    8160
caccgccaga atcggtggtt gtggtgatgt acgtggcgaa ctccgttgta gtgcctgtgg    8220
tggcatccgt ggccactctc gttgcacggt tcgttgtgcc gttacaggcc ccgttgacag    8280
ctcaccgaac gtagttaaaa catgctggtc aaactaggtt taccaacgat acgagtcagc    8340
tcatctaggg ccagttctag gcgttgttcg ttgcgcggtt cgttgcgcat gtttcgtgtg    8400
gttgctagat ggctccgcaa ccacacgctt cgaggttgag tgcttccagc acgggcgcga    8460
tccagaagaa cttcgtcgtg cgactgtcct cgttgggatc tagcccgcct aatgagcggg    8520 ctttttttg gatc                                                      8534
```

<210> SEQ ID NO 32
<211> LENGTH: 8801
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<221> NAME/KEY: modified_base
<222> LOCATION: (5756)..(5756)
<223> OTHER INFORMATION: a, c, t, g, unknown or other

<400> SEQUENCE: 32

```
cggaccgcta ccggacagcg aggtccgcgc catcgccaac agcatttggc gttggatcac    60
```

```
aaccaagtcg cgcatttggg cggacgggat cgtggtctac gaggccacac tcagtgcgcg    120
ccagtcggcc atctcgcgga agggcgcagc agcgcgcacg gcggcgagca cagttgcgcg    180
gcgcgcaaag tccgcgtcag ccatggaggc attgctatga gcgacggcta cagcgacggc    240
tacaaccgga agccgactgt ccgcaaaaag cggcgcgtga ccgccgccga aggcgctcga    300
atcaccggac tatccgaacg ccacgtcgtc cggctcgtgg cgcaggaacg cagcgagtgg    360
ctcgccgagc aggctgcacg ccgcgaacgc atccgcgcct atcacgacga cgagggccac    420
tcttggccgc aaacggccaa acatttcggg ctgcatctgg acaccgttaa gcgactcggc    480
tatcgggcga ggaagagcg tgcggcagaa caggaagcgg ctcaaaaggc ccacaacgaa     540
gccgacaatc caccgctgtt ctaacgcaat tggggagcgg gtgtcgcggg ggttccgtgg    600
ggggttccgt tgcaacgggt cggacaggta aaagtcctgg tagacgctag ttttctggtt    660
tgggccatgc ctgtctcgtt gcgtgtttcg ttgcgcccgt tttgaatacc agccagacga    720
gacggggttc tacgaatctt ggtcgatacc aagccatttc cgctgaatat cggggagctc    780
accgccagaa tcggtggttg tggtgatgta cgtggcgaac tccgttgtag tgcctgtggt    840
ggcatccgtg gcgcggccgc ggtaccagat ctttaaatct agataaagaa gtgacgcggt    900
ctcaagcgtc gagcgtcgcc agcgtgtcga ggatgtcgaa gtcgtagccg tcggcgctgg    960
cgatgtagac ctgctggtcg aattgactgt cgcgcataca catcgggccc cggggcccgt   1020
cgaacccgac atcgtgcgcg gatgccatca ggtccggtat ctcggggag tgggcccgct    1080 ggaagatggc ctcgagcgca agcagaccct cgtaacagga ttcggccatc gcgttgagcg   1140
gtggcgcgtc ggcgccgtag cgggcgacgt agctgcccat caggtccatg gcacccgcgg   1200
tggccagtga actgaagtac gccgcggcga catagaggtt ttcggtggag ccggcgccgc   1260
tggccagcag catgttctcc tccatcagcg ggctgaaccg cgccatgcgg tcgtgcccgc   1320
cggcgcgcgc gaactcgcgg ttgaacaaca cggcgtcctg gccgacgagc agcatcaaca   1380
cggcctgcgc ccccgacgcg atggccttgc ggacaggtgc gcggaaatcg tcggtgccgt   1440 acggacgta gatctcccgt ctgagctcga ggtccagatc tcggcagtac gcgcgggcgg    1500
ccgcggcgga acggcgcggc cagatgtagt catcgccgac caggcaccag gaccggatgc   1560
cgaagtggtc gcgcagccag gcgagcgcgg gcgcgatctg gatctgcggt gtctcgcctg   1620
tgcagaacac gcccggtgtg cgttcaccgc cctcgtacaa cgaggtgtag acgtacggga   1680
tgcggtcgcg gaccaccggg gagatgcggt tgcgcacggc cgagatgtgc cagccggtca   1740
cggcgtcgag accgtgacct cgcaaccggt cggcgacggt ccgggcgacg tcgtcgccgg   1800
gcgctccgcc gtcgagcacc tcgatggtga ccttgcggcc ctgcaggccg cctcggtcgt   1860
tgacctcctt ggccgcgagc tcggccacgg cctcgcacga aggcgcgaag attcccgctg   1920
gcccttgaag cggaatcacc agcccgacgc ggaactcaac ctcgccgtcc tgcactccag   1980
atcaccgtcg atcccgtgta gtctgcgctt caaagctttc tagcagaaat aattcattct   2040
gaacagaccc cgccgtcgac acgaggagac acccaccatg gccgccggac agcagcgccg   2100
ccccaacctc ctgctgccgt tggtgcgtct gacccacctc gcggagtcgg cgatcgaacg   2160
cgtgctcgcg gactcgtcgc tcaagatcga ggactgcgc gtgctcgacg agttggccgg    2220
acggcgcacc gtgcccatga gcgatctcgc gcaggccacg ctgatcacgg gtccgactct   2280
caccagaacc gtcgatcgcc ttgtgtcgca agggatcatc taccgactg ccgatctgca    2340 tgaccgccgg cgggtgctcg tggcgttgac cccgcggggg cggacgctgc gcaaccgcct   2400
```

```
ggtggacgcg gtagccgagg ccgagtgtgc ggcttttgaa tcgtgcgggc tggacgtcga    2460
ccagttgcgc gaactcgtcg acaccacctc gaatttgact tcgtaaccac ccgcgcccgg    2520
cgcgggcgtt cacccttgac ttttattttc atctggatat atttcgggtg aatggaaagg    2580
ggtgaccatg ccgacctaca cattccgttg ttcccactgc ggtcccttcg atctcacctg    2640
cgcgatctcc gagcgcgatg cggcggcgac ctgtccggag tgccggacgc cggcgcgccg    2700
ggtcttcggt tcggtagggc tgacgacatt caccgcggga catcaccgcg cattcgacgc    2760
ggcgtccgcg agcgccgaaa gtcccacggt ggtgaagtcg attcccgcag gcgcggaccg    2820
cccgcgggcc ccgcgccgca atcccggtct accgagtctg ccgaggtact agcgacatgg    2880
gtggcgtcgg gctcttctac gtgggtgcgg tgctcatcat cgacgggctg atgctgctgg    2940
gccgcatcag cccacgaggc gcaacaccgc tgaacttctt cgtcggcgga ctgcaggtgg    3000
tgacgcctac ggtgctgatc ctgcagtccg gcggagacgc ggccgtgatc ttcgcggcct    3060
ccgggctcta cctgttcggc ttcacctacc tgtgggtggc catcaacaac gtgaccgact    3120
gggacggaga aggtctcgga tggttctcgc tgttcgtcgc gatcgccgca ctcggctact    3180
cgtggcacgc gttcaccgcc gaggccgacc cggcgttcgg ggtgatctgg ctgctgtggg    3240
cagtgctgtg gttcatgctg ttcctgctgc tcggcctggg gcacgacgca ctggggcccg    3300
ccgtcgggtt cgtcgcggtg gccgaaggcg tgatcaccgc cgccgtgccg gccttcctga    3360
tcgtgtcggg caactgggaa accggcccgc tccccgccgc ggtcatcgcc gtgatcggtt    3420
ttgccgcagt tgttctcgca taccccatcg ggcgccgtct cgcagcgccg tcagtcacca    3480
accctccacc ggccgcgctc gcggccacca cccgataaga gaaagggagt ccacatatgt    3540
aacggatcca gctgcagaat tcgaagctta tcgatgtcga cgtagttacg agatcggcgg    3600
ccgcatatga gtgtgcccac acaggacgga atgcaccggt tcgtcgacga ggacgtctac    3660
cacgctgacc ggggctcgct gtcggtatcc ggcgcgaagc tgctgttgcc gccgtcgtgt    3720
cccgcgaaat tccgctggga gatggacaac acccggaagc cgaaaaaggt ctgggacttc    3780
ggacatgtcg cgcacaaact ggtgctcggc aagggtgccg agttcgagat cctcgacccc    3840
gaggtgcacg gctgaaggc ggacggtacg ccgtcggaga agccgaccgc gacgggcatg    3900
tggcgcaagg ccgaggctga ggctcgcaaa cagggcaagg tgccgattca cgtcgacctg    3960
ttcacgaagg cgtacgacat ggccgaaaag gtgcgtcagc acccgacagc cggcccgatc    4020
ttcgccaatc ctgacggcga ggccgaggtc gcgctgtact acaccgaccc cgagaccggc    4080
gtgcggctgc gtgccggat cgactggctc actgacgata tcgatgatta caagacgtcg    4140
atgaccgcga accggccga gctgaaaacc aagttctaca agctcggcta tttcatgcag    4200
gcggcctggt acatcgatct actggtcgcc ctcgggctcg ccgagaaccc gcgattccgg    4260
ttcatcacgc aggagaaaga accgccctac gtcgtgactc cgatccagta cgacgacgag    4320
gcgatcgaag aggggcggcg ccgcaaccgc caggcgatcc ggctctacgc cgactgcatg    4380
gaatcgggca gtggcctga ctacagcgac gacgtggtca cgatcagcct gccctcgtgg    4440
gggctgccgc gaccgcagac cgtcggcgac gtcgtcaccg acagctatat ctacgacacc    4500
gacccgctcg aagaggccga cccgattgaa ggggattaca tctatggctg aaaatgctgt    4560
caccaagcag gattcgccca aggcacccga gacgatctcg caagtgctgc aggtgctcgt    4620
gccgcagctg gcgcgtgcag tgcccaaggg tatggacccc gaccgcatcg gcggatcgt    4680
gcaaaccgag atccgcaagt cgcgcaacgc gaaagctgct ggcatcgcta agcagtccct    4740
cgacgactgc acgcaagagt catttgccgg tgcgctgctg acctcggccg cgctcggtct    4800
```

-continued

```
cgagcccggt gtcaacggcg agtgctacct cgtgccctac cgcgacaccc ggcgcggcgt   4860
ggtcgagtgc cagctgatca tcggctacca gggcatcgtc aaactgttct ggcagcaccc   4920
gcgcgcctcc cggatcgacg cgcagtgggt cggcgcgaac gacgaattcc attacaccat   4980
gggcctcaat ccgacgctga aacacgtgaa ggccaagggt gatcggggta atccggtcta   5040
cttctacgcg atcgtcgagg tgaccggcgc tgagccgctg tgggacgtgt tcaccgccga   5100
cgagatcagg gaattgcgtc gcggcaaggt cggatcctcg ggcgacatca aggacccgca   5160
gcgctggatg gagcggaaga ccgcgctcaa acaggtgctg aagctggcac gaagacgac   5220 gcggctcgac gcggcgatcc gcgccgacga tcgcccgggc accgacctgt cacagtcgca   5280
ggcgctcgcg ctgccgtcga ccgtcaagcc gacggccgac tacatcgacg gcgagatcgc   5340
cgagccgcac gaggtcgata cgccaccgaa gtcgtcgcgc gcacaacgcg cgcagcgcgc   5400
caccgcgccg gcgcccgacg tgcagatggc caatcccgat cagctgaagc gcctcggcga   5460
gatccagaag gccgaaaagt acaacgacgc cgattggttc aagttcctcg ccgattcggc   5520
cggcgtcaaa gccacgcgcg ccgccgacct cacgttcgac gaggcgaagg ctgtcatcga   5580
catgttcgac gggcccaacg catgagcgcc cggcgaatt ccgacgcggt ggttgatctg   5640
caactagcgt acgatcgact gccaggcatc aaataaaacg aaaggctcag tcgaaagact   5700 gggccttttcg ttttatgcca tcatggccgc ggtgatcagc tagccacctg acgtcnggg   5760 gggggaaag ccacgttgtg tctcaaaatc tctgatgtta cattgcacaa gataaaaata   5820
tatcatcatg aacaataaaa ctgtctgctt acataaacag taatacaagg ggtgttatga   5880
gccatattca acgggaaacg tcttgctcga ggccgcgatt aaattccaac atggatgctg   5940
atttatatgg gtataaatgg gctcgcgata atgtcgggca atcaggtgcg acaatctatc   6000
gcttgtatgg gaagcccat cgccagagt tgtttctgaa acatggcaaa ggtagcgttg   6060
ccaatgatgt tacagatgag atggtcagac taaactggct gacggaattt atgcctcttc   6120
cgaccatcaa gcattttatc cgtactcctg atgatgcatg gttactcacc actgcgatcc   6180
ccgggaaaac agcattccag gtattagaag aatatcctga ttcaggtgaa atattgttg   6240 atgcgctggc agtgttcctg cgccggttgc attcgattcc tgtttgtaat tgtccttta   6300 acagcgatcg cgtatttcgt ctcgctcagg cgcaatcacg aatgaataac ggtttggttg   6360
atgcgagtga ttttgatgac gagcgtaatg gctggcctgt tgaacaagtc tggaaagaaa   6420
tgcataatct tttgccattc tcaccggatt cagtcgtcac tcatggtgat ttctcacttg   6480
ataaccttat ttttgacgag gggaaattaa taggttgtat tgatgttgga cgagtcggaa   6540
tcgcagaccg ataccaggat cttgccatcc tatggaactg cctcggtgag ttttctcctt   6600
cattacagaa acggcttttt caaaatatg gtattgataa tcctgatatg aataaattgc   6660
agtttcattt gatgctcgat gagttttct aatcagaatt ggttaattgg ttgtaacact   6720
ggcagagcat tacgctgact tgacgggacg gcggctttgt tgaataaatc gaacttttgc   6780
tgagttgaag gatcagatca cgcatcttcc cgacaacgca gaccgttccg tggcaaagca   6840
aaagttcaaa atcaccaact ggtccaccta acaaagct ctcaccaacc gtggctccct   6900
cactttctgg ctggatgatg gggcgattca ggcctggtat gagtcagcaa caccttcttc   6960
acgaggcaga cctcactagt tccatgagcg tcagacccg tagaaaagat caaaggatct   7020
tcttgagatc ctttttttct gcgcgtaatc tgctgcttgc aaacaaaaaa accaccgcta   7080
ccagcggtgg tttgtttgcc ggatcaagag ctaccaactc ttttccgaa ggtaactggc   7140
```

-continued

```
ttcagcagag cgcagatacc aaatactgtc cttctagtgt agccgtagtt aggccaccac   7200
ttcaagaact ctgtagcacc gcctacatac ctcgctctgc taatcctgtt accagtggct   7260
gctgccagtg gcgataagtc gtgtcttacc gggttggact caagacgata gttaccggat   7320
aaggcgcagc ggtcgggctg aacgggggt cgtgcacac agcccagctt ggagcgaacg    7380
acctacaccg aactgagata cctacagcgt gagctatgag aaagcgccac gcttcccgag   7440
gggagaaagg cggacaggta tccggtaagc ggcagggtcg aacaggaga gcgcacgagg    7500 gagcttccag ggggaaacgc ctggtatctt tatagtcctg tcgggtttcg ccacctctga   7560
cttgagcgtc gattttttgtg atgctcgtca gggggggcgga gcctatggaa aaacgccagc 7620
aacgcggcct ttttacggtt cctggccttt tgctggcctt ttgctcacat gttctttcct   7680
gcgttatccc ctgattctgt ggataaccgt attaccgcct ttgagtgagc tgataccgct   7740
cgccgcagcc gaacgaccga cgcaacgcg tgagcccacc agctccgtaa gttcgggcgc    7800
tgtgtggctc gtaccgcgc attcaggcg caggggggtct aacgggtcta aggcggcgtg    7860
tacggccgcc acagcggctc tcagcggccc ggaaacgtcc tcgaaacgac gcatgtgttc   7920
ctcctggttg gtacaggtgg ttgggggtgc tcggctgtcg ctggtgttcc accaccaggg   7980
ctcgacggga gagcggggga gtgtgcagtt gtggggtggc ccctcagcga aatatctgac   8040
ttggagctcg tgtcggacca tacaccggtg attaatcgtg gtctactacc aagcgtgagc   8100
cacgtcgccg acgaatttga gcagctctgg ctgccgtact ggccgctggc aagcgacgat   8160
ctgctcgagg ggatctaccg ccaaagccgc gcgtcggccc taggccgccg gtacatcgag   8220
gcgaacccaa cagcgctggc aaacctgctg gtcgtggacg tagaccatcc agacgcagcg   8280
ctccgagcgc tcagcgcccg ggggtcccat ccgctgccca acgcgatcgt gggcaatcgc   8340
gccaacggcc acgcacacgc agtgtgggca ctcaacgccc ctgttccacg caccgaatac   8400
gcgcggcgta agccgctcgc atacatggcg gcgtgcgccg aaggccttcg gcgcgccgtc   8460
gatggcgacc gcagttactc aggcctcatg accaaaaaacc ccggccacat cgcctgggaa   8520
acggaatggc tccactcaga tctctacaca ctcagccaca tcgaggccga gctcggcgcg   8580
aacatgccac cgccgcgctg gcgtcagcag accacgtaca aagcggctcc gacgccgcta   8640
gggcggaatt gcgcactgtt cgattccgtc aggttgtggg cctatcgtcc cgccctcatg   8700
cggatctacc tgccgacccg gaacgtggac ggactcggcc gcgcgatcta tgccgagtgc   8760
cacgcgcgaa acgccgaatt tccgtgcaac gacgtgtgtc c                     8801
```

<210> SEQ ID NO 33
<211> LENGTH: 2145
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

```
ggggaattcg aggacatcag ccggctgccg gatacctgct tcgggatcac cgcggccgac    60
gacgtcgggt atgcgatcgg acagtcactg gttcttgaga tgggcgggga gccgttttgt   120
gtgcgcgaaa cgcccgcat cctctaccac gcggcgctgg cccatgcgag caaccacatc   180
gtcaccgtgc tggccgatgc gctcgaggcg ttgcgggccg ccctgagcgg ggggaactg    240 ctcggccaac aaaccgtcga cgaccagccg ggcgggatcg tggagcgcat cgtcgggccg   300
ctggccagag cggcgctgga gaacacgctg cagcggggac aggccgcgct caccggaccg   360
```

```
gtcgcccgcg gcgatgcggc agcggtcgcg gatcatctgg cggccctcgc ggacgtcgac    420
gcagcgctgg cccaggcata ccggataaac gcgctgcgga ccgcgcagcg cgcacacgcc    480
cccgcggatg tcgtcgaggt tttgacggcc ttgacataat gtcgcttatc ggcttaatcg    540
atctagaccg gccgtgcgga attaagccgg cccgtaccct gtgaatagag gtccgctgtg    600
acacaagaat ccctgttact tctcgaccgt attgattcgg atgattccta cgcgagcctg    660
cggaacgacc aggagttctg ggagccgctg gcccgccgag ccctggagga gctcgggctg    720
ccggtgccgc cggtgctgcg ggtgcccggc gagagcacca accccgtact ggtcggcgag    780
cccggcccgg tgatcaagct gttcggcgag cactggtgcg gtccggagag cctcgcgtcg    840
gagtcggagg cgtacgcggt cctggcggac gccccggttc cggtgccccg cctcctcggc    900
cgcggcgagc tgcggcccgg caccggagcc tggccgtggc cctacctggt gatgagccgg    960
atgaccggca ccacctggcg gtccgcgatg gacggcacga ccgaccggaa cgcgctgctc   1020
gccctggccc gcgaactcgg ccgggtgctc ggacggctgc acagggtgcc gctgaccggg   1080
aacaccgtgc tcaccccca ttccgaggtc ttccggaaac tgctgcggga acgccgcgcg   1140
gcgaccgtcg aggaccaccg cgggtggggc tacctctcgc cccggctgct ggaccgcctg   1200
gaggactggc tgccggacgt ggacacgctg ctggccggcc gcgaacccg gttcgtccac    1260 ggcgacctgc acgggaccaa catcttcgtg gacctggccg cgaccgaggt caccgggatc   1320
gtcgacttca ccgacgtcta tgcgggagac tcccgctaca gctggtgca actgcatctc   1380 aacgccttcc ggggcgaccg cgagatcctg gccgcgctgc tcgacggggc gcagtggaag   1440
cggaccgagg acttcgcccg cgaactgctc gccttcacct tcctgcacga cttcgaggtg   1500
ttcgaggaga ccccgctgga tctctccggc ttcaccgatc cggaggaact ggcgcagttc   1560
ctctgggggc gccggacac cgccccggc gcctgatcta acccgggac ttgacataat   1620 gtcgcttatc ggcttaccgt gctgctggcg attgacgtcc gcaacaccca caccgttgtg   1680
ggcctgctgt ccggaatgaa agagcacgca aaggtcgtgc agcagtggcg gatacgcacc   1740
gaatccgaag tcaccgccga cgaactggca ctgacgatcg acgggctgat cggcgaggat   1800
tccgagcggc tcaccggtac cgccgccttg tccacggtcc cgtccgtgct gcacgaggtg   1860
cggataatgc tcgaccagta ctggccgtcg gtgccgcacg tgctgatcga gcccggagta   1920
cgcaccggga tccctttgct cgtcgacaac ccgaaggaag tgggcgcaga ccgcatcgtg   1980
aactgtttgg ccgcctatga ccggttccgg aaggccgcca tcgtcgttga ctttggatcc   2040
tcgatctgtg ttgatgttgt atcggccaag ggtgaatttc ttggcggcgc catcgcgccc   2100
ggggtgcagg tgtcttccga tgccgcggcg gcccgcaagc ttggg              2145

<210> SEQ ID NO 34
<211> LENGTH: 1128
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
acttgacata atgtcgctta tcggcttaat cgatctagac cggccgtgcg gaattaagcc     60
ggcccgtacc ctgtgaatag aggtccgctg tgacacaaga atccctgtta cttctcgacc    120
gtattgattc ggatgattcc tacgcgagcc tgcggaacga ccaggagttc tgggagccgc    180
tggcccgccg agccctggag gagctcgggc tgccggtgcc gccggtgctg cgggtgcccg    240
```

| | |
|---|---|
| gcgagagcac caaccccgta ctggtcggcg agcccggccc ggtgatcaag ctgttcggcg | 300 |
| agcactggtg cggtccggag agcctcgcgt cggagtcgga ggcgtacgcg gtcctggcgg | 360 |
| acgccccggt tccggtgccc cgcctcctcg gccgcggcga gctgcggccc ggcaccggag | 420 |
| cctggccgtg gccctacctg gtgatgagcc ggatgaccgg caccacctgg cggtccgcga | 480 |
| tggacggcac gaccgaccgg aacgcgctgc tcgccctggc ccgcgaactc ggccgggtgc | 540 |
| tcggacggct gcacagggtg ccgctgaccg gaacaccgt gctcaccccc cattccgagg | 600 |
| tcttcccgga actgctgcgg gaacgccgcg cggcgaccgt cgaggaccac cgcgggtggg | 660 |
| gctacctctc gccccggctg ctggaccgcc tggaggactg gctgccggac gtggacacgc | 720 |
| tgctggccgg ccgcgaaccc cggttcgtcc acggcgacct gcacgggacc aacatcttcg | 780 |
| tggacctggc cgcgaccgag gtcaccggga tcgtcgactt caccgacgtc tatgcgggag | 840 |
| actcccgcta cagcctggtg caactgcatc tcaacgcctt ccggggcgac cgcgagatcc | 900 |
| tggccgcgct gctcgacggg gcgcagtgga agcggaccga ggacttcgcc cgcgaactgc | 960 |
| tcgccttcac cttcctgcac gacttcgagg tgttcgagga gaccccgctg gatctctccg | 1020 |
| gcttcaccga tccggaggaa ctggcgcagt tcctctgggg gccgccggac accgcccccg | 1080 |
| gcgcctgatc tagacccggg acttgacata atgtcgctta tcggctta | 1128 |

<210> SEQ ID NO 35
<211> LENGTH: 3879
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 35

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcaggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt cgagctcggt acctcgcgaa | 420 |
| tgcatctaga tatcggatcc cgggatgcat cagatctctc gagacttgac ataatgtcgc | 480 |
| ttatcggctt aatcgatcta gaccggccgt gcggaattaa gccggccgt accctgtgaa | 540 |
| tagaggtccg ctgtgacaca agaatccctg ttacttctcg accgtattga ttcggatgat | 600 |
| tcctacgcga gcctgcggaa cgaccaggag ttctgggagc cgctggcccg ccgagccctg | 660 |
| gaggagctcg ggctgccggt gccgccggtg ctgcgggtgc ccggcgagag caccaaccc | 720 |
| gtactggtcg gcgagcccgg cccggtgatc aagctgttcg gcgagcactg gtgcggtccg | 780 |
| gagagcctcg cgtcggagtc ggaggcgtac gcggtcctgg cggacgcccc ggttccggtg | 840 |
| ccccgcctcc tcggccgcgg cgagctgcgg cccggcaccg gagcctggcc gtggccctac | 900 |
| ctggtgatga gccggatgac cggcaccacc tggcggtccg cgatggacgg cacgaccgac | 960 |
| cggaacgcgc tgctcgccct ggcccgcgaa ctcggccggg tgctcggacg gctgcacagg | 1020 |
| gtgccgctga ccgggaacac cgtgctcacc ccccattccg aggtcttccc ggaactgctg | 1080 |
| cgggaacgcc gcgcggcgac cgtcgaggac caccgcgggt ggggctacct ctcgccccgg | 1140 |

```
ctgctggacc gcctggagga ctggctgccg gacgtggaca cgctgctggc cggccgcgaa    1200
ccccggttcg tccacggcga cctgcacggg accaacatct tcgtggacct ggccgcgacc    1260
gaggtcaccg ggatcgtcga cttcaccgac gtctatgcgg gagactcccg ctacagcctg    1320
gtgcaactgc atctcaacgc cttccggggc gaccgcgaga tcctgccgcg ctgctcgac     1380
ggggcgcagt ggaagcggac cgaggacttc gcccgcgaac tgctcgcctt caccttcctg    1440
cacgacttcg aggtgttcga ggagacccgc ctggatctct ccggcttcac cgatccggag    1500
gaactggcgc agttcctctg ggggccgccg gacaccgccc ccggcgcctg atctagaccc    1560
gggacttgac ataatgtcgc ttatcggctt actcgagatt atccatggcg gccgcactag    1620
tctgcagagg cctgcatgca agcttggcgt aatcatggtc atagctgttt cctgtgtgaa    1680
attgttatcc gctcacaatt ccacacaaca tacgagccgg aagcataaag tgtaaagcct    1740
ggggtgccta atgagtgagc taactcacat taattgcgtt gcgctcactg cccgctttcc    1800
agtcgggaaa cctgtcgtgc cagctgcatt aatgaatcgg ccaacgcgcg gggagaggcg    1860
gtttgcgtat tgggcgctct tccgcttcct cgctcactga ctcgctgcgc tcggtcgttc    1920
ggctgcggcg agcggtatca gctcactcaa aggcggtaat acggttatcc acagaatcag    1980
gggataacgc aggaaagaac atgtgagcaa aaggccagca aaaggccagg aaccgtaaaa    2040
aggccgcgtt gctggcgttt ttccataggc tccgcccccc tgacgagcat cacaaaaatc    2100
gacgctcaag tcagaggtgg cgaaacccga caggactata agataccagg cgtttccccc    2160
ctggaagctc cctcgtgcgc tctcctgttc cgaccctgcc gcttaccgga tacctgtccg    2220
cctttctccc ttcgggaagc gtggcgcttt ctcatagctc acgctgtagg tatctcagtt    2280
cggtgtaggt cgttcgctcc aagctgggct gtgtgcacga accccccgtt cagcccgacc    2340
gctgcgcctt atccggtaac tatcgtcttg agtccaaccc ggtaagacac gacttatcgc    2400
cactggcagc agccactggt aacaggatta gcagagcgag gtatgtaggc ggtgctacag    2460
agttcttgaa gtggtggcct aactacggct acactagaag aacagtattt ggtatctgcg    2520
ctctgctgaa gccagttacc ttcggaaaaa gagttggtag ctcttgatcc ggcaaacaaa    2580
ccaccgctgg tagcggtggt ttttttgttt gcaagcagca gattacgcgc agaaaaaaag    2640
gatctcaaga agatcctttg atcttttcta cggggtctga cgctcagtgg aacgaaaact    2700
cacgttaagg gattttggtc atgagattat caaaaaggat cttcacctag atccttttaa    2760
attaaaaatg aagttttaaa tcaatctaaa gtatatatga gtaaacttgg tctgacagtt    2820
accaatgctt aatcagtgag gcacctatct cagcgatctg tctatttcgt tcatccatag    2880
ttgcctgact ccccgtcgtg tagataacta cgatacggga gggcttacca tctggcccca    2940
gtgctgcaat gataccgcga gacccacgct caccggctcc agatttatca gcaataaacc    3000
agccagccgg aagggccgag cgcagaagtg gtcctgcaac tttatccgcc tccatccagt    3060
ctattaattg ttgccgggaa gctagagtaa gtagttcgcc agttaatagt ttgcgcaacg    3120
ttgttgccat tgctacaggc atcgtggtgt cacgctcgtc gtttggtatg gcttcattca    3180
gctccggttc ccaacgatca aggcgagtta catgatcccc catgttgtgc aaaaaagcgg    3240
ttagctcctt cggtcctccg atcgttgtca gaagtaagtt ggccgcagtg ttatcactca    3300
tggttatggc agcactgcat aattctctta ctgtcatgcc atccgtaaga tgcttttctg    3360
tgactggtga gtactcaacc aagtcattct gagaatagtg tatgcggcga ccgagttgct    3420
cttgcccggc gtcaatacgg gataataccg cgccacatag cagaacttta aaagtgctca    3480
tcattggaaa acgttcttcg gggcgaaaac tctcaaggat cttaccgctg ttgagatcca    3540
```

| | |
|---|---|
| gttcgatgta acccactcgt gcacccaact gatcttcagc atcttttact ttcaccagcg | 3600 |
| tttctgggtg agcaaaaaca ggaaggcaaa atgccgcaaa aaagggaata agggcgacac | 3660 |
| ggaaatgttg aatactcata ctcttccttt ttcaatatta ttgaagcatt tatcagggtt | 3720 |
| attgtctcat gagcggatac atatttgaat gtatttagaa aaataaacaa ataggggttc | 3780 |
| cgcgcacatt tccccgaaaa gtgccacctg acgtctaaga aaccattatt atcatgacat | 3840 |
| taacctataa aaataggcgt atcacgaggc cctttcgtc | 3879 |

<210> SEQ ID NO 36
<211> LENGTH: 4891
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt cgagctcggt acctcgcgaa | 420 |
| tgcatctaga tatcggatcc cgggatgcat cagatctctc gaggaattcg aggacatcag | 480 |
| ccggctgccg gataccgtgc tcgggatcac gcggccgac gacgtcgggt atgcgatcgg | 540 |
| acagtcactg gttcttgaga tgggcgggga gccgttttgt gtgcgcgaag acgcccgcat | 600 |
| cctctaccac gcgcgctgg cccatgcgag caaccacatc gtcaccgtgc tggccgatgc | 660 |
| gctcgaggcg ttgcgggccg ccctgagcgg gggggaactg ctcggccaac aaaccgtcga | 720 |
| cgaccagccg ggcgggatcg tggagcgcat cgtcgggccg ctggccagag cggcgctgga | 780 |
| gaacacgctg cagcggggac aggccgcgct caccggaccg gtcgcccgcg gcgatgcggc | 840 |
| agcggtcgcg gatcatctgg cggccctcgc ggacgtcgac gcagcgctgg cccaggcata | 900 |
| ccggataaac gcgctgcgga ccgcgcagcg cgcacacgcc cccgcggatg tcgtcgaggt | 960 |
| tttgacggca cttgacataa tgtcgcttat cggcttaatc gatctagacc ggccgtgcgg | 1020 |
| aattaagccg gcccgtaccc tgtgaataga ggtccgctgt gacacaagaa tccctgttac | 1080 |
| ttctcgaccg tattgattcg gatgattcct acgcgagcct gcggaacgac caggagttct | 1140 |
| gggagccgct ggcccgccga gccctggagg agctcgggct gccggtgccg ccggtgctgc | 1200 |
| gggtgcccgg cgagagcacc aaccccgtac tggtcggcga gcccggcccg gtgatcaagc | 1260 |
| tgttcggcga gcactggtgc ggtccggaga gcctcgcgtc ggagtcggag gcgtacgcgg | 1320 |
| tcctggcgga cgccccggtt ccggtgcccc gcctcctcgg ccgcggcgag ctgcggcccg | 1380 |
| gcaccggagc ctggccgtgg ccctacctgg tgatgagccg gatgaccggc accacctggc | 1440 |
| ggtccgcgat ggacggcacg accgaccgga acgcgctgct cgccctggcc cgcgaactcg | 1500 |
| gccgggtgct cggacggctg cacagggtgc cgctgaccgg gaacaccgtg ctcacccccc | 1560 |
| attccgaggt cttcccggaa ctgctgcggg aacgccgcgc ggcgaccgtc gaggaccacc | 1620 |
| gcgggtgggg ctacctctcg ccccggctgc tggaccgcct ggaggactgg ctgccggacg | 1680 |

```
tggacacgct gctggccggc cgcgaacccc ggttcgtcca cggcgacctg cacgggacca    1740
acatcttcgt ggacctggcc gcgaccgagg tcaccgggat cgtcgacttc accgacgtct    1800
atgcgggaga ctcccgctac agcctggtgc aactgcatct caacgccttc cggggcgacc    1860
gcgagatcct ggccgcgctg ctcgacgggg cgcagtggaa gcggaccgag gacttcgccc    1920
gcgaactgct cgccttcacc ttcctgcacg acttcgaggt gttcgaggag accccgctgg    1980
atctctccgg cttcaccgat ccggaggaac tggcgcagtt cctctggggg ccgccggaca    2040
ccgcccccgg cgcctgatct agacccggga cttgacataa tgtcgcttat cggcttaccg    2100
tgctgctggc gattgacgtc cgcaacaccc acaccgttgt gggcctgctg tccggaatga    2160
aagagcacgc aaaggtcgtg cagcagtggc ggatacgcac cgaatccgaa gtcaccgccg    2220
acgaactggc actgacgatc gacgggctga tcggcgagga ttccgagcgg ctcaccggta    2280
ccgccgcctt gtccacggtc ccgtccgtgc tgcacgaggt gcggataatg ctcgaccagt    2340
actggccgtc ggtgccgcac gtgctgatcg agcccggagt acgcaccggg atcccctttgc    2400
tcgtcgacaa cccgaaggaa gtgggcgcag accgcatcgt gaactgtttg gccgcctatg    2460
accggttccg gaaggccgcc atcgtcgttg actttggatc ctcgatctgt gttgatgttg    2520
tatcggccaa gggtgaattt cttggcggcg ccatcgcgcc cggggtgcag gtgtcttccg    2580
atgccgcggc ggcccgcaag cttctcgaga ttatccatgg cggccgcact agtctgcaga    2640
ggcctgcatg caagcttggc gtaatcatgg tcatagctgt ttcctgtgtg aaattgttat    2700
ccgctcacaa ttccacacaa catacgagcc ggaagcataa agtgtaaagc ctggggtgcc    2760
taatgagtga gctaactcac attaattgcg ttgcgctcac tgcccgcttt ccagtcggga    2820
aacctgtcgt gccagctgca ttaatgaatc ggccaacgcg cggggagagg cggtttgcgt    2880
attgggcgct cttccgcttc ctcgctcact gactcgctgc gctcggtcgt tcggctgcgg    2940
cgagcggtat cagctcactc aaaggcggta atacggttat ccacagaatc aggggataac    3000
gcaggaaaga acatgtgagc aaaaggccag caaaaggcca ggaaccgtaa aaaggccgcg    3060
ttgctggcgt ttttccatag gctccgcccc cctgacgagc atcacaaaaa tcgacgctca    3120
agtcagaggt ggcgaaaccc gacaggacta taaagatacc aggcgtttcc ccctggaagc    3180
tccctcgtgc gctctcctgt tccgaccctg ccgcttaccg gatacctgtc cgcctttctc    3240
ccttcgggaa gcgtggcgct ttctcatagc tcacgctgta ggtatctcag ttcggtgtag    3300
gtcgttcgct ccaagctggg ctgtgtgcac gaaccccccg ttcagcccga ccgctgcgcc    3360
ttatccggta actatcgtct tgagtccaac ccggtaagac acgacttatc gccactggca    3420
gcagccactg gtaacaggat tagcagagcg aggtatgtag gcggtgctac agagttcttg    3480
aagtggtggc ctaactacgg ctacactaga agaacagtat ttggtatctg cgctctgctg    3540
aagccagtta ccttcggaaa aagagttggt agctcttgat ccggcaaaca accaccgct    3600
ggtagcggtg ttttttttgt ttgcaagcag cagattacgc gcagaaaaaa aggatctcaa    3660
gaagatcctt tgatctttc tacggggtct gacgctcagt ggaacgaaaa ctcacgttaa    3720
gggattttgg tcatgagatt atcaaaaagg atcttcacct agatcctttt aaattaaaaa    3780
tgaagtttta aatcaatcta agtatatat gagtaaactt ggtctgacag ttaccaatgc    3840
ttaatcagtg aggcacctat ctcagcgatc tgtctatttc gttcatccat agttgcctga    3900
ctccccgtcg tgtagataac tacgatacgg gagggcttac catctggccc cagtgctgca    3960
atgataccgc gagacccacg ctcaccggct ccagatttat cagcaataaa ccagccagcc    4020
```

```
ggaagggccg agcgcagaag tggtcctgca actttatccg cctccatcca gtctattaat   4080
tgttgccggg aagctagagt aagtagttcg ccagttaata gtttgcgcaa cgttgttgcc   4140
attgctacag gcatcgtggt gtcacgctcg tcgtttggta tggcttcatt cagctccggt   4200
tcccaacgat caaggcgagt tacatgatcc cccatgttgt gcaaaaaagc ggttagctcc   4260
ttcggtcctc cgatcgttgt cagaagtaag ttggccgcag tgttatcact catggttatg   4320
gcagcactgc ataattctct tactgtcatg ccatccgtaa gatgcttttc tgtgactggt   4380
gagtactcaa ccaagtcatt ctgagaatag tgtatgcggc gaccgagttg ctcttgcccg   4440
gcgtcaatac gggataatac cgcgccacat agcagaactt taaaagtgct catcattgga   4500
aaacgttctt cggggcgaaa actctcaagg atcttaccgc tgttgagatc cagttcgatg   4560
taacccactc gtgcacccaa ctgatcttca gcatctttta ctttcaccag cgtttctggg   4620
tgagcaaaaa caggaaggca aaatgccgca aaaaagggaa taagggcgac acggaaatgt   4680
tgaatactca tactcttcct ttttcaatat tattgaagca tttatcaggg ttattgtctc   4740
atgagcggat acatatttga atgtatttag aaaaataaac aaataggggt tccgcgcaca   4800
tttccccgaa aagtgccacc tgacgtctaa gaaaccatta ttatcatgac attaacctat   4860
aaaaataggc gtatcacgag gccctttcgt c                                 4891
```

<210> SEQ ID NO 37
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ggggactagt aacaccccctt gtattactg                                   29

<210> SEQ ID NO 38
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ggggtgatca tcagaattgg ttaattggtt g                                 31

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ggggactagt acgaccagcc g                                            21

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40

```
ggggtgatca gctatcccac accg                                          24
```

<210> SEQ ID NO 41
<211> LENGTH: 935
<212> TYPE: DNA
<213> ORGANISM: Mycobacterium bovis

<400> SEQUENCE: 41

```
atgacgattc ctgcgttcca tcccggtgaa ctcaatgt gtatttcgtc tcgctcaggc                                        20

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gcgatggtgg cttctccctc g                                      21

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ccatcttgca cagctcgcgt ag                                     22

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
taaggccaac cgtgaaaaga tg                                     22

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ctggatggct acgtacatgg ct                                     22

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gaccctcaca ctcagatcat c                                      21

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gctgctcctc cacttggt                                                 18

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ccacagccct ctccatcaac                                               20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ctccgtcatc tccataggga                                               20

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ctgcaagaga cttccatcca g                                             21

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
caggtctgtt gggagtgg                                                 18

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
agcggctgac tgaactcaga ttgt                                          24

<210> SEQ ID NO 56
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gtcacagttt tcagctgtat aggg                                          24

<210> SEQ ID NO 57
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
ggagagtgtg gatcccaa                                              18

<210> SEQ ID NO 58
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gtggagtttg agtctgcag                                             19

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ggctcagcca gatgcagtta ac                                         22

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gatcctcttg tagctctcca gc                                         22

<210> SEQ ID NO 61
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gaaagacgtt tatgttgtag agg                                        23

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gactccatgt ctctggtctg                                            20

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ggagttcgag gaaccctagt g                                      21

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gggatttgta gtggatcgtg c                                      21

<210> SEQ ID NO 65
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gtgggactca agggatccct ctc                                    23

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gcttccctat ggccctcatt c                                      21

<210> SEQ ID NO 67
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
gttctcagcc caacaataca ag                                     22

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ggaacattct gtgctgtccc                                        20

```
<210> SEQ ID NO 69
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ctctgatgca ggtccctatg gtg                                              23

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ggcagagggt gacggatgta g                                                21

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
ctcgcttcgg cagcacatat ac                                               22

<210> SEQ ID NO 72
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
aatatggaac gcttcacgaa tttg                                             24

<210> SEQ ID NO 73
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
caacttgctt ggattcctac aaag                                             24

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
tattcaagcc tcccattcaa ttg                                              23

<210> SEQ ID NO 75
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
ggtacatcct cgacggcatc t                                              21

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gtgcctcttt gctgctttca c                                              21

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
caggattcat gtgccagggt                                                20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
ccaaagacca catgcttgcc                                                20

<210> SEQ ID NO 79
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gagtcttcac actcctggc                                                 19

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
gtccttcagg catgagacag                                                20

<210> SEQ ID NO 81
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
gcgttcctgc tgtgcttctc                                                    20

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
ccattcagct gcctcaggag c                                                  21

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
cgtcttggtt ttgcagctct                                                    20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
cgtccttttg ccagttcctc                                                    20

<210> SEQ ID NO 85
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
ggtgagggga ctggactttt ag                                                 22

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
ttgttgggct gggaatagca                                                    20

<210> SEQ ID NO 87
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 87
tccacctccc tttacccagt                                                 20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
agagctagga gagccgtcat                                                 20

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
caggtctctg tcacgcttct g                                               21

<210> SEQ ID NO 90
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
gccagtgaat gagtagcagc ag                                              22

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
acaagcgcac cctctgttac                                                 20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
ggtcaggaaa atgacacccg                                                 20

<210> SEQ ID NO 93
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 93
gacttcacca tggaacccgt                                                 20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
ggagactgcc cattctcgac                                                 20

<210> SEQ ID NO 95
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
cgtccctctc atacactgg                                                  19

<210> SEQ ID NO 96
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
catgctttcc gtgctcatg                                                  19

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
tgacgtcact ggagttgtcc                                                 20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
cctcgacgtt tgggactgat                                                 20

<210> SEQ ID NO 99
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 99
cctctggata cagctgcgac                                              20

<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
tgccgggtgg ttcaattttt c                                            21

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
tactagcggt tttacgggcg                                              20

<210> SEQ ID NO 102
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
tcgaacagga ggagcagaga gcga                                         24

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
cggtgaagaa tggatgacct                                              20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
aaacgagacc cttgcacaac                                              20

<210> SEQ ID NO 105
<211> LENGTH: 24
<212> TYPE: DNA
<213> ORGANISM: Artificial Sequence
<220> FEATURE:
<223> OTHER INFORMATION: Description of Artificial Sequence: Synthetic
```

-continued

```
      primer

<400> SEQUENCE: 105
atcagtcagt ggcccagaag accc                                              24

<210> SEQ ID NO 106
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
ccacgtcccg gatcatgctt cag                                               23

<210> SEQ ID NO 107
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
gggcatcata tgcacgctgt gactcgtc                                          28
```

RECOMBINANT THERAPEUTIC INTERVENTIONS FOR CANCER

CROSS-REFERENCE TO RELATED APPLICATIONS

This application is a 35 USC § 371 National Stage application of International Application No. PCT/US2021/018007 filed Feb. 12, 2021, now pending; which is a continuation application of U.S. application Ser. No. 16/790,161 filed Feb. 13, 2020, now abandoned. The disclosure of each of the prior applications is considered part of and is incorporated by reference in the disclosure of this application.

STATEMENT OF GOVERNMENTAL INTEREST

This invention was made with government support under grant nos. AI036973, AI037856, awarded by the National Institutes of Health. The government has certain rights in the invention.

INCORPORATION OF SEQUENCE LISTING

The material in the accompanying sequence listing is hereby incorporated by reference into this application. The accompanying sequence listing text file, named JHU4280-3_ST25.txt, was created on Jul. 8, 2022 and is 154 kB in size. The file can be accessed using Microsoft Word on a computer that uses Windows OS.

BACKGROUND OF THE INVENTION

Urothelial cancer of the bladder is the most common type of bladder cancer (BC) in North America, South America, Europe and Asia. Non-Muscle Invasive Bladder Cancer (NMIBC) is associated with a high recurrence rate, frequent intravesical treatments, risk of progression to advanced stages and the highest lifetime treatment among all cancers. Intravesical BCG (bacillus Calmette Guerin) instillation has been the standard of care treatment for NMIBC for 30 years. It is effective in 60-70% patients. BCG has shown to be a very effective vehicle for delivery of antigens. Many studies corroborating an underlying immune response skewed towards a Type I interferon and Th1 induced mediated immune response show promise. Efforts to generate recombinant BCG (rBCG) strains for NMIBC have focused on developing strains that augment these anti-tumor immune responses. To date such efforts have not yielded demonstrable improvement over traditional BCG.

SUMMARY OF THE INVENTION

One embodiment of the present invention provides a vector including a nucleic acid sequence expressing a protein or functional part thereof that makes a STING agonist including c-di-AMP (also known as 3'-5' c-di-AMP); c-di-GMP (also known as 3'-5' c-di-GMP); 3'-3'cGAMP (also known as 3'-5',3'-5'cGAMP, the product of the *Vibrio cholerae* DncV protein); 2'-3'cGAMP (also known as 2'-5',3'-5' cGAMP, the product of the human cGAS protein) and a combination thereof, as examples. Some vectors of the present invention include a nucleic acid sequence selected from the group consisting of a first nucleic acid sequence encoding a Rv1354c protein, or a functional part thereof; a second nucleic acid sequence encoding a 3'-3' cyclic GMP-AMP synthase (DncV) protein, or a functional part thereof; a third nucleic acid sequence encoding a 2'-3'cyclic GMP-AMP synthase (cGAS) protein, or a functional part thereof; a fourth nucleic acid sequence encoding a DNA integrity scanning (disA) protein, or a functional part thereof and a combination thereof. Each of these nucleic acid sequences express proteins that make one or more of the STING agonist as described in the definition section of the specification. Some vectors of the present invention include in addition to one or more of the sequences listed above a fifth nucleic acid sequence encoding a PanC protein and a PanD protein or functional part thereof. Vectors including a nucleic acid sequence encoding a PanC protein and a PanD protein or functional part thereof are typically free of an antibiotic resistance gene. Suitable vectors used in the present invention may include vectors that replicate episomally in multiple copies, or vectors that integrate into a bacterial chromosome in single copy or are otherwise present in the bacterial cell. A vector of the present invention may stably integrate into a bacterial genome or it may stably replicate as an episomal plasmid. Suitable third nucleic acid sequences include those that overexpress the cyclase domains of the cyclic GMP-AMP synthase (cGAS) protein. Other suitable third nucleic acid sequence may express a cyclic GMP-AMP synthase (cGAS) protein having a regulatory DNA recognition capability that is non-functional. Vectors of the present invention may also include nucleic acid sequences that encode sequences or proteins that knock out the expression of PDE genes of a strain of Mycobacteria used in the present invention.

Another embodiment of the present invention provides a strain of Mycobacteria including any one of the vectors of the present invention including a vector comprising a protein or functional part thereof that makes a STING agonist. As mentioned above, examples of STING agonist include c-di-AMP (also known as 3'-5' c-di-AMP); c-di-GMP (also known as 3'-5' c-di-GMP); 3'-3'cGAMP (also known as 3'-5',3'-5'cGAMP, the product of the Vibrio cholerae DncV protein); 2'-3'cGAMP (also known as 2'-5',3'-5' cGAMP, the product of the human cGAS protein) and a combination thereof, as examples. Examples of suitable nucleic acid sequence includes a nucleic acid sequence selected from the group consisting of a first nucleic acid sequence encoding a Rv1354c protein, or a functional part thereof; a second nucleic acid sequence encoding a 3'-3' cyclic GMP-AMP synthase (DncV) protein, or a functional part thereof; a third nucleic acid sequence encoding a 2'-3' cyclic GMP-AMP synthase (cGAS) protein, or a functional part thereof; a fourth nucleic acid sequence encoding a DNA integrity scanning (disA) protein, or a functional part thereof and a combination thereof. Examples of suitable strains of *Mycobacterium* used in the present invention include *Mycobacterium tuberculosis, Mycobacterium bovis*, or a combination thereof, for example. Another strain used in the present invention is *Mycobacterium bacillus* Calmette Guerin (BCG). A strain of Mycobacteria used in the present invention may be a panthothenate auxotroph of BCG lacking its panCD genetic operon. panCD auxotoph strains lack genomic sequences able to encode functional PanC and/or PanD protein. In some embodiments, strains of Mycobacteria that are pantothenate auxotrophs comprise vectors of the present invention including a panCD nucleic acid encoding the PanC and PanD proteins or functional parts thereof. Vectors of the present invention that include panCD nucleic acid sequences are preferably free of antibiotic resistant genes or nucleic acid sequences that encode functional proteins providing antibiotic resistance. Mycobacteria that are pantothenate auxotrophs of the present invention are preferably free of a genomic antibiotic resistant gene or unable to encode functional proteins that provide antibiotic resistance.

Another embodiment of the present invention provides a pharmaceutical composition, including any one of the strains of Mycobacteria of the present invention, and a pharmaceutically acceptable carrier.

Another embodiment of the present invention provides a method of eliciting a type 1 interferon response, enhancing the expression of pro-inflammatory cytokine, and/or eliciting trained immunity in a subject including the steps of: administering a pharmaceutical composition including anyone of the strains of the present invention into a subject; and eliciting a type 1 interferon response, enhancing the expression of pro-inflammatory cytokine, and/or eliciting trained immunity in the subject. In one aspect, the pharmaceutical composition is administered into the bladder of the subject by a catheter.

Another embodiment provides a method of using a strain of Mycobacteria of the present invention to treat or prevent cancer in a subject. The method includes the steps of: administering a pharmaceutical composition including a strain of Mycobacteria including a vector expressing a protein that makes a STING agonist or a functional part thereof to a subject having cancer; and treating or preventing cancer in the subject. The present invention may be used to treat or prevent cancers including epithelial cancers, breast cancer, non-muscle invasive bladder cancer, as examples. In some aspects, the cancer is a BCG-unresponsive non-muscle invasive bladder cancer (BCG-unresponsive NMIBC) and the pharmaceutical composition is administered by intravesical instillation. In some aspects, the cancer is a BCG-naïve non-muscle invasive bladder cancer (BCG-naïve NMIBC) and the pharmaceutical composition is administered by intravesical instillation. In other aspects, the cancer is selected from the group consisting of colon cancer, uterine cancer, cervical cancer, vaginal cancer, esophageal cancer, nasopharyngeal cancer, endobronchial cancer, and a combination thereof and the pharmaceutical composition is administered to a luminal surface of the epithelial cancer. In some aspetcs, the cancer is selected from a solid tumor or a liquid tumor and the pharmaceutical composition is administered by intratumoral injection and/or by systemic infusion. The methods of the present invention may include the step of administering a checkpoint inhibitor, such as an anti-PD1 antibody, an anti-PDL1 antibody, or a combination thereof, as example. In another aspect, the cancer is bladder cancer and the pharmaceutical composition is administered via a catheter.

One embodiment of the present invention provides an expression vector including a first nucleic acid sequence encoding a Rv1354c protein, or a functional part thereof; a second nucleic acid sequence encoding a cyclic GMP-AMP synthase (DncV) protein, or a functional part thereof; a third nucleic acid sequence encoding a cyclic GMP-AMP synthase (cGAS) protein, or a functional part thereof; a fourth nucleic acid sequence encoding a DNA integrity scanning (disA) protein which functions as a diadenylate cyclase, or a functional part thereof, or a combination thereof. Some expression vectors of the present invention include a first nucleic acid sequence that overexpresses the cyclase domains of the Rv1354c protein when compared to the expression of a native Rv1354c protein as a reference. Some expression vectors of the present invention include a second nucleic acid sequence that overexpresses the cyclic GMP-AMP synthase (DncV) protein, when compared to the expression of a native DncV protein. Some expression vectors of the present invention include a third nucleic acid sequence that overexpresses the cyclase domains of the cyclic GMP-AMP synthase (cGAS) protein when compared to the expression of a native cGAS protein. Suitable Rv1354 proteins used in the present invention include a *Mycobacterium tuberculosis* Rv1354 protein. Suitable DncV proteins used in the present invention include a *Vibrio cholera* DncV protein. Suitable cGAS proteins used in the present invention include a *Homo sapiens* cGAS protein. Suitable DisA proteins used in the present invention include a *Mycobacterium tuberculosis* disA protein.

Another embodiment of the present invention provides a strain of BCG including a cdnP gene, an Rv1354c gene, an Rv1357c gene, or a combination thereof, wherein the cdnP gene is unable to express a functional cyclic di-nucleotide phosphodiesterase (CdnP) protein, the Rv1354c gene is unable to express a functional Rv1345c protein, and/or the Rv1357c gene is unable to express a functional Rv1357 protein. Some BCG strains of the present invention may have an Rv1354c gene that includes a non-functional EAL domain. The BCG strains of the present invention may include any of the expression vectors of the present invention.

Another embodiment of the present invention provides a method of treating or preventing bladder cancer including the steps of: administering a pharmaceutical composition including a strain of BCG including an expression vector of the present invention into the bladder of a subject; and treating or preventing bladder cancer in the subject when compared to a reference subject who was not administered the pharmaceutical composition. The pharmaceutical composition may be administered by any suitable means including by a catheter.

Another embodiment of the present invention provides a method of eliciting a type 1 interferon response in a subject including the steps of: administering a pharmaceutical composition including a strain of BCG including an expression vector of the present invention into the subject such as the subject's bladder; and enhancing a type 1 interferon response in the subject compared to a reference subject not administered the pharmaceutical composition.

Another embodiment of the present invention provides a method of treating or preventing cancer in a subject including the steps of: administering a pharmaceutical composition comprising a strain of BCG including an expression vector of the present invention into a tumor of a subject having cancer; and treating or preventing cancer in the subject when compared to a reference subject not administered the pharmaceutical composition. The pharmaceutical composition may be administered by any suitable means including injection into the tumor. Cancers that may be treated or prevented by this method include, but are not limited to, breast cancer, and/or non-muscle invasive bladder cancer.

Examples of Mycobacteria used in the present invention include *Mycobacterium tuberculosis, Mycobacterium bovis, Mycobacterium bovis Bacillus Calmette Guerin* (referred to a BCG), *Mycobacterium smegmatis, Mycobacterium avium* complex, and other non-tuberculous mycobacteria (NTM). Examples of BCG strains used in the present invention including those that overexpress STING agonists, include BCG Pasteur, BCG-Pasteur-Aeras, BCG Tice (also known as BCG Chicago), BCG-Connaught (also known as BCG Toronto), BCG Danish, BCG-Prague (also known as BCG Czechoslovakian), BCG Russia (also known as BCG Moscow), BCG Moreau (also known as BCG Brazil), BCG Japan (also known as BCG Tokyo), BCG Sweden (also known as BCG Gothenburg), BCG Birkhaug, BCG Glaxo, BCG Frappier (also known as BCG Montreal), BCG Phipps, or other available BCG strains.

Another embodiment of the present invention provides a method of treating diabetes including the steps of: administering a pharmaceutical composition including a strain of Mycobacteria including a vector expressing a protein or a functional part thereof that makes a STING agonist to a subject having diabetes; and treating or preventing diabetes in the subject by providing trained immunity. Trained immunity refers to the ability of one antigenic stimulus to elicit more potent immune responses to a second, different antigenic stimulus introduced at a later time. Trained immunity is antigen independent, based on heterologous CD4 and CD8 memory activation, cytokine mediated, and is associated with epigenetic and metabolic changes. The method results in the upregulation of glycolysis mediated by the trained immunity. The aforementioned up-regulation of glycolysis is beneficial in preventing and treating type 1 and type 2 diabetes mellitus.

Another embodiment of the present invention provide a method of stimulating trained immunity in a subject including the steps of: administering a pharmaceutical composition including a strain of Mycobacteria including a vector expressing a protein or a functional part thereof that makes a STING agonist to a subject; and stimulating trained immunity in the subject. Upregulating glycolysis in the subject and/or stimulating episomal changes in histone methylation in the subject mediate trained immunity in the subject.

Another embodiment of the present invention provides a method of treating or preventing a viral infection in a subject including the steps of: administering a pharmaceutical composition including a strain of Mycobacteria including a vector expressing a protein or a functional part thereof that makes a STING agonist to a subject; and treating or preventing the viral infection in the subject. Stimulating trained immunity in the subject treats or prevents the viral infection in the subject. Upregulating glycolysis in the subject and/or stimulating episomal changes in histone methylation in the subject mediate trained immunity in the subject.

Another embodiment of the present invention provides a method of treating or preventing a bacterial infection, or a drug-resistant bacterial infection in a subject including the steps of: administering a pharmaceutical composition including a strain of Mycobacteria including a vector expressing a protein or a functional part thereof that makes a STING agonist to a subject; and treating or preventing the bacterial infection or the drug-resistant bacterial infection in the subject. Stimulating trained immunity in the subject treats or prevents the bacterial infection in the subject. Upregulating glycolysis in the subject and/or stimulating episomal changes in histone methylation in the subject mediate trained immunity in the subject. The methods of the present invention may use one or more of the vectors of the present invention or one or more strain of bacteria including a vector of the present invention.

Another embodiment of the present invention provides a method of suppressing the expression of myeloid-derived suppressor cells (MDSCs), M2 macrophages, and Treg cells in a tumor and inducing the expression of macrophages, dendritic cells (DCs), and T effector cells in a tumor. The method includes the steps of administering a pharmaceutical composition including a strain of Mycobacteria including a vector expressing a protein that makes a STING agonist or a functional part thereof to a subject having a tumor; suppressing the expression of MDSCs, M2 macrophages, and Treg cells in the tumor; and inducing the expression of macrophages, DCs, and T effector cells in the tumor. An example of M1 macrophages having induced expression in a tumor includes M1 macrophages. An example of T effector cells having induced expression in a tumor includes CD4+ T cells and CD8+ T cells. Suppressing the expression of MDSCs, M2 macrophages, and Treg cells in the tumor of subjects administered a Mycobacteria including a vector of the present invention is observed when compared to the expression of MDSCs, M2 macrophages, and Treg cells in a tumor of a referenced subject not administered a pharmaceutical composition including the strain of Mycobacteria. Inducing the expression of macrophages, DCs, and T effector cells in a tumor is observed when compared to the expression of macrophages, DCs, and T effector cells in a tumor of a referenced subject not administered a pharmaceutical composition comprising the strain of Mycobacteria. Examples of suitable STING agonist include 3'-5' c-di-AMP (also known as c-di-AMP); 3'-5' c-di-GMP (also known as c-diGMP); 3'-3' cGAMP; 2'-3'cGAMP and a combination thereof. A suitable vector of the present invention may include a nucleic acid sequence selected from the group consisting of a first nucleic acid sequence encoding a Rv1354c protein, or a functional part thereof; a second nucleic acid sequence encoding a 3'-3' cyclic GMP-AMP synthase (DncV) protein, or a functional part thereof; a third nucleic acid sequence encoding a 2'-3' cyclic GMP-AMP synthase (cGAS) protein, or a functional part thereof; a fourth nucleic acid sequence encoding a DNA integrity scanning (DisA) protein, or a functional part thereof and a combination thereof. The tumor may be a epithelial cancer, a breast cancer, or a non-muscle invasive bladder cancer, and melanoma as examples. In some aspects, the tumor may be a non-muscle invasive bladder cancer such as a BCG-unresponsive non-muscle invasive bladder cancer (BCG-unresponsive NMIBC) and the pharmaceutical composition can be administered by intravesical instillation. In other aspects, the tumor may be a non-muscle invasive bladder cancer such as a BCG-naïve non-muscle invasive bladder cancer (BCG-naïve NMIBC) and the pharmaceutical composition can be administered by intravesical instillation. In other aspects, the tumor may be an epithelial cancer selected from the group consisting of colon cancer, uterine cancer, cervical cancer, vaginal cancer, esophageal cancer, nasopharyngeal cancer, endobronchial cancer, and a combination thereof and the pharmaceutical composition can be administered to a luminal surface of the epithelial cancer. In other aspects, the tumor is a solid tumor and the pharmaceutical composition is administered by intratumoral, intravenous, intradermal, transdermal, intravesical topical, intramuscular or subcutaneous injection. In other aspects, the tumor is a liquid tumor and the pharmaceutical composition is administered by intravenous, intradermal, transdermal, intravesical topical, intramuscular or subcutaneous injection. Methods of the present invention may further comprise the step of administering a checkpoint inhibitor. Suitable checkpoint inhibitors that may be used in the present invention include ipilimumab (anti-CTLA-4 antibody), nivolumab (anti-PD-1 antibody), pembrolizumab (anti-PD-1 antibody), cemiplimab (anti-PD-1 antibody), atezolizumab (anti-PD-L1 antibody), avelumab (anti-PD-L1 antibody), durvalumab (anti-PD-L1 antibody) and a combination thereof.

BRIEF DESCRIPTION OF THE DRAWINGS

This application is continuation-in-part (CIP) of Ser. No. 16/638,943, all the figures from U.S. Ser. No. 16/638,943 are herein incorporated by reference in their entirety.

FIG. 1A. J774 macrophages infected with *M.tb* harboring the pSD5B $P_{hsp60}$::disA plasmid or wild type *M.tb* (CDC1551) at an MOI of 1:20. Intramacrophage levels of c-di-AMP were determined by LC-MS/MS after 24 hours of infection. As can be seen, the *M.tb*-disA-OE strain produces ~15-fold more c-di-AMP than wild type *M.tb* (CDC1551). The BCG-disA-OE would be expected to show similarly high levels of c-di-AMP. (Data are from Dey B, Dey R J, Cheung L S, Pokkali S, Guo H, Lee J H, Bishai W R. A bacterial cyclic dinucleotide activates the cytosolic surveillance pathway and mediates innate resistance to tuberculosis. Nat Med. 2015; 21:401-6. PMID: 25730264.) FIG. 1B. BCG-Pasteur harboring the pSD5B $P_{hsp60}$::disA plasmid or BCG-Pasteur-WT were grown to mid-exponential phase. Bacteria were lysed and mRNA was prepared. The levels of disA mRNA were determined by quantitative RT-PCR. The BCG-disA-OE strain produces ~50-fold more disA mRNA than BCG-Pasteur-WT.

FIG. 4A shows differential expression of TNF-α. FIG. 4B shows differential expression of IL-6. FIG. 4C shows differential expression of IL-1β. Mouse BMDMs were challenged with wild-type and disA overexpression strains of BCG-Pasteur. Culture supernatants were assayed by ELISA for different cytokines.

FIG. 10 Summary of relative gene expression by BCG-disA-OE versus BCG-WT in different cells or tissues. Mouse bone marrow-derived macrophages (BMDM), human immortalized bladder cancer cell lines RT4 and 5637, and rat immortalized bladder cancer cell lines were infected with BCG-disA-OE and BCG-WT for 24 hours and mRNA was prepared from the cells. Rats were exposed to MNU by intravesical instillation over 8 weeks and then treated with either BCG-disA-OE or BCG-WT by intravesical instillation for 8 weeks. Bladders were removed upon necropsy at week 16, and mRNA was prepared. Quantitative RT-PCR for the cytokine or chemokine genes indicated was performed. The changes shown are the fold-induction or reduction observed with BCG-disA-OE normalized to that seen with BCG-WT. BCG-WT is BCG Pasteur and BCG-disA-OE was derived from BCG Pasteur.

FIG. 11. Diagram of two cyclic dinucleotide cyclase and phosphodiesterase proteins present in BCG: BCG_RS07340 and BCG_AHM07112. BCG_RS07340 is a bifunctional protein with both CDN cyclase and CDN PDE activities. BCG_AHM07112 is a CDN PDE. The domains are: GAF (regulatory), GGDEF (diguanylate cyclase), and EAL diguanylate phosphodiesterase.

FIG. 12. *M. tuberculosis* harboring the pSD5B $P_{hsp60}$::disA plasmid (Mtb-disA-OE or Mtb-OE) is significantly attenuated for virulence in mice compared to wild type *M.tb* (Mtb-CDC1551). 6-7-week-old female BALB/c mice (n=10 per group) were infected as described above with ~3.5 $\log_{10}$ CFU by aerosol infection. Day 1 CFU counts were performed on 3 mice in each group and confirmed the implantation of 3.5 log 10 CFU units. Mice were held until death. As can be seen, the median time to death for wild-type *M. tuberculosis* infection was 150.5 days. In contrast, mice infected with the same inoculum of *M.tb*-disA-OE (Mtb-OE) had a median time to death of 321.5 days (p=0.001). The BCG-disA-OE is expected to show similar loss of virulence in mice compared with BCG-WT. (Data are from Dey B, Dey R J, Cheung L S, Pokkali S, Guo H, Lee J H, and Bishai W R. A bacterial cyclic dinucleotide activates the cytosolic surveillance pathway and mediates innate resistance to tuberculosis. Nat Med. 2015; 21: 401-6. PMID: 25730264.)

FIG. 13A shows Bdifferential expression pattern of TNF-α. FIG. 13B shows differential expression of IL-6. Mouse BMDM were challenged with the two different strains of BCG. The BCG-Tice strain was from the commercially available Onco-Tice product.

FIGS. 17A-17B show that BCG-disA-OE is safer than BCG-WT in two mouse models. FIG. 17A shows that groups of BALB/c mice (immunocompetent) were exposed to 1×10$^3$ CFU (confirmed by sacrificing a group of mice and determining day 1 lung CFU counts) of either BCG-WT or BCG-disA-OE using a Glas-Col aerosolization chamber. After 4 weeks, the mice were sacrificed from each group, their lungs were removed, homogenized, and plated on 7H11 agar plates. The figure shows the mean CFU counts for the BCG-WT and BCG-disA-OE-infected mouse lungs. As may be seen a statistically significantly lower lung CFU burden was observed with BCG-disA-OE compared with BCG-WT. FIG. 17B shows that groups of SCID mice (immunosuppressed) were exposed to 1×10$^2$ CFU (confirmed by sacrificing a group of mice and determining day 1 lung CFU counts) of either BCG-WT or BCG-disA-OE using a Glas-Col aerosolization chamber. A third group was uninfected. The figure shows a Kaplan-Meier survival curve for the groups of mice. As may be seen BCG-disA-OE-infected mice had a statistically significantly longer survival time than BCG-WT-infected mice.

FIG. 18 shows that BCG-disA-OE elicits statistically significantly higher levels of "Trained Immunity immunological and epigenetic marks" in CD14$^+$ human monocytes than does BCG-WT. "Trained Immunity" refers to the ability of a first immunologic stimulus to induce increased immune responses to a second antigenically different stimulus give subsequently. In this experiment, CD14$^+$ human monocytes were prepared from LeukoPaks collected by apheresis. On day 0 they were infected with either BCG-WT or BCG-disA-OE at a MOI of 5:1 for 3 hours. A third group of cells were not infected. After infection, cells were washed multiple times (every two days). After a 6-day rest period, the monocytes were re-stimulated with the TLR1/2 agonist PAM3CSK4 for 2 hours. Cells were washed repeatedly and were subsequently incubated for 24 h. Th levels of secreted IL-1β were measured in the culture supernatants by ELISA. As may be seen, while BCG-WT itself elicited statistically significantly higher levels of immune response to the second stimulus compared to uninfected cells, BCG-disA-OE elicit statistically significantly more of a response than either BCG-WT or uninfected cells.

FIG. 19 shows that BCG-disA-OE elicits a greater histone activation mark (H3K4-trimethylation) in the IL6 and TNF gene promoter regions than BCG-WT. "Trained Immunity" refers to the ability of a first immunologic stimulus to induce increased immune responses to a second antigenically different stimulus give subsequently. Trained immunity has been associated with epigenetic modifications, such as histone methylation, in the promoter region of cytokines and other immune mediators. The experiment shown in FIG. 19 was performed in the same set of cells and exactly the same way as that described in FIG. 18 except that after the second stimulus with the TLR1/2 agonist PAM3CSK4 (abbreviated PAM3), cells were harvested fixed, chromatins were crosslinked and DNA was collected for chromatin immunoprecipitation analysis (ChIP) using an antibody specific for the H3K4-me3 histone methylation mark. H3K4-me3 is known to be a gene activating mark. The graph shows the relative fold change in abundance of immunoprecipitated DNA as measured by quantitative PCR using primers for the IL6 and TNF gene promoter region. As may be seen both BCG-Pasteur-disA-OE and BCG-Tice-disA-OE led to significantly greater levels of H3K4 histone trimethylation in the IL6 and TNF promoter regions than did their corresponding BCG-WT strains following challenge with the second stimulus, PAM3CSK4.

FIG. 24A shows interferon-β levels in murine BMDMs. FIG. 24B shows interferon-β levels in murine BMDCs. FIG. 24C shows interferon-β levels in murine J774.1 macrophages.

FIG. 25A shows IL-6 levels in murine BMDMs. FIG. 25B shows IL-6 levels in murine BMDCs. FIG. 25C shows IL-6 levels in murine J774.1 macrophages.

FIG. 26A shows TNF levels in murine BMDMs. FIG. 26B shows TNF levels in murine BMDCs. FIG. 26C shows TNF levels in murine J774.1 macrophages.

FIG. 27A shows TNF levels in NBT-II cells. FIG. 27B shows IFN-γ levels in NBT-II cells.

FIG. 28A shows IFN-β levels in RT4 cells. FIG. 28B shows IFN-γ levels in RT4 cells. FIG. 28C shows TNF levels in RT4 cells. FIG. 28D shows IL-1β levels in RT4 cells.

FIG. 30A shows IFN-β levels in BCG-WT and BCG-disA-OE-infected mouse lungs. FIG. 30B shows IFN-γ levels in BCG-WT and BCG-disA-OE-infected mouse lungs. FIG. 30C shows IL-6 levels in BCG-WT and BCG-disA-OE-infected mouse lungs. FIG. 30D shows TNF levels in BCG-WT and BCG-disA-OE-infected mouse lungs.

FIG. 31A shows IFN-β levels in BCG-WT and BCG-disA-OE-infected mouse spleens. FIG. 31B shows IFN-γ levels in BCG-WT and BCG-disA-OE-infected mouse spleens. FIG. 31C shows IL-6 levels in BCG-WT and BCG-disA-OE-infected mouse spleens. FIG. 31D shows TNF levels in BCG-WT and BCG-disA-OE-infected mouse spleens.

FIG. 39A shows colony PCR using Kanamycin gene specific primer confirms the presence of recombinant plasmid pSD5-hsp60-MT3692 in the BCG-disA-OE (Tice) clones selected against Kanamycin (25 μg/mL). FIG. 39B shows real time PCR showing differential disA expression in different clones of BCG Tice BCG-disA-OE Tice. Transcript levels were measured in total RNA isolated from the late log phase cultures using log phase culture. *M. tuberculosis* sigA (Rv2703) was used as a reference gene, and relative expression was calculated by $2^{\Delta\Delta CT}$ method.

FIG. 39C shows measurement of IRF activation BY quantification of IRF induction based on ISRE (RLU, relative light units) in 24-h-post infection (MOI=1:20) culture supernatants of RAW-Lucia ISG cells. Data represent mean±SEM (n=3 replicates). Student's t-test (two-tailed) *P<0.05, P<0.01, *P<0.001, ****P<0.0001

FIG. 40A shows quantitative measurement of IFN-β in culture supernatants of wild-type C57BL/6-derived BMDMs and STING-KO BMDM (C57BL/6J-Tmem173gt/J) 24 h after BCG-disA-OE (Tice) infection. FIG. 40B shows quantitative measurement of IFN-β in culture supernatants of wild-type C57BL/6-derived BMDMs, BMDCs, J774.1 macrophages and human monocyte-derived macrophages (HMDMs) 24 h post-infection. FIG. 40C shows quantitative measurement of IFN-β in culture supernatants of wild-type C57BL/6-derived BMDMs, BMDCs, J774.1 macrophages and human monocyte-derived macrophages (HMDMs) 24 h post-infection. Macrophage to BCG infection ratio=1:20. Data represent mean±SEM (n=3 replicates). Student's t-test (two-tailed) *P<0.05, P<0.01, *P<0.001, ****P<0.0001

FIG. 41A shows measurements 24 h post-infection with BCG-disA-OE (Tice). FIG. 41B shows measurements 24 h post-infection with BCG-disA-OE (Pasteur). (C-D) Quantitative measurement of IL-6 in culture supernatants of wild-type C57BL/6-derived BMDMs, BMDCs, J774.1 macrophages and human monocyte-derived macrophages (HMDMs). FIG. 41C shows measurements 24 h post-infection with BCG-disA-OE (Tice). FIG. 41D shows measurements 24 h post-infection with BCG-disA-OE (Pasteur). Macrophage to BCG infection ratio=1:20. Data represent mean±SEM (n=3 replicates). Student's t-test (two-tailed) *P<0.05, P<0.01, *P<0.001, ****P<0.0001

FIGS. 43A-43E show BCG-disA-OE induces significantly higher Th1 cytokines and chemokines as compared to WT BCG. FIG. 43A shows relative gene expression analyses of different cytokines and chemokines in IFN-γ activated macrophages at 6 h post-infection by wild-type BCG (Tice) and BCG-disA-OE (Tice) strains. (B-D) Relative gene expression analyses of IL-6, IL-12 and MCP-1 IFN-γ activated macrophages at 6 h post-infection by wild-type BCG (Pasteur) and BCG-disA-OE (Pasteur) strains. β-actin was used as a reference gene, and relative expression was calculated by $2^{\Delta\Delta CT}$ method. Data represent mean±SEM (n=3 replicates). Student's t-test (two-tailed). FIG. 43B shows IL-6 relative gene expression. FIG. 43C shows IL-12 relative gene expression. FIG. 43D shows MCP-1 relative gene expression. FIG. 43E shows quantitative measurement of MCP-1 in culture supernatants of wild-type C57BL/6-derived BMDMs 24 h after BCG-disA-OE (Tice) infection.

Macrophage to BCG infection ratio=1:20. Data represent mean±SEM (n=3 replicates). Student's t-test (two-tailed) *P<0.05, P<0.01, *P<0.001, ****P<0.0001

Figure 44C:
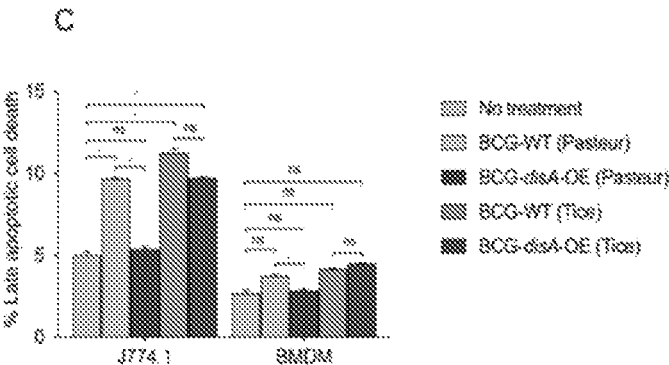

FIGS. 44A-44C show differential apoptotic induction in murine BMDMs and J774.1 macrophage after infection with different BCG strains. (A-B) Murine BMDMs and J774.1 macrophages were challenged with WT or BCG-disA-OE strains of BCG at a MOI of 1:10 for 24 h and apoptotic cell death was accessed by Annexin and PI staining. Representative data from individual infection assay. FIG. 44A shows measurements in murine BMDMs. FIG. 44B shows measurements in J774.1 macrophages. FIG. 44C shows a bar diagram showing quantifications of late apoptotic cell death following infection. Data represent mean±SEM (n=3 replicates). Student's t-test (two-tailed) *P<0.05

Figures 45A, 45B, 45C:
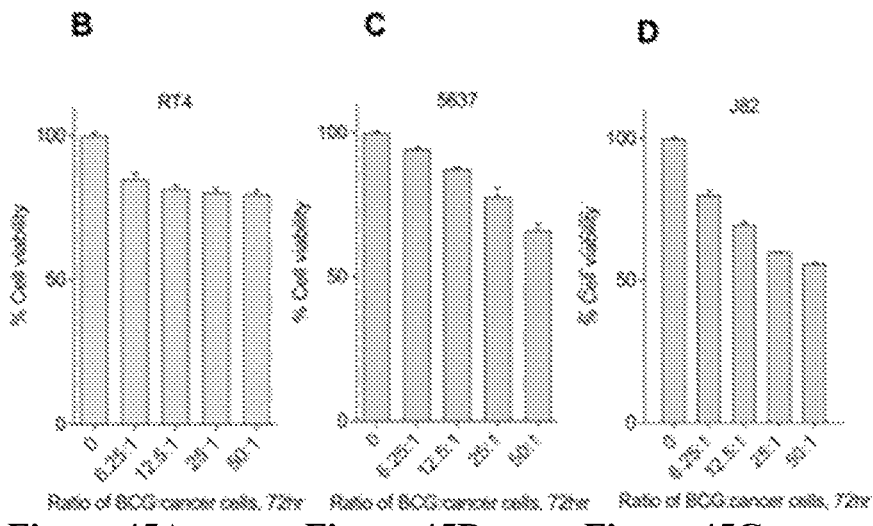

FIGS. 45A-45C show internalization and differential toxicity of WT and BCG-disA-OE strains in human urothelial carcinoma cells. (A-C) Cell viability of RT4 (Human bladder cancer cell line representing grade I carcinoma), 5637 (Human bladder cancer cell line representing grade II carcinoma) and J82 (Human bladder cancer cell line representing grade III) cells exposed to different MOIs of wild-type BCG. Cell viability was measured using CellTiter-Glo Luminescent Cell Viability assay. FIG. 45A shows cell viability of RT4 cells. FIG. 45B shows cell viability of 5637 cells. FIG. 45C shows cell viability of J82 cells.

Figures 46A, 46B:
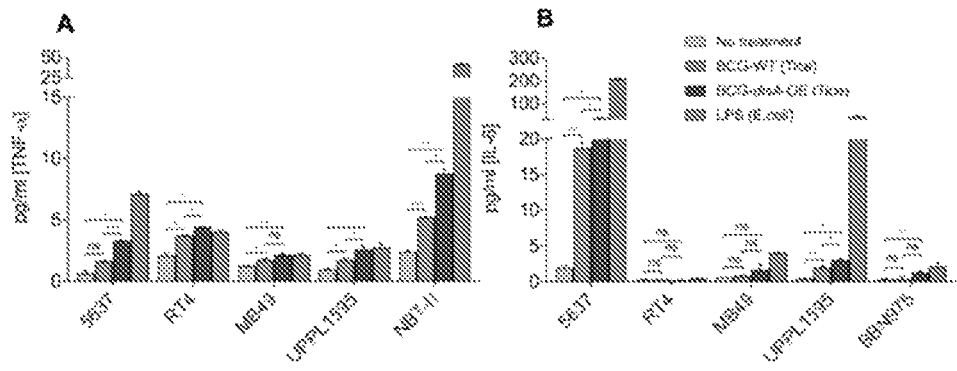

FIGS. 46A-46D show BCG Tice overexpressing c-di-AMP as a stronger inducer of antitumor cytokine response in urothelial carcinoma cells. (A-D) Quantitative measurement of differential TNF-α, IL-6, IL-1β and IFN-γ levels using ELISA in different urothelial carcinoma cells 24 h after infection with different wild-type BCG (Tice) and BCG-disA-OE (Tice) strains. Cells to BCG infection ratio=1:20, data represent mean±SEM (n=3 replicates). Student's t-test (two-tailed) *P<0.05, P<0.01, *P<0.001, ****P<0.0001. FIG. 46A shows TNF-α levels. FIG. 46B shows IL-6 levels. FIG. 46C shows IL-10 levels. FIG. 46D shows IFN-γ levels.

FIGS. 47A-47G show BCG Pasteur overexpressing c-di-AMP as a stronger inducer of antitumor cytokine response in urothelial carcinoma cells. (A-G) Quantitative measurement of differential cytokine levels using ELISA in different urothelial carcinoma cells 24 h after infection with different wild-type BCG (Pasteur) and BCG-disA-OE (Pasteur) strains. Cells to BCG infection ratio=1:20. Data represent mean±SEM (n=3 replicates). Student's t-test (two-tailed) *P<0.05, P<0.01, *P<0.001, ****P<0.0001. FIG. 47A shows TNF-α levels in 5637 cells. FIG. 47B shows TNF-α levels in BBN975 cells. FIG. 47C shows 11-6 levels in UPPL1595 cells. FIG. 47D shows IL-1β levels in MB49 cells. FIG. 47E shows IL-1β levels in UPPL1595 cells. FIG. 47F shows IFN-γ levels in BBN975 cells. FIG. 47G shows IFN-γ levels in NBT-II cells.

FIGS. 48A-48B show stronger macrophage reprogramming towards M1 phenotype after infection with BCG strains overexpressing c-di-AMP. FIG. 48A shows wild-type BMDMs infected with different BCG strains and for 24 h at 1:10 MOIs. Cell surface and intracellular straining was carried out and cells were analyzed using flow-cytometry (BD LSR II flow cytometer. Bar diagram showing percentage of TNF-α positive antigen presenting mouse macrophages (MHC Class II$^+$CD11b$^+$F4/80$^+$) following infection with wild-type and c-di-AMP overexpressing BCG Tice and Pasteur strains. Data were processed using FlowJo software (Tree Star v10). FIG. 48B shows representative flow plots showing different cell phenotypes of antigen producing M1 macrophages. Data represent mean±SEM (n=3 replicates). Student's t-test (two-tailed) *P<0.05, P<0.01, *P<0.001, ****P<0.0001

FIGS. 49A-49B show stronger reprogramming of M2 macrophages after infection with BCG strains overexpressing c-di-AMP. FIG. 49A shows percentage of M2 macrophage surface markers (CD206$^+$CD124$^+$) positivity on mouse BMDM macrophages (CD11b$^+$F4/80$^+$) after infection with wild-type. FIG. 49B shows percentage of IL-10 producing macrophages of M2 macrophage (CD206 CD124 mouse macrophages) population. Briefly, wild-type BMDMs were generated in presence of murine M-CSF. Macrophages were infected with different BCG strains and for 24 h at 1:10 MOIs. Cell surface and intracellular straining were carried out and cells were analyzed using flow-cytometry (BD LSR II flow cytometer. Data were processed using FlowJo software (Tree Star v10). Data represent mean±SEM (n=3 replicates). Student's t-test (two-tailed) *P<0.05, P<0.01, *P<0.001, ****P<0.0001

Figure 50B:
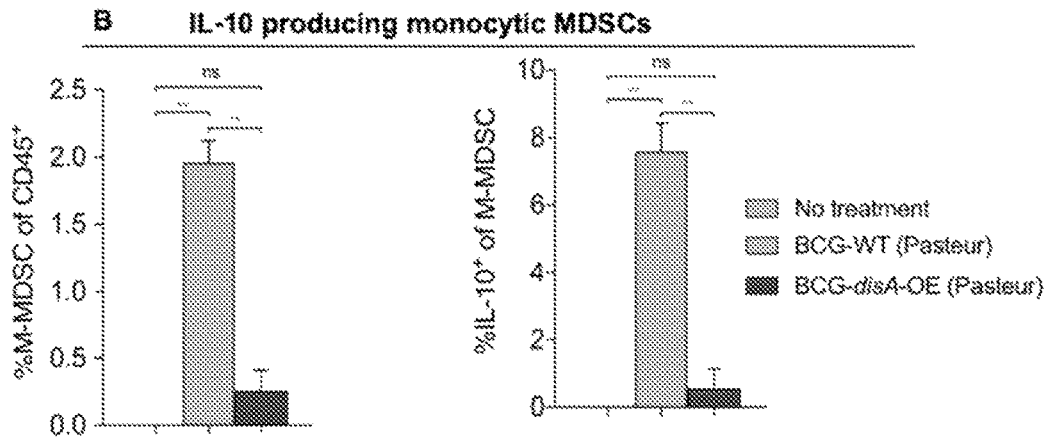

FIGS. 50A-50B show stronger induction of monocytic MDSCs secreting IL-10 in murine BMDMs after infection with wild-type and c-di-AMP overexpressing BCG strains. FIG. 50A shows the percentage of M-MDSCs of total myeloid cells (CD45+). FIG. 50B shows the percentage of IL-10 producing M-MDSCs after infection of murine BMDMs with WT and BCG-disA-OE strains. Briefly, wild-type BMDM macrophages were infected with different BCG strains and for 24 h at 1:10 MOIs. Cell surface and intracellular straining was carried out and cells were analyzed using flow-cytometry (BD LSR II flow cytometer. Data was processed using FlowJo software (Tree Star v10). Data represent mean±SEM (n=3 replicates). Student's t-test (two-tailed) *P<0.05, P<0.01, *P<0.001, ****P<0.0001

Figure 51A:
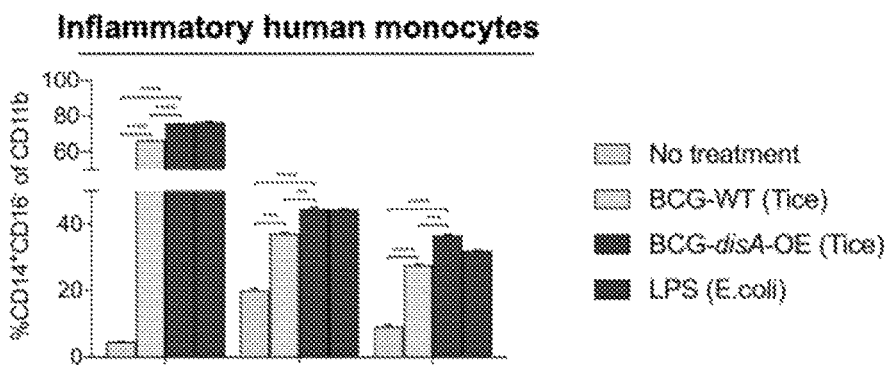
Figure 51B:
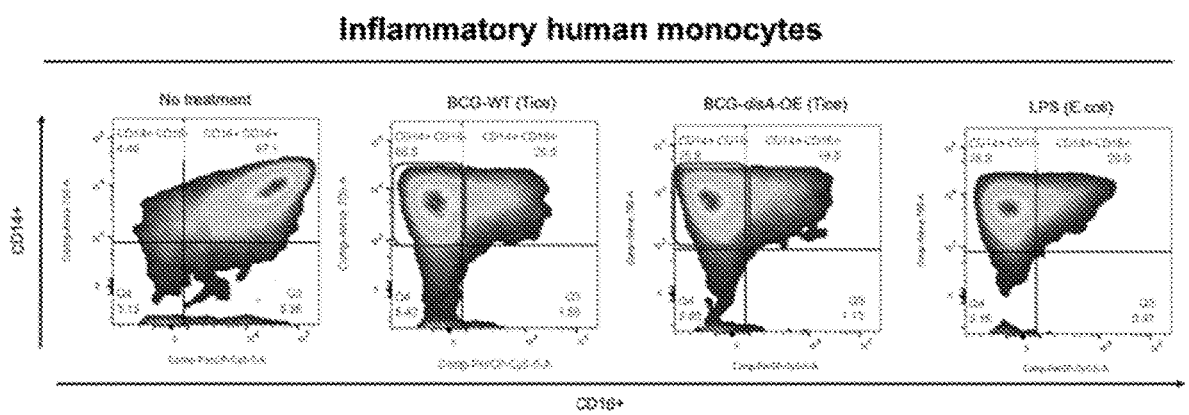

FIGS. 51A-51B show differential induction of classical (inflammatory) monocytes after infection with wild-type and c-di-AMP overexpressing BCG Tice. FIG. 51A shows a bar diagram showing percentage of classical monocytes (CD14 CD16) of CD11b populations. Briefly, human monocytes were isolated from PBMCs drawn from different healthy blood donors. Negatively selected human monocytes were infected with wild-type and BCG-disA-OE strains for 24 h (1:10 MOIs). FIG. 51B shows representative flow-cytometry plots showing different percentage of monocyte populations. Cell surface staining was carried out and cells were analyzed using flow-cytometry (BD LSR II flow cytometer). Data were processed using FlowJo software (Tree Star v10). Student's t-test (two-tailed) *P<0.05, P<0.01, *P<0.001, ****P<0.0001

Figure 52A:
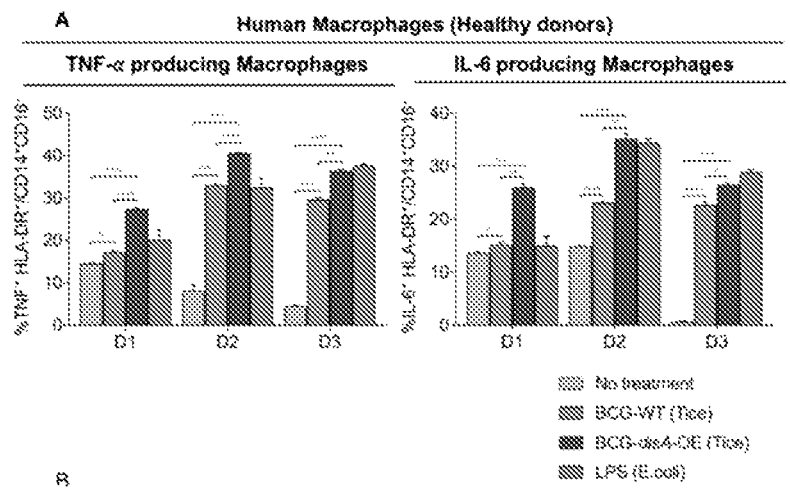
Figure 52B:
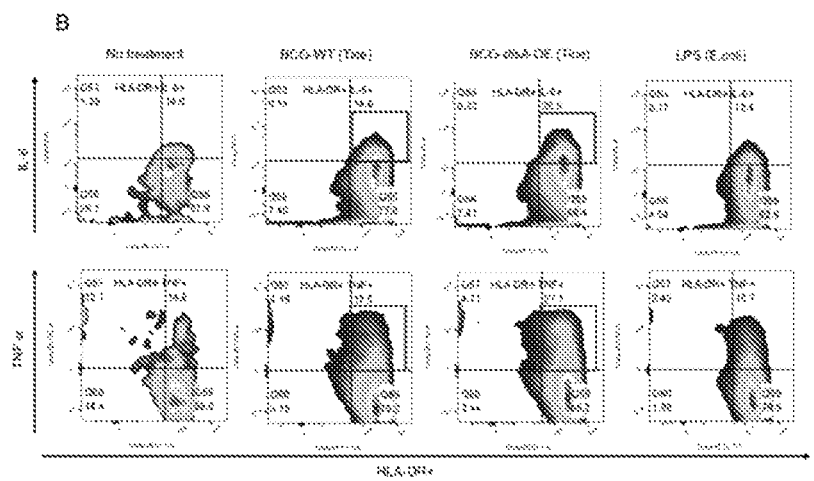

FIGS. 52A-52B show BCG overexpressing c-di-AMP as a potent inducer of proinflammatory cytokines in human monocyte-derived macrophages. FIG. 52A is a bar diagram showing percentage of MHC class II positive classical macrophages producing TNF-α (TNF-α$^+$HLA-DR$^+$/CD14$^+$CD16$^-$) and IL-6 (IL-6$^+$HLA-DR$^+$/CD14$^+$CD16$^-$). Briefly, human monocytes were isolated from PBMCs drawn from different healthy blood donors. Negatively selected human monocytes were differentiated into macrophages. Macrophages were infected with wild-type and BCG-disA-OE strains for 24 h (1:10 MOIs). FIG. 52B shows representative flow-cytometry plots showing different percentage of macrophage populations. Cell surface staining was carried out and cells were analyzed using flow-cytometry (BD LSR II flow cytometer. Data were processed using FlowJo software (Tree Star v10). Student's t-test (two-tailed) *P<0.05, P<0.01, *P<0.001, ****P<0.0001

Figures 53A, 53B:
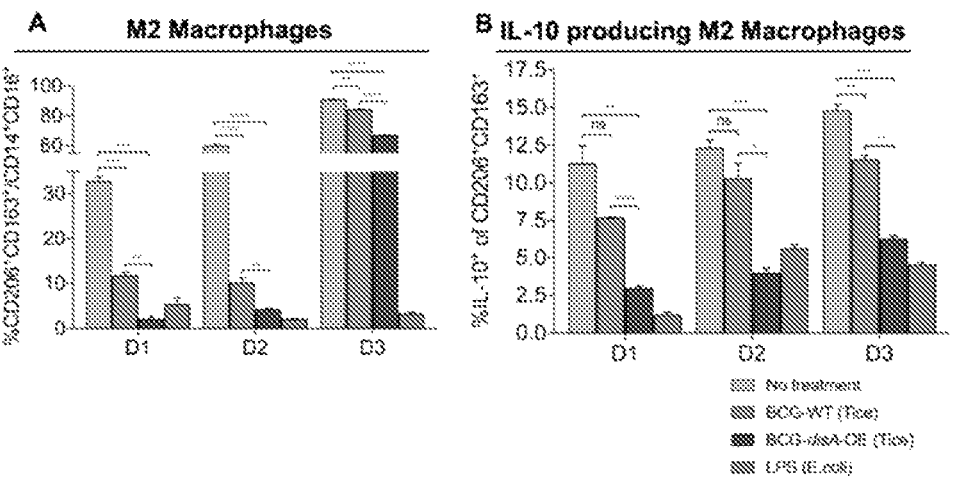
Figure 53C:
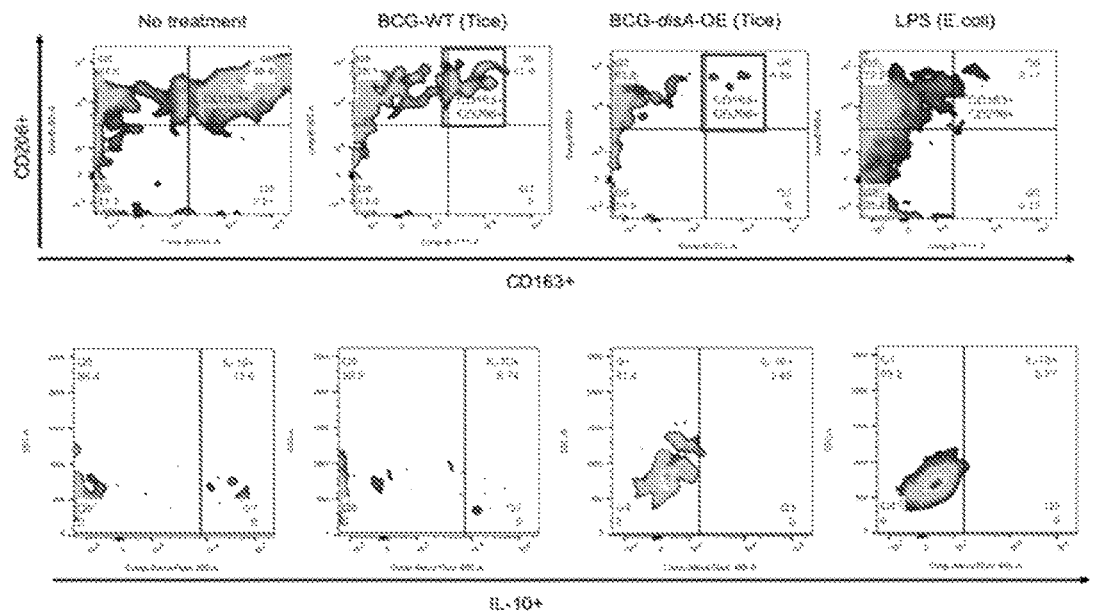

FIGS. 53A-53C show BCG overexpressing c-di-AMP strongly suppressing M2 macrophage phenotypes. FIG. 53A shows percentage of immunosuppressive M2 (CD206+ CD163+) macrophages of total transitional (CD14+CD16+) macrophages. FIG. 53B shows percentage of IL-10 producing macrophages of total M2 macrophages (CD206+ CD163+) after infection of HMDMs with WT and BCG-disA-OE Tice strains. FIG. 53C shows representative flow-cytometry plots showing M2 cell surface phenotypes and IL-10 producing cells of M2 macrophages. Briefly, human monocytes were isolated from PBMCs drawn from different healthy blood donors. Negatively selected human monocytes were differentiated into M2 macrophages in presence of M-CSF. Infections were carried out for 24 h (1:10 MOIs), cell surface staining and intracellular staining was performed. Data are mean±SEM (n=3 replicate experiments performed on monocytes-derived macrophages from healthy human donors). Student's t-test (two-tailed). *P<0.05, P<0.01, *P<0.001, ****P<0.0001

Figures 54, 55A, 55B:
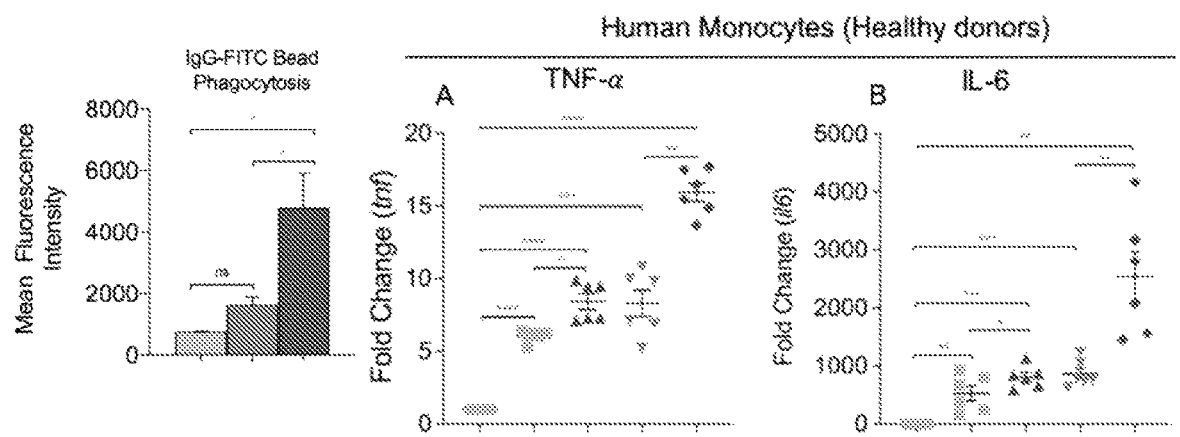

FIGS. 54 shows BCG overexpressing c-di-AMP infected macrophages enhanced phagocytosis. HMDMs were infected with WT BCG and BCG-disA-OE strains for 6 h and phagocytic activity was measured by quantifying intracellular FITC-labeled IgG-opsonized latex beads. Images were acquired on live cells. Nuclear staining was done using Hoechst . Image acquisition was carried out using LSM700 confocal microscope at 63× magnification. Images were process using Fiji software. Cells to BCG infection ratio=1:10. Data are mean±SEM (n=3 replicate experiments performed on monocytes-derived macrophages from healthy human donors). Student's t-test (two-tailed). *P<0.05, P<0.01, *P<0.001, ****P<0.0001. FIG. 54 is a bar graph showing the quantification of the fluorescence.

FIGS. 55A-55B show BCG overexpressing c-di-AMP as a potent inducer of proinflammatory cytokines in primary human monocytes. (A-B) BCG-disA-OE induces significantly higher gene expression of TNF-α and IL-6 in primary human monocytes as compared to WT BCG. TNF-α and IL-6 expression was accessed in primary human monocytes isolated from different healthy donors using qRT-PCR. RNU6A was used as reference gene, and relative expression was calculated by $2^{\Delta\Delta CT}$ method. Data represent mean±SEM (n=6 different healthy donors). Student's t-test (two-tailed) *P<0.05, P<0.01, *P<0.001, ****P<0.0001. FIG. 55A shows TNF-α levels. FIG. 55B shows IL-6 levels.

Figures 56A, 56B:
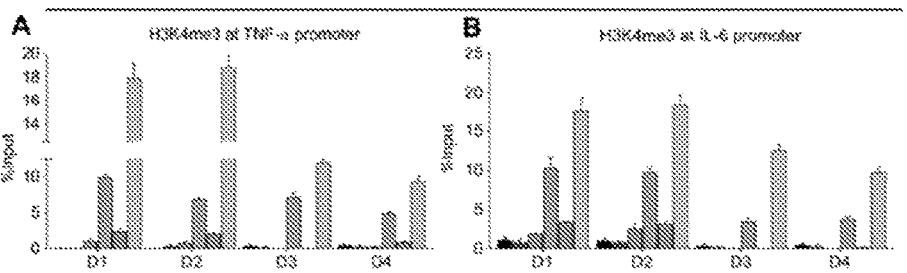
Figures 56C, 56D, 56E:
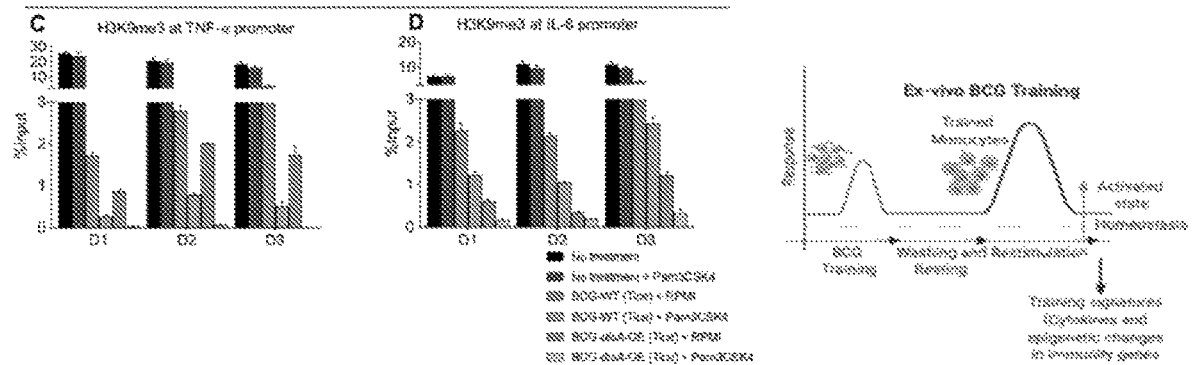

FIGS. 56A-56E show BCG overexpressing c-di-AMP as a stronger inducer of trained immunity epigenetic marks in human monocytes after training. (A-B) Bar diagram showing epigenetic active chromatin mark H3K4me3 on TNF-α and IL-6 gene promoters. Fold enrichment of epigenetically modified TNF-α and IL-6 gene promoters in BCG-trained human monocytes isolated from different donors (n=4 different healthy donors) following re-stimulation by Pam3CSK4. H3K4-trimethylated promoters were enriched and quantified using ChIP-PCR. FIG. 56A shows H3K4me3 levels on TNF-α gene promoter. FIG. 56B shows H3K4me3 levels on IL-6 gene promoter. (C-D) Bar diagram showing epigenetic inactive chromatin mark, H3K9me3 on TNF-α and IL-6 gene promoters. Fold enrichment of epigenetically modified TNF-α and IL-6 gene promoters in BCG-trained human monocytes isolated from different donors (n=4 different healthy donors) following re-stimulation by Pam3CSK4. H3K9-trimethylated promoters were enriched and quantified using ChIP-PCR. Student's t-test (two-tailed) *P<0.05, P<0.01, *P<0.001, ****p<0.0001. FIG. 56C shows H3K9me3 levels on TNF-α gene promoter. FIG. 56D shows H3K9me3 levels on IL-6 gene promoter. FIG. 56E shows schematic representation of ex-vivo BCG training.

Figure 57A:
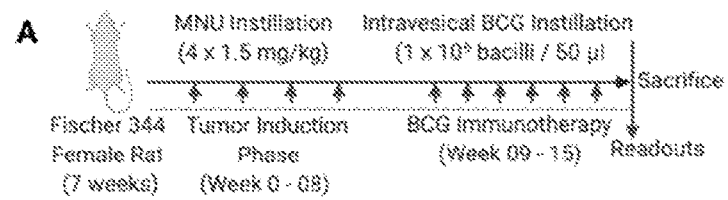
Figures 57B, 57C:
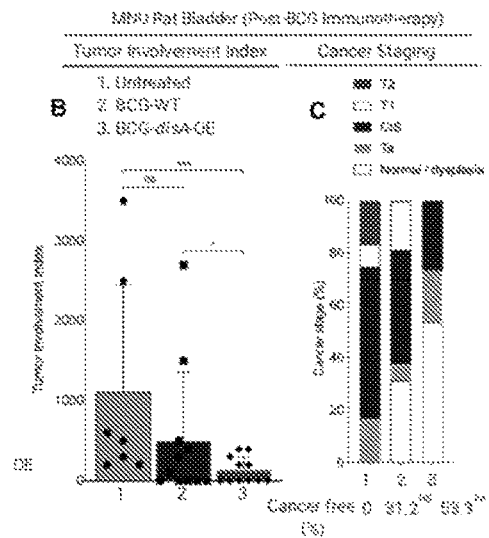

FIGS. 57A-57C shows BCG overexpressing c-di-AMP demonstrating improved antitumor activity in the MNU carcinogen model of NMIBC. FIG. 57A Schematic of intravesical treatment strategy of BCG in MNU carcinogen model of NMIBC. FIG. 57B is a graph bar showing tumor involvement index. FIG. 57C is a graph showing staging of tumors. Student's t-test (two-tailed) *P<0.05, P<0.01, *P<0.001, ****P<0.0001

Figure 58A:
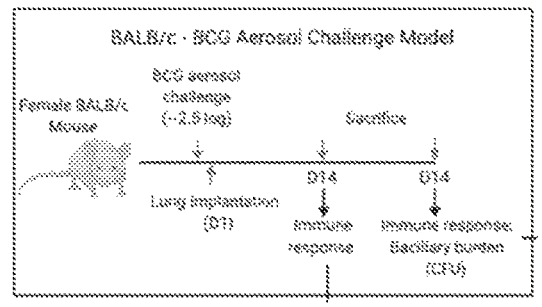
Figures 58B, 58C:
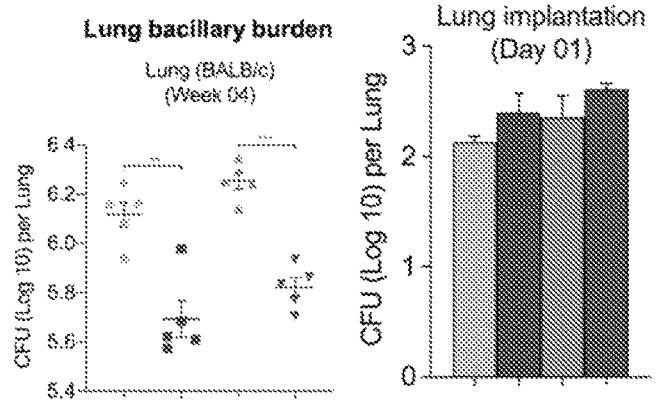

FIGS. 58A-58C show BCG-disA-OE strains attenuated for virulence in vivo. FIG. 58A illustrates BALB/c BCG aerosol challenge model. FIG. 58B shows BALB/c mice lung bacillary burden of wild-type and BCG-disA-OE strains in mouse lungs 4-week post infection. Data are mean±S.E.M. (n=5 animals/group). FIG. 58C shows implantation (day 01) of BCG strains following aerosol challenge in BALB/c mice. Student's t-test (two-tailed) *P<0.05, P<0.01, *P<0.001, ****P<0.0001

Figure 59A:
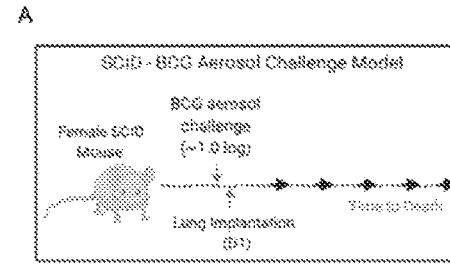
Figure 59B:
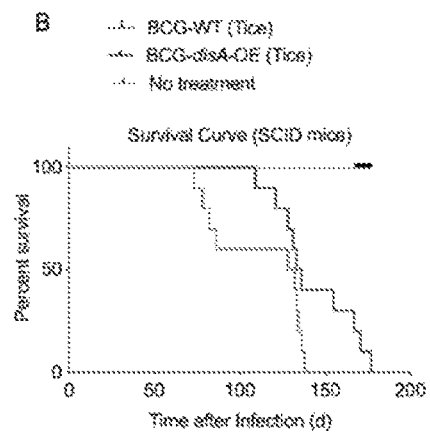
Figure 59C:
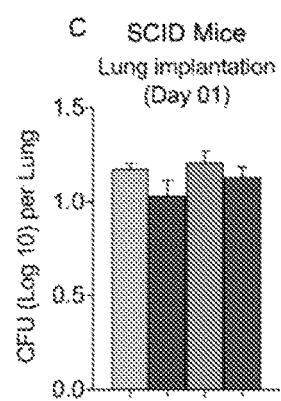

FIGS. 59A-59C show BCG strain overexpressing c-di-AMP attenuated for virulence in a severely immunocompromised (SCID) mouse model of aerosol infection. FIG. 59A illustrates SCID mice model of BCG aerosol infection. FIG. 59B shows survival of SCID mice (n=10) after infection with different BCG strains. FIG. 59C shows implantation (day 01) of BCG strains following aerosol challenge in SCID mice. Student's t-test (two-tailed) *P<0.05, P<0.01, *P<0.001, ****P<0.0001

Figures 60A, 60B, 60C:
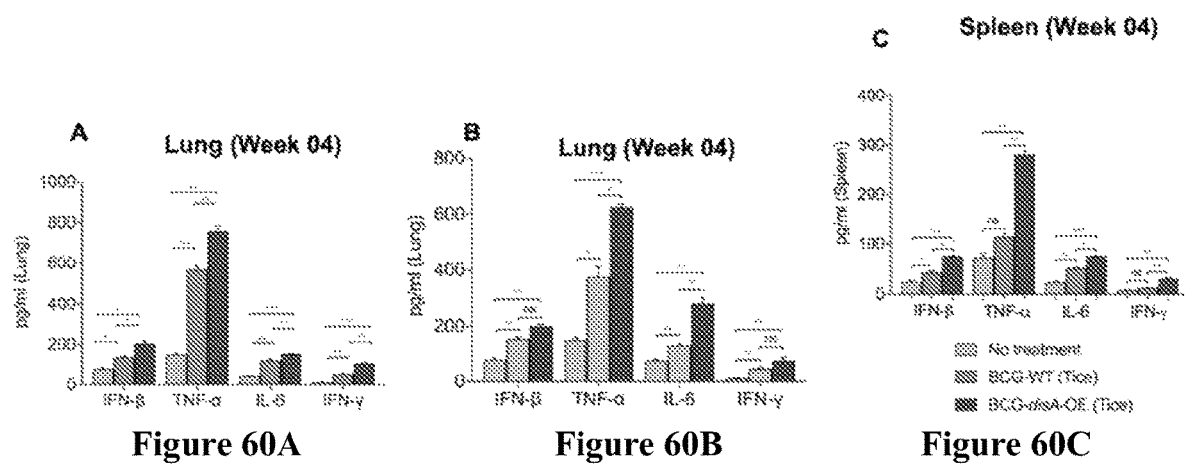
Figures 60D, 61A:
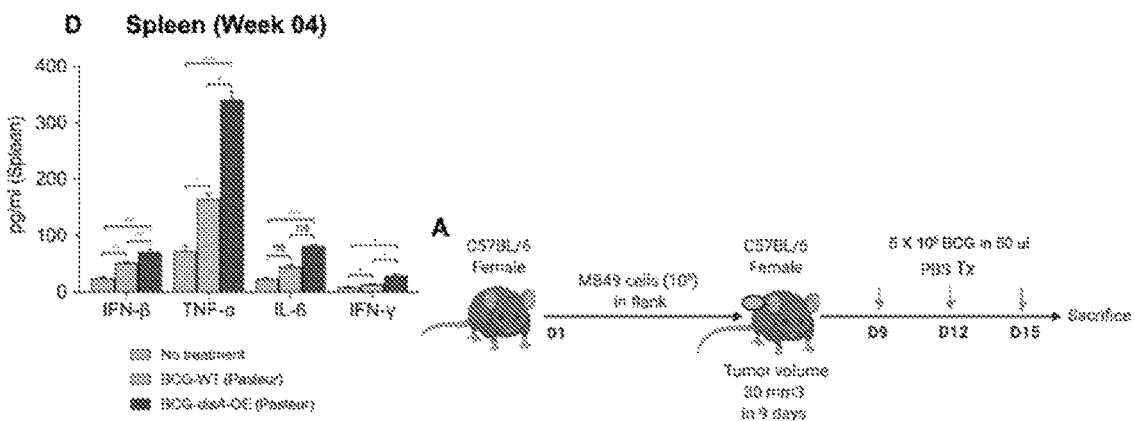

FIGS. 60A-60D show BCG overexpressing c-di-AMP as a stronger inducer of Th1 cytokines in vivo. (A-B) Quantitative levels of IFN-β, TNF-α, IL-6 and IFN-γ in lung homogenates from BALB/c mice at 4 weeks after infection with different BCG strains using ELISA. FIG. 60A shows results with WT BCG (Tice) and BCD-disA-OE (Tice). FIG. 60B shows results with WT BCG (Pasteur) and BCD-disA-OE (Pasteur). (C-D) Quantitative levels of IFN-β, TNF-α, IL-6 and IFN-γ in lung homogenates from BALB/c mice at 4 weeks after infection with different BCG strains using ELISA. FIG. 60C shows results with WT BCG (Tice) and BCD-disA-OE (Tice). FIG. 60D shows results with WT BCG (Pasteur) and BCD-disA-OE (Pasteur). Results are represented as the mean (pg/ml)±SEM (n=4 animals/group). Student's t-test. Student's t-test (two-tailed) *P<0.05, P<0.01, *P<0.001, ****P<0.0001

Figures 61B, 62A, 62B:
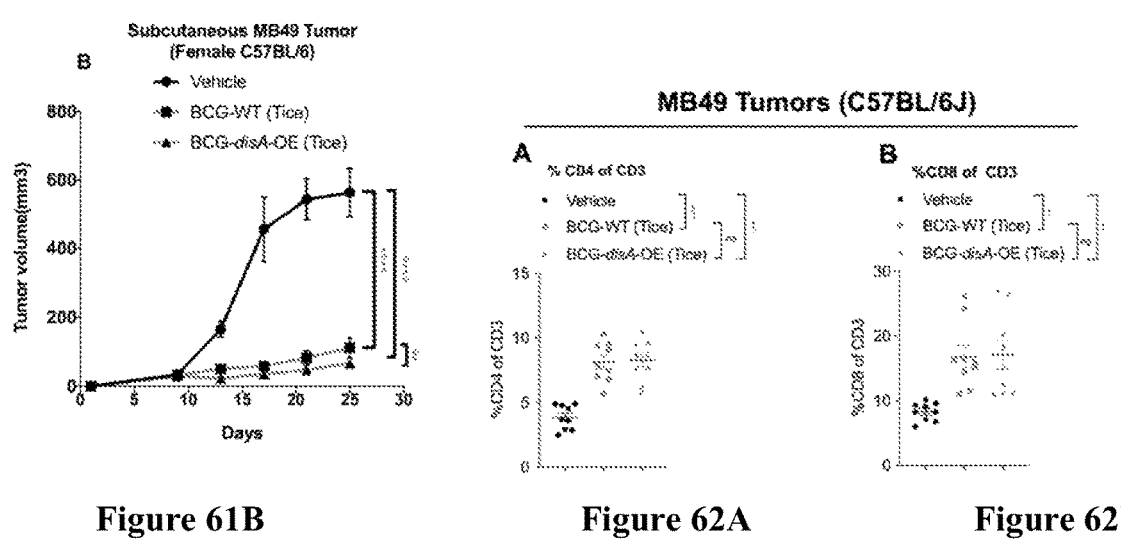

FIGS. 61A-61B show therapeutic intratumoral injection of BCG overexpressing c-di-AMP leading to greater antitumor activities in MB49 model of bladder cancer. FIG. 61A shows a schematic representation of intratumoral injection of tumors. Mice were implanted with $1\times10^5$ MB49 cells on day 0, then accessed for tumor volume until the group averaged ~40 mm³. At that time, mice were treated with $5\times10^6$ wild-type or BCG-disA-OE strain in a total volume of 50 μL or with PBS alone every $3^{rd}$ day for a total of 3 treatments. FIG. 61B shows tumor outgrowth of MB49 bearing animals treated with vehicle (PBS), wild-type and BCG-disA-OE following treatments as shown in FIG. 61A. Two-way ANOVA.

Figure 62C:
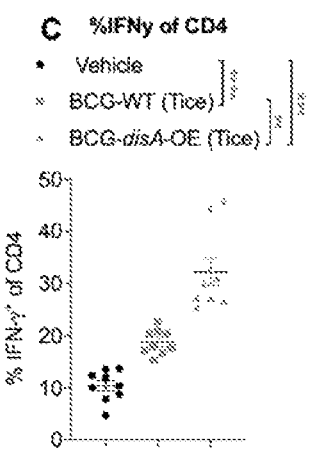
Figure 62D:
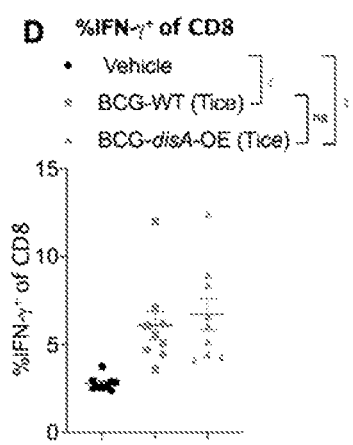

FIGS. 62A-62D show BCG overexpressing c-di-AMP inducing stronger infiltration of IFN-γ at tumor site following intratumoral administration. (A-B) Dot plot showing relative abundance of percentage of CD4 or CD8 of total CD3 populations in single cells isolated from tumor. FIG. 62A shows percentage of CD4 cells. FIG. 62B shows percentage of CD8 cells. (C-D) Dot plot showing higher percentage of interferon-γ producing CD4 T cells inside single cells isolated from tumors receiving BCG-disA-OE. FIG. 62C shows percentage of INF-γ⁺ cells among CD4 cells. FIG. 62D shows percentage of INF-γ⁺ cells among CD8 cells. No significant changes in percentage of interferon-γ producing CD8 T cells were observed. Briefly, single cells were prepared from excised tumors after intratumoral administration of PBS or BCG strains. Cell surface and intracellular cytokine staining was performed, and cells were analyzed using flow cytometry. Student's t-test. Student's t-test (two-tailed) *P<0.05, P<0.01, *P<0.001, ****P<0.0001

DETAILED DESCRIPTION OF THE INVENTION

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant any small molecule chemical compound, antibody, nucleic acid molecule, or polypeptide, or fragments thereof.

By "alteration" is meant a change (increase or decrease) in the expression level or activity of a gene or polypeptide as detected by standard methods known in the art such as those described herein. As used herein, an alteration includes a 10% change in expression level, preferably a 25% change, more preferably a 40% change, and most preferably a 50% or greater change in expression level.

By "ameliorate" is meant decrease, suppress, attenuate, diminish, arrest, or stabilize the development or progression of a disease.

By "analog" is meant a molecule that is not identical but has analogous functional or structural features. For example, a polypeptide analog retains the biological activity of a corresponding naturally occurring polypeptide, while having certain biochemical modifications that enhance the analog's function relative to a naturally occurring polypeptide. Such biochemical modifications could, for example, increase the analog's protease resistance, membrane permeability, or half-life, without altering, for example, ligand binding. An analog may include an unnatural amino acid, in another example.

By "cdnP" is meant either 1) a cdnP gene or nucleic acid sequence that encodes a cyclic di-nucleotide phosphodiesterase (cdnP) protein or 2) the cyclic di-nucleotide phosphodiesterase protein. Examples include the M. tuberculosis cdnP gene in H37Rv, Rv2837c, having NCBI Gene ID 888920, and a cdnP protein of UniProtKB/Swiss-Prot P71615.2.

By "cGas" is meant either 1) a cGas gene or nucleic acid sequence that encodes a cyclic GMP-AMP synthase (cGAS) protein, or 2) the cyclic GMP-AMP synthase protein. Examples of cGas include the H. sapiens cGAS gene (NCBI Gene ID: 115004) and the protein encoded by this gene (UniProtKB/Swiss-Prot: Q8N884.2). The cGas protein is a cyclic GMP-AMP synthase from humans that makes 2'3' cGMP. 2'3' cGMP is a STING agonist in humans.

"Cyclase domains" of cGAS for example, refers to a portion or fragment of the 522 amino acids of the human cGAS protein described in Kranzusch et al. (Cell Reports 2013; 3:1362-1368 PMID 23707061). A cyclase domain may be described as having an NTase core situated from amino acid 160-330, and a regulatory-sensor domain that is the C-domain situated from amino acids 330-522. Mutants of the NTase core sequence as well as mutants of the regulatory-sensor domain can be used to generate constitutively active variants of cGAMP designed to produce high levels of cGAMP without the normal requirement for activation by DNA binding. Another example of a cyclase domain includes M. tuberculosis Rv1354c of NCBI Gene ID: 887485, and the protein encoded by this gene (UniProtKB/Swiss-Prot: P9WM13) that encodes a 623 amino acid-long protein capable of both c-di-GMP (cyclic diguanylate or cyclic di-GMP) synthesis (via its GGDEF domain, amino acids 201-400) and degradation (via its EAL domain, amino acids 401-623). The GAF domain (amino acids 1-200) is a regulatory domain. The GGDEF domain as well as mutants of the regulatory-sensor GAF domain and polypeptides truncated to remove the EAL domain (phosphodiesterase activity) can be used to generate constitutively active variants of Rv1354c designed to produce high levels of c-di-GMP.

By "DisA" or "disA" is meant either 1) a Dis A gene or nucleic acid sequence that encodes a DNA integrity scanning (DisA) protein or 2) the DNA integrity scanning protein. Examples include M tuberculosis disA gene Rv3586 of NCBI Gene ID: 887485, and the protein encoded by this gene is UniProtKB/Swiss-Prot: P9WNW5.1. The protein is a 358 amino acid-long diadenylate cyclase as described by Dey & Bishai et al. Nature Medicine 2015; 21:401-6. PMID: 25730264. A DisA protein is a diadenylate cyclase that makes c-di-AMP. c-di-AMP is a STING agonist.

By "disease" is meant any condition or disorder that damages or interferes with the normal function of a cell, tissue, or organ. Examples of diseases include, but are not limited to, bladder cancer.

By "dncV" is meant a gene that encodes a Cyclic GMP-AMP synthase that catalyzes the synthesis of 3'3'-cyclic GMP-AMP (3'3'-cGAMP) from GTP and ATP, a second messenger in cell signal transduction. dncV is also able to produce c-di-AMP and c-di-GMP from ATP and GTP, respectively; however, 3'3'-cGAMP is the dominant molecule produced by DncV in vivo, contrary to the 2'3'-cGAMP produced by eukaryotes. dncV is required for efficient V. cholerae intestinal colonization, and down-regulates the colonization-influencing process of chemotaxis. dncV is not active with dATP, TTP, UTP, and CTP. The DncV protein is a cyclic GMP-AMP synthase from V. cholerae that makes 3'3'cGAMP. 3'3'cGAMP is a STING agonist.

"EAL domain" means a conserved protein domain that is found in diverse bacterial signaling proteins. The EAL domain may function as a diguanylate phosphodiesterase and has been shown to stimulate degradation of a second messenger, cyclic di-GMP. A non-functional EAL domain will not have one or more of these functions. An example of an EAL domain includes M. tuberculosis Rv1357c gene of NCBI Gene ID: 886815, and the 307 amino acid-long protein encoded by this gene is UniProtKB/Swiss-Prot: P9WM07 that encodes a c-di-GMP phosphodiesterase (PDE) and is comprised of a sole EAL domain. This enzyme's activity is to serve as a c-di-GMP phosphodiesterase, cleaving the cyclic dinucleotide (which has signaling activity) into 2 GMP molecules (which lack signaling activity), as described in the article titled, "A full-length bifunctional protein involved in c-di-GMP turnover is required for long-term survival under nutrient starvation in Mycobacterium smegmatis," Bharati B K, Sharma I M, Kasetty S, Kumar M, Mukherjee R, Chatterji D. Microbiology. 2012 June; 158(Pt 6):1415-27. doi: 10.1099/ mic.0.053892-0. Epub 2012 Feb. 16. PMID: 22343354. Another example of an EAL domain includes the 336 amino acid-long protein encoded by *M. tuberculosis* cdnP gene in H37Rv (Rv2837c), a c-di-AMP phosphodiesterase comprising an EAL domain with the capability of hydrolyzing human 2'-3'cGAMP (the product of the human cGAS enzyme) as shown by Jain-Dey Bishai et al. Nat Chem Biol. 2017; 13:210-217 PMID 28106876. The structural characteristics of the EAL domains (cyclic dinucleotide phosphodiesterase activity) and GGDEF domains (cyclic dinucleotide cyclization-biosynthetic activity) are known and well described (for example, in Schirmer T, Jenal U. Structural and mechanistic determinants of c-di-GMP signaling. Nat Rev Microbiol. 2009; 7:724-35. PMID: 19756011).

By "effective amount" is meant the amount required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "dncV" is meant either 1) a dncV gene or nucleic acid sequence that encodes a cyclic GMP-AMP synthase (DncV) protein, or 2) the Cyclic GMP-AMP synthase protein. Examples include, but are not limited to, the Vibrio cholerae dncV gene of NCBI Gene ID: 2614190 and the protein encoded by this gene is UniProtKB/Swiss-Prot: Q9KVG7.1

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain, for example, 10, 20, 30, 40, 50, 60, 70, 80, 90, 100, 200, 300, 400, 500, 600, 700, 800, 900, or 1000 nucleotides or amino acids.

By "gene deletion" is meant using allelic exchange methodologies well-known to one skilled in the art to delete the full gene coding region of the gene of interest from the chromosome of BCG. Gene replacement with selectable markers such as antibiotic resistance cassettes is a form of allelic exchange and may be performed. Technologies are also available to generate unmarked deletions (no selectable marker) in which the gene is entirely deleted, and no selectable marker is introduced in its place.

By "gene domain deletion" is meant using the above allelic exchange methodologies to remove the portion of a gene encoding a particular domain (in the case of the present invention the EAL domain of Rv1354c which encodes the CDN phosphodiesterase domain of a multifunctional polypeptide) leaving the other portions of the polypeptide intact and in frame.

By "*H. sapiens*" is meant Homo sapiens.

By "obtaining" as in "obtaining an agent" is meant synthesizing, purchasing, or otherwise acquiring the agent.

By "overexpression" is meant, in a general sense, a gene expressing its corresponding protein in a greater quantity than a wild type or reference gene. An example of creating a gene overexpressing a protein in the present invention includes fusing the DNA encoding the gene of interest to a strong promoter in BCG such as Phsp60 or to a strong conditionally active promoter such as PtetOFF. In PtetOFF, gene expression is turned off in the presence of tetracycline, anhydrotetracycline, or doxycycline; however, when the recombinant BCG is administered as an immunotherapy in a human or an animal model, the gene of interest will be turned on. This conditionally active strategy has the advantage of preventing any deleterious effects on viability or growth rate that strong overexpression of cyclic dinucleotide producing enzyme might have on the BCG organisms while the BCG is being grown, and it allows for strong expression ("overexpression") only when the BCG immunotherapy is given as a therapeutic to a mammalian host.

By "Mtb" is meant *Mycobacterium tuberculosis*.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins.

By "reduce" or "decrease" is meant a negative alteration of at least about 10%, 25%, 50%, 75%, or 100%, for example, or any percentage in between.

By "increase" is meant a positive alteration of at least about 10%, 25%, 50%, 75%, or 100%, for example, or any percentage in between.

By "reference" is meant a standard or control condition.

A "reference sequence" is meant a defined sequence used as a basis for sequence comparison. A reference sequence may be a subset of or the entirety of a specified sequence, for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or there between.

By "reference BCG strain" is meant, for example, a conventional BCG strain that does not contain the expression vectors of the present invention and/or the endogenous genes unable to express a cdnP functional protein, a Rv1354c functional protein, a Rv1357c functional protein, or a combination thereof By "regulatory DNA recognition capability" is meant the ability of a protein to detect or bind DNA. For example, a cGAS protein is known to bind DNA, such as cytosolic DNA, and triggers the reaction of GTP and ATP to form cyclic GMP-AMP (cGAMP). cGAMP binds to the Stimulator Interferon Genes (STING) which triggers phosphorylation of IRF3 via TBK1.

By "Rv1354c" is meant either 1) a Rv1354c gene or nucleic acid sequence that encodes a Rv1354c protein or 2) the Rv1354c protein (e.g., Gupta, Kumar, and Chatterji; PLoS ONE (November, 2010); Vol. 5; Issue 11; and Bhariati, Sharma, Kasetty, Kumar, Mukherjee, and Chatterji; Microbiology (2012), 158, 1415-1427). The Rv1354c protein is a diguanylate cyclase that mkes c-di-GMP. C-di-GMP is a STING agonist.

By "Rv1357c" is meant either 1) a Rv1357 gene or nucleic acid sequence that encodes a cyclic di-GMP phosphodiesterase protein (Rv1357) protein or 2) the cyclic di-GMP phosphodiesterase protein (e.g., Gupta, Kumar, and Chatterji; PLoS ONE (November, 2010); Vol. 5; Issue 11; and Bhariati, Sharma, Kasetty, Kumar, Mukherjee, and Chatterji; Microbiology(2012), 158, 1415-1427). The Rv1357c protein is a diguanylate cyclase that mkes c-di-GMP. C-di-GMP is a STING agonist.

By "STING agonist" is meant a molecule which binds to STING (stimulator of interferon genes, or TMEM173), activates it, and triggers activation of the IRF3-TBK1 pathway leading to increased transcription of type 1 interferon and other genes.

By "CDN" is meant cyclic dinuculeotide such as 3'-5' c-di-AMP, 3'-5' c-di-GMP, 3'-3' cGAMP (also known as 3'-5',3'-5'cGAMP, the product of the Vibrio cholerae DncV protein), or 2'-3' cGAMP (also known as 2'-5',3'-5' cGAMP, the product of the human cGAS protein).

By "PAMP" is meant pathogen associated molecular pattern. PAMPs are microbial products including small molecules which are recognized by innate immune sensors. Examples of PAMPs are 3'-5' c-di-AMP, 3'-5' c-di-GMP, 3'-3' cGAMP.

By "DAMP" is meant danger associated molecular pattern. DAMPs are host-derived (that is human, mouse, or other mammalian model of disease) molecules that are produced to signal danger such as infection or other derangement of normal physiology. An example of a DAMP is 2'-3' cGAMP which is produced by the host sensor enzyme cGAS upon detection of double-stranded DNA in the cytosol as occurs during viral or certain intracellular bacterial infections.

By "panCD" is meant the genetic operon from bacteria or other species the encodes the biosynthetic gene panC (encoding the PanC protein which has pantoate-beta-alanine ligase enzymatic activity) and the biosynthetic gene panD (encoding the PanD protein which has aspartate 1-decarboxylase enzymatic activity). The PanC and PanD proteins are required for the biosynthesis of pantothenic acid or pantothenate also called vitamin B5 (a B vitamin). Pantothenic acid, a water-soluble vitamin, is an essential nutrient for bacteria and for all mycobacteria including BCG. Pantothenic acid is required in order to synthesize coenzyme-A (CoA), as well as to synthesize and metabolize proteins, carbohydrates, and fats.

By "specifically binds" is meant a compound, nucleic acid, peptide, protein, or antibody, for example, that recognizes and binds a polypeptide or nucleic acid sequence, but which does not substantially recognize and bind other molecules in a sample.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison. Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline.

By "sensitivity" is meant the percentage of subjects with a particular disease.

By "specificity" is meant the percentage of subjects correctly identified as having a particular disease, i.e., normal or healthy subjects. For example, the specificity is calculated as the number of subjects with a particular disease as compared to normal healthy subjects (e.g.,non-cancer subjects).

By "trained immunity" is meant the ability of one antigenic stimulus to elicit more potent immune responses to a second, different antigen administered at a later time. Trained immunity is antigen-independent, based on heterologous CD4 and CD8 memory activation, cytokine mediated, and is associated with epigenetic and metabolic changes.

By "Phsp60" or "Phsp65" is meant a strong mycobacterial promoter derived from the Mycobacterium leprae Hsp65 5'UTR.

By "5'UTR" is meant the 5' untranslated region of a gene.
By "3'UTR" is meant the 3' untranslated region of a gene.
By "WT" is meant wild type.
By "BCG-WT" is meant a wild type strain of *Mycobacterium bovis* bacillus Calmette Guerin.

Ranges provided herein are to be understood to be shorthand for all of the values within the range. For example, a range of 1 to 50 is to be understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used herein, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Any compositions or methods provided herein can be combined with one or more of any of the other compositions and methods provided herein.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

Such treatment (surgery and/or chemotherapy) will be suitably administered to subjects, particularly humans, suffering from, having, susceptible to, or at risk for bladder cancer or disease, disorder, or symptom thereof. Determination of those subjects "at risk" can be made by any objective or subjective determination by a diagnostic test or opinion of a subject or health care provider (e.g., genetic test, enzyme or protein marker, a marker (as defined herein), family history, and the like). In some embodiments, determination of subjects susceptible to or having a urothelial cancer is determined by measuring levels of at least one of the markers.

In some embodiments, the present invention relates to genetic alterations of *Mycobacterium bovis* BCG (hereafter, "BCG") which generate recombinant BCG (hereafter "rBCG") strains. These strains have greater potency as (i) tuberculosis vaccines and/or (ii) immunotherapies for non-muscle invasive bladder cancer (NMIBC). Some embodiments of the present invention relate to BCG strains that synthesize and secrete high levels of cyclic dinucleotides (CDNs) which are known to elicit valuable immunomodulatory responses from human phagocytic cells such as macrophages, dendritic cells, and others. Another embodiment of this invention is to combine genetic modifications of BCG to generate multivalent CDN-overexpression modifications that include addition of novel CDN-synthesizing genetic material and/or mutations of endogenous BCG phosphodiesterase genes or genetic domains that will enhance the accumulation and release of CDNs.

BCG

BCG (bacillus Calmette Guerin) is a mutant version of *Mycobacterium bovis* generated by the French microbiologists Calmette and Guerin in 1921 by 13 years of serial passage of virulent M bovis. Between 1921 and 1960 BCG was carried by serial passage in numerous world laboratories, until defined seedlots were established and banked in reference laboratories. As such, many dozen variants of BCG exist worldwide such as BCG Pasteur, BCG Tice, BCG Tokyo, BCG Danish, BCG Montreal, etc. The majority of existing BCG strains have now been defined by whole genome sequencing. Major differences between virulent *M. bovis* and the various BCG strains include the deletion of at least 15 regions of difference that comprise genomic deletions in BCG compared with virulent *M. tuberculosis*. Key regions of difference in the development of BCG were RD1 (9.5 kb deletion leading to loss of the Esx-1 secretion system and inability to release antigens ESAT-6 and CFP-10) and RD3 (9.2 kb deletion). Regions of difference RD4-RD11 are absent in all BCG strains compared with virulent *M. tuberculosis*.

Since the 1920s, BCG has been used as a vaccine for prevention of tuberculosis (TB). In 2004 it was estimated that BCG was given to about 100 million children, hence since its introduction BCG has been given to approximately 5 billion humans and as such is the most widely utilized vaccine in history. It is most commonly given intradermally at birth, and to date it is still given in most countries except the United States, Canada, and parts of Europe. BCG has been shown to reduce the incidence of childhood disseminated TB, but BCG-vaccinated individuals are not fully protected from the risk of TB.

Since 1977, BCG has also achieved wide use as a cancer immunotherapy for non-muscle invasive bladder cancer (NMIBC). It is given intravesically weekly for six weeks and in some instances, such as high-risk disease, it is given as maintenance therapy weekly for three weeks at 3, 6, 12, 18, 24, 30, and 36 months after initial therapy. Intravesical BCG has been shown to (i) induce a mononuclear cell infiltrate comprised predominantly of CD4 T cells and macrophages, (ii) increase the expression of interferon gamma (IFNy) in the bladder, and (iii) increase urinary cytokine levels of IL-1, IL-2, IL-6, IL-8, IL-12, IFNγ, and TNFα.

Despite the wide global use of BCG as (i) a vaccine for TB and (ii) an immunotherapy for NMIBC, there is considerable room for improvement in its efficacy. For TB, BCG gives only partial protection predominantly against childhood disseminated tuberculosis. For NMIBC, approximately 30% of patients have BCG-resistant disease. These individuals require riskier treatments with systemic chemotherapy and have higher rates of progression to more invasive forms of bladder cancer.

Urothelial Cancer

Urothelial cancer of the bladder is the most common malignancy of the urinary tract. It is the fourth most common cancer in males and 11th most common in females. It is estimated that approximately 79,000 new cases of bladder cancer will be diagnosed in the USA in 2017, associated with 19,870 deaths. Although the estimated five-year survival for bladder cancer patients is 78%, the rates decline dramatically for patients with locally advanced or metastatic disease. Approximately 75% of patients with bladder cancer present with a disease that is confined to the mucosa (stage Ta, carcinoma in situ) or submucosa (stage T1), known as non-muscle invasive bladder cancer (NMIBC). Transurethral resection is the initial treatment of choice for NMIBC. For patients with muscle invasive bladder cancer (MIBC; T2 or greater), the first-line treatment option is platinum-containing chemotherapy followed by bladder removal. For those patients with NMIBC who do not respond to intravesical treatments, there is high risk of progression to MIBC. Thus, the high rates of recurrence and significant risk of progression mandate that additional therapy be implemented. Improving clinical outcomes for patients with high risk-NMIBC therefore requires the development of novel treatments.

Intra-vesical administration of Bacillus-Calmette Guerin (BCG), developed in the 1970s for NMIBC, provided the first successful immunotherapy against an established solid cancer, and it remains the standard of care for patients with NMIBC. (Askeland E J, Newton M R, O'Donnell M A, Luo Y. Bladder Cancer Immunotherapy: BCG and Beyond. Adv Urol. 2012; 2012:181987. PMID: 22778725. Morales A. BCG: A throwback from the stone age of vaccines opened the path for bladder cancer immunotherapy. Can J Urol. 2017; 24:8788-8793. PMID: 28646932). The exact mechanism of the anti-tumor effects of BCG, which is an attenuated strain of *Mycobacterium bovis*, remains unclear, but it is believed to orchestrate a vigorous immune cellular and humoral immune response, predominantly Th1 response, after binding to the urothelium through fibronectin and integrin a5131 (Redelman-Sidi G, Glickman M S, Bochner B H. The mechanism of action of BCG therapy for bladder cancer—a current perspective. Nat Rev Urol. 2014; 11:153-62. PMID: 24492433). However, typical complete response rates for BCG treatment are 55-65% for papillary tumors and 70-75% for carcinoma in situ (CIS). (Askeland E J, Newton M R, O'Donnell M A, Luo Y. Bladder Cancer Immunotherapy: BCG and Beyond. Adv Urol. 2012; 2012: 181987. PMID: 22778725. Morales A. BCG: A throwback from the stone age of vaccines opened the path for bladder cancer immunotherapy. Can J Urol. 2017; 24:8788-8793. PMID: 28646932). The burden of patients with BCG unresponsive and relapsing disease and of those intolerant to treatment has therefore prompted the need for further improving the efficacy of BCG against NMIBC.

CDNs are Important PAMPs and DAMPs that Generate Valuable Immune Responses for TB and NMIBC.

Bacterial pathogen-associated molecular patterns (PAMPs). Human cells utilize an innate immune monitoring system known as the cytosolic surveillance program (CSP) to detect nucleic acid including cyclic dinucleotides in the cytosol. Originally characterized as a viral defense system, the CSP has now been shown to be important in antibacterial defenses particularly against intracellular bacteria such as *Mycobacterium tuberculosis, Listeria monocytogenes, Salmonella* species, and others. Cytosolic pattern recognition receptors (PRRs) including STING, cGAS, DDX41 and many others are capable of binding to cytosolic CDNs and nucleic acids leading to their activation. A key signaling event is STING activation which leads to activation of TBK1 and IRF3 and subsequent upregulation of type I interferon expression. STING activation by cyclic dinucleotides also leads to the induction of STAT6 which induces chemokines such as CCL2 and CCL20 independently of the TBK1-IRF3 pathway. STING activation is also believed to activate the transcription factor NFKB through the IκB kinase (IKK) activation.

Human danger associated molecular patterns (DAMPs). Cyclic cGAMP (cGAS) synthase is a cytosolic PRR which recognized cytosolic DNA. Upon binding to DNA it undergoes a conformational change that activates its core enzymatic activity which is to catalyze the formation of 2'3' cGAMP. 2'3' cGAMP in turn is a potent DAMP which activates the STING-TBK1-IRF3 axis leading to increased type 1 interferon expression as well as the STAT6 activation and IKK activation.

STING-mediated mechanism of CDN-triggered immune responses. Type I IFNs, produced both by innate immune cells in the tumor microenvironment and by the tumor cells themselves, are known to mediate anti-tumor effects against several malignancies, due to their ability to intervene in all phases of cancer immune-editing. (Zitvogel L, Galluzzi L, Kepp O, Smyth M J, Kroemer G. Type I interferons in anticancer immunity. Nat Rev Immunol. 2015; 15:405-14. PMID: 26027717). STING (stimulator of interferon genes), is a major regulator of type I IFN innate immune responses to pathogens, following recognition of cytosolic DNA by the sensor cyclic GMP-AMP synthase (cGAS). cGAS catalyzes the synthesis of cyclic GMP-AMP (cGAMP), which in turn functions as a second messenger that binds to and activates STING. (Zhao G N, Jiang D S, Li H. Interferon regulatory factors: at the crossroads of immunity, metabolism, and disease. Biochim Biophys Acta. 2015; 1852:365-78. PMID: 24807060). Novel anticancer immunotherapies based on recombinant type I IFNs, type I IFN-encoding vectors, type I IFN-expressing cells, and STING agonists are therefore currently being developed as novel tumor immunotherapies.

Overexpression of the PAMP immunomodulator, 3'-5' c-di-AMP. 3'-5' c-di-AMP is a strong inducer of the STING-TBK1-IRF3 axis. It is produced by mycobacteria including BCG by the disA gene which encodes the DisA protein (BCG protein WP_010950916.1 in BCG, M tuberculosis protein Rv3586 or P9WNW5.1). Mycobacterium tuberculosis (Mtb) synthesizes and secretes c-di-AMP, which activates the interferon regulatory factor (IRF) pathway and type I IFN responses through STING-signaling and cGAS. (Ahmed D, Cassol E. Role of cellular metabolism in regulating type I interferon responses: Implications for tumour immunology and treatment. Cancer Lett. 2017; 409:20-29. PMID: 28888999.). c-di-AMP overexpressing *M.tb* strains showed attenuation of TB in a mouse model. As a mucosal adjuvant, c-di-AMP exerts immune stimulatory effects causing maturation of dendritic cells, up-regulation of co-stimulatory molecules and production of pro-inflammatory cytokines, and strong Th1, Th17 and CD8 T cell responses against pathogens. A c-di-AMP—overexpressing BCG strain (rBCG-disA or BCG-disA-OE) has been constructed and it was surprisingly found that it produced a significantly higher IRF and IFN-β response than BCG itself, indicating that bacteria-derived c-di-AMP gains access to the host cell cytosol despite the absence of the ESX-1 protein secretion system. (Ahmed D, Cassol E. Role of cellular metabolism in regulating type I interferon responses: Implications for tumour immunology and treatment. Cancer Lett. 2017; 409:20-29. PMID: 28888999.). These findings suggest that rBCG strains modified to overexpress c-di-AMP could induce better protective immunity against bladder tumors than BCG itself.

Figure 1A:
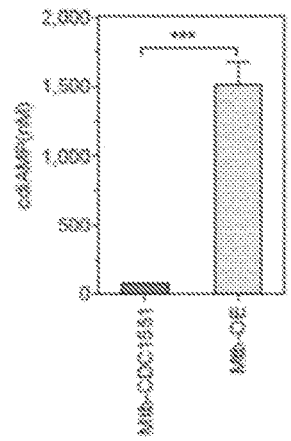
FIGS. 1A-1B Mycobacteria overexpressing disA from the pSD5B $P_{hsp60}$::disA plasmid construct release large amounts of c-di-AMP into the macrophage cytosol and transcribe high levels of disA mRNA.
Figure 1B:
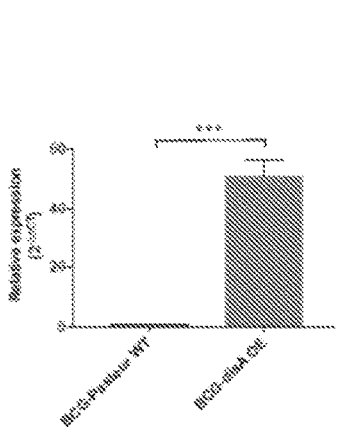

Induction of pro-inflammatory Th1 cytokines in mouse bone marrow-derived macrophages (BMDMs) in response to BCG overexpressing *M.tb* disA (MT3692): *M.tb* genome encodes a di-adenylate cyclase enzyme (DisA, also called DacA, P9WNW5.1 in the UniProtKB/Swiss-Prot databases) that synthesizes c-di-AMP from ATP or ADP. The BCG protein WP_010950916.1 (NCBI reference number) is 100% identical to *M. tuberculosis* DisA. *M.tb* strains overexpressing disA intoxicate macrophages by releasing excessive c-di-AMP, a unique bacterial PAMP that activates STING-dependent IFN-β production. (Ahmed D, Cassol E. Role of cellular metabolism in regulating type I interferon responses: Implications for tumour immunology and treatment. Cancer Lett. 2017; 409:20-29. PMID: 28888999.). To expand the antigenic repertoire of a non-pathogenic vaccine strain, BCG Pasteur was transformed with a kanamycin-resistance (Kan-R)-conferring plasmid that harbors the disA gene (*M. tuberculosis* Rv3586 or MT3692) from *M.tb* (the *M.tb* and BCG disA genes are 100% identical) fused to the strong mycobacterial promoter, $P_{hsp60}$. Addition of this plasmid to BCG-Pasteur increased the level of disA mRNA by 50-fold (FIG. 1b). The closely related *M.tb*-disA-OE strain releases 15-fold more c-di-AMP into the macrophage cytosol than wild type *M.tb*. (FIG. 1a), and hence it is expected that BCG-disA-OE also releases significantly more c-di-AMP into the host cytosol. These disA overexpressor recombinants (rBCG or BCG-disA-OE) were better inducers of STING-dependent IFN-β as compared to the parental strain. Most importantly as reported in PCT/US2016/017248, filed Feb. 10, 2016, guinea pigs vaccinated with rBCG were significantly better protected against aerosol infection with virulent *M.tb*, suggesting improved protective efficacy over existing BCG strain.

Figure 2:
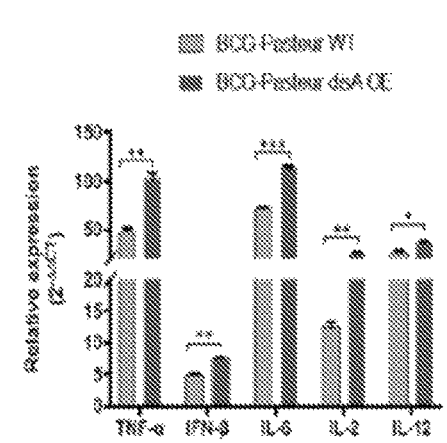
FIG. 2. BCG overexpressing disA augments pro-inflammatory cytokines. Gene expression profiling (qPCR) of pro-inflammatory cytokines and IFN-β in mouse BMDMs challenged with wild-type and disA overexpression strains of BCG-Pasteur.

As shown in FIG. 2, immune responses elicited by BCG-Pasteur disA-OE were tested in an in vitro macrophage infection model. BMDMs from C57BL/6 mice infected with BCG-Pasteur disA-OE showed significant upregulation of IFN-β, TNF-α, IL-6 and IL-2 in comparison to uninfected or wild-type BCG infected macrophages.

Figure 3:
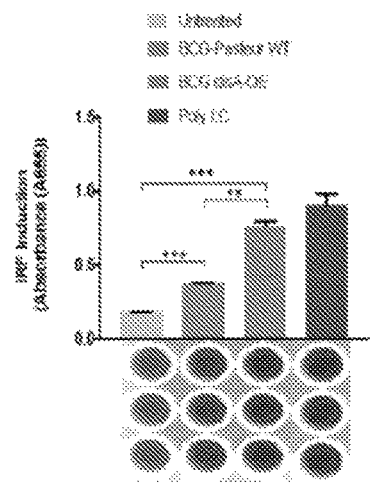
FIG. 3. BCG overexpressing disA augments IRF3 signaling. Effect of disA overexpression on activation of IRF pathway measured by IRF-SEAP QUANTI Blue reporter assay. The culture supernatants of infected RAW-Blue ISG cells were assayed for IRF activation. The image below the IRF-activation graph represents QUANTI Blue assay plate and sample wells; treatment parameters for column of wells correspond to those defined for the bars above aligned with the wells. BCG-disA-OE in this figure is derived from BCG Pasteur.

As shown in FIG. 3, augmented c-di-AMP-based STING activation was confirmed in RAWBlue ISG macrophages. RAWBlue macrophages showed increased IRF3 levels when infected with BCG-Pasteur disA-OE, as compared to parental control.

Figure 4A:
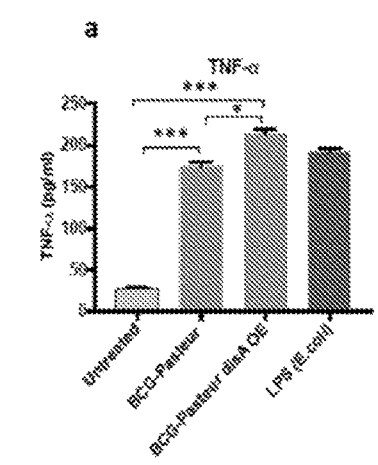
FIGS. 4A-4C. Increased pro-inflammatory cytokines in response to disA overexpression.
Figure 4B:
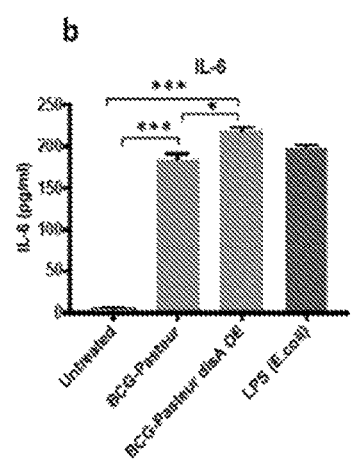
Figure 4C:
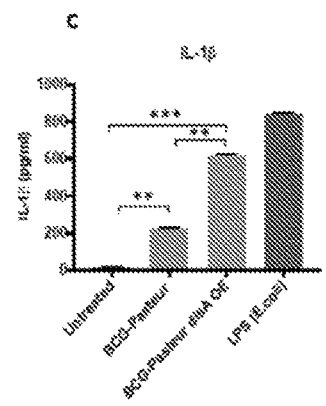

As shown in FIGS. 4A-4C, a significant increase in secreted pro-inflammatory cytokines (TNF-α, IL-6 and IL-1β) was found in culture supernatants of BCG-Pasteur-disA-OE infected mouse BMDMs. These findings indicate that BCG-Pasteur-disA-OE with increased antigenic repertoire acts like a STING agonist, and hence a potent inducer of STING-dependent type I IFNs. Furthermore, the immune responses in macrophages in response to BCG-Pasteur disA-OE were skewed towards Th1, a phenotype largely attributed for control of NMIBC by BCG immunotherapy.

Figure 5:
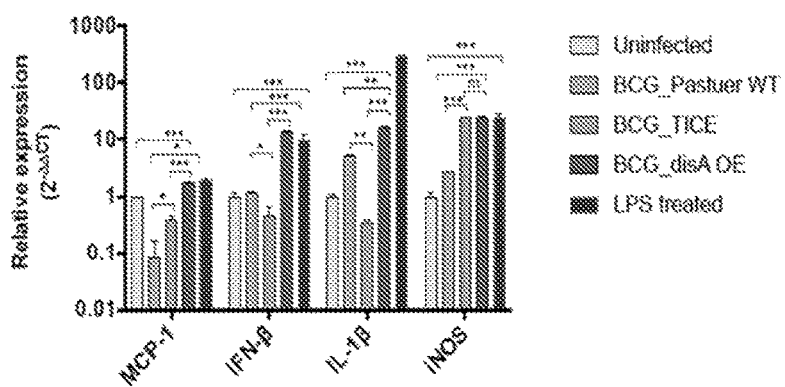
FIG. 5. BCG overexpressing disA induces differential immune response in human bladder cancer cells (RT4). Differential gene expression in human RT4 bladder cancer cells challenged with wild-type BCG-Pasteur, wild-type BCG-Tice strain, and BCG-Pasteur-disA-OE Expression levels of mRNA was measured using a SYBR green-based quantitative real-time PCR.

As shown in FIG. 5, BCG-disA-OE elicits anti-tumor immune responses in human bladder carcinoma (RT4) cells. BCG-Pasteur-disA-OE was tested to determine whether it elicits similar immune responses in bladder cancer (BC) cells, in comparison to WT strains BCG-Pasteur and OncoTICE (the current immunotherapeutic BCG strain). Human RT4 BC cells, derived from human NMIBC tumors, were challenged with the wild-type (both Pasteur and TICE) and recombinant BCG Pasteur disA-OE strain at 1:20 (RT4 BCG) for 3h, and differential gene expression profile was determined in comparison to uninfected cells. Key immune mediators such as, monocyte chemoattractant protein 1 (MCP-1)/CCL2, IFN-β and IL-1β were found to be significantly increased in bladder cancer cells exposed to BCG-Pasteur-disA-OE compared to responses to wild type strains.

Figure 6:
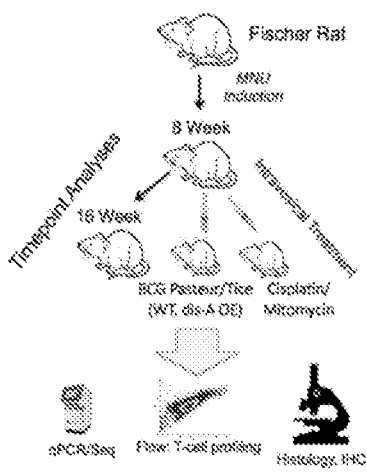
FIG. 6. Schematic workflow of testing relative therapeutic efficacy of wild-type and BCG-disA-OE strains.

As shown in FIG. 6, an experimental system was set up to test whether intravesical BCG-disA-OE immunotherapy leads to heightened Th1 responses and anti-tumor efficacy in the MNU carcinogen model of NMIBC. Results from the aforementioned experiments with RT4 cells encouraged the inventors to test the relative therapeutic efficacy of BCG-Pasteur disA OE in an in vivo rat NMIBC model, pioneered in Bivalacqua lab. (Kates M, Nirschl T, Sopko N A, Matsui H, Kochel C M, Reis L O, Netto G J, Hogue M O, Hahn N M, McConkey D J, Baras A S, Drake C G, Bivalacqua T J. Intravesical BCG Induces CD4(+) T-Cell Expansion in an Immune Competent Model of Bladder Cancer. Cancer Immunol Res. 2017; 5:594-603. PMID: 28588015). In this model, N-methyl-N-nitrosourea (MNU), a carcinogenic alkylating agent, is used to induce urothelial cancer in female Fischer rats.

Figure 7:
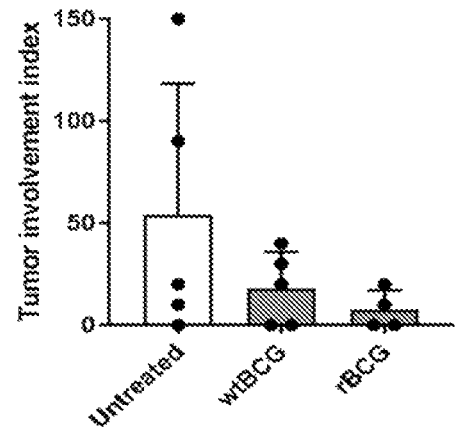
FIG. 7. Tumor involvement index of tumor-bearing rats untreated or treated with WT BCG or rBCG overexpressing disA (rBCG=BCG-Pasteur-disA-OE; wtBCG=BCG-Pasteur).

As can be seen in FIG. 7, BCG-disA-OE has significant immunotherapeutic effects in the rat bladder cancer model. Urothelial dysplasia develops within eight weeks of MNU instillation, and by the 16th week after the first instillation, all rats display carcinoma-in-situ, papillary Ta, or high-grade T1 urothelial carcinoma with histopathologic and immunophenotypic features similar to those observed in human urothelial cancer. Using this model, it was showed that intravesical BCG immunotherapy lead to a large, transient rise in the $CD4^+$ T cell population in the urothelium. (Kates M, Nirschl T, Sopko N A, Matsui H, Kochel C M, Reis L O, Netto G J, Hogue M O, Hahn N M, McConkey D J, Baras A S, Drake C G, Bivalacqua T J. Intravesical BCG Induces CD4(+) T-Cell Expansion in an Immune Competent Model of Bladder Cancer. Cancer Immunol Res. 2017; 5:594-603. PMID: 28588015). Intravesical instillation of BCG-disA-OE strain was performed in MNU-treated rats, administered sequentially every week for 6 weeks starting eight weeks after MNU induction when tumors are visible. Bladder tumors were staged by a GU pathologist according to WHO-ISUP classifications with percent tumor involvement (sum of Ta, T1 and CIS) calculated for each group according to criteria as described. (Kates M, Nirschl T, Sopko N A, Matsui H, Kochel C M, Reis L O, Netto G J, Hogue M O, Hahn N M, McConkey D J, Baras A S, Drake C G, Bivalacqua T J. Intravesical BCG Induces CD4(+) T-Cell Expansion in an Immune Competent Model of Bladder Cancer. Cancer Immunol Res. 2017; 5:594-603. PMID: 28588015). A significant decrease in tumor involvement index in rats treated with BCG-Pasteur disA-OE was found in comparison to bladders from untreated or BCG-Pasteur treated rats.

Figure 8:
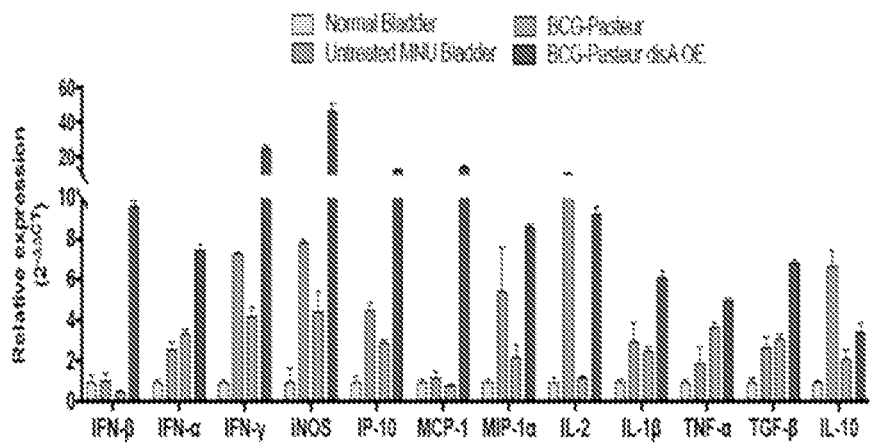
FIG. 8. Immune profiling of MNU-induced Fisher rat urinary bladder tumors in response to intravesical therapy using different strains of BCG. Differential gene expression in rat bladder tumor cells after therapy with wild-type and disA overexpression strains of *Mycobacterium bovis* BCG-Pasteur. Expression levels of mRNA were measured using a TaqMan-based quantitative real-time PCR. BCG-WT is BCG Pasteur and BCG-disA-OE was derived from BCG Pasteur.

As can be seen in FIG. 8, BCG-disA-OE induces a characteristic cytokine and chemokine signature in rat bladders undergoing immunotherapy. Rat urinary bladders from rats treated with BCG-disA-OE showed a significant induction of IFN-α/β, IFN-γ, IL-1β, TNF-α, TGF-β, iNOS, IP-10, MCP-1 and MIP-1α in comparison to untreated or BCG-Pasteur treated rats.

Figure 9:
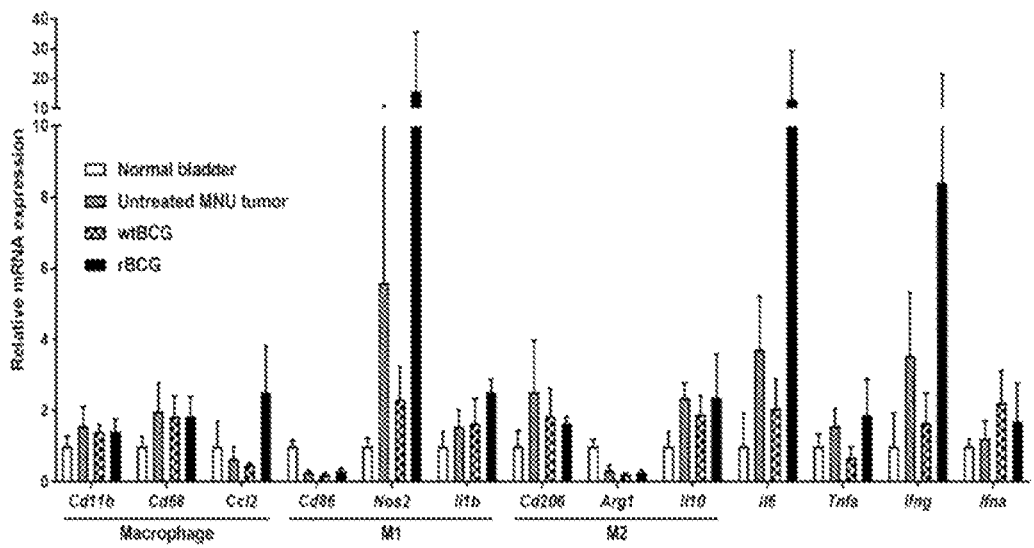
FIG. 9. Gene expression profiling of bladders from MNU tumor bearing rats untreated or treated with WT or rBCG overexpressing disA.
Figure 13A:
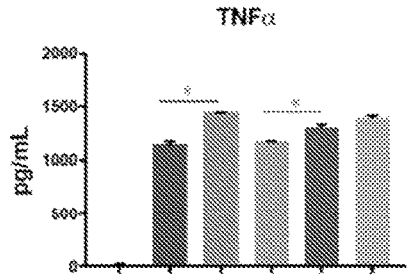
FIGS. 13A-13B. Other BCG strains are also active: BCG Tice strain overexpressing disA also shows induction of proinflammatory cytokines similar to BCG Pasteur overexpressing disA. Bone marrow derived macrophages were challenged with wild-type and disA overexpressing strains of both BCG Pasteur and BCG Tice strains at an M.O.I of 1:20 for 15 h. Culture supernatants were harvested and probed for cytokines using ELISA.
Figure 13B:
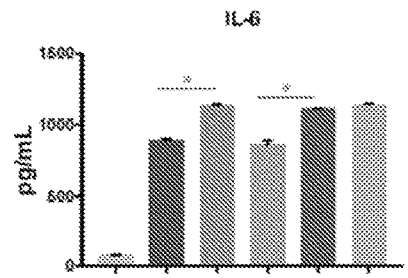
Figure 14:
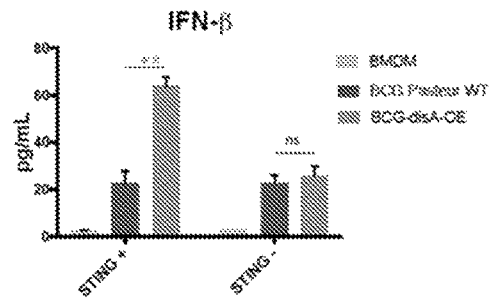
FIG. 14. Type I interferon responses in macrophages in response to BCG-disA-OE are STING-dependent. Bone marrow-derived macrophages from STING-ablated (KO) and control mouse were challenged with wild-type and disA OE strains of BCG Pasteur for 24 h. Culture supernatants were probed for IFN-β levels using ELISA.

As shown in FIG. 9, evidence was found for increased infiltration of $CCL2^+$ macrophages, $Nos2^+$ and $IL-1\beta^+$ M1 macrophages, accompanied by increased IL-6 and IFN-expression in bladders of rats treated with BCG-Pasteur-disA-OE. Interestingly, increased levels of IP-10 were found, which together with increased IFN-γ is known to promote a strong T cell recruitment at the site of infection and inflammation.

FIG. 10 shows a summary of the cytokine expression level changes observed with BCG-disA-OE versus BCG-WT in primary cells, cancer cell lines, and in rat bladder cancer tissues. As can be seen, cytokines associated with Th1 T cell and M1 macrophage expansion, two type 1 interferons, and three pro-inflammatory chemokines were significantly upregulated by BCG-disA-OE compared to BCG-WT (2-fold to 30-fold) across these cells, cell lines and tissues. In contrast, cytokines associated with Th2 T cell and M2 macrophage expansion were generally down-regulated by BCG-disA-OE in comparison to BCG-WT (1-fold to 10-fold).

BCG immunotherapy may be effective via three immune mechanisms: (i) increased generation of tumor-specific cytotoxic CD8 T cells, (ii) cytokine environment which promotes macrophage-mediated CD4 cell activation against tumor antigens, and (iii) macrophage M1 shift promoting enhanced tumoricidal activity. The findings reported herein strongly indicate that BCG overexpressing c-di-AMP is taken up by bladder tumor cells, and myeloid cells that are either resident or recruited to the tumor microenvironment, and induces host immune responses, including activation of STING and type I IFN responses, and NF-κB signaling, that promotes secretion of cytokines and chemokines, macrophage recruitment and apoptotic mechanisms, all of which collectively reduce tumor progression.

In addition to overexpression of disA generating increased levels of the PAMP molecule c-di-AMP, there are additional recombinant DNA modification which may be made to BCG to enhance its production of other PAMP and DAMP molecules. Genes for other CDN cyclases—(i) the GGDEF domain of the BCG_RS07340 protein or *M. tuberculosis* Rv1354c protein (100% identical to each other), (ii) the *Vibrio cholerae* DncV protein, Q9KVG7 in Swiss-Prot, which is a 2'-5'c-GAMP synthase, and (iii) the human cGAS protein Q8N884 in Swiss-Prot which is a 2'-3' cGAMP synthase—may be added to BCG. These added CDN cyclase genes may be added alone or in combination. Such combinations would represent multivalent CDN overexpressing BCG. Also, as shown in FIG. 11, BCG possess several CDN phosphodiesterase genes or genes which contain phosphodiesterase domains. Recombinant technology methods to remove these endogenous phosphodiesterase genes and intragenic phosphodiesterase domains: (i) the BCG WP_003414507 gene which encodes a CDN PDE in BCG that is 100% identical to the *M. tuberculosis* Rv2837c (also called CdnP or CnpB), (ii) the DNA encoding the EAL domain of protein BCG_RS07340 (previously BCG_1416c) which is 100% identical to the known CDN PDE *M. tuberculosis* Rv1354c protein, and (iii) the gene encoding BCG AHM07112 which is homologous the known CDN PDE *M. tuberculosis* Rv1357c. Removal of the genes encoding these PDEs will serve to further increase the levels of CDN PAMP and DAMP molecules produced by the rBCG strains disclosed herein.

SEQ ID NO:1

Diadenylate cyclase DisA from BCG and other related mycobacteria, amino acid sequence (358 amino acids; BCG protein AOQ92_RS18745; NCBI Reference Sequence: NZ_CUWL01000001.1). The identical sequence is present in other strains of BCG, e.g., *Mycobacterium tuberculosis* as protein Rv3586 or MT3692, and in *Mycobacterium bovis* as protein Mb3617.

```
MHAVTRPTLREAVARLAPGTGLRDGLERIL
RGRTGALIVLGHDENVEAICDGGFSLDVRY
AATRLRELCKMDGAVVLSTDGSRIVRANVQ
LVPDPSIPTDESGTRHRSAERAAIQTGYPV
ISVSHSMNIVTVYVRGERHVLTDSATILSR
ANQAIATLERYKTRLDEVSRQLSRAEIEDF
VTLRDVMTVVQRLELVRRIGLVIDYDVVEL
GTDGRQLRLQLDELLGGNDTARELIVRDYH
ANPEPPSTGQINATLDELDALSDGDLLDFT
ALAKVFGYPTTTEAQDSTLSPRGYRAMAGI
PRLQFAHADLLVRAFGTLQGLLAASAGDLQ
SVDGIGAMWARHVREGLSQLAESTISDQ
```

SEQ ID NO:2

Diadenylate cyclase disA from BCG and other related mycobacteria, DNA sequence (1077 nucleotides [358 codons, 1 stop codon]; encodes BCG gene AOQ92_RS18745; NCBI Reference Sequence: NZ_CUWL01000001.1) Identical sequence is present in other strains of BCG, e.g., *Mycobacterium tuberculosis* as gene Rv3586 or MT3692, *Mycobacterium bovis* as gene Mb3617.

```
   1 atgcacgctg tgactcgtcc gaccctgcgt
     gaggctgtcg cccgcctagc ccccgggcact
  61 gggctgcggg acggcctgga gcgtatcctg
     cgcggccgca ctggtgccct gatcgtgctg
 121 ggccatgacg agaatgtcga ggccatctgc
     gatggtggct tctccctcga tgtccgctat
```

-continued

```
 181 gcagcaaccc ggctacgcga gctgtgcaag
     atggacggcg ccgtggtgct gtccaccgac
 241 ggcagccgca tcgtgcgggc caacgtgcaa
     ctggtaccgg atccgtcgat ccccaccgac
 301 gaatcgggga cccggcaccg ctcggccgag
     cgggccgcga tccagaccgg ttacccggtg
 361 atctcagtga gccactcgat gaacatcgtg
     accgtctacg tccgcgggga acgtcacgta
 421 ttgaccgact cggcaaccat cctgtcgcgg
     gccaaccagg ccatcgcaac cctggagcgg
 481 tacaaaacca ggctcgacga ggtcagccgg
     caactgtcca gggcagaaat cgaggacttc
 541 gtcacgctgc gcgatgtgat gacggtggtg
     caacgcctcg agctggtccg gcgaatcggg
 601 ctggtgatcg actacgacgt ggtcgaactc
     ggcactgatg gtcgtcagct gcggctgcag
 661 ctcgacgagt tgctcggcgg caacgacacc
     gcccgggaat tgatcgtgcg cgattaccac
 721 gccaacccgg aaccaccgtc cacggggcaa
     atcaatgcca ccctggacga actggacgcc
 781 ctgtcggacg gcgacctcct cgatttcacc
     gcgctggcaa aggttttcgg atatccgacg
 841 accacggaag cgcaggattc ggcgctgagc
     ccgcgtggct accgcgcgat ggccggtatc
 901 ccccggctcc agttcgccca tgccgacctg
     ctggtccggg cgttcggaac gttgcagggt
 961 ctgctggcgg ccagcgccgg cgatctgcaa
     tcagtggacg gcatcggcgc catgtgggcc
1021 cgtcatgtgc gcgatgggtt gtcacagctg
     gcggaatcga ccatcagcga tcaataa
```

SEQ ID NO:3.

Plasmid pSD5B-$P_{hsp60}$::disA is an episomally replicating *E. coli*-mycobacterial shuttle plasmid that overexpresses the BCG disA gene from the $P_{hsp60}$ promoter, DNA sequence. (7742 nucleotides; promoter $P_{hsp60}$ DNA comprised of a portion of the *M. leprae* hsp65 gene nucleotides 13 to 180 is underlined; disA coding sequence nucleotides 242 to 1318; ATG start codon and TAA stop codon shown in boldface, underline).

| | |
|---|---|
| GGATCCTTCTAGAATTCCGGAATTGCACTCGCCTTAGGGGAGTGCTAAAAATGATCCTGGCACTCGCGATCAGCGAG | 1-77 |
| TGCCAGGTCGGGACGGTGAGACCCAGCCAGCAAGCTGTGGTCGTCCGTCGCGGGCACTGCACCCGGCCAGCGTAAGT | 78-154 |
| AATGGGGGTTGTCGGCACCCGGTGACCTAGACACATGCATGCATGCTTAATTAATTAAGCGATATCCGGAGGAATCA | 155-231 |
| CTTCCATATGATGCACGCTGTGACTCGTCCGACCCTGCGTGAGGCTGTCGCCCGCCTAGCCCCGGGCACTGGGCTGC | 232-308 |
| GGGACGGCCTGGAGCGTATCCTGCGCGGCCGCACTGGTGCCCTGATCGTGCTGGGCCATGACGAGAATGTCGAGGCC | 309-385 |
| ATCTGCGATGGTGGCTTCTCCCTCGATGTCCGCTATGCAGCAACCCGGCTACGCGAGCTGTGCAAGATGGACGGCGC | 386-462 |
| CGTGGTGCTGTCCACCGACGGCAGCCGCATCGTGCGGGCCAACGTGCAACTGGTACCGGATCCGTCGATCCCCACCG | 463-539 |
| ACGAATCGGGGACCCGGCACCGCTCGGCCGAGCGGGCCGCGATCCAGACCGGTTACCCGGTGATCTCAGTGAGCCAC | 540-616 |
| TCGATGAACATCGTGACCGTCTACGTCCGCGGGGAACGTCACGTATTGACCGACTCGGCAACCATCCTGTCGCGGGC | 617-693 |
| CAACCAGGCCATCGCAACCCTGGAGCGGTACAAAACCAGGCTCGACGAGGTCAGCCGGCAACTGTCCAGGGCAGAAA | 694-770 |
| TCGAGGACTTCGTCACGCTGCGCGATGTGATGACGGTGGTGCAACGCCTCGAGCTGGTCCGGCGAATCGGGCTGGTG | 771-847 |
| ATCGACTACGACGTGGTCGAACTCGGCACTGATGGTCGTCAGCTGCGGCTGCAGCTCGACGAGTTGCTCGGCGGCAA | 848-924 |
| CGACACCGCCCGGGAATTGATCGTGCGCGATTACCACGCCAACCCGGAACCACCGTCCACGGGGCAAATCAATGCCA | 925-1001 |
| CCCTGGACGAACTGGACGCCCTGTCGGACGGCGACCTCCTCGATTTCACCGCGCTGGCAAAGGTTTTCGGATATCCG | 1002-1078 |
| ACGACCACGGAAGCGCAGGATTCGACGCTGAGCCCGCGTGGCTACCGCGCGATGGCCGGTATCCCCCGGCTCCAGTT | 1079-1155 |
| CGCCCATGCCGACCTGCTGGTCCGGGCGTTCGGAACGTTGCAGGGTCTGCTGGCGGCCAGCGCCGGCGATCTGCAAT | 1156-1232 |
| CAGTGGACGGCATCGGCGCCATGTGGGCCCGTCATGTGCGCGAGGGGTTGTCACAGCTGGCGGAATCGACCATCAGC | 1233-1309 |
| GATCAATAAACGCGTTCTGGCGTAATAGCGAAGAGGCCCGCACCGATCGCCCTTCCCAACAGTTGCGCAGCCTGAAT | 1310-1386 |
| GGCGAATGGCGCTTTGCCTGGTTTCCGGTCGAAGCTTGGCCGGATCTAAAGTTTTGTCGTCTTTCCAGACGTTAGTA | 1387-1463 |
| AATGAATTTTCTGTATGAGGTTTTGCTAAACAACTTTCAACAGTTTCAGCGGAGTGAGAATAGAAAGGAACAACTAA | 1464-1540 |
| AGGAATTGCGAATAATAATTTTTTCACGTTGAAAATCTCCAAAAAAAAAGGCTCAAAAGGAGCCTTTAATTGTATC | 1541-1617 |
| GGTTTATCAGCTTGCTTTCGAGGTGAATTTCTTAAACAGCTTGATACCGATAGTTGCGCCGACAATGACAACAACCA | 1618-1694 |
| TCGCCCACGCATAACCGATATATTCGGTCGCTGAGGCTTGCAGGGAGTCAAAGGCCGCTTTTGCGGGGATCCGCTCG | 1695-1771 |
| GAGGCGCGGTCGCGGCGCGGCTGTGGCATGTCGGGGCGTGCCGCTCCCCCGGCGCCGCCCATCGGCCCGCCCATTGG | 1772-1848 |
| CATTCCGCCCATGCCGCCCATCATTCCTGTGGAGCCAGAACTGATCCAGCCTGTGCCACAGCCGACAGGATGGTGAC | 1849-1925 |
| CACCATTTGCCCCATATCACCGTCGGTACTGATCCCGTCGTCAATAAACCGAACCGCTACACCCTGAGCATCAAACT | 1926-2002 |
| CTTTTATCAGTTGGATCATGTCGGCGGTGTCGCGGCCAAGACGGTCGAGCTTCTTCACCAGAATGACATCACCTTCC | 2003-2079 |
| TCCACCTTCATCCTCAGCAAATCCAGCCCTTCCCGATCTGTTGAACTGCCGGATGCCTTGTCGGTAAAGATGCGGTT | 2080-2156 |
| AGCTTTTACCCCTGCATCTTTGAGCGCTGAGGTCTGCCTCGTGAAGAAGGTGTTGCTGACTCATACCAGGCCTGAAT | 2157-2233 |
| CGCCCCATCATCCAGCCAGAAAGTGAGGGAGCCACGGTTGATGAGAGCTTTGTTGTAGGTGGACCAGTTGGTGATTT | 2234-2310 |
| TGAACTTTTGCTTTGCCACGGAACGGTCTGCGTTGTCGGGAAGATGCGTGATCTGATCCTTCAACTCAGCAAAGTT | 2311-2387 |
| CGATTTATTCAACAAAGCCGCCGTCCCGTCAAGTCAGCGTAATGCTCTGCCAGTGTTACAACCAATTAACCAATTCT | 2388-2464 |
| GATTAGAAAAACTCATCGAGCATCAAATGAAACTGCAATTTATTCATATCAGGATTATCAATACCATATTTTTGAAA | 2465-2541 |
| AAGCCGTTTCTGTAATGAAGGAGAAAACTCACCGAGGCAGTTCCATAGGATGGCAAGATCCTGGTATCGGTCTGCGA | 2542-2618 |
| TTCCGACTCGTCCAACATCAATACAACCTATTAATTTCCCCTCGTCAAAAATAAGGTTATCAAGTGAGAAATCACCA | 2619-2695 |
| TGAGTGACGACTGAATCCGGTGAGAATGGCAAAAGCTTATGCATTTCTTTCCAGACTTGTTCAACAGGCCAGCCATT | 2696-2772 |
| ACGCTCGTCATCAAAATCACTCGCATCAACCAAACCGTTATTCATTCGTGATTGCGCCTGAGCGAGACGAAATACGC | 2773-2849 |
| GATCGCTGTTAAAAGGACAATTACAAACAGGAATCGAATGCAACCGGCGCAGGAACACTGCCAGCGCATCAACAATA | 2850-2926 |
| TTTTCACCTGAATCAGGATATTCTTCTAATACCTGGAATGCTGTTTTCCCGGGGATCGCAGTGGTGAGTAACCATGC | 2927-3003 |
| ATCATCAGGAGTACGGATAAAATGCTTGATGGTCGGAAGAGGCATAAATTCCGTCAGCCAGTTTAGTCTGACCATCT | 3004-3080 |
| CATCTGTAACATCATTGGCAACGCTACCTTTGCCATGTTTCAGAAACAACTCTGGCGCATCGGGCTTCCCATACAAT | 3081-3157 |

```
CGATAGATTGTCGCACCTGATTGCCCGACATTATCGCGAGCCCATTTATACCCATATAAATCAGCATCCATGTTGGA  3158-3234
ATTTAATCGCGGCCTCGAGCAAGACGTTTCCCGTTGAATATGGCTCATAACACCCCTTGTATTACTGTTTATGTAAG  3235-3311
CAGACAGTTTTATTGTTCATGATGATATATTTTTATCTTGTGCAATGTAACATCAGAGATTTTGAGACACAACGTGG  3312-3388
CTTTGTTGAATAAATCGAACTTTTGCTGAGTTGAAGGATCAGATCACGCATCTTCCCGACAACGCAGACCGTTCCGT  3389-3465
GGCAAAGCAAAAGTTCAAAATCACCAACTGGTCCACCTACAACAAAGCTCTCATCAACCGTGGCTCCCTCACTTTCT  3466-3542
GGCTGGATGATGGGCGATTCAGGCCTGGTATGAGTCAGCAACACCTTCTTCACGAGGCAGACCTCAGCGCTAGCGG  3543-3619
AGTGTATACTGGCTTACTATGTTGGCACTGATGAGGGTGTCAGTGAAGTGCTTCATGTGGCAGGAGAAAAAGGCTG  3620-3696
CACCGGTGCGTCAGCAGAATATGTGATACAGGATATATTCCGCTTCCTCGCTCACTGACTCGCTACGCTCGGTCGTT  3697-3773
CGACTGCGGCGAGCGGAAATGGCTTACGAACGGGCGGAGATTTCCTGGAAGATGCCAGGAAGATACTTAACAGGGA  3774-3850
AGTGAGAGGGCCGCGGCAAAGCCGTTTTTCCATAGGCTCCGCCCCCCTGACAAGCATCACGAAATCTGACGCTCAAA  3851-3927
TCAGTGGTGGCGAAACCCGACAGGACTATAAAGATACCAGGCGTTTCCCCCTGGCGGCTCCCTCGTGCGCTCTCCTG  2928-4004
TTCCTGCCTTTCGGTTTACCGGTGTCATTCCGCTGTTATGGCCGCGTTTGTCTCATTCCACGCCTGACACTCAGTTC  4005-4081
CGGGTAGGCAGTTCGCTCCAAGCTGGACTGTATGCACGAACCCCCCGTTCAGTCCGACCGCTGCGCCTTATCCGGTA  4082-4158
ACTATCGTCTTGAGTCCAACCCGGAAAGACATGCAAAAGCACCACTGGCAGCAGCCACTGGTAATTGATTTAGAGGA  4159-4235
GTTAGTCTTGAAGTCATGCGCCGGTTAAGGCTAAACTGAAAGGACAAGTTTTGGTGACTGCGCTCCTCCAAGCCAGT  4236-4312
TACCTCGGTTCAAAGAGTTGGTAGCTCAGAGAACCTTCGAAAAACCGCCCTGCAAGGCGGTTTTTTCGTTTTCAGAG  4313-4389
CAAGAGATTACGCGCAGACCAAAACGATCTCAAGAAGATCATCTTATTAAGGGGTCTGACGCTCAGTGGAACGAAAA  4390-4466
CTCACGTTAAGGGATTTTGGTCATGAGATTATCAAAAAGGATCTTCACCTAGATCCTTTTAAAAGTGCTCATCATTG  4467-4543
GAAAACGTTCTTCGGGGCGAAAACTCTCAAGGATCTTACCGCTGTTGAGATCCAGTTCGATGTAACCCACTCGTGCA  4544-4620
CCCAACTGATCTTCAGCATCTTTTACTTTCACCAGCGTTTCTGGGTGAGCAAAAACAGGAAGGCAAAATGCCGCAAA  4621-4697
AAAGGGAATAAGGGCGACACGGAAATGTTGAATACTCATACTCTTCCTTTTTCAATATTATTGAAGCATTTATCAGG  4698-4774
GTTATTGTCTCATGAGCGGATACATATTTGAATGTATTTAGAAAAATAAACAAATAGGGGTTCCGCGCACATTTCCC  4775-4851
CGAAAAGTGCCACCTGACGTCTAAGAAACCATTATTATCATGACATTAACCTATAAAAATAGGCGTATCACGAGGCC  4852-4928
CTTTCGTCTTCAAGAATTCCCAGGCATCAAATAAAACGAAAGGCTCAGTCGAAAGACTGGGCCTTTCGTTTTATCTG  4929-5005
TTGTTTGTCGGTGAACGCTCTCCTGAGTAGGACAAATCCGCCGGGAGCGGATTTGAACGTTGCGAAGCAACGGCCCG  5006-5082
GAGGGTGGCGGGCAGGACGCCCGCCATAAACTGCCAGGGAATTCCCATCGAGCCGAGAACGTTATCGAAGTTGGTCA  5083-5159
TGTGTAATCCCCTCGTTTGAACTTTGGATTAAGCGTAGATACACCCTTGGACAAGCCAGTTGGATTCGGAGACAAGC  5160-5236
AAATTCAGCCTTAAAAAGGGCGAGGCCCTGCGGTGGTGGAACACCGCAGGGCCTCTAACCGCTCGACGCGCTGCACC  5237-5313
AACCAGCCCGCGAACGGCTGGCAGCCAGCGTAAGGCGCGGCTCATCGGGCGGCGTTCGCCACGATGTCCTGCACTTC  5314-5390
GAGCCAAGCCTCGAACACCTGCTGGTGTGCACGACTCACCCGGTTGTTGACACCGCGCGCGGCCGTGCGGGCTCGGT  5391-5467
GGGGCGGCTCTGTCGCCCTTGCCAGCGTGAGTAGCGCGTACCTCACCTCGCCCAACAGGTCGCACACAGCCGATTCG  5468-5544
TACGCCATAAAGCCAGGTGAGCCCACCAGCTCCGTAAGTTCGGGCGCTGTGTGGCTCGTACCCGCGCATTCAGGCGG  5545-5621
CAGGGGGTCTAACGGGTCTAAGGCGGCGTGTACGCGGCCACAGCGGCTCTCAGCGGCCCGGAAACGTCCTCGAAACG  5622-5698
ACGCATGTGTTCCTCCTGGTTGGTACAGGTGGTTGGGGGTGCTCGGCTGTCGCGGTTGTTCCACCACCAGGGCTCGA  5699-5775
CGGGAGAGCGGGGAGTGTGCAGTTGTGGGGTGGCCCCTCAGCGAAATATCTGACTTGGAGCTCGTGTCGGACCATA  5776-5852
CACCGGTGATTAATCGTGGTCTACTACCAAGCGTGAGCCACGTCGCCGACGAATTTGAGCAGCTCTGGCTGCCGTAC  5853-5929
TGGCCGCTGGCAAGCGACGATCTGCTCGAGGGGATCTACCGCCAAAGCCGCGCGTCGGCCCTAGGCCGCCGGTACAT  5930-6006
CGAGGCGAACCCAACAGCGCTGGCAAACCTGCTGGTCGTGGACGTAGACCATCCAGACGCAGCGCTCCGAGCGCTCA  6007-6083
GCGCCCGGGGGTCCCATCCGCTGCCCAACGCGATCGTGGGCAATCGCGCCAACGGCCACGCACACGCAGTGTGGGCA  6084-6160
CTCAACGCCCCTGTTCCACGCACCGAATACGCGCGGCGTAAGCCGCTCGCATACATGGCGGCGTGCGCCGAAGGCCT  6161-6237
```

-continued

```
TCGGCGGCCGTCGACGGCGACCGCAGTTACTCAGGCCTCATGACCAAAAACCCCGGCCACATCGCCTGGGAAACGGA   6238-6314

ATGGCTCCACTCAGATCTCTACACACTCAGCCACATCGAGGCCGAGCTCGGCGCGAACATGCCACCGCCGCGCTGGC   6315-6391

GTCAGCAGACCACGTACAAAGCGGCTCCGACGCCGCTAGGGCGGAATTGCGCACTGTTCGATTCCGTCAGGTTGTGG   6392-6468

GCCTATCGTCCCGCCCTCATGCGGATCTACCTGCCGACCCGGAACGTGGACGGACTCGGCCGCGCGATCTATGCCGA   6469-6545

GTGCCACGCGCGAAACGCCGAATTCCCGTGCAACGACGTGTGTCCCGGACCGCTACCGGACAGCGAGGTCCGCGCCA   6546-6622

TCGCCAACAGCATTTGGCGTTGGATCACAACCAAGTCGCGCATTTGGGCGGACGGGATCGTGGTCTACGAGGCCACA   6623-6699

CTCAGTGCGCGCCAGTCGGCCATCTCGCGGAAGGGCGCAGCAGCGCGCACGGCGGCGAGCACAGTTGCGCGGCGCGC   6700-6776

AAAGTCCGCGTCAGCCATGGAGGCATTGCTATGAGCGACGGCTACAGCGACGGCTACAGCGACGGCTACAACCGGCA   6777-6853

GCCGACTGTCCGCAAAAAGCCGTGACGCGCCGAAGGCGCTCGAATCACCGGACTATCCGAACGCCACGTCGTCCGGC   6854-6930

TCGTGGCGCAGGAACGCAGCGAGTGGCTCGCCGAGCAGGCTGCACGCGCGCGAAGCATCCGCGCCTATCACGACGAC   6931-7007

GAGGGCCACTCTTGGCCGCAAACGGCCAAACATTTCGGGCTGCATCTGGACACCGTTAAGCGACTCGGCTATCGGGC   7008-7084

GAGGAAAGAGCGTGCGGCAGAACAGGAAGCGGCTCAAAAGGCCCACAACGAAGCCGACAATCCACCGCTGTTCTAAC   7085-7161

GCAATTGGGGACGGGTGTCGCGGGGGTTCCGTGGGGGGTTCCGTTGCAACGGGTCGGACAGGTAAAAGTCCTGGTAG   7162-7238

ACGCTAGTTTTCTGGTTTGGGCCATGCCTGTCTCGTTGCGTGTTTCGTTGCGCCGTTTTGAATACCAGCCAGACGAG   7239-7315

ACGGGGTTCTACGAATCTTGGTCGATACCAAGCCATTTCCGCTGAATATCGGGGAGCTCACCGCCAGAATCGGTGGT   7316-7392

TGTGGTGATGTACGTGGCGAACTCCGTTGTAGTGCCTGTGGTGGCATCCGTGGCCACTCTCGTTGCACGGTTCGTTG   7393-7469

TGCCGTTACAGGCCCCGTTGACAGCTCACCGAACGTAGTTAAAACATGCTGGTCAAACTAGGTTTACCAACGATACG   7470-7546

AGTCAGCTCATCTAGGGCCAGTTCTAGGCGTTGTTCGTTGCGCGGTTCGTTGCGCATGTTTCGTGTGGTTGCTAGAT   7547-7623

GGCTCCGCAACCACACGCTTCGAGGTTGAGTGCTTCCAGCACGGGCGCGATCCAGAAGAACTTCGTCGTGCGACTGT   7624-7700

CCTCGTTGGGATCTAGCCCGCCTAATGAGCGGGCTTTTTTT                                       7701-7742
```

Mycobacteria overexpressing disA are attenuated for virulence. As shown in FIG. 12, when mice are infected with 3.5 $\log_{10}$ units by the aerosol route of either *M. tuberculosis* harboring the pSD5B P$_{hsp60}$::disA plasmid (*M. tb*-disA-OE or *Mtb*-OE) or wild type *M. tuberculosis* (Mtb-CDC1551), there are profound differences in the median time to death (MTD) of the animals. As can be seen, wild type *M. tuberculosis* (Mtb-CDC1551) gave an MTD of 150.5 days, while *M. tuberculosis* harboring the pSD5B P$_{hsp60}$::disA plasmid (*M.tb*-disA-OE or *Mtb*-OE) was a significantly weaker pathogen giving an MTD of 321.5 days. A similar reduction in the pathogenicity is to be expected with BCG-disA-OE compared with BCG-WT. Hence, it is likely that should BCG-disA-OE be used as a cancer immunotherapy, one would anticipate reduced rates of bloodstream dissemination, reduced dysuria, reduced urgency and reduced malaise compared with BCG-WT.

Addition of CDN Cyclase Genes to rBCG Other than disA

Overexpression of the PAMP immunomodulator, 3'-5' c-di-GMP by overexpressing the GGDEF domain of protein BCG RS07340. 3'-5' c-di-GMP is a strong inducer of the STING-TBK1-IRF3 axis. It is produced by mycobacteria including BCG by the GGDEF domain of protein BCG_RS07340 (previously BCG 1416c) and by the *M. tuberculosis* Rv1354c gene. The BCG_RS07340 protein (100% identical to the *M. tuberculosis* Rv1354c protein) encodes a bifunctional diguanylate cyclase/diguanylate phosphodiesterase. Hence the portion that functions as a diguanylate cyclase is an endogenous CDN-producing enzyme in BCG. The full-length BCG_RS07340 polypeptide is 623 amino acids in length, and its domain structure is: N-terminus-GAF-GGDEF-EAL-C-terminus. The GAF domain (approximately amino acids 1-190) is a regulatory domain which influences the activity of the other domains. The GGDEF domain (approximately amino acids 190-350) is a diguanylate cyclase catalyzing the reaction 2 GTP→c-di-GMP+2 pyrophosphates. The EAL domain (approximately amino acids 350-623) is a diguanylate phosphodiesterase catalyzing the reaction c-di-GMP→2 GMP. By genetically removing the DNA sequences that encode the C-terminal EAL domain, it is possible to use the DNA encoding the GGDEF domain to generate a recombinant BCG that will overexpress diguanulate cyclase activity. This may be accomplished by also deleting the DNA encoding the regulatory-sensor GAF domain and/or the use of mutations in the DNA encoding the GAF domain to relieve any cyclase inhibitory activity it may possess. Such techniques to generate constitutively active recombinant forms of the BCG_RS07340 protein will produce high levels of c-di-GMP in recombinant BCG.

SEQ ID NO:4

Bifunctional diguanylate cyclase/phosphodiesterase BCG_RS07340 from BCG and other related mycobacteria, amino acid sequence (623 amino acids; BCG protein BCG_RS07340; NCBI Reference Sequence: NC_008769.1; Protein ID WP 003898837.1; old locus tag BCG_1416c). The identical sequence is present in other strains of BCG, e.g., *Mycobacterium tuberculosis* as protein Rv1354c or MT1397, and in *Mycobacterium bovis* as protein Mb1389c. The EAL domain is from amino acid 354 to 623 and is underlined.

MCNDTATPQLEELVTTVANQLMTVDAATSAEVSQRVLAYLVEQL

GVDVSFLRHNDRDRRATRLVAEWPPRLNIPDPDPLRLIYFADAD

PVFALCEHAKEPLVFRPEPATEDYQRLIEEARGVPVTSAAAVPL

VSGEITTGLLGFIKFGDRKWHEAELNALMTIATLFAQVQARVAA

EARLRYLADHDDLTGLHNRRALLQHLDQRLAPGQPGPVAALFLD

LDRLKAINDYLGHAAGDQFIHVFAQRIGDALVGESLIARLGGDE

FVLIPASPMSADAAQPLAERLRDQLKDHVAIGGEVLTRTVSIGV

ASGTPGQHTPSDLLRRADQAALAAKHAGGDSVAIFTADMSVSGE

LRNDIELHLRRGIESDALRLVYLPEVDLRTGDIVGTEALVRWQH

PTRGLLAPGCFIPVAESINLAGELDRWVLRRACNEFSEWQSAGL

GHDALLRINVSAGQLVTGGFVDFVADTIGQHGLDASSVCLEITE

NVVVQDLHTARATLARLKEVGVHIAIDDFGTGYSAISLLQTLPI

DTLKIDKTFVRQLGTNTSDLVIVRGIMTLAEGFQLDVVAEGVET

EAAARILLDQRCYRAQGFLFSRPVPGEAMRHMLSARRLPPTCIP

ATDPALS

SEQ ID NO:5

Bifunctional diguanylate cyclase/phosphodiesterase BCG_RS07340 from BCG and other related mycobacteria, DNA sequence (1872 nucleotides [623 codons+1 stop codons]; encodes BCG protein BCG_RS07340; NCBI Reference Sequence: NC_008769.1; Protein ID WP 003898837.1; old locus tag BCG_1416c; DNA from NC_008769.1: c1548390-1546519 *Mycobacterium bovis* BCG Pasteur 1173P2). The identical sequence is present in other strains of BCG, e.g., *Mycobacterium tuberculosis* as protein Rv1354c or MT1397, and in *Mycobacterium bovis* as protein Mb1389c. EAL domain is encoded from nucleotide 1060 to 1872 and is underlined.

ATGTGCAACGACACCGCGACGCCGCAGCTTGAGGAGCTCGTCACCACCGTAGCCAACCAGCTCATGACAG

TCGACGCTGCCACGTCAGCCGAAGTCAGTCAGCGCGTTTTGGCCTATCTAGTGGAACAGCTGGGCGTAGA

TGTCAGCTTTTTGCGTCATAACGATCGCGACAGGCGCGCGACGAGGCTGGTGGCCGAATGGCCACCTCGC

CTCAACATACCGGACCCCGATCCGCTCAGGCTGATCTACTTCGCTGATGCCGACCCGGTGTTTGCGCTAT

GCGAACACGCCAAAGAGCCTCTCGTGTTCCGGCCCGAGCCGGCCACCGAGGACTATCAACGCCTCATCGA

AGAAGCCCGCGGGGTTCCGGTAACGTCGGCTGCCGCCGTGCCGCTGGTATCTGGCGAGATCACCACTGGA

CTGCTGGGGTTCATCAAGTTCGGTGATCGGAAATGGCACGAGGCCGAGCTTAACGCCCTCATGACCATCG

CTACACTCTTCGCCCAGGTGCAGGCTCGCGTCGCCGCCGAGGCGCGGCTTCGCTATCTGGCCGACCATGA

CGATCTGACCGGACTGCATAACCGTCGCGCGTTGCTGCAGCACCTGGACCAAAGACTGGCCCCCGGACAA

CCTGGCCCGGTCGCGGCGCTATTTCTCGACTTGGACCGCCTCAAGGCCATCAACGACTACCTGGGCCACG

CCGCCGGTGACCAGTTCATCCATGTGTTCGCCCAACGGATCGGTGACGCACTCGTTGGCGAGAGCCTGAT

CGCCCGACTCGGCGGCGACGAATTCGTCCTCATACCCGCATCTCCAATGAGTGCCGATGCCGCTCAACCG

CTCGCCGAACGTCTTCGCGACCAGCTCAAGGACCACGTCGCTATCGGCGGTGAGGTGCTCACCCGCACCG

TCAGTATCGGTGTCGCCTCAGGGACTCCCGGACAGCACACACCGTCGGACCTCCTGCGCCGAGCCGACCA

AGCCGCTCTGGCAGCCAAACACGCCGGCGGAGATAGCGTCGCGATTTTCACCGCGGACATGTCGGTCAGC

GGCGAACTGCGCAACGATATTGAACTACACCTTCGACGTGGTATCGAATCCGACGCCCTTCGCCTGGTCT

ACCTACCCGAGGTCGACCTACGGACCGGCGACATTGTCGGGACCGAGGCATTGGTCCGGTGGCAGCACCC

CACCCGTGGGCTGCTGGCACCGGGCTGCTTCATCCCTGTGGCCGAATCCATCAACCTTGCAGGCGAATTG

GATAGATGGGTGCTGCGGAGGGCCTGCAATGAATTCTCCGAGTGGCAGTCAGCCGGTTTGGGCCACGACG

CGCTGCTGCGTATCAACGTCTCAGCTGGACAGCTGGTGACGGGCGGGTTTGTTGACTTCGTCGCAGACAC

GATCGGCCAGCACGGTCTGGACGCCTCGTCCGTGTGTTTGGAAATCACCGAAAACGTTGTGGTGCAAGAC

CTACATACCGCCAGAGCCACCCTGGCTCGACTCAAAGAAGTCGGCGTTCACATCGCTATCGACGATTTCG

GCACCGGCTATAGCGCCATATCACTGTTGCAGACGCTACCGATCGACACGCTCAAGATCGACAAAACATT

CGTGCGGCAACTCGGAACCAACACTAGCGATCTGGTCATTGTGCGCGGCATCATGACACTCGCCGAAGGC

TTCCAACTCGATGTAGTAGCCGAAGGCGTCGAGACCGAGGCTGCCGCCAGAATTCTATTGGATCAGCGCT

GTTACCGTGCGCAAGGCTTCTTGTTCTCCCGGCCTGTCCCCGGGGAGGCCATGCGGCACATGTTGTCCGC

ACGACGACTACCGCCGACCTGCATACCTGCAACTGACCCGGCGTTATCTTGA

SEQ ID NO:6

Modified bifunctional diguanylate cyclase/phosphodiesterase from BCG and other related mycobacteria, with its EAL domain deleted so that it acts as a monofunctional diguanylate cyclase, amino acid sequence (353 amino acids; a fragment of BCG protein BCG_RS07340; NCBI Reference Sequence: NC_008769.1; Protein ID WP 003898837.1; old locus tag BCG_1416c). The identical sequence fragment is present in other strains of BCG, e.g., *Mycobacterium tuberculosis* as protein Rv1354c or MT1397, and in *Mycobacterium bovis* as protein Mb1389c.

MCNDTATPQLEELVTTVANQLMTVDAATSAEVSQRVLAYLVEQLGVDVSF

LRHNDRDRRATRLVAEWPPRLNIPDPDPLRLIYFADADPVFALCEHAKEP

LVFRPEPATEDYQRLIEEARGVPVTSAAAVPLVSGEITTGLLGFIKFGDR

KWHEAELNALMTIATLFAQVQARVAAEARLRYLADHDDLTGLHNRRALLQ

HLDQRLAPGQPGPVAALFLDLDRLKAINDYLGHAAGDQFIHVFAQRIGDA

LVGESLIARLGGDEFVLIPASPMSADAAQPLAERLRDQLKDHVAIGGEVL

TRTVSIGVASGTPGQHTPSDLLRRADQAALAAKHAGGDSVAIFTADMSVS

GEL

SEQ ID NO:7

Modified, bifunctional diguanylate cyclase/phosphodiesterase from BCG and other related mycobacteria, with sequences encoding its EAL domain deleted so that it encodes a monofunctional diguanylate cyclase, DNA sequence (1059 nucleotides [353 codons+0 stop codons]; encodes a fragment of BCG protein BCG_RS07340; NCBI Reference Sequence: NC_008769.1; Protein ID WP 003898837.1; old locus tag BCG 1416c; DNA from NC_008769.1: c1548390-1546519 *Mycobacterium bovis* BCG Pasteur 1173P2). The identical sequence is present in other strains of BCG, e.g., *Mycobacterium tuberculosis* as a fragment of gene Rv1354c or MT1397, and in *Mycobacterium bovis* as a fragment of gene Mb1389c.

ATGTGCAACGACACCGCGACGCCGCAGCTTGAGGAGCTCGTCACCACCGT

AGCCAACCAGCTCATGACAGTCGACGCTGCCACGTCAGCCGAAGTCAGTC

AGCGCGTTTTGGCCTATCTAGTGGAACAGCTGGGCGTAGATGTCAGCTTT

TTGCGTCATAACGATCGCGACAGGCGCGCGACGAGGCTGGTGGCCGAATG

GCCACCTCGCCTCAACATACCGGACCCCGATCCGCTCAGGCTGATCTACT

TCGCTGATGCCGACCCGGTGTTTGCGCTATGCGAACACGCCAAAGAGCCT

CTCGTGTTCCGGCCCGAGCCGGCCACCGAGGACTATCAACGCCTCATCGA

AGAAGCCCGCGGGGTTCCGGTAACGTCGGCTGCCGCCGTGCCGCTGGTAT

CTGGCGAGATCACCACTGGACTGCTGGGGTTCATCAAGTTCGGTGATCGG

AAATGGCACGAGGCCGAGCTTAACGCCCTCATGACCATCGCTACACTCTT

CGCCCAGGTGCAGGCTCGCGTCGCCGCCGAGGCGCGGCTTCGCTATCTGG

CCGACCATGACGATCTGACCGGACTGCATAACCGTCGCGCGTTGCTGCAG

CACCTGGACCAAAGACTGGCCCCCGGACAACCTGGCCCGGTCGCGGCGCT

ATTTCTCGACTTGGACCGCCTCAAGGCCATCAACGACTACCTGGGCCACG

CCGCCGGTGACCAGTTCATCCATGTGTTCGCCCAACGGATCGGTGACGCA

CTCGTTGGCGAGAGCCTGATCGCCCGACTCGGCGGCGACGAATTCGTCCT

CATACCCGCATCTCCAATGAGTGCCGATGCCGCTCAACCGCTCGCCGAAC

GTCTTCGCGACCAGCTCAAGGACCACGTCGCTATCGGCGGTGAGGTGCTC

ACCCGCACCGTCAGTATCGGTGTCGCCTCAGGGACTCCCGGACAGCACAC

ACCGTCGGACCTCCTGCGCCGAGCCGACCAAGCCGCTCTGGCAGCCAAAC

ACGCCGGCGGAGATAGCGTCGCGATTTTCACCGCGGACATGTCGGTCAGC

GGCGAACTG

Overexpression of the PAMP immunomodulator, 2'-5'c-GAMP synthase: Q9KVG7 (Swiss-Prot). 2'-5' c-GAMP is a strong inducer of the STING-TBK1-IRF3 axis. The *Vibrio cholerae* Q9KVG7 protein (436 amino acids) encoded by the dncV gene is a known 2'-5'c-GAMP synthase. It is possible to generate a recombinant dncV gene which is codon-optimized for BCG. The codon-optimized structural gene may be overexpressed in BCG by fusion to a strong promoter (such as Phsp60) or a conditionally active strong promoter such as PTET-off. Such techniques to generate a constitutively active recombinant forms of the Q9KVG7 protein will produce high levels of 2'-5'c-GAMP in recombinant BCG.

SEQ ID NO:8

Cyclic GMP-AMP synthase, DncV, from *Vibrio cholerae*, amino acid sequence (436 amino acids; UniProtKB/Swiss-Prot Protein ID Q9KVG7.1).

MRMTWNFHQYYTNRNDGLMGKLVLTDEEKNNLKALRKIIRLRTRDVFEEA

KGIAKAVKKSALTFEIIQEKVSTTQIKHLSDSEQREVAKLIYEMDDDARD

EFLGLTPRFWTQGSFQYDTLNRPFQPGQEMDIDDGTYMPMPIFESEPKIG

HSLLILLVDASLKSLVAENHGWKFEAKQTGCRIKIEAEKTHIDVPMYAIP

KDEFQKKQIALEANRSFVKGAIFESYVADSITDDSETYELDSENVNLALR

EGDRKWINSDPKIVEDWFNDSCIRIGKHLRKVCRFMKAWRDAQWDVGGPS

SISLMAATVNILDSVAHDASDLGETMKIIAKHLPSEFARGVESPDSTDEK

PLFPPPSYKHGPREMDIMSKLERLPEILSSAESADSKSEALKKINMAFGNR

VTNSELIVLAKALPAFAQEPSSASKPEKISSTMVSG

SEQ ID NO: 9

Cyclic GMP-AMP synthase, DncV, from *Vibrio cholerae*, DNA sequence (1311 nucleotides [436 codons+1 stop codon]; encodes UniProtKB/Swiss-Prot Protein ID Q9KVG7.1; NCBI Reference Sequence: NC_002505.1: *Vibrio cholerae* O1 biovar El Tor str. N16961 chromosome I, complete sequence, and nucleotides 180419-181729)

GTGAGAATGACTTGGAACTTTCACCAGTACTACACAAACCGAAATGATGG

CTTGATGGGCAAGCTAGTTCTTACAGACGAGGAGAAGAACAATCTAAAGG

CATTGCGTAAGATCATCCGCTTAAGAACACGAGATGTATTTGAAGAAGCT

AAGGGTATTGCCAAGGCTGTGAAAAAAGTGCTCTTACGTTTGAAATTAT

TCAGGAAAAGGTGTCAACGACCCAAATTAAGCACCTTTCTGACAGCGAAC

AACGAGAAGTGGCTAAGCTTATTTACGAGATGGATGATGATGCTCGTGAT

GAGTTTTTGGGATTGACACCTCGCTTTTGGACTCAGGGAAGCTTTCAGTA

```
TGACACGCTGAATCGCCCGTTTCAGCCTGGTCAAGAAATGGATATTGATG

ATGGAACCTATATGCCAATGCCTATTTTTGAGTCAGAGCCTAAGATTGGT

CATTCTTTACTAATTCTTCTTGTTGACGCGTCACTTAAGTCACTTGTAGC

TGAAAATCATGGCTGGAAATTTGAAGCTAAGCAGACTTGTGGGAGGATTA

AGATTGAGGCAGAGAAAACACATATTGATGTACCAATGTATGCAATCCCT

AAAGATGAGTTCCAGAAAAAGCAAATAGCTTTAGAAGCAAATAGATCATT

TGTTAAAGGTGCCATTTTTGAATCATATGTTGCAGATTCAATTACTGACG

ATAGTGAAACTTATGAATTAGATTCAGAAAACGTAAACCTTGCTCTTCGT

GAAGGTGATCGGAAGTGGATCAATAGCGACCCCAAAATAGTTGAAGATTG

GTTCAACGATAGTTGTATACGTATTGGTAAACATCTTCGTAAGGTTTGTC

GCTTTATGAAAGCGTGGAGAGATGCGCAGTGGGATGTTGGAGGTCCGTCA

TCGATTAGTCTTATGGCTGCAACGGTAAATATTCTTGATAGCGTTGCTCA

TGATGCTAGTGATCTCGGAGAAACAATGAAGATAATTGCTAAGCATTTAC

CTAGTGAGTTTGCTAGGGGAGTAGAGAGCCCTGACAGTACCGATGAAAAG

CCACTCTTCCCACCCTCTTATAAGCATGGCCCTCGGGAGATGGACATTAT

GAGCAAACTAGAGCGTTTGCCAGAGATTCTGTCATCTGCTGAGTCAGCTG

ACTCTAAGTCAGAGGCCTTGAAAAAGATTAATATGGCGTTTGGGAATCGT

GTTACTAATAGCGAGCTTATTGTTTTGGCAAAGGCTTTACCGGCTTTCGC

TCAAGAACCTAGTTCAGCCTCGAAACCTGAAAAAATCAGCAGCACAATGG

TAAGTGGCTGA
```

Overexpression of the DAMP immunomodulator, 2'-3' cGAMP synthase: Q8N884 (Swiss-Prot). 2'-3' cGAMP is a strong inducer of the STING-TBK1-IRF3 axis. The cGAS protein is produced by the human cGAS gene to yield a 522 amino acid polypeptide which senses cytosolic DNA and functions as a 2'-3' cGAMP synthase. The synthase or cyclase domain of cGAS becomes activated when cGAS binds to DNA. It is possible to generate a recombinant cGAS gene which contains only the cyclase domain and is hence constitutively active. This recombinant gene can also be codon-optimized for BCG. The codon-optimized structural gene may be overexpressed in BCG by fusion to a strong promoter (such as Phsp60) or a conditionally active strong promoter such as PTET-off. Such techniques to generate a constitutively active recombinant forms of the cGAS protein will produce high levels of 2'-3'c-GAMP in recombinant BCG.

SEQ ID NO:10

Cyclic 2'3'-GMP-AMP synthase, cGAS, from Homo sapiens, amino acid sequence (522 amino acids, UniProtKB/Swiss-Prot Protein ID Q8N884.2).

MQPWHGKAMQRASEAGATAPKASARNARGAPMDPTESPAAPEAALPKAGK

FGPARKSGSRQKKSAPDTQERPPVRATGARAKKAPQRAQDTQPSDATSAP

GAEGLEPPAAREPALSRAGSCRQRGARCSTKPRPPPGPWDVPSPGLPVSA

PILVRRDAAPGASKLRAVLEKLKLSRDDISTAAGMVKGVVDHLLLRLKCD

SAFRGVGLLNTGSYYEHVKISAPNEFDVMFKLEVPRIQLEEYSNTRAYYF

VKFKRNPKENPLSQFLEGEILSASKMLSKFRKIIKEEINDIKDTDVIMKR

-continued

KRGGSPAVTLLISEKISVDITLALESKSSWPASTQEGLRIQNWLSAKVRK

QLRLKPFYLVPKHAKEGNGFQEETWRLSFSHIEKEILNNHGKSKTCCENK

EEKCCRKDCLKLMKYLLEQLKERFKDKKHLDKFSSYHVKTAFFHVCTQNP

QDSQWDRKDLGLCFDNCVTYFLQCLRTEKLENYFIPEFNLFSSNLIDKRS

KEFLTKQIEYERNNEFPVFDEF

SEQ ID NO:11

Cyclic 2'3'-GMP-AMP synthase, cGAS, from *Homo sapiens*, DNA sequence of mRNA with nucleotide T used in place of U (1802 nucleotides; encodes UniProtKB/Swiss-Prot Protein ID Q8N884.2; NCBI Reference Sequence: NM_138441.2. Coding sequence is 1569 nucleotides [522 codons, 1 stop codon], start codon ATG [bold underlined] at nucleotide 140; Stop codon TGA (bold, underlined) at nucleotide 17061).

AGCCTGGGGTTCCCCTTCGGGTCGCAGACTCTTGTGTGCCCGCCAGTAGT

GCTTGGTTTCCAACAGCTGCTGCTGGCTCTTCCTCTTGCGGCCTTTTCCT

GAAACGGATTCTTCTTTCGGGGAACAGAAAGCGCCAGCC <u>ATG</u>CAGCCT

TGGCACGGAAAGGCCATGCAGAGAGCTTCCGAGGCCGGAGCCACTGCCCCC

AAGGCTTCCGCACGGAATGCCAGGGGCGCCCCGATGGATCCCACCGAGTC

TCCGGCTGCCCCCGAGGCCGCCCTGCCTAAGGCGGGAAAGTTCGGCCCCG

CCAGGAAGTCGGGATCCCGGCAGAAAAAGAGCGCCCCGGACACCCAGGAG

AGGCCGCCCGTCCGCGCAACTGGGGCCCGCGCCAAAAAGGCCCCTCAGCG

CGCCCAGGACACGCAGCCGTCTGACGCCACCAGCGCCCCTGGGGCAGAGG

GGCTGGAGCCTCCTGCGGCTCGGGAGCCGGCTCTTTCCAGGGCTGGTTCT

TGCCGCCAGAGGGGCGCGCGCTGCTCCACGAAGCCAAGACCTCCGCCCGG

GCCCTGGGACGTGCCCAGCCCCGGCCTGCCGGTCTCGGCCCCCATTCTCG

TACGGAGGGATGCGGCGCCTGGGGCCTCGAAGCTCCGGGCGGTTTTGGAG

AAGTTGAAGCTCAGCCGCGATGATATCTCCACGGCGGCGGGGATGGTGAA

AGGGGTTGTGGACCACCTGCTGCTCAGACTGAAGTGCGACTCCGCGTTCA

GAGGCGTCGGGCTGCTGAACACCGGGAGCTACTATGAGCACGTGAAGATT

TCTGCACCTAATGAATTTGATGTCATGTTTAAACTGGAAGTCCCCAGAAT

TCAACTAGAAGAATATTCCAACACTCGTGCATATTACTTTGTGAAATTTA

AAAGAAATCCGAAAGAAAATCCTCTGAGTCAGTTTTTAGAAGGTGAAATA

TTATCAGCTTCTAAGATGCTGTCAAAGTTTAGGAAAATCATTAAGGAAGA

AATTAACGACATTAAAGATACAGATGTCATCATGAAGAGGAAAAGAGGAG

GGAGCCCTGCTGTAACACTTCTTATTAGTGAAAAAATATCTGTGGATATA

ACCCTGGCTTTGGAATCAAAAAGTAGCTGGCCTGCTAGCACCCAAGAAGG

CCTGCGCATTCAAAACTGGCTTTCAGCAAAAGTTAGGAAGCAACTACGAC

TAAAGCCATTTTACCTTGTACCCAAGCATGCAAAGGAAGGAAATGGTTTC

CAAGAAGAAACATGGCGGCTATCCTTCTCTCACATCGAAAAGGAAATTTT

GAACAATCATGGAAAATCTAAAACGTGCTGTGAAAACAAAGAAGAGAAAT

GTTGCAGGAAAGATTGTTTAAAACTAATGAAATACCTTTTAGAACAGCTG

AAAGAAAGGTTTAAAGACAAAAAACATCTGGATAAATTCTCTTCTTATCA

-continued
```
TGTGAAAACTGCCTTCTTTCACGTATGTACCCAGAACCCTCAAGACAGTC

AGTGGGACCGCAAAGACCTGGGCCTCTGCTTTGATAACTGCGTGACATAC

TTTCTTCAGTGCCTCAGGACAGAAAAACTTGAGAATTATTTTATTCCTGA

ATTCAATCTATTCTCTAGCAACTTAATTGACAAAAGAAGTAAGGAATTTC

TGACAAAGCAAATTGAATATGAAAGAAACAATGAGTTTCCAGTTTTTGAT

GAATTTTGAGATTGTATTTTTAGAAAGATCTAAGAACTAGAGTCACCCTA

AATCCTGGAGAATACAAGAAAAATTTGAAAAGGGGCCAGACGCTGTGGCT

CAC
```

SEQ ID NO:12
Cyclic 2'3'-GMP-AMP synthase, cGAS, from *Homo sapiens* with mycobacterial codon optimization, DNA sequence. (1569 nucleotides [522 codons, 1 stop codon]; encodes UniProtKB/Swiss-Prot Protein ID Q8N884.2).

```
ATGCAACCATGGCACGGGAAAGCCATGCAGCGTGCGAGCGAAGCCGGGGC

GACGGCCCCCAAGGCGTCGGCGCGTAACGCGCGGGGTGCGCCCATGGACC

CGACGGAGTCCCCCGCGGCGCCGGAGGCGGCCCTGCCGAAAGCGGGTAAG

TTCGGTCCAGCGCGGAAAAGCGGGAGCCGCCAAAAGAAGTCCGCGCCCGA

CACCCAGGAGCGTCCCCGGTCCGGGCCACCGGCGCGCGTGCCAAAAAAG

CCCCGCAACGGGCGCAAGATACGCAGCCAAGCGATGCGACCTCCGCCCCC

GGGGCGGAGGGTCTGGAGCCCCGGCCGCCCGGGAGCCAGCGCTCTCGCG

CGCGGGTTCCTGCCGTCAGCGGGGCGCGCGGTGTTCCACGAAACCCCGTC

CCCCACCAGGTCCCTGGGACGTGCCGTCGCCGGGTTTGCCGGTGAGCGCG

CCAATCCTGGTCCGGCGCGACGCGGCCCCGGGGCGTCGAAATTGCGTGC

GGTGCTCGAGAAATTGAAGTTGTCGCGCGACGACATCTCCACGGCCGCGG

GTATGGTCAAGGGCGTGGTCGATCATTTGTTGTTGCGGCTCAAGTGTGAT

TCGGCGTTCCGCGGGGTGGGCTTGCTGAACACGGGGTCCTACTATGAGCA

TGTCAAAATCAGCGCCCCAACGAATTTGACGTGATGTTTAAGCTGGAAG

TGCCACGTATCCAATTGGAAGAGTATTCCAATACCCGTGCGTATTATTTC

GTCAAATTTAAGCGCAATCCGAAGGAAAATCCACTCAGCCAATTCTTGGA

GGGCGAAATTCTGTCGGCCTCGAAAATGCTCTCCAAATTTCGTAAGATTA

TCAAGGAGGAGATCAACGACATTAAGGACACGGATGTGATCATGAAACGT

AAACGTGGCGGTTCCCCCGCGGTGACGCTCCTCATTTCGGAAAAAATTTC

GGTGGACATTACCCTGGCGTTGGAATCGAAGTCCAGCTGGCCGGCGTCGA

CCCAGGAGGGCCTGCGGATTCAAAACTGGTTGAGCGCCAAAGTGCGGAAG

CAGCTGCGTCTCAAACCCTTTTATTTGGTCCCGAAACATGCCAAAGAGGG

TAACGGTTTTCAAGAGGAAACCTGGCGTTTGAGCTTCTCCCACATTGAGA

AGGAGATTTTGAACAACCATGGTAAGTCCAAAACGTGCTGCGAGAATAAG

GAAGAAAAATGTTGTCGCAAAGATTGTCTCAAATTGATGAAATATTTGCT

GGAACAACTCAAAGAGCGTTTTAAGGACAAGAAGCATCTCGACAAGTTCT

CCTCGTATCACGTCAAGACCGCCTTCTTTCATGTCTGTACGCAGAACCCG

CAAGATAGCCAGTGGGATCGCAAGGACTTGGGGTTGTGTTTTGACAATTG

CGTCACCTATTTCTTGCAATGTTTGCGGACCGAGAAATTGGAGAACTACT

TTATTCCAGAATTCAACTTGTTTTCCTCGAATCTGATTGACAAACGCTCC

AAAGAGTTTCTGACGAAGCAGATTGAATACGAGCGTAACAATGAGTTTCC

GGTCTTTGACGAGTTTTGA
```

SEQ ID NO:13
Plasmid pMH94H-P$_{hsp60}$::disA::hcGASco::mCherry which is an *E. coli*-mycobacterial shuttle plasmid that overexpresses the BCG disA gene, the human cGAS gene (with mycobacterial codon optimization), and mCherry from the P$_{hsp60}$ promoter, DNA sequence. When introduced into BCG, *M. tuberculosis, M. bovis* or highly related strains, this plasmid integrates as a single copy in the mycobacterial chromosome (10842 nucleotides; promoter $P_{hsp60}$ DNA comprised of a portion of the *M. leprae* hsp65 gene nucleotides 901 to 1068 is underlined; disA coding sequence are from nucleotides 1069 to 2145; human cGAS with mycobacterial codon optimization sequences are from nucleotides 2158 to 3726; ATG start codons and TAA or TGA stop codons are shown in boldface, underline).

TCGCGCGTTTCGGTGATGACGGTGAAAACCTCTGACACATGCAGCTCCCGGAGACGGTCACAGCTTGTCTGTAAGCGGATGCC 1-83

GGGAGCAGACAAGCCCGTCAGGGCGCGTCAGCGGGTGTTGGCGGGTGTCGGGGCTGGCTTAACTATGCGGCATCAGAGCAGAT 84-166

TGTACTGAGAGTGCACCAAAATTGTAAACGTTAATATTTTGTTAAAATTCGCGTTAAATTTTTGTTAAATCAGCTCATTTTTT 167-249

AACCAATAGGCCGAAATCGGCAAAATCCCTTATAAATCAAAAGAATAGCCCGAGATAGGGTTGAGTGTTGTTCCAGTTTGGA 250-331

ACAAGAGTCCACTATTAAAGAACGTGGACTCCAACGTCAAAGGGCGAAAAACCGTCTATCAGGGCGATGGCCCACTACGTGAA 332-414

CCATCACCCAAATCAAGTTTTTTGGGGTCGAGGTGCCGTAAAGCACTAAATCGGAACCCTAAAGGGAGCCCCCGATTTAGAGC 415-497

TTGACGGGGAAAGCCGGCGAACGTGGCGAGAAAGGAAGGGAAGAAAGCGAAAGGAGCGGGCGCTAGGGCGCTGGCAAGTGTAG 498-580

CGGTCACGCTGCGCGTAACCACCACACCCGCCGCGCTTAATGCGCCGCTACAGGGCGCGTACTATGGTTGCTTTGACGTGCGG 581-663

TGTGAAATACCGCACAGATGCGTAAGGAGAAAATACCGCATCAGGCGCCATTCGCCATTCAGGCTGCGCAACTGTTGGGAAGG 664-746

GCGATCGGTGCGGGCCTCTTCGCTATTACGCCAGCTGGCGAAAGGGGGATGTGCTGCAAGGCGATTAAGTTGGGTAACGCCAG 747-829

GGTTTTCCCAGTCACGACGTTGTAAAACGACGGCCAGTGAATTCGAGCTCGGTACCCGGGGATCCTCTAGAAATTCCGGAATT 830-912

GCACTCGCCTTAGGGGAGTGCTAAAAATGATCCTGGCACTCGCGATCAGCGAGTGCCAGGTCGGGACGGTGAGACCCAGCCAG 913-995

CAAGCTGTGGTCGTCCGTCGCGGGCACTGCACCCGGCCAGCGTAAGTAATGGGGGTTGTCGGCACCCGGTGACATGCACGCTG 996-1078

```
TGACTCGTCCGACCCTGCGTGAGGCTGTCGCCCGCCTAGCCCCGGGCACTGGGCTGCGGGACGGCCTGGAGCGTATCCTGCGC    1079-1161
GGCCGCACTGGTGCCCTGATCGTGCTGGGCCATGACGAGAATGTCGAGGCCATCTGCGATGGTGGCTTCTCCCTCGATGTCCG    1162-1244
CTATGCAGCAACCCGGCTACGCGAGCTGTGCAAGATGGACGGCGCCGTGGTGCTGTCCACCGACGGCAGCCGCATCGTGCGGG    1245-1327
CCAACGTGCAACTGGTACCGGATCCGTCGATCCCCACCGACGAATCGGGGACCCGGCACCGCTCGGCCGAGCGGGCCGCGATC    1228-1410
CAGACCGGTTACCCGGTGATCTCAGTGAGCCACTCGATGAACATCGTGACCGTCTACGTCCGCGGGGAACGTCACGTATTGAC    1411-1493
CGACTCGGCAACCATCCTGTCGCGGGCCAACCAGGCCATCGCAACCCTGGAGCGGTACAAAACCAGGCTCGACGAGGTCAGCC    1494-1576
GGCAACTGTCCAGGGCAGAAATCGAGGACTTCGTCACGCTGCGCGATGTGATGACGGTGGTGCAACGCCTCGAGCTGGTCCGG    1577-1659
CGAATCGGGCTGGTGATCGACTACGACGTGGTCGAACTCGGCACTGATGGTCGTCAGCTGCGGCTGCAGCTCGACGAGTTGCT    1660-1742
CGGCGGCAACGACACCGCCCGGGAATTGATCGTGCGCGATTACCACGCCAACCCGGAACCACCGTCCACGGGGCAAATCAATG    1743-1825
CCACCCTGGACGAACTGGACGCCCTGTCGGACGGCGACCTCCTCGATTTCACCGCGCTGGCAAAGGTTTTCGGATATCCGACG    1826-1908
ACCACGGAAGCGCAGGATTCGACGCTGAGCCCGCGTGGCTACCGCGCGATGGCCGGTATCCCCCGGCTCCAGTTCGCCCATGC    1909-1991
CGACCTGCTGGTCCGGGCGTTCGGAACGTTGCAGGGTCTGCTGGCGGCCAGCGCCGGCGATCTGCAATCAGTGGACGGCATCG    1992-2074
GCGCCATGTGGGCCCGTCATGTGCGCGAGGGGTTGTCACAGCTGGCGGAATCGACCATCAGCGATCAATAAGAGCACATCGAT    2075-2157
ATGCAACCATGGCACGGGAAAGCCATGCAGCGTGCGAGCGAAGCCGGGGCGACGGCCCCAAGGCGTCGGCGCGTAACGCGCG    2158-2240
GGGTGCGCCCATGGACCCGACGGAGTCCCCGCGGCGCCGGAGGCGGCCCTGCCGAAAGCGGGTAAGTTCGGTCCAGCGCGGA    2241-2323
AAAGCGGGAGCCGCCAAAAGAAGTCCGCGCCCGACACCCAGGAGCGTCCCCGGTCCGGGCCACCGGCGCGCGTGCCAAAAAA    2324-2406
GCCCCGCAACGGGCGCAAGATACGCAGCCAAGCGATGCGACCTCCGCCCCCGGGGCGGAGGGTCTGGAGCCCCGGCCGCCCG    2407-2489
GGAGCCAGCGCTCTCGCGCGCGGGTTCCTGCCGTCAGCGGGGCGCGCGGTGTTCCACGAAACCCGTCCCCCACCAGGTCCCT    2490-2572
GGGACGTGCCGTCGCCGGGTTTGCCGGTGAGCGCGCCAATCCTGGTCCGGCGCGACGCGGCCCCGGGGGCGTCGAAATTGCGT    2573-2655
GCGGTGCTCGAGAAATTGAAGTTGTCGCGCGACGACATCTCCACGGCCGCGGGTATGGTCAAGGGCGTGGTCGATCATTTGTT    2656-2738
GTTGCGGCTCAAGTGTGATTCGGCGTTCCGCGGGGTGGGCTTGCTGAACACGGGGTCCTACTATGAGCATGTCAAAATCAGCG    2739-2821
CCCCCAACGAATTTGACGTGATGTTTAAGCTGGAAGTGCCACGTATCCAATTGGAAGAGTATTCCAATACCCGTGCGTATTAT    2822-2904
TTCGTCAAATTTAAGCGCAATCCGAAGGAAAATCCACTCAGCCAATTCTTGGAGGGCGAAATTCTGTCGGCCTCGAAAATGCT    2905-2987
CTCCAAATTTCGTAAGATTATCAAGGAGGAGATCAACGACATTAAGGACACGGATGTGATCATGAAACGTAAACGTGGCGGTT    2988-3070
CCCCCGCGGTGACGCTCCTCATTTCGGAAAAAATTTCGGTGGACATTACCCTGGCGTTGGAATCGAAGTCCAGCTGGCCGGCG    3071-3153
TCGACCCAGGAGGGCCTGCGGATTCAAAACTGGTTGAGCGCCAAAGTGCGGAAGCAGCTGCGTCTCAAACCCTTTTATTTGGTC    3154-3237
CCGAAACATGCCAAAGAGGGTAACGGTTTTCAAGAGGAAACCTGGCGTTTGAGCTTCTCCCACATTGAGAAGGAGATTTTGAAC    3238-3321
AACCATGGTAAGTCCAAAACGTGCTGCGAGAATAAGGAAGAAAAATGTTGTCGCAAAGATTGTCTCAAATTGATGAAATATTTG    3322-3405
CTGGAACAACTCAAAGAGCGTTTTAAGGACAAGAAGCATCTCGACAAGTTCTCCTCGTATCACGTCAAGACCGCCTTCTTTCAT    3406-3489
GTCTGTACGCAGAACCCGCAAGATAGCCAGTGGGATCGCAAGGACTTGGGGTTGTGTTTTGACAATTGCGTCACCTATTTCTTG    3490-3573
CAATGTTTGCGGACCGAGAAATTGGAGAACTACTTTATTCCAGAATTCAACTTGTTTTCCTCGAATCTGATTGACAAACGCTCC    3574-3657
AAAGAGTTTCTGACGAAGCAGATTGAATACGAGCGTAACAATGAGTTTCCGGTCTTTGACGAGTTTTGAAAGCTTGAGATGGTG    3658-3741
AGCAAGGGCGAGGAGGATAACATGGCCATCATCAAGGAGTTCATGCGCTTCAAGGTGCACATGGAGGGCTCCGTGAACGGCCAC    3742-3825
GAGTTCGAGATCGAGGGCGAGGGCGAGGGCCGCCCCTACGAGGGCACCCAGACCGCCAAGCTGAAGGTGACCAAGGGTGGCCCC    3826-3909
CTGCCCTTCGCCTGGGACATCCTGTCCCCTCAGTTCATGTACGGCTCCAAGGCCTACGTGAAGCACCCCGCCGACATCCCCGAC    3919-3993
TACTTGAAGCTGTCCTTCCCCGAGGGCTTCAAGTGGGAGCGCGTGATGAACTTCGAGGACGGCGGCGTGGTGACCGTGACCCAG    3994-4077
GACTCCTCCCTGCAGGACGGCGAGTTCATCTACAAGGTGAAGCTGCGCGGCACCAACTTCCCCTCCGACGGCCCCGTAATGCAG    4078-4161
AAGAAGACCATGGGCTGGGAGGCCTCCTCCGAGCGGATGTACCCCGAGGACGGCGCCCTGAAGGGCGAGATCAAGCAGAGGCTG    4162-4225
AAGCTGAAGGACGGCGGCCACTACGACGCTGAGGTCAAGACCACCTACAAGGCCAAGAAGCCCGTGCAGCTGCCCGGCGCCTAC    4226-4329
AACGTCAACATCAAGTTGGACATCACCTCCCACAACGAGGACTACACCATCGTGGAACAGTACGAACGCGCCGAGGGCCGCCAC    4330-4413
```

| | |
|---|---|
| TCCACCGGCGGCATGGACGAGCTGTACAAGTAGACTAGTTGCCTGGCGGCAGTAGCGCGGTGGTCCCACCTGACCCCATGCCGA | 4414-4497 |
| ACTCAGAAGTGAAACGCCGTAGCGCCGATGGTAGTGTGGGGTCTCCCCATGCGAGAGTAGGGAACTGCCAGGCATCAAATAAAA | 4498-4581 |
| CGAAAGGCTCAGTCGAAAGACTGGGCCTTTCGTTTTATCTGTTGTTTGTCGGTGAACGCTCTCCTGAGTAGGACAAATCCGCCG | 4582-4665 |
| GGAGCGGATTTGAACGTTGCGAAGCAACGGCCCGGAAGGGTGGCGGGCAGGACGCCCGCCATAAACTGCCAGGCATCAAATTAA | 4667-4749 |
| GCAGAAGGCCATCCTGACGGATGGCCTTTTTTCTAGAGTCGACCACCAAGGGCACCATCTCTGCTTGGGCCACCCCGTTGGCCG | 4750-4833 |
| CAGCCAGCTCGCTGAGAGCCGTGAACGACAGGGCGAACGCCAGCCCGCCGACGGCGAGGGTTCCGACCGCTGCAACTCCCGGTG | 4834-4917 |
| CAACCTTGTCCCGGTCTATTCTCTTCACTGCACCAGCTCCAATCTGGTGTGAATGCCCCTCGTCTGTTCGCGCAGGCGGGGGGC | 4918-5001 |
| TCTATTCGTTTGTCAGCATCGAAAGTAGCCAGATCAGGGATGCGTTGCAACCGCGTATGCCCAGGTCAGAAGAGTCGCACAAGA | 5002-5085 |
| GTTGCAGACCCCTGGAAAGAAAAATGGCCAGAGGGCGAAAACACCCTCTGACCAGCGGAGCGGGCGACGGGAATCGAACCCGCG | 5086-5169 |
| TAGCTAGTTTGGAAGAATGGGTGTCTGCCGACCACATATGGGCCGGTCAAGATAGGTTTTTACCCCCTCTCGGCTGCATCCTCT | 5170-5253 |
| AAGTGGAAAGAAATTGCAGGTCGTAGAAGCGCGTTGAAGCCTGAGAGTTGCACAGGAGTTGCAACCCGGTAGCCTTGTTCACGA | 5254-5337 |
| CGAGAGGAGACCTAGTTGGCACGTCGCGGATGGGATCGCTGAAGACTCAGCGCAGCGGGAGGATCCAAGCCTCATACGTCAAC | 5338-5421 |
| CCGCAGGACGGTGTGAGGTACTACGCGCTGCAGACCTACGACAACAAGATGGACGCCGAAGCCTGGCTCGCGGGCGAGAAGCGG | 5422-5505 |
| CTCATCGAGATGGAGACCTGGACCCCTCCACAGGACCGGGCGAAGAAGGCAGCCGCCAGCGCCATCACGCTGGAGGAGTACACC | 5506-5589 |
| CGGAAGTGGCTCGTGGAGCGCGACCTCGCAGACGGCACCAGGGATCTGTACAGCGGGCACGCGGAGCGCCGCATCTACCCGGTG | 5590-5673 |
| CTAGGTGAAGTGGCGGTCACAGAGATGACGCCAGCTCTGGTGCGTGCGTGGTGGGCCGGGATGGGTAGGAAGCACCCGACTGCC | 5674-5757 |
| CGCCGGCATGCCTACAACGTCCTCCGGGCGGTGATGAACACAGCGGTCGAGGACAAGCTGATCGCAGAGAACCCGTGCCGGATC | 5768-5841 |
| GAGCAGAAGGCAGCCGATGAGCGCGACGTAGAGGCGCTGACGCCTGAGGAGCTGGACATCGTCGCCGCTGAGATCTTCGAGCAC | 5842-5925 |
| TACCGGATCGCGGCATACATCCTGGCGTGGACGAGCCTCCGGTTCGGAGAGCTGATCGAGCTTCGCCGCAAGGACATCGTGGAC | 5926-6009 |
| GACGGCATGACGATGAAGCTCCGGGTGCGCCGTGGCGCTTCCCGCGTGGGAACAAGATCGTCGTTGGCAACGCCAAGACCGTC | 6010-6093 |
| CGGTCGAAGCGTCCTGTGACGGTTCCGCCTCACGTCGCGGAGATGATCCGAGCGCACATGAAGGACCGTACGAAGATGAACAAG | 6094-6177 |
| GGCCCCGAGGCATTCCTGGTGACCACGACGCAGGGCAACCGGCTGTCGAAGTCCGCGTTCACCAAGTCGCTGAAGCGTGGCTAC | 6178-6261 |
| GCCAAGATCGGTCGGCCGGAACTCCGCATCCACGACCTCCGCGCTGTCGGCGCTACGTTCGCCGCTCAGGCAGGTGCGACGACC | 6262-6345 |
| AAGGAGCTGATGGCCCGTCTCGGTCACACGACTCCTAGGATGGCGATGAAGTACCAGATGGCGTCTGAGGCCCGCGACGAGGCT | 6346-6429 |
| ATCGCTGAGGCGATGTCCAAGCTGGCCAAGACCTCCTGAAACGCAAAAAGCCCCCTCCCAAGGACACTGAGTCCTAAAGAGGG | 6430-6513 |
| GGGTTTCTTGTCAGTACGCGAAGAACCACGCCTGGCCGCGAGCGCCAGCACCGCCGCTCTGTGCGGAGACCTGGGCACCAGCCC | 6514-6597 |
| CGCCGCCGCCAGGAGCATTGCCGTTCCCGCCAGCTGAGTTCTGTTGTGCGCCGCCTATGTAGAGCTGGTCGTTGTAGGTCCGA | 6598-6680 |
| TCTCCAGGCGACTTTCCGGCGACGCTGAGGATGTCGATCACAGAGCCTCCGGGACCGCCGGTTGCGGTCAAACCTGACCATCC | 6681-6763 |
| GACAGCGGACGCCGTGGTGTTTCCTCCAGGGCCTCCGGCCTTGCCTGAGAATACAGAGCCAGCTCCCGCTGCGCCTCCAGCTC | 6764-6846 |
| CGACGAGCCCGGTGATCGTCTTGGTCGACCTGCAGGCATGCAAAAGCTGATCCTTGCCGAGCTGGGATGGAAGCCCGGCCGAC | 6847-6929 |
| CCACCCTGGAGGAGATGATCGAGGATGCCAGGGCCTTTCACGCCCGCCGCTGCTGAGCGTCCGCCGCCGGGCCCGCACCGCCG | 6830-7012 |
| TCGGCCGGCCCGCTCCGGGCTCGCAGCAGCGGGCTTCGGCGCGGGCCCGGGGCTCCGGGCCGCGGGCGGGGCTCCGCCCGG | 7013-7095 |
| CGGCCGCCGGGGGCCGGGGCGGCGCCGGGCGGCCCGGGGCGTCAGGCGCCGGGGCGGTGTCCGGCGGCCCCCAGAGGAACT | 7096-7178 |
| GCGCCAGTTCCTCCGGATCGGTGAAGCCGGAGAGATCCAGCGGGGTCTCCTCGAACACCTCGAAGTCGTGCAGGAAGGTGAAG | 7179-7261 |
| GCGAGCAGTTCGCGGGCGAAGTCCTCGGTCCGCTTCCACTGCGCCCCGTCGAGCAGCGCGGCCAGGATCTCGCGGTCGCCCCG | 7262-7344 |
| GAAGGCGTTGAGATGCAGTTGCACCAGGCTGTAGCGGGAGTCTCCCGCATAGACGTCGGTGAAGTCGACGATCCCGGTGACCT | 7345-7427 |
| CGGTCGCGGCCAGGTCCACGAAGATGTTGGTCCCGTGCAGGTCGCCGTGGACGAACCGGGGTTCGCGGCCGGCCAGCAGCGTG | 7428-7510 |
| TCCACGTCCGGCAGCCAGTCCTCCAGGCGGTCCAGCAGCGGGGCGAGAGGTAGCCCACCCGCGGTGGTCCTCGACGGTCGC | 7511-7593 |
| CGCGCGGCGTTCCCGCAGCAGTTCCGGGAAGACCTCGGAATGGGGGGTGAGCACGGTGTTCCCGGTCAGCGGCACCCTGTGCA | 7594-7676 |
| GCCGGCCGAGCACCCGGCCGAGTTCGCGGGCCAGGGCGAGCAGCGCGTTCCGGTCGGTCGTGCCGTCCATCGCGGACCGCCAG | 7677-7759 |
| GTGGTGCCGGTCATCCGGCTCATCACCAGGTAGGGCCACGGCCAGGCTCCGGTGCCGGGCCGCAGCTCGCCGCGGCCGAGGAG | 7760-7842 |

| | |
|---|---|
| GCGGGGCACCGGCACCGGGGCGTCCGCCAGGACCGCGTACGCCTCCGACTCCGACGCGAGGCTCTCCGGACCGCACCAGTGCT | 7743-7925 |
| CGCCGAACAGCTTGATCACCGGGCCGGGCTCGCCGACCAGTACGGGGTTGGTGCTCTCGCCGGGCACCCGCAGCACCGGCGGC | 7926-8008 |
| ACCGGCAGCCCGAGCTCCTCCAGGGCTCGGCGGGCCAGCGGCTCCCAGAATTCCTGGTCGTTCCGCAGGCTCGCGTAGGAATC | 8009-8091 |
| ATCCGAATCAATACGGTCGAGAAGTAACAGGGATTCTTGTGTCACAGCGGACCTCTATTCACAGGGTACGGGCCGGCTTAATT | 8092-8174 |
| CCGCACGGCCGGTCGCGACACGGCCTGTCCGCACCGCGGATCAGGCGTTGACGATGACGGGCTGGTCGGCCACGTCGGGGACG | 8175-8257 |
| TTCTCGGTGGTGCTGCGGTCGGGATCGCCAATCTCTACGGGCCGACCGAGGCGACGGTGTACGCCACCGCCTGGTTCTGCGAC | 8258-8340 |
| GGCGAGGCGCCGTCCCAGGCCCCGCCGATCCCCGTCCCCGCGTCGTCGAGCGCGGTGCCGACGACACCGCCGCGTGGCTCGT | 8341-8423 |
| CACGGAGGCCGTCCCCGGCGTCGCGGCGGCCGAGGAGTGGCCCGAGCACCAGCGGTTCGCCGTGGTCGAGGCGATGGCGGAGC | 8424-8506 |
| TGGCCCGCGCCCTCCACGAGCTGCCCGTGGAGGACTGCCCCTTCGACCGGCGCCTCGACGCGGCGGTCGCCGAGGCCCGGCGG | 8507-8589 |
| AACGTCGCCGAGGGCCTGTGGACCTCGACGACCTGCAGGCATGCAAGCTAGCTTTTGTTATCCGCTCACAATTCCACACAACA | 8590-8672 |
| TACGAGCCGGAAGCATAAAGTGTAAAGCCTGGGGTGCCTAATGAGTGAGCTAACTCACATTAATTGCGTTGCGCTCACTGCCC | 8673-8755 |
| GCTTTCCAGTCGGGAAACCTGTCGTGCCAGCTGCATTAATGAATCGGCCAACGCGCGGGGAGAGGCGGTTTGCGTATTGGGCG | 8756-8838 |
| CTCTTCCGCTTCCTCGCTCACTGACTCGCTGCGCTCGGTCGTTCGGCTGCGGCGAGCGGTATCAGCTCACTCAAAGGCGGTAA | 8839-8921 |
| TACGGTTATCCACAGAATCAGGGGATAACGCAGGAAAGAACATGTGAGCAAAAGGCCAGCAAAAGGCCAGGAACCGTAAAAAG | 8922-9004 |
| GCCGCGTTGCTGGCGTTTTTCCATAGGCTCCGCCCCCCTGACGAGCATCACAAAAATCGACGCTCAAGTCAGAGGTGGCGAAA | 9005-9087 |
| CCCGACAGGACTATAAAGATACCAGGCGTTTCCCCCTGGAAGCTCCCTCGTGCGCTCTCCTGTTCCGACCCTGCCGCTTACCG | 9088-9170 |
| GATACCTGTCCGCCTTTCTCCCTTCGGGAAGCGTGGCGCTTTCTCAATGCTCACGCTGTAGGTATCTCAGTTCGGTGTAGGTC | 9171-9253 |
| GTTCGCTCCAAGCTGGGCTGTGTGCACGAACCCCCCGTTCAGCCCGACCGCTGCGCCTTATCCGGTAACTATCGTCTTGAGTC | 9254-9336 |
| CAACCCGGTAAGACACGACTTATCGCCACTGGCAGCAGCCACTGGTAACAGGATTAGCAGAGCGAGGTATGTAGGCGGTGCTA | 9337-9419 |
| CAGAGTTCTTGAAGTGGTGGCCTAACTACGGCTACACTAGAAGGACAGTATTTGGTATCTGCGCTCTGCTGAAGCCAGTTACC | 9420-9502 |
| TTCGGAAAAAGAGTTGGTAGCTCTTGATCCGGCAAACAAACCACCGCTGGTAGCGGTGGTTTTTTTGTTTGCAAGCAGCAGAT | 9503-9585 |
| TACGCGCAGAAAAAAAGGATCTCAAGAAGATCCTTTGATCTTTTCTACGGGGTCTGACGCTCAGTGGAACGAAAACTCACGTT | 9586-9668 |
| AAGGGATTTTGGTCATGAGATTATCAAAAAGGATCTTCACCTAGATCCTTTTAAATTAAAAATGAAGTTTTAAATCAATCTAA | 9669-9751 |
| AGTATATATGAGTAAACTTGGTCTGACAGTTACCAATGCTTAATCAGTGAGGCACCTATCTCAGCGATCTGTCTATTTCGTTC | 8752-9834 |
| ATCCATAGTTGCCTGACTCCCCGTCGTGTAGATAACTACGATACGGGAGGGCTTACCATCTGGCCCCAGTGCTGCAATGATAC | 9835-9917 |
| CGCGAGACCCACGCTCACCGGCTCCAGATTTATCAGCAATAAACCAGCCAGCCGGAAGGGCCGAGCGCAGAAGTGGTCCTGCA | 9918-10000 |
| ACTTTATCCGCCTCCATCCAGTCTATTAATTGTTGCCGGGAAGCTAGAGTAAGTAGTTCGCCAGTTAATAGTTTGCGCAACGTT | 10001-10085 |
| GTTGCCATTGCTACAGGCATCGTGGTGTCACGCTCGTCGTTTGGTATGGCTTCATTCAGCTCCGGTTCCCAACGATCAAGGCGA | 10086-10169 |
| GTTACATGATCCCCCATGTTGTGCAAAAAAGCGGTTAGCTCCTTCGGTCCTCCGATCGTTGTCAGAAGTAAGTTGGCCGCAGTG | 10170-10253 |
| TTATCACTCATGGTTATGGCAGCACTGCATAATTCTCTTACTGTCATGCCATCCGTAAGATGCTTTTCTGTGACTGGTGAGTAC | 10254-10337 |
| TCAACCAAGTCATTCTGAGAATAGTGTATGCGGCGACCGAGTTGCTCTTGCCCGGCGTCAATACGGGATAATACCGCGCCACAT | 10338-10421 |
| AGCAGAACTTTAAAAGTGCTCATCATTGGAAAACGTTCTTCGGGGCGAAAACTCTCAAGGATCTTACCGCTGTTGAGATCCAGT | 10422-10505 |
| TCGATGTAACCCACTCGTGCACCCAACTGATCTTCAGCATCTTTTACTTTCACCAGCGTTTCTGGGTGAGCAAAAACAGGAAGG | 10506-10589 |
| CAAAATGCCGCAAAAAAGGGAATAAGGGCGACACGGAAATGTTGAATACTCATACTCTTCCTTTTTCAATATTATTGAAGCATT | 10590-10673 |
| TATCAGGGTTATTGTCTCATGAGCGGATACATATTTGAATGTATTTAGAAAAATAAACAAATAGGGGTTCCGCGCACATTTCCC | 10674-10757 |
| CGAAAAGTGCCACCTGACGTCTAAGAAACCATTATTATCATGACATTAACCTATAAAAATAGGCGTATCACGAGGCCCTTTCGT | 10758-10841 |
| C | 10842-10842 |

Knocking Out Endogenous BCG Phosphodiesterase Genes and Intragenic Segments Encoding Phosphodiesterase Domains in Order to Increase CDN PAMP and DAMP Levels Overexpression of CDNs by Knocking Out an Endogenous BCG Phosphodiesterase: WP_003414507

The BCG AHM08589.1 protein encodes a 316 amino acid endogenous bifunctional c-di-AMP and cGAMP phosphodiesterase in BCG that is 100% identical to the *M. tuberculosis* Rv2837c over the C-terminal 316 amino acids (also called CdnP, CnpB, 3'-to-5' oligoribonuclease A, bifunctional oligoribonuclease, or PAP phosphatase NrnA). The *M. tuberculosis* Rv2837c protein is known to hydrolyze both 3'-5' c-di-AMP (bacterial PAMP molecule) and 2'-3'cGAMP (host DAMP molecule). Since the BCG protein is 100% identical over the C-terminal 315 amino acids, knockout (gene replacement) of the BCG AHM08589.1 protein will lead to increased levels of CDNs (3'-5' c-di-AMP and 2'-3'cGAMP) in recombinant BCG.

SEQ ID NO:14

Bifunctional c-di-AMP and cGAMP phosphodiesterase CdnP (also called CnpB, 3'-to-5' oligoribonuclease A, bifunctional oligoribonuclease, PAP phosphatase NrnA) from BCG, amino acid sequence (316 amino acids; BCG protein AHM08589.1; NCBI Reference DNA Sequence: CP003494.1 from BCG strain ATCC 35743; NCBI Reference Protein Identifier WP_003414507). A similar sequence is present in *Mycobacterium tuberculosis* as protein Rv2837c or MT2903, and in *Mycobacterium bovis* as protein Mb2862c.

```
MDAVGAAALLSAAARVGVVCHVHPDADTIGAGLALALVLDGCGKRVEVSF

AAPATLPESLRSLPGCHLLVRPEVMRRDVDLVVTVDIPSVDRLGALGDLT

DSGRELLVIDHHASNDLFGTANFIDPSADSTTTMVAEILDAWGKPIDPRV

AHCIYAGLATDTGSFRWASVRGYRLAARLVEIGVDNATVSRTLMDSHPFT

WLPLLSRVLGSAQLVSEAVGGRGLVYVVVDNREWVAARSEEVESIVDIVR

TTQQAEVAAVFKEVEPHRWSVSMRAKTVNLAAVASGFGGGGHRLAAGYTT

TGSIDDAVASLRAALG
```

SEQ ID NO:15

Bifunctional c-di-AMP and cGAMP phosphodiesterase gene, cdnP (also called cnpB or gene for 3'-to-5' oligoribonuclease A, bifunctional oligoribonuclease, or PAP phosphatase NrnA) from BCG, DNA sequence (951 nucleotides [316 codons and 1 stop codon]; encodes BCG protein AHM08589.1; NCBI Reference Sequence: CP003494.1 from BCG strain ATCC 35743). A similar sequence is present in *Mycobacterium tuberculosis* encoding protein Rv2837c or MT2903, and in *Mycobacterium bovis* encoding protein Mb2862c.

```
GTGGACGCCGTCGGTGCCGCTGCGCTGTTGTCGGCCGCTGCCAGGGTCGG

GGTAGTCTGCCACGTCCACCCCGATGCCGACACCATCGGCGCCGGATTGG

CATTGGCATTGGTGTTGGACGGGTGCGGCAAGCGGGTAGAGGTCAGCTTT

GCCGCGCCGGCGACACTGCCCGAGTCGCTGCGTTCGCTGCCGGGCTGCCA

TCTGCTGGTCCGCCCTGAGGTGATGCGCCGCGATGTCGATTTGGTTGTGA

CTGTTGACATTCCGAGTGTTGATCGGCTCGGTGCTCTGGGCGATCTAACT
```

-continued

```
GATTCCGGGCGGGAGCTCCTGGTAATCGACCATCACGCCTCCAACGACCT

GTTCGGCACCGCGAATTTCATTGACCCGTCGGCGGATTCCACCACGACGA

TGGTTGCCGAGATCCTCGACGCGTGGGGGAAACCGATAGACCCGCGCGTC

GCGCACTGCATCTACGCCGGGTTGGCGACCGACACGGGGTCGTTTCGCTG

GGCCAGTGTGCGGGGGTATCGGCTGGCGGCGCGGCTGGTAGAGATCGGTG

TGGACAACGCCACCGTCAGCAGGACCTTGATGGACAGCCATCCCTTCACC

TGGTTGCCGTTGCTATCGCGGGTGTTGGGTTCGGCGCAGCTGGTGTCCGA

GGCGGTCGGTGGCCGCGGGCTGGTTTACGTCGTCGTCGACAACCGGGAGT

GGGTCGCTGCGCGCTCGGAGGAAGTGGAAAGCATCGTCGACATCGTCCGC

ACCACGCAACAAGCCGAGGTCGCGGCGGTGTTCAAGGAGGTCGAACCGCA

TCGGTGGTCGGTGTCGATGCGGGCTAAGACCGTGAATTTGGCCGCGGTTG

CCTCTGGGTTCGGTGGCGGTGGTCACCGGCTGGCCGCGGGGTATACGACC

ACCGGCTCGATCGACGACGCTGTGGCGTCGTTGCGCGCGGCGCTTGGTTA

G
```

SEQ ID NO:16

Bifunctional c-di-AMP and cGAMP phosphodiesterase CdnP (also called CnpB, Rv2837c, or MT2903, 3'-to-5' oligoribonuclease A, bifunctional oligoribonuclease, PAP phosphatase NrnA) from *Mycobacterium tuberculosis*, amino acid sequence (336 amino acids; *M. tuberculosis* protein WP_003905944.1; NCBI/GenBank Reference Sequence: AL123456 from *M. tuberculosis* strain H37Rv). The *M. tuberculosis* protein has 20 additional amino acids at its N-terminus compared with the BCG protein (SEQ ID NO:14) which are underlined and boldfaced.

MTTIDPRSELVDGRRRAGARVDAVGAAALLSAAARVGVVCHVHPDADTIG

AGLALALVLDGCGKRVEVSFAAPATLPESLRSLPGCHLLVRPEVMRRDVD

LVVTVDIPSVDRLGALGDLTDSGRELLVIDHHASNDLFGTANFIDPSADS

TTTMVAEILDAWGKPIDPRVAHCIYAGLATDTGSFRWASVRGYRLAARLV

EIGVDNATVSRTLMDSHPFTWLPLLSRVLGSAQLVSEAVGGRGLVYVVVD

NREWVAARSEEVESIVDIVRTTQQAEVAAVFKEVEPHRWSVSMRAKTVNL

AAVASGFGGGGHRLAAGYTTTGSIDDAVASLRAALG

Overexpression of CDNs by knocking out an endogenous BCG phosphodiesterase domain: EAL domain of protein BCG RS07340 (previously BCG 1416c). The BCG_RS07340 protein (SEQ ID NO:4) is encoded by the DNA sequence shown in SEQ ID NO:5. The BCG_RS07340 protein is 100% identical to the *M. tuberculosis* Rv1354c protein and is an endogenous CDN PDE in BCG. The full-length polypeptide is 623 amino acids in length, and it encodes a bifunctional diguanylate cyclase/diguanylate phosphodiesterase. The domain structure is: N-terminus-GAF-GGDEF-EAL-C-terminus as shown. The GAF domain (approximately amino acids 1-190) is a regulatory domain which influences the activity of the other domains. The GGDEF domain (approximately amino acids 190-350) is a diguanylate cyclase catalyzing the reaction 2 GTP→4 c-di-GMP+2 pyrophosphates. The EAL domain (amino acids 354 to 623, highlighted in SEQ ID No: 4) is a diguanylate phosphodiesterase catalyzing the reaction c-di-GMP→2 GMP. As the EAL domain of this protein is known to cleave 3'-5' c-di-GMP, knockout of this endogenous cyclic dinucleotide phosphodiesterase domain will increase the levels of c-di-GMP produced by BCG. Targeted knockout of the EAL domain may be accomplished by gene replacement of the full-length WT BCG_RS07340 gene with one which encodes only amino acids 1-353 (the GAF-GGDEF domains), that is truncating the coding sequence of the gene to exclude the sequences that encode amino acids 354-623 (shown as the underlined DNA sequence in SEQ ID NO:5) and including an appropriate stop codon and transcription termination sequence. Recombinant BCG lacking the EAL domain of BCG_RS07340 will lead to increased levels of the CDN PAMP c-di-GMP.

Overexpression of CDNs by knocking out an endogenous BCG phosphodiesterase: BCG AHM07112. The BCG_AHM07112 protein is an endogenous diguanylate phosphodiesterase in BCG (homologous the 307 amino acid *M. tuberculosis* Rv1357c protein). Some strains of BCG lack BCG_AHM07112 altogether while others such as BCG Tice harbor it. Among the BCG strains that have this polypeptide, the protein may be 288 amino acids in length (such as in BCG ATCC 35743) or 307 amino acids in length (such as in BCG Pasteur 1173 P2). The BCG_AHM07112 protein from BCG ATCC 35743 is 288 amino acids in length and is 100% identical to the *M. tuberculosis* Rv1357c protein over its C-terminal 287 amino acids. The domain structure of BCG_AHM07112 is that of a single EAL domain. As the *M. tuberculosis* Rv1357c protein is known to cleave 3'-5' c-di-GMP, it is highly likely that the BCG protein performs the same reaction. Knockout of this endogenous cyclic dinucleotide phosphodiesterase in BCG is anticipated to increase the levels of c-di-GMP produced by BCG. Targeted knockout of the EAL domain may be accomplished by gene replacement of the full-length WT BCG_AHM07112 gene and subsequent generation of an unmarked deletion.

SEQ ID NO:17

Diguanylate phosphodiesterase AHM07112.1 from BCG and other related mycobacteria, amino acid sequence (288 amino acids; GenBank Reference Sequence: CP003494.1; from BCG strain ATCC 35743). AHM07112.1 is 100% identical to the C-terminal 287 amino acids of the diguanylate phosphodiesterase of *Mycobacterium tuberculosis* protein Rv1357c or MT1400 and of *Mycobacterium bovis* as protein Mb1392c.

```
MIDYEEMFRGAMQARAMVANPDQWADSDRDQVNTRHYLSTSMRVALDRGE
FFLVYQPIIRLADNRIIGAEALLRWEHPTLGTLLPGRFIDRAENNGLMVP
LTAFVLEQACRHVRSWRDHSTDPQPFVSVNVSASTICDPGFLVLVEGVLG
ETGLPAHALQLELAEDARLSRDEKAVTRLQELSALGVGIAIDDFGIGFSS
LAYLPRLPVDVVKLGGKFIECLDGDIQARLANEQITRAMIDLGDKLGITV
TAKLVESPSQAARLRAFGCKAAQGWHFAKALPVDFFRE
```

SEQ ID NO:18

Diguanylate phosphodiesterase AHM07112.1 from BCG and other related mycobacteria, DNA sequence (867 nucleotides [288 codons, 1 stop codon]; GenBank Reference Sequence: CP003494.1; from BCG strain ATCC 35743). AHM07112.1 is 100% identical to the C-terminal 287 amino acids of the diguanylate phosphodiesterase of *Mycobacterium tuberculosis* protein Rv1357c or MT1400 and of *Mycobacterium bovis* as protein Mb1392c.

```
  1  ttgatcgact acgaagagat gtttaggggc gcgatgcaag
     cgcgagcgat ggtagccaat
 61  cctgaccaat gggcggactc cgaccgcgac caggtcaaca
     ctcgccatta tctgtccact
121  tcgatgcgcg tggcactgga tcgcggtgaa ttcttcctcg
     tctaccagcc aatcatccgg
181  cttgccgaca accgcatcat cggcgccgag gccctgctgc
     gctgggaaca cccgacgttg
241  ggcacgctac tcccgggccg gttcatcgac cgtgccgaga
     acaacggact gatggtgccg
301  ctcacggcct tcgtgctcga gcaggcctgc cgccacgtcc
     gcagttggcg tgaccacagc
361  accgaccgc aaccgtttgt cagcgtcaac gtctccgcca
     gcaccatctg cgatcccggc
421  ttcctggtgc tggtcgaagg tgtgctcggc gaaaccggcc
     tgcccgccca tgccctgcag
481  ctcgaactgg ccgaggacgc gcgccttagc agagacgaga
     aggcggtgac caggctacaa
541  gaattgtccg ctctcggcgt cggcatcgcc atcgacgact
     tcggcattgg attctccagc
601  ctcgcctacc ttccccgcct ccccgtcgac gtggtcaaac
     tcgggggaaa gttcatcgag
661  tgcctcgatg gcgacattca agctcggctg gccaacgaac
     agatcacccg ggcaatgatc
721  gaccttggcg acaagctcgg tatcaccgtc actgcaaagc
     tagtcgaaag ccccagccaa
781  gccgcccggt tgcgcgcctt cggctgtaaa gccgcacaag
     gctggcactt tgccaaggca
841  ctgccggtcg acttttttcag agagtag
```

SEQ ID NO:19

Diguanylate phosphodiesterase Rv1357c or MT1400 from *Mycobacterium tuberculosis* and BCG Pasteur 1173 P2, amino acid sequence (307 amino acids, NCBI/GenBank Reference Sequence: AL123456 from *M. tuberculosis* strain H37Rv). The 19 amino acid N-terminal extension is present in the *M. tuberculosis* and in BCG Pasteur strain 1173 P2 but absent in several other BCG strains. The 19 amino acid N-terminal extension is underlined and boldfaced. The C-terminal 287 amino acids of *M. tuberculosis* Rv1357c are 100% identical to the BCG diguanylate phosphodiesterase AHM07112.1.

<u>MDRCCORATAFACALRPTK</u>LIDYEEMFRGAMQARAMVANPDQWADSDRDQ
VNTRHYLSTSMRVALDRGEFFLVYQPIIRLADNRIIGAEALLRWEHPTLG

-continued

TLLPGRFIDRAENNGLMVPLTAFVLEQACRHVRSWRDHSTDPQPFVSVNV

SASTICDPGFLVLVEGVLGETGLPAHALQLELAEDARLSRDEKAVTRLQE

LSALGVGIAIDDFGIGFSSLAYLPRLPVDVVKLGGKFIECLDGDIQARLA

-continued

NEQITRAMIDLGDKLGITVTAKLVETPSQAARLRAFGCKAAQGWHFAKAL

PVDFFRE

The sequences referenced in the application are summarized in Table 1 below.

TABLE 1

| SEQUENCE NUMBER | DESCRIPTION |
|---|---|
| SEQ ID NO: 1 | Diadenylate cyclase DisA from BCG and other related mycobacteria, amino acid sequence |
| SEQ ID NO: 2 | Diadenylate cyclase disA from BCG and other related mycobacteria, DNA sequence |
| SEQ ID NO: 3 | Plasmid pSD5B-P$_{hsp60}$::disA which overexpresses the disA gene, DNA sequence |
| SEQ ID NO: 4 | Bifunctional diguanylate cyclase/phosphodiesterase BCG_RS07340 from BCG and other related mycobacteria, amino acid sequence |
| SEQ ID NO: 5 | Bifunctional diguanylate cyclase/phosphodiesterase BCG_RS07340 from BCG and other related mycobacteria, DNA sequence |
| SEQ ID NO: 6 | Modified, bifunctional diguanylate cyclase/phosphodiesterase from BCG and other related mycobacteria lacking the EAL domain so that it functions as a monofunctional diguanylate cyclase, amino acid sequence |
| SEQ ID NO: 7 | Modified, bifunctional diguanylate cyclase/phosphodiesterase from BCG and other related mycobacteria lacking the EAL domain so that it functions as a monofunctional diguanylate cyclase, DNA sequence |
| SEQ ID NO: 8 | Cyclic GMP-AMP synthase DncV from *Vibrio cholerae*, amino acid sequence |
| SEQ ID NO: 9 | Cyclic GMP-AMP synthase dncV from *Vibrio cholerae*, DNA sequence |
| SEQ ID NO: 10 | Cyclic GMP-AMP synthase cGAS from *Homo sapiens*, amino acid sequence |
| SEQ ID NO: 11 | Cyclic GMP-AMP synthase cGAS from *Homo sapiens*, DNA sequence |
| SEQ ID NO: 12 | Cyclic GMP-AMP synthase cGAS gene from *Homo sapiens* with mycobacterial codon optimization, DNA sequence |
| SEQ ID NO: 13 | Plasmid pMH94H- P$_{hsp60}$::disA::COcGAS::mCherry which overexpresses the disA gene, the codon-optimized human cGAS gene, and mCherry, DNA sequence |
| SEQ ID NO: 14 | Bifunctional c-di-AMP & cGAMP phosphodiesterase CdnP from BCG, amino acid sequence |
| SEQ ID NO: 15 | Bifunctional c-di-AMP & cGAMP phosphodiesterase CdnP from BCG, DNA sequence |
| SEQ ID NO: 16 | Bifunctional c-di-AMP & cGAMP phosphodiesterase CdnP from *M. tuberculosis* with 20 amino acid N-terminal extension, amino acid sequence. |
| SEQ ID NO: 17 | Diguanylate phosphodiesterase AHM07112.1 from BCG and other related mycobacteria, amino acid sequence |
| SEQ ID NO: 18 | Diguanylate phosphodiesterase AHM07112.1 from BCG and other related mycobacteria, DNA sequence |
| SEQ ID NO: 19 | Diguanylate phosphodiesterase Rv1357c or MT1400 from *Mycobacterium tuberculosis* and BCG Pasteur 1173 P2 with 19 amino acid N-terminal extension, amino acid sequence |
| SEQ ID NO: 20 | DNA sequence for the 1350 bp panCD operon from BCG Pasteur |
| SEQ ID NO: 21 | Protein sequence for the 301 aa PanC polypeptide from BCG Pasteur |
| SEQ ID NO: 22 | Protein sequence for the 139 aa PanD polypeptide from BCG Pasteur |
| SEQ ID NO: 23 | DNA sequence for the 2501 bp panCD-containing region from BCG |
| SEQ ID NO: 24 | Protein sequence for the 724 aa mutant PanC polypeptide from BCG |
| SEQ ID NO: 25 | Protein sequence for the 139 aa PanD polypeptide from BCG Tice |
| SEQ ID NO: 26 | DNA sequence alignment of the BCG Pasteur and BCG Tice panC |
| SEQ ID NO: 27 | DNA sequence alignment of the BCG Pasteur and BCG Tice panD |
| SEQ ID NO: 28 | L primer to amplify the panCD operon (diagnostically) |
| SEQ ID NO: 29 | R primer to amplify the panCD operon (diagnostically) |
| SEQ ID NO: 30 | pSD5.hsp65-disA.Kan |
| SEQ ID NO: 31 | pSD5.hsp65-disA.panCD—"No Kan |
| SEQ ID NO: 32 | DNA sequence for pJV53 (recombineering plasmid) |
| SEQ ID NO: 33 | DNA fragment containing panCD allelic exchange substrate cassette |
| SEQ ID NO: 34 | dif-Hyg-dif cassette |
| SEQ ID NO: 35 | pUC-Hyg Plasmid |
| SEQ ID NO: 36 | pUC-Hyg-panCD KO plasmid |
| SEQ ID NO: 37 | Left primer used to generate the backbone of "pSD5.hsp65- |
| SEQ ID NO: 38 | Right primer used to generate the backbone of "pSD5.hsp65- |
| SEQ ID NO: 39 | Left primer used to generate the panCD portion of "pSD5.hsp65- |
| SEQ ID NO: 40 | Right primer used to generate the panCD portion of "pSD5.hsp65- |

In one embodiment, the present invention relates to an expression cassette or expression vector including a nucleic acid sequence encoding a Rv1354c protein, or a functional part thereof; a nucleic acid sequence encoding a cyclic GMP-AMP synthase (DncV) protein, or a functional part thereof; a nucleic acid sequence encoding a cyclic GMP-AMP synthase (cGAS) protein, or a functional part thereof; or a combination thereof. In some aspects, the expression vector or expression cassette further includes a nucleic acid sequence encoding a DNA integrity scanning (disA) protein which functions as a diadenylate cyclase, or a functional part thereof. In other aspects, the nucleic acid sequence encoding a Rv1354c protein does not contain a phosphodiesterase gene or phosphodiesterase domain. In some aspects, the expression vector or expression cassette does not contain a phosphodiesterase gene or phosphodiesterase domain.

Methods for generating expression vectors and expression cassettes, transforming Mycobacteria and isolating the same have been described. In some embodiments, an expression vector or expression cassette of the invention includes one or more regulatory sequences, e.g., a promoter and/or enhancer element, operably linked to a nucleic acid of the invention which controls or influences transcription of the nucleic acid. In some aspects, an expression vector or expression cassette of the invention includes one or more sequences operably linked to a nucleic acid of the invention which direct termination of transcription, post-transcriptional cleavage, and/or polyadenylation. In some aspects, an expression vector or expression cassette of the invention includes a variable length intervening sequence and/or a selectable marker gene operably linked to a nucleic acid of the invention.

In one embodiment, the present invention relates to a strain of *Mycobacterium* including an expression vector or expression cassette of the invention described herein. In some aspects, the strain of *Mycobacterium* is *Mycobacterium tuberculosis*, *Mycobacterium bovis*, or a combination thereof. In other aspects, the strain of *Mycobacterium* is BCG. In some aspects, the strain includes the plasmid of SEQ ID NO:13.

In another embodiment, the present invention relates to a strain of *Mycobacterium* that expresses or overexpresses diadenylate cyclase and/or expresses or overexpresses one or more other cyclase genes or domains (e.g., those described herein). In some aspects, the expression or over-expression results in the release of one or more STING agonists (e.g., c-di-AMP, c-di-GMP, 2'-3' cGAMP, and/or 3'-3' cGAMP). In some aspects, the present invention relates to a strain of *Mycobacterium* that expresses or overexpresses diadenylate cyclase and/or does not express a phosphodiesterase (PDE) that hydrolyzes STING agonists (e.g., contains a deletion of a PDE gene that hydrolyzes STING agonists). In some aspects, the strain of *Mycobacterium* is *Mycobacterium tuberculosis*, *Mycobacterium bovis*, or a combination thereof. In some aspects, the strain of *Mycobacterium* is BCG.

Statistically Significant Anti-Tumor Effects with BCG-disA-OE in the Rat MNU Bladder Cancer Model The rat MNU bladder cancer model is a validated model of bladder cancer in which administration of intravesical BCG can be shown to be therapeutic (FIG. 6 and Kates et al. PMID 28588015). The inventors extended their previous findings of the therapeutic effect of BCG-disA-OE versus BCG-WT which were shown in FIG. 7. The inventors have now performed the 16-week rat MNU model twice. FIG. 7 was based on Experiment 1 and shows that BCG-disA-OE displays a trend towards a better outcome versus BCG-WT.

Figure 15:
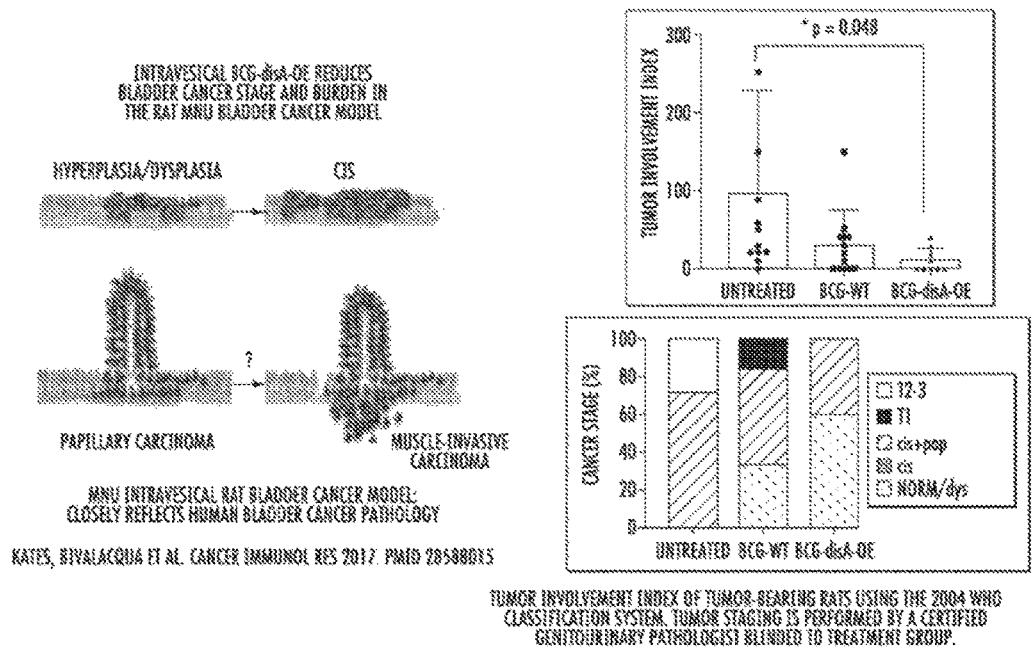
FIG. 15 shows that intravesical instillation of BCG-disA-OE displays greatest antitumor efficacy (statistically significant improvement in pathology) in the MNU carcinogen model of non-muscle invasive bladder cancer (NIMBC). Groups of rats received 4 intravesical treatments with MNU over the first 8 weeks (one treatment every 2 weeks) to elicit NIMBC. Over the next 8 weeks they received 4 intravesical treatments with either PBS (untreated), BCG-WT, or BCG-disA-OE (one treatment every 2 weeks). At the end of the 16-week experiment, rats were sacrificed, and their bladders were removed. A portion of the bladder was fixed and subjected to H&E staining and then interpreted in a blinded fashion by a Board-certified urologic pathologist. The tumor involvement score and cancer stage (T2-3, T1, CIS+papillary lesions, CIS alone, or normal-dysplastic) were determined and are shown. As may be seen BCG-disA-OE instillation resulted into statistically significantly lower tumor involvement index than PBS (untreated) while BCG-WT was not statistically significantly superior to PBS. This 16-week experiment was performed twice. The data in FIG. 7 represent the results of Experiment 1. The data in this figure (FIG. 15) represent the combined results of Experiment 1 plus Experiment 2. The qPCR data shown in FIG. 8 and FIG. 9 were obtained using bladder tissue at necropsy from the end of Experiment 1.

After performing Experiment 2 and combining its data with Experminent 1, it is now shown that BCG-disA-OE is statistically significantly superior to no treatment (p=0.048) whereas BCG-WT is not statistically significantly superior to no treatment (data shown in FIG. 15).

Reduction of Tumor-Suppressive Treg Cells by BCG-disA-OE in a Murine Syngeneic Bladder Cancer Tumor Model.

Figure 16:
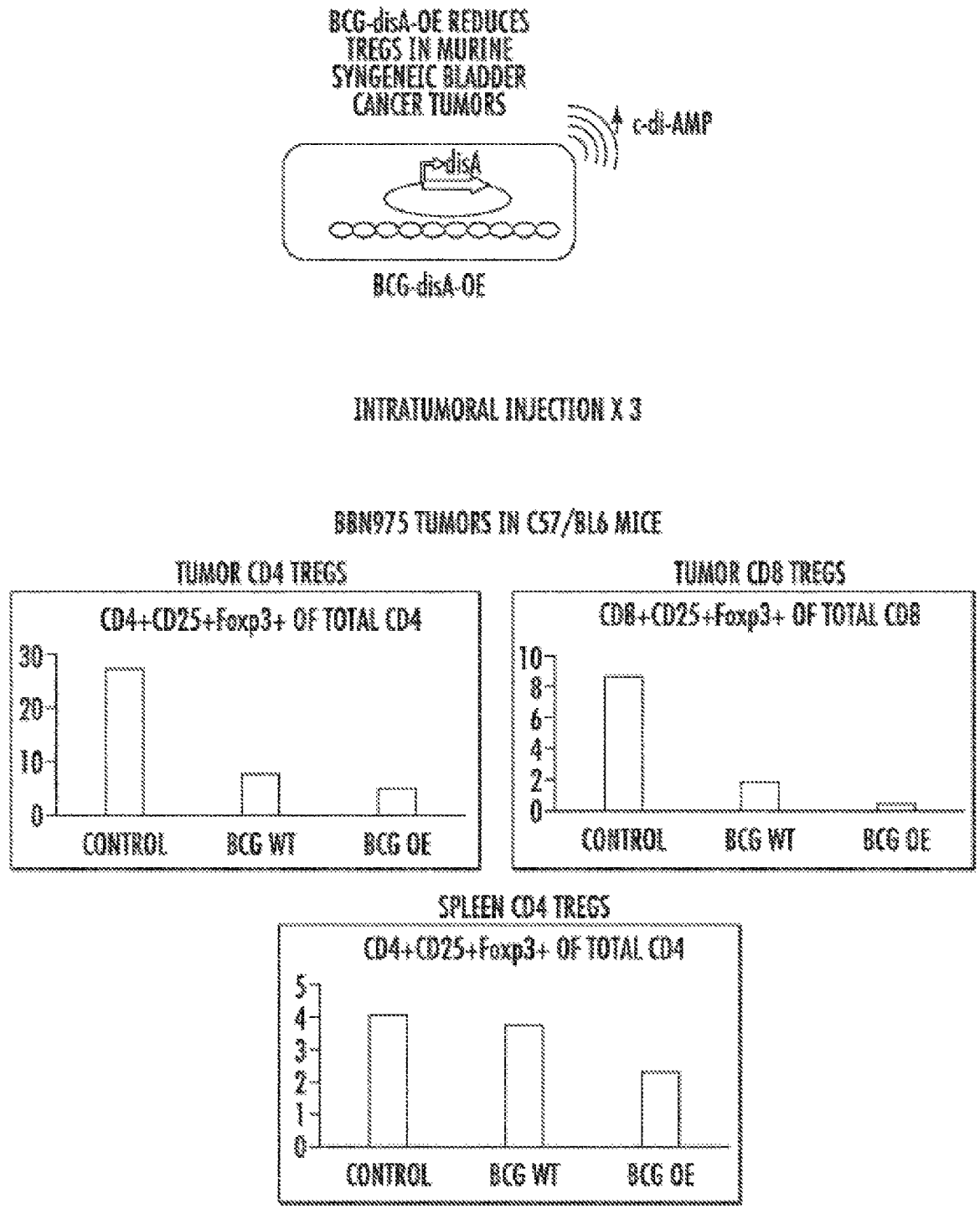
FIG. 16 shows that BCG-disA-OE reduces Tregs (CD4$^+$CD25$^+$Foxp3$^+$) in murine syngeneic bladder cancer tumors. Mice were implanted on the flank with 5×10$^6$ BBN975 murine bladder cancer tumor cells. When the tumors were 1.5 cm in diameter, mice received 3 intratumoral injections of either PBS (control), BCG-WT, or BCG-disA-OE (one treatment every 2 days). Two days after the last intratumoral treatment, mice were sacrificed, and their spleens and tumors were removed. After tumor cell dispersal, the cell preparations were stained and subjected to flow cytometry. As may be seen BCG-disA-OE led to reduced tumor CD4$^+$ Tregs, reduced tumor CD8$^+$ Tregs, and reduced spleen CD4$^+$ Tregs.
Figure 20:
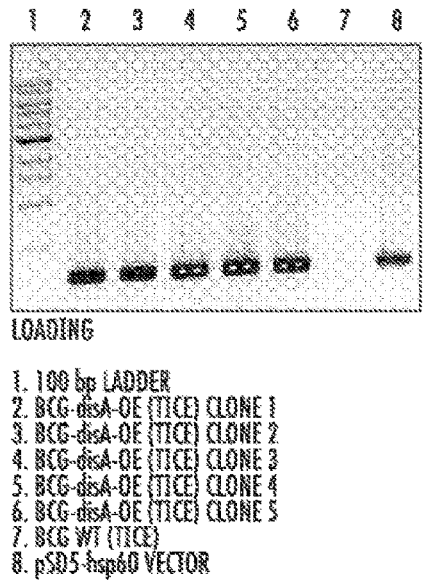
FIG. 20 shows the successful construction of BCG-Tice-disA-OE. The inventors' previous work had utilized BCG-Pasteur to construct BCG-Pasteur-disA-OE. This strain was provided to one of the inventors by Dr. Frank Collins in 1995. It is the same strain known as BCG-Pasteur-Aeras. BCG-Tice is manufactured and sold by Merck and is the sole FDA-approved BCG available in the United States. The inventors purchased BCG-Tice, prepared electrocompetent BCG-Tice, and electroporated the pSD5-hsp60-MT3692 plasmid into BCG-Tice. The drawing shows the results of colony PCRs for 5 kanamycin-resistant candidate clones of transformed BCG-Tice and confirms the successful preparation of BCG-Tice-disA-OE by electroporation of the pSD5-hsp65-MT3692 plasmid into BCG-Tice. Note on nomenclature, the inventors had previously referred to this same plasmid pSD5-hsp60-MT3692. However, the actual promoter in this strain is the promoter for the hsp65 gene of M leprae. Thus, the inventors now more correctly refer to the plasmid as pSD5-hsp65-MT3692.

In the MNU rat bladder cancer model the amount of bladder tissue at the end of the 16-week experiment is insufficient to perform flow cytometry. In order to study the cell population changes elicited by BCG-disA-OE a murine syngeneic bladder cancer tumor model using BBN975 cells was developed. The model allows for large tumors (>1.5 cm in diameter) to develop on the mouse flank. Mice were treated with BCG-disA-OE and BCG-WT by intratumoral injection. As is shown in FIG. 16, the use of BCG-disA-OE led to reduced levels of tumor-associated CD4+ Treg cells, tumor-associated CD8+ Treg cells, and splenic CD4+ Treg cells.

BCG-disA-OE Delivers Sustained STING Agonist from the Intracellular Compartment.

Persistence of BCG in the Bladder.

Bowyer et al (The persistence of bacilli Calmette-Guerin in the bladder after intravesical treatment for bladder cancer. Brit J Urol. 1995; 75: 188-192. PMID 7850324) evaluated 125 bladder cancer patients from 1986- 1992 who received intravesical BCG. Patients were asked to provide monthly urine samples which were then sent for mycobacterial culture. 90 patients survived and were compliant with the monthly urine samples. 4/90 patients (4.4%) had persistent BCG in their urine, one for up to 16.5 months. A fifth patient required a cystectomy 7 weeks after completing intravesical BCG treatments and was found to have microscopic evidence of acid-fast bacilli in the bladder by microscopy.

Figure 38:
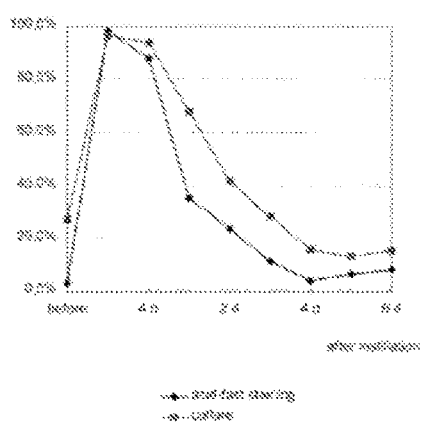
FIG. 38 shows the number of positive specimens.

Durek et al. (The fate of bacillus Calmette-Guerin after intravesical instillation. J Urol. 2001; 165: 1765-1768. PMID 11342972) studied 49 patients with serial urine cultures following intravesical BCG. BCG was in the urine detected in 96.4% of the specimens after 2 hours and in 67.9% after 24 hours after instillation. The number of positive specimens decreased, and was 27.1% on day 7 immediately before the next instillation (FIG. 38). The investigators also evaluated bladder biopsies by PCR for mycobacterial DNA within 1 week after the $6^{th}$ instillation (instillations were given monthly). In 14 of 44 bladder biopsies (31.8%) mycobacterial ribosomal DNA was found. Additionally, positive PCRs for mycobacterial DNA was evident up to 24 months in between 4.2% and 37.5% of the investigated biopsies.

The fact that BCG is known to persist in bladder tissue represents an important advantage of the BCG-disA-OE strategy for STING agonist deliver in cancer. While numerous technologies have focus on generating small molecule STING agonists, such agents have relatively short exposure times. In contrast, as an intracellular microorganism and as demonstrated by the Bowyer and Durek studies, BCG persists in cells and tissues for many weeks. The persistence of BCG-disA-OE in tissue offers sustained long-term deliver of the STING agonist in the tumor microenvironment.

BCG-disA-OE is Safer than BCG-WT in Two Separate Mouse Models

Intravesical BCG treatment in humans is associated with dysuria, fatigue, and malaise in treated patients. Additional more severe adverse effects are persistent cystitis with BCG and disseminated BCGosis. The patient safety of BCG was reviewed extensively in O'Donnell et al (Up-to-date, 2019).

The incidence of dissemination of BCG into the bloodstream after intravesical instillation is estimated at 1/15,000 patients.

To test the safety of BCG-disA-OE compared to BCG-WT the inventors used two mouse models of BCG infection where the BCG strains were aerosolized into the lungs of immunocompetent BABL/c mice or immunosuppressed SCID mice. As shown in FIGS. 17A-17B, BCG-disA-OE was less capable of proliferating in immunocompetent mouse lungs than BCG-WT, and it was less lethal in a time-to-death assay in immunosuppressed mice.

BCG has been Shown to Elicit Trained Immunity which has been Associated with its Therapeutic Benefit in Solid and Liquid Tumors and for Diabetes. STING Agonist Overexpressing BCG Strains Elicit Stronger Trained Immunity Changes than BCG-WT Trained immunity. Trained immunity refers to the ability of one antigenic stimulus to elicit more potent immune responses to a second, different antigen. Trained immunity is antigen independent, based on heterologous CD4 and CD8 memory activation, cytokine mediated, and is associated with epigenetic and metabolic changes. BCG is a potent tool as the first antigenic stimulus to elicit trained immunity to subsequent antigenic stimuli such as tumors, viral infection, or drug-resistant bacterial infections (Netea et al. Trained immunity: a program of innate immune memory in health and disease. Science 2016. PMID 27102489; and Arts et al. BCG vaccination protects against experimental viral infection in humans through the induction of cytokines associated with trained immunity. Cell Host Microbe 2018. PMID 29324233).

BCG for solid and liquid tumors. BCG has a long history of therapeutic benefit as an immunotherapy for both solid and liquid tumors in humans (Hersh et al. BCG as adjuvant immunotherapy for neoplasia. Annu Rev Med 1977. PMID 324372). It has been used both systemically and intratumorally for malignancies that include melanoma, non-small cell lung cancer (NSCLC), and acute lymphoblastic leukemia (ALL). Recently there have been trials of BCG together with checkpoint inhibitors for forms of bladder cancer.

BCG for diabetes. BCG vaccination has recently been shown to have therapeutic benefits in glucose control for various forms of diabetes mellitus including Type 1 diabetes mellitus (Stienstra and Netea. Firing up glycolysis: BCG vaccination effects on Type 1 diabetes mellitus. Trends Endoc Metab 2018. PMID: 30327169). The effect is believed to be mediated by the trained immunity effects of BCG which have been shown to lead to epigenetic modifications which promote pro-inflammatory cytokine expression as well as the expression of metabolic enzymes such as those for glycolosis.

BCG-disA-OE and trained immunity. To investigate the ability of STING agonist overexpressing strains of BCG to stimulate trained immunity, the inventors tested the ability of BCG-WT versus BCG-disA-OE to elicit potentiation of second antigen stimulation in rested human monocytes following an exposure to the BCG strains six days prior. The first antigen was a BCG strain on day 0, and after six days of rest, the second antigen was the unrelated TLR-1/2 antigen PAM3CSK4. As may be seen in FIG. 18, upon receiving the second stimulus, the immune response tested (secretion of IL-1β) was potentiated by both BCG-WT and BCG-disA-OE, but the degree of stimulation by BCG-disA-OE was statistically significantly greater than that of either no BCG first stimulus or BCG-WT as the first stimulus. This reveals that STING overexpressing BCG strains such as BCG-disA-OE are a more potent stimulators of trained immunity than BCG-WT.

In a related experiment, the inventors conduced the same BCG-first stimulation/6 day rest/TLR-1, 2 second antigen stimulation with PAM3CSK4 experiment with human monocytes. At the end of the experiment cellular DNA was collected and subjected to chromatin immunoprecipitation (ChIP) using an antibody for the H3K4 histone methylation mark. The H3K4 mark is a known transcriptional activation mark. Upon quantitative PCR amplification of the IL-6 promoter region of the immunoprecipitated DNA, the results showed that BCG-Pasteur-disA-OE and BCG-Tice-disA-OE were statistically significantly more potent in eliciting the H3K4 mark in the IL-6 promoter (IL-6 is a pro-inflammatory cytokine) than their respective BCG-WT strains. These results showed that STING overexpressing BCG strains such as BCG-disA-OE are a more potent stimulators of epigenetic changes associated with trained immunity than BCG-WT.

BCG-Tice-disA-OE Expresses Much Higher Levels of the disA Gene than BCG-WT

Figure 21:
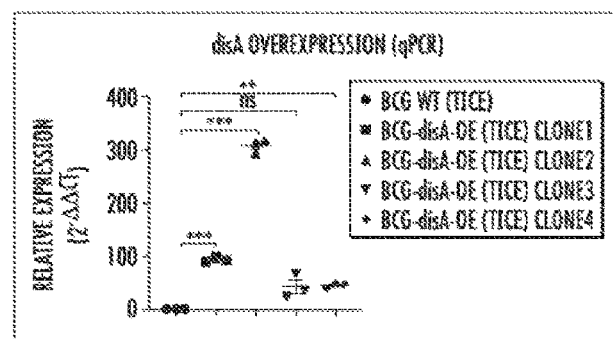
FIG. 21 shows that clone 2 of BCG-Tice-disA-OE from the transformation experiment shown in FIG. 20 strongly expresses the disA gene. Real time PCR was used to show differential disA expression in four different BCG-Tice-disA-OE clones. Gene expression was measured in total RNA isolated from the late log phase cultures using log phase cultures using SYBR green based quantitative real-time PCR. The graphical data points represent the mean of 3 independent experiments ±standard error mean (SEM). M tuberculosis sigA (Rv2703) was used as an internal control. Data analysis was performed using $2^{-\Delta\Delta CT}$ method. Student's t test followed by Welch correction (*P<0.001; P<0.01). The inventors created seedlots of BCG-TicedisA-OE clone 2 and refer to this clone as simply "BCG-Tice-disA-OE" in all subsequent work.

As may be seen in FIG. 21, the relative expression of BCG-Tice-disA-OE clone 2 (which was selected for seed-lot preparation and storage) was 300:1 using the $2^{-\Delta\Delta CT}$ method of comparison. This indicates that disA is strongly overexpressed by being on a multicopy plasmid and driven by the *M. leprae* hsp65 promoter in pSD5-hsp65-MT3692 plasmid. This strong overexpression leads to much higher levels of release of the STING agonist, c-di-AMP.

STING Agonist Overexpression BCG Strains such as BCG-disA-OE Elicit Pro-Inflammatory Changes in Signaling Pathways and Cytokine Secretion Profiles in Multiple Model Systems.

The inventors tested STING agonist overexpressing strains such as BCG-disA-OE compared to BCG-WT in multiple model systems to evaluate its relative capacity to elicit proinflammatory cytokine changes. BCG-disA-OE was statistically significantly superior than BCG-WT in the majority of their tests. When the comparisons were not statistically significant, BCG-disA-OE gave the stronger of the two responses.

Figure 23:
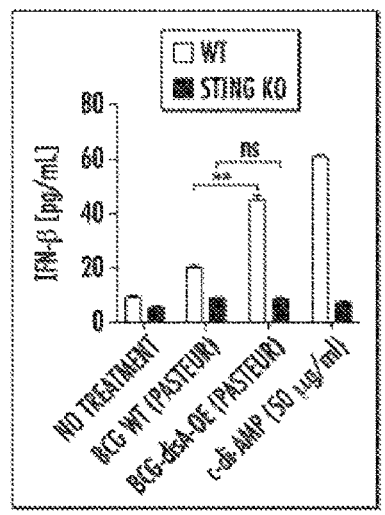
FIG. 23 shows that STING is required for enhanced type I IFN (IFN-β) induction in response to BCG-WT and BCG-disA-OE. Mouse (C57BL/6) bone marrow-derived macrophages from STING ablated (STING-KO) wild-type animals were infected with different strains of BCG (MOI=1:20) for 3 h. Cell were washed using warm DPBS to removed non-internalized bacilli and were subsequently incubated in for another 24 h before culture supernatants were harvested. ELISA for IFN-β was performed in culture supernatants as per the manufacturer's instruction. Data points represent the mean of three independent biological experiments±standard error mean (S.E.M.). Student's t test followed by Welch correction (**P<0.01).

FIG. 23 also shows that the elevation of type 1 IFN secretion in both BCG-disA-OE and BCG-WT is STING-dependent.

In summary, BCG-disA-OE is a more potent stimulator of pro-inflammatory cytokine expression and proinflammatory pathway induction than BCG-WT The table below summarizes the data:

TABLE 2

Figure 22:
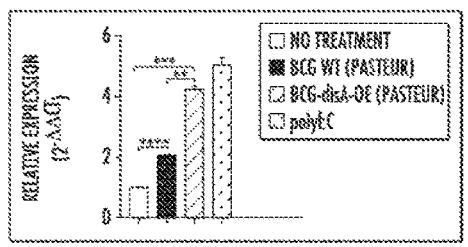
FIG. 22 shows potent, statistically significantly enhanced IRF3 induction in mouse bone marrow-derived macrophages infected with BCG-Pasteur-disA-OE compared with BCG-Pasteur-WT. Mouse (C57BL/6) bone marrow-derived macrophages were infected with wild-type and disA overexpressing strains of BCG Pasteur (20 MOI) for 3 h. Cells were washed with warm DPBS to remove non-internalized bacilli and were subsequently incubated for another 3 hours. IRF3 expression was measured in total RNA isolated from the cell lysate using SYBR green based quantitative real-time PCR. The graphical data points represent the mean of 3 independent experiments±standard error mean (SEM). Mouse beta-actin was used as an internal control. Data analysis was performed using $2^{-\Delta\Delta C_T}$ method. Student's t test followed by Welch correction (*P<0.001; P<0.01).
Figure 24A:
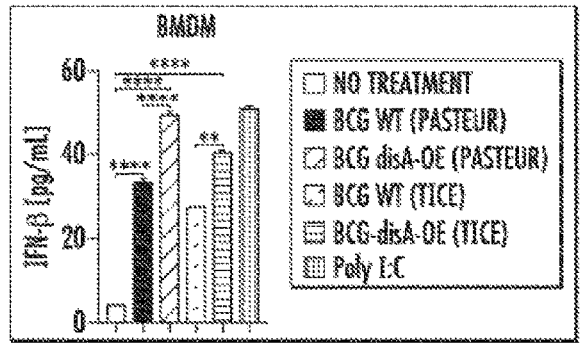
FIGS. 24A-24C shows that interferon-β is induced murine BMDMs, BMDCs and J774.1 macrophages in upon exposure to disA overexpressing BCG strains and that the IFN-β response is statistically significantly greater for BCG-Pasteur-disA-OE and BCG-Tice-disA-OE than for the corresponding BCG-WT strains. Mouse (C57BL/6) bone marrow-derived macrophages (BMDMs), and J774.1 macrophages were infected for 3h using different strains of BCG (MOI: 20). Non-internalized bacilli were washed using warm DPBS and cell were incubated for another 24 hours. IFN-β levels were quantified in culture supernatants using ELISA as per manufacturer's instruction. Data points represent three independent biological experiments±standard error mean (S.E.M.). Data analysis was performed using unpaired t-test (*P<0.001; P<0.01; *P<0.05).
Figure 24B:
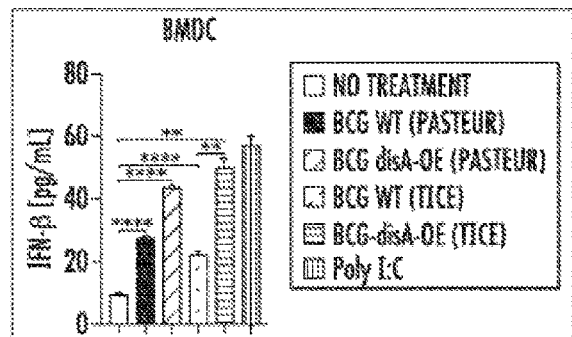
Figure 24C:
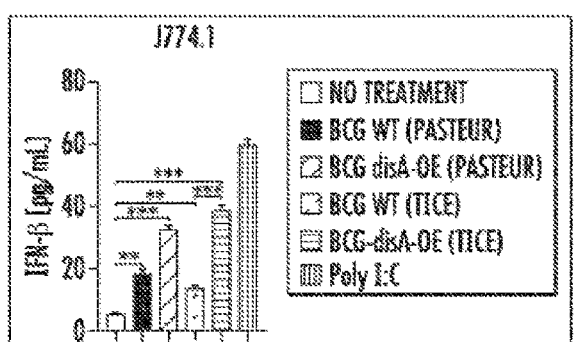
Figure 25A:
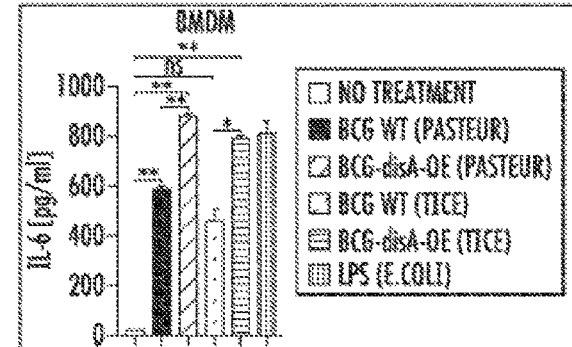
FIGS. 25A-25C show that IL-6 is induced in mouse BMDMs, BMDCs and J774.1 macrophages in response to exposure to disA overexpressing BCG strains and that the IL-6 response is statistically significantly greater for BCG-Pasteur-disA-OE and BCG-Tice-disA-OE than for the corresponding BCG-WT strains. Mouse (C57BL/6) bone marrow-derived macrophages (BMDMs), and J774.1 macrophages were infected for 3 h using different strains of BCG (MOI: 20). Non-internalized bacilli were washed using warm DPBS and cell were incubated for another 24 hours. IL-6 levels were quantified in culture supernatants using ELISA as per manufacturer's instruction. Data points represent three independent biological experiments±standard error mean (S.E.M.). Data analysis was performed using unpaired t-test (*P<0.001; P<0.01; *P<0.05).
Figure 25B:
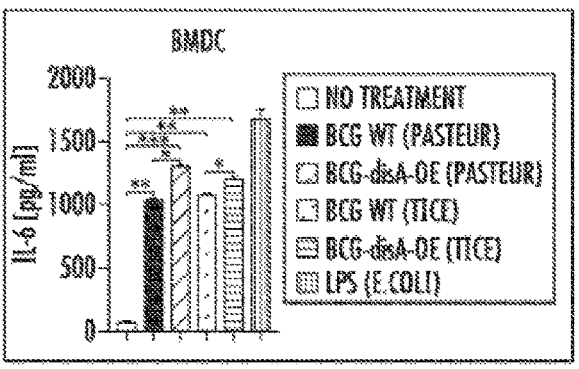
Figure 25C:
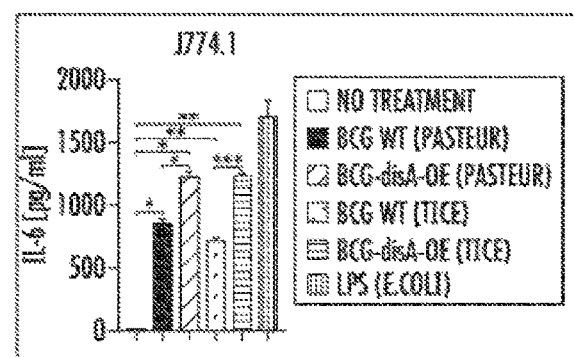

| | | | | |
|---|---|---|---|---|
| Mouse BMDM in vitro | IRF3 | qRT-PCR | BCG-disA-OE > BCG-WT | FIG. 22 |
| Mouse BMDM, BMDC, J774 macrophage cell line in vitro | IFN-β | ELISA | BCG-disA-OE > BCG-WT | FIG. 24 |
| Mouse BMDM; BMDC. J774 macrophage cell line in vitro | IL-6 | ELISA | BCG-disA-OE > BCG-WT | FIG. 25 |

TABLE 2-continued

Figure 26A:
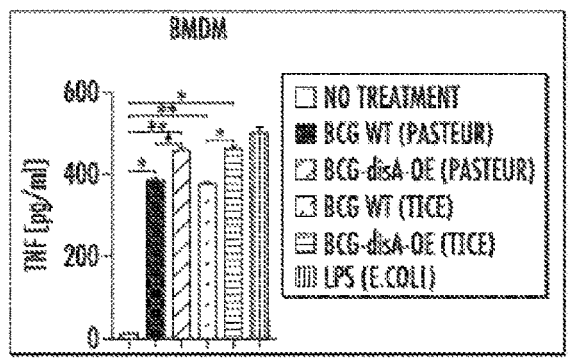
FIGS. 26A-26C shows that TNF is induced in mouse BMDMs, BMDCs and J774.1 macrophages in response to exposure to disA overexpressing BCG strains and that the responses are statistically significantly greater for BCG-Pasteur-disA-OE and BCG-Tice-disA-OE than for the corresponding BCG-WT strains. Mouse (C57BL/6) bone marrow-derived macrophages (BMDMs), and J774.1 macrophages were infected for 3h using different strains of BCG (MOI: 20). Non-internalized bacilli were washed using warm DPBS and cell were incubated for another 24 hours. TNF levels were quantified in culture supernatants using ELISA as per manufacturer's instruction. Data points represent three independent biological experiments±standard error mean (S.E.M.). Data analysis was performed using unpaired t-test (*P<0.001; P<0.01; *P<0.05).
Figure 26B:
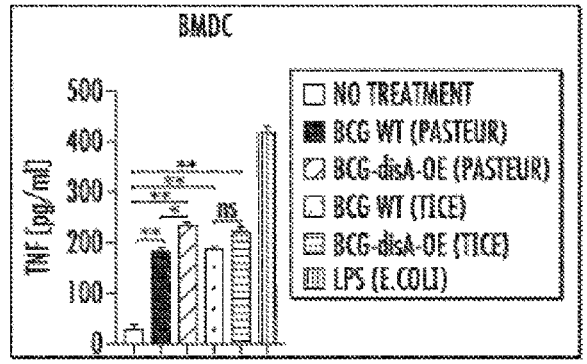
Figure 26C:
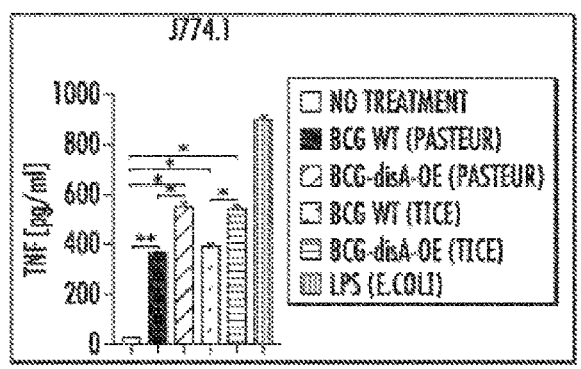
Figure 27A:
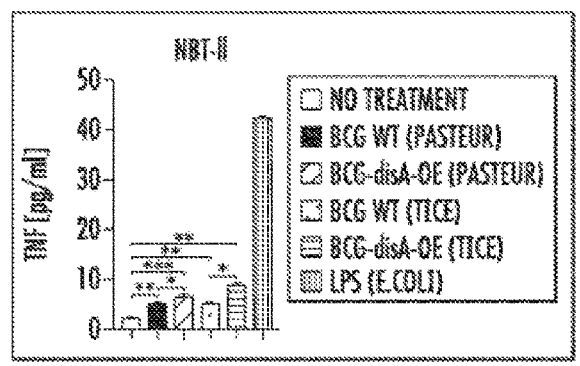
FIGS. 27A-27B shows that TNF and IFN-γ are induced in the rat bladder carcinoma NBT-II cell line in response to exposure to disA overexpressing BCG strains and that the two responses are statistically significantly greater for BCG-Pasteur-disA-OE and BCG-Tice-disA-OE than for the corresponding BCG-WT strains. NBT-II cells were infected with wild-type and recombinant strains of BCG for 3 h. Non-internalized bacilli were repeatedly washed using warm DPBS and cells were incubated for another 24 h. Culture supernatants were used for quantification of TNF and IFN-γ. Data points represent three independent biological experiments±standard error mean (S.E.M.). Data analysis was performed using unpaired t-test (*P<0.0001; P<0.001; *P<0.05).
Figure 27B:
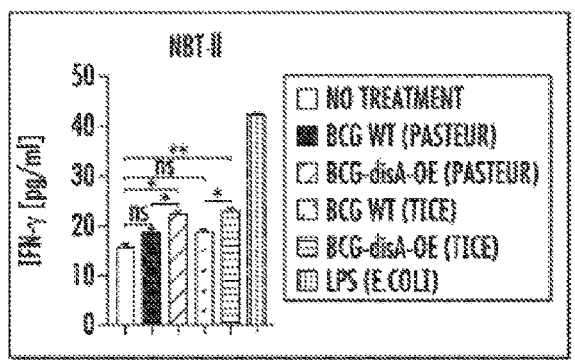
Figure 28A:
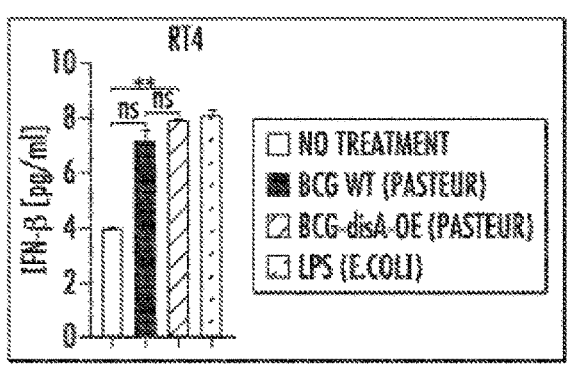
FIGS. 28A-28D shows that of IFN-β, IFN-γ, TNF and IL-1β in are induced the in the human transitional cell papilloma RT4 bladder cancer cell line in response to exposure to disA overexpressing BCG strains and that the two responses are greater for BCG-Pasteur-disA-OE and BCG-Tice-disA-OE than for the corresponding BCG-WT strains. RT4 cells were infected with wild-type and recombinant strains of BCG for 3 h. Non-internalized bacilli were repeatedly washed using warm DPBS and cells were incubated for another 24 h. Culture supernatants were used for quantification of cytokines as per manufacturer's instruction. Data points represent two independent biological experiments±standard error mean (S.E.M.). Data analysis was performed using unpaired t-test (*P<0.001; P<0.01; *P<0.05).
Figure 28B:
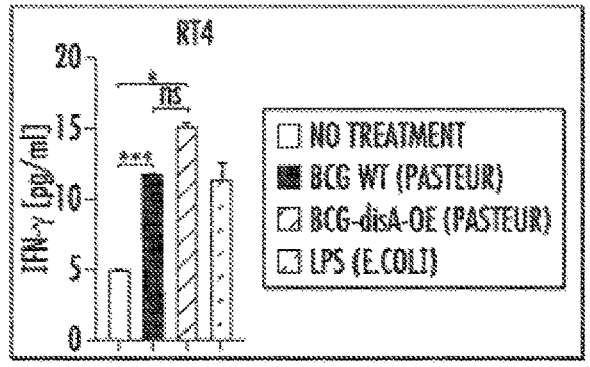
Figure 28C:
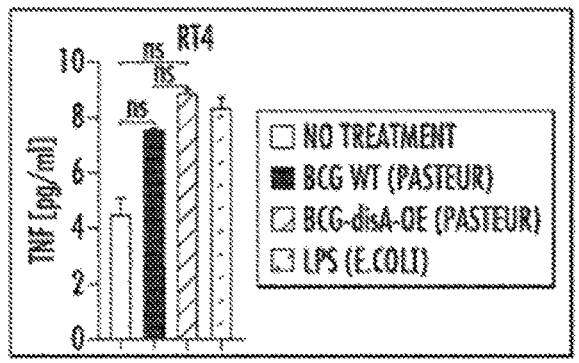
Figure 28D:
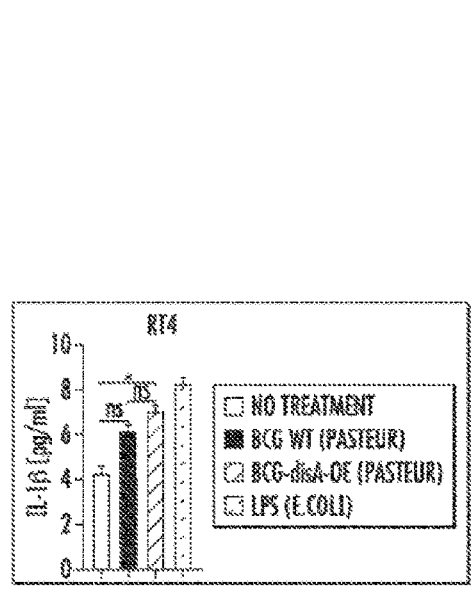
Figure 29:
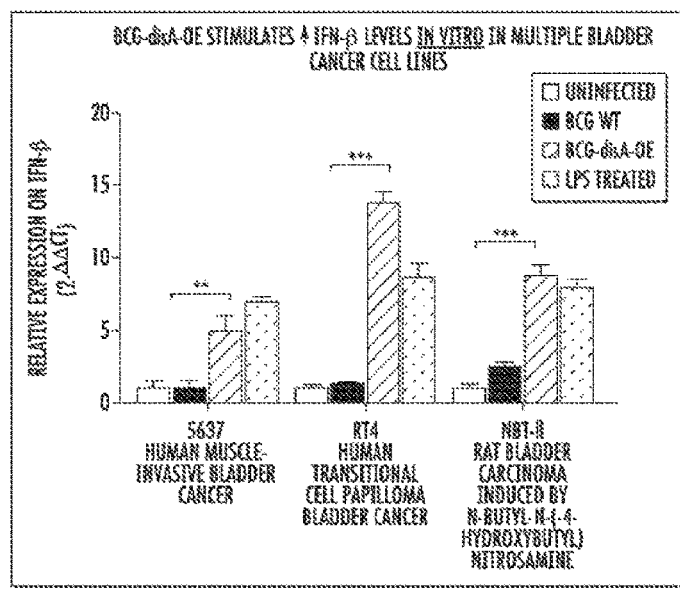
FIG. 29 shows that BCG-disA-OE stimulates increased IFN-β levels in multiple bladder cancer cell lines to a greater degree than BCG-WT. The drawing shows the levels of IFN-β mRNA (relative expression by the $2^{-\Delta\Delta C_T}$ method) following exposure to BCG-WT, BCG-disA-OE, and LPS. 5637 cells are human muscle-invasive bladder cancer cells, RT4 cells are human transitional cell papilloma bladder cancer cells, and NBT-II cells are rat bladder carcinoma cells induced by N-butyl-N-(-4-hydroxybutyl) nitrosamine.
Figure 30A:
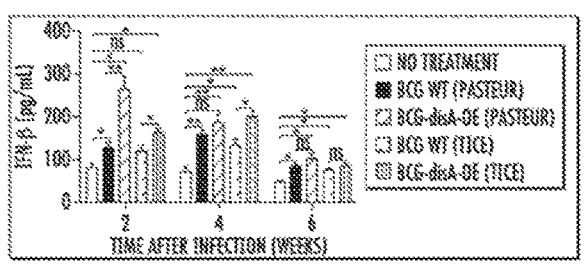
FIGS. 30A-30D shows the cytokine responses for IFN-β, IFN-γ, IL-6, and TNF in BCG-WT and BCG-disA-OE-infected mouse lungs at different time points following aerosol infection. The drawing reveals that at most time points for most cytokines, the responses are greater for BCG-Pasteur-disA-OE and BCG-Tice-disA-OE than for the corresponding BCG-WT strains. BALB/c mice were infected by the aerosol route as described in FIG. 19. Groups of mice were sacrificed at 2, 4, and 6 weeks after infection. Lung homogenates were prepared, and cytokine levels were quantified using ELISA as per manufacturer's protocol (n=4 animals/treatment group±S.E.M.). Data analysis was performed using paired t-test (*P<0.001; P<0.01; *P<0.05).
Figure 30B:
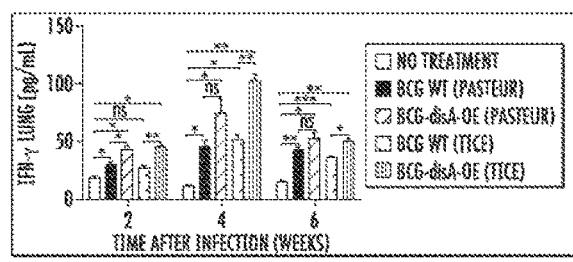
Figure 30C:
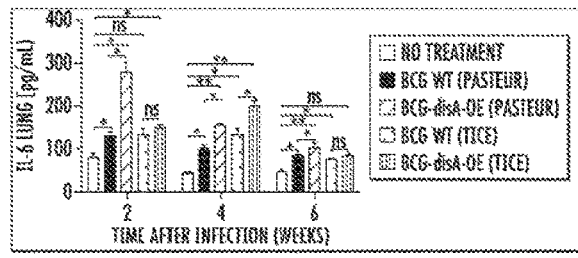
Figure 30D:
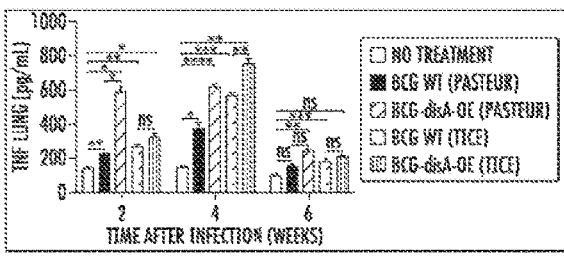
Figure 31A:
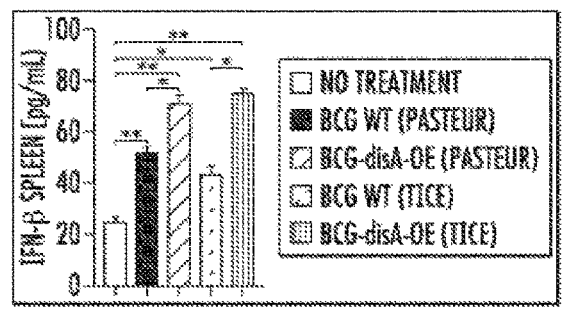
FIGS. 31A-31D shows the cytokine responses for IFN-β, IFN-γ, IL-6, and TNF in BCG-WT and BCG-disA-OE-infected mouse spleens at 4 weeks following aerosol infection. The drawing reveals that for most cytokines, the responses are greater for BCG-Pasteur-disA-OE and BCG-Tice-disA-OE than for the corresponding BCG-WT strains. BALB/c mice were infected by the aerosol route as described in FIG. 17. Groups of mice were sacrificed at 4 weeks after infection. Spleen homogenates were prepared, and cytokine levels were quantified using ELISA as per manufacturer's protocol (n=4 animals/treatment group±S.E.M.). Data analysis was performed using paired t-test (*P<0.001; P<0.01; *P<0.05).
Figure 31B:
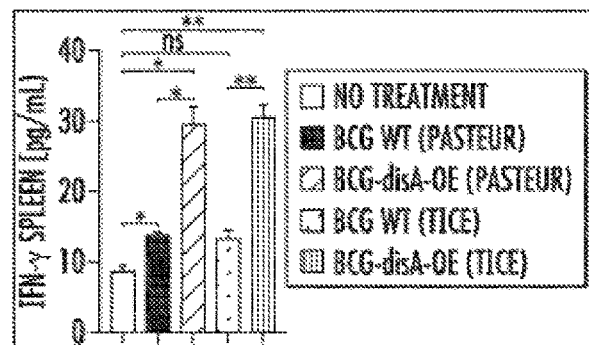
Figure 31C:
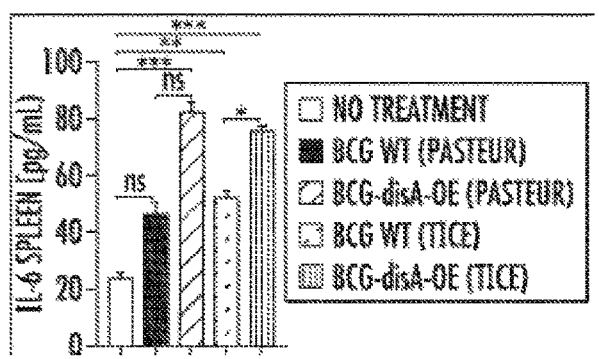
Figure 31D:
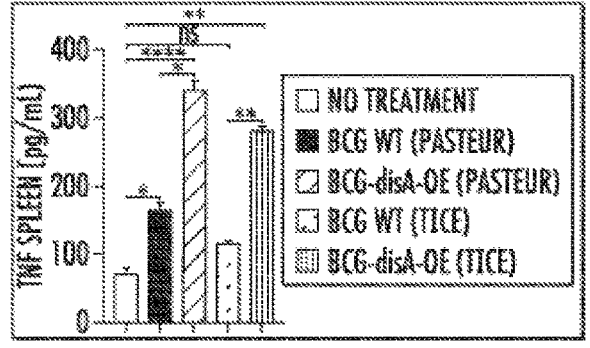
Figure 32:
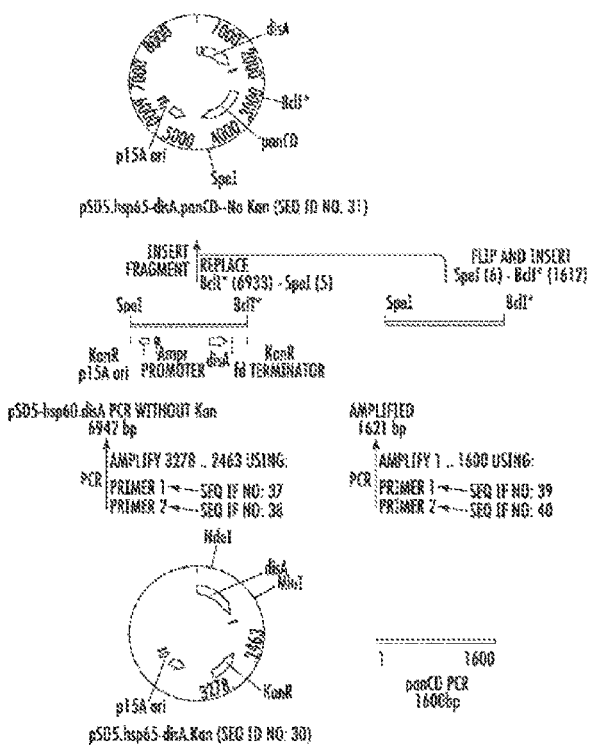
FIG. 32 shows the strategy used to generate "pSD5.hsp65-disA.panCD—No Kan" (SEQ ID NO: 31). The scheme replaces Kan cassette "pSD5. hsp65-disA.Kan" (SEQ ID NO:30) with the panCD operon to generate "pSD5.hsp65-disA.panCD—No Kan" (SEQ ID NO:31).
Figure 33:
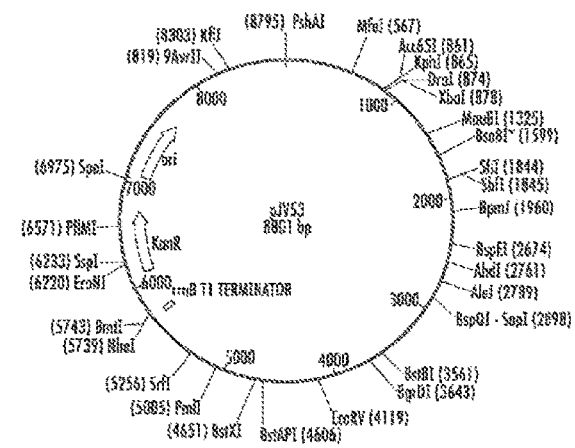
FIG. 33 shows the molecular structure of the pJV53, the recombineering plasmid which is SEQ ID NO:32
Figure 34:
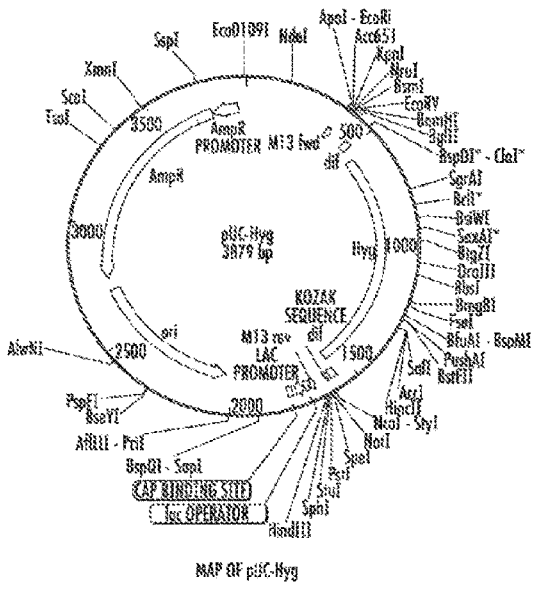
FIG. 34 shows the molecular structure of the pUC-Hyg, a plasmid with dif sites flanking a Hyg cassette which is SEQ ID NO:35. pUC-Hyg is used to generate the plasmid "pUC-Hyg-panCD-KO" (SEQ ID NO:36).
Figure 35:
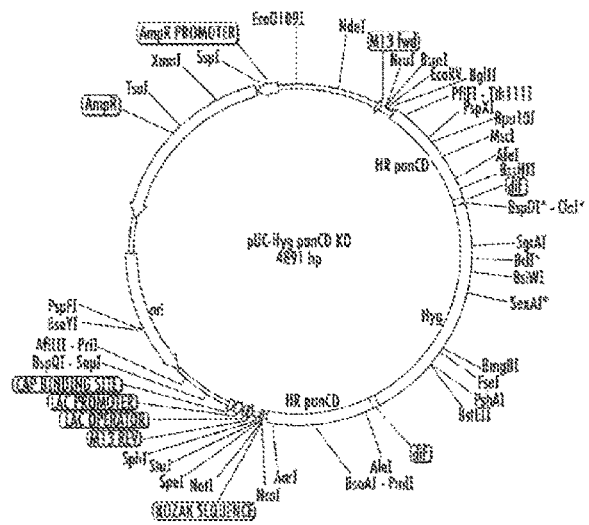
FIG. 35 shows the molecular structure of the plasmid "pUC-Hyg-panCD-KO" which is SEQ ID NO:36. "pUC-Hyg-panCD-KO" is generated by cloning 500 bp of the panCD 5'UTR on one flank of the Hyg cassette, and cloning 500 bp of the panCD 3'UTR the other flank.
Figure 36:
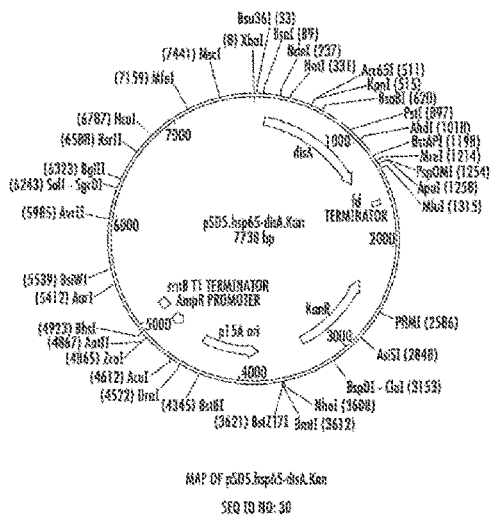
FIG. 36 shows the molecular structure of the plasmid "pSD5. hsp65-disA.Kan" which is SEQ ID NO:30.
Figure 37:
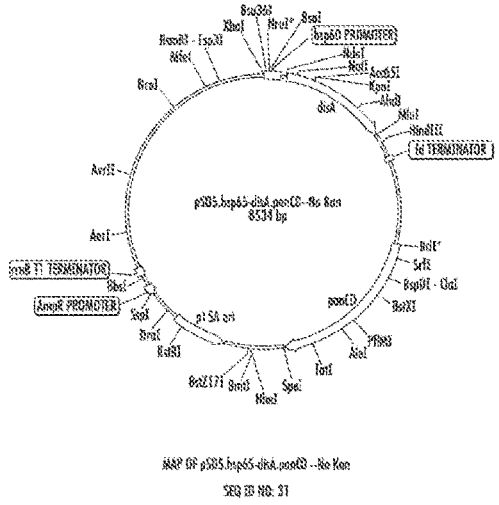
FIG. 37 shows the molecular structure of the plasmid "pSD5. hsp65-disA.panCD—No Kan" which is SEQ ID NO:31. This plasmid is generated using the scheme illustrated in FIG. 32.

| Mouse BMDM, BMDC, J774 macrophage cell line in vitro | TNF | ELISA | BCG-disA-OE > BCG-WT | FIG. 26 |
|---|---|---|---|---|
| Rat bladder cancer NBT-II line in vitro | TNF, IFN-γ | ELISA | BCG-disA-OE > BCG-WT | FIG. 27 |
| Human bladder cancer RT4 line in vitro | IFN-β, IFN-γ, TNF, IL-1β | ELISA | BCG-disA-OE > BCG-WT | FIG. 28 |
| 5637, RT4, NBT-II bladder cancer cell lines In vitro | IFN-β | qRT-PCR | BCG-disA-OE > BCG-WT | FIG. 29 |
| Mouse lungs in vivo (different time points) In vivo | IFN-β, IFN-γ, IL-6, TNF | ELISA | BCG-disA-OE > BCG-WT | FIG. 30 |
| Mouse spleens in vivo (4 weeks). In vivo | IFN-β; IFN-γ IL-6; TNF | ELISA | BCG-disA-OE > BCG-WT | FIG. 31 |

A Method to Produce an Antibiotic Gene Cassette-Free Recombinant BCG which Overexpresses a STING Agonist Biosynthetic Gene.

The disA-overexpressing plasmid pSD5-hsp65-MT3692 carries a Kan resistance gene cassette conferring resistance to the antibiotic kanamycin. The inventors disclose a method to generate an antibiotic gene cassette-free recombinant BCG which overexpresses a STING agonist biosynthetic gene.

The mycobacterial genetic operon panCD encodes for the biosynthetic gene panC (Pantoate—beta-alanine ligase gene) and panD (aspartate 1-decarboxylase gene). The gene products PanC and PanD are required for the biosynthesis of pantothenic acid also called vitamin B5 (a B vitamin). Pantothenic acid, a water-soluble vitamin, is an essential nutrient for mycobacteria such as BCG. Animals require pantothenic acid in order to synthesize coenzyme-A (CoA), as well as to synthesize and metabolize proteins, carbohydrates, and fats. The anion is called pantothenate.

Genetic deletion of panCD in mycobacteria has been shown to yield mutant strains that can only grow in the presence of added pantothenate. As such they are auxotroph for pantothenate. ΔpanCD mutants of *Mycobacterium tuberculosis*, have been shown to be highly attenuated in animal infection, being rapidly cleared, because of their inability to grow in mammalian tissues where pantothenate is not available to them.

The inventors disclose a detailed method for generating an unmarked (no antibiotic gene cassettes) ΔpanCD deletion mutant of BCG. This mutant will only be able to grow in the presence of pantothenate and would not be expected to survive during infection or be an effective delivery vector for STING agonist expression.

The inventors disclose a detailed method for generating a shuttle plasmid which harbors the mycobacterial panCD gene as well as an overexpression construct for the biosynthesis of STING agonists (such as the Phsp65::disA construct which overexpresses the disA gene and releases excess STING agonist, c-di-AMP). The shuttle plasmid is capable of replication in *E. coli* or in mycobacteria. It harbors an antibiotic cassette that can be conveniently removed by cleavage with a rare-cutting restriction enzyme and re-ligation. Alternatively, the shuttle plasmid may be generated by PCR amplification of the backbone of the plasmid excluding the antibiotic resistance cassette that generates unique restriction sites at the termini and ligating in a PCR product consisting of an amplified panCD operon with the same unique restriction sites at its termini. In either manner the antibiotic resistance gene-free shuttle plasmid (ligation product) may be electroporated into a BCG or *E. coli* auxotroph and selected for on pantothenate-free agar plates.

In the final manifestation of this disclosure, the inventors show a method to introduce the antibiotic-cassette-free plasmid harboring the mycobacterial panCD gene as well as an overexpression construct for the biosynthesis of STING agonists (such as the Phsp65::disA construct) into an unmarked BCG ΔpanCD mutant. The end result is a BCG strain that harbors no antibiotic resistance genes, and that strongly overexpresses a STING agonist biosynthetic gene (s). In a mammalian host or a human, such a BCG strain would be under strong selective pressure to retain the plasmid due to its requirement for panCD complementation from the plasmid.

In another manifestation of the disclosure, the panCD cassette and the construct for the biosynthesis of STING agonists (such as the Phsp65::disA construct) could be introduced into a chromosomally integrating vector such as pMH94. Using similar methods, the antibiotic cassette could be eliminated from pMH94. Introduction of this chromosomally integrating plasmid into an unmarked BCG ΔpanCD mutant would also yield a BCG strain that harbors no antibiotic resistance genes, and that strongly overexpresses a STING agonist biosynthetic gene(s). A disadvantage of this strategy is that the overexpression construct would be in single copy on the bacterial chromosome, rather than being in multicopy on a plasmid, and this could result in lower levels of STING agonist release.

BCG-Tice (ATCC 35743) is a Natural Pantothenate Auxotroph.

The inventors disclose that the *Mycobacterium bovis* BCG Tice strain (ATCC 35743) is a natural pantothenate auxotroph. This strain carries a 5 bp DNA insertion in its panC gene at base pairs 739-743. This insertion mutation change leads to a frameshift mutation after the 246$^{th}$ amino acid of PanC (wild type PanC is 309 amino acids in length). As a result of the 5 bp insertion mutation, the mutant PanC polypeptide in the Mycobacterium bovis BCG Tice strain (ATCC 35743) is comprised of 246 amino acids of the wild type PanC sequence at its N-terminus followed by a 478 amino acid nonsense polypeptide at its C-terminus. This mutant PanC polypeptide is highly unlikely to retain any functional pantoate—beta-alanine ligase activity (the normal enzymatic function of PanC). Additionally, the PanD polypeptide in BCG Tice (ATCC 35743) is highly unlikely to be translated because the stop codon for the panC gene (which overlaps with the ATG for panD translation initiation in the wild type sequence) is out of frame. Ribosomal termination of PanC translation is coupled with ribosomal initiation of PanD translation in the wild type panCD operon. Since there is no ribosomal termination immediately upstream of the panD start codon, ribosomal initiation of translation of the panD gene is highly unlikely to occur.

The inventors disclose that this natural auxotrophy enables the more rapid construction of an antibiotic gene cassette-free recombinant BCG which overexpresses a STING agonist biosynthetic gene.

The inventors disclose a method for introducing an anti-biotic-cassette-free plasmid harboring the mycobacterial panCD gene as well as an overexpression construct for the biosynthesis of STING agonists (such as the Phsp65::disA construct) directly into BCG-Tice (ATCC 35743).

pSD5-hsp60-MT3692 is the same as pSD5-hsp65-MT3692. The inventors had previously referred to this same plasmid as pSD5-hsp60-MT3692. However, the actual promoter in this strain is the promoter for the hsp65 gene of *M. leprae*. Thus, the inventors may refer to the plasmid pSD-hsp60-MT3692 as pSD5-hsp65-MT3692.

In one embodiment, the present invention relates to a pharmaceutical composition including an expression vector, expression cassette, or strain of the invention described herein and a pharmaceutically acceptable carrier.

In another embodiment, the present invention relates to methods and/or compositions for treating and/or preventing cancer comprising administration of an expression vector, expression cassette, strain or pharmaceutical composition described herein to a subject. In some aspects, the cancer is bladder cancer (e.g., non-muscle invasive bladder cancer (NMIBC)), breast cancer, or a solid tumor. Additional embodiments of the disclosure concern methods and/or compositions for treating and/or preventing a bladder cancer in which modulation of a type 1 interferon (IFN) response is directly or indirectly related. In certain aspects, individuals with a bladder cancer such as NMIBC are treated with a modulator of the type 1 interferon response, and in some aspects an individual with bladder cancer is provided a modulator of expression type 1 interferon expression, such as an inducer of its expression.

In certain aspects, the level to which an inducer of type 1 interferon expression increases type 1 interferon expression may be any level so long as it provides amelioration of at least one symptom of bladder cancer, including non-muscle-invasive bladder cancer (NMIBC). The level of expression of type 1 interferon may increase by at least 2, 3, 4, 5, 10, 25, 50, 100, 1000, or more fold expression compared to the level of expression in a standard, in at least some cases. An individual may monitor expression levels of type 1 interferon using standard methods in the art, such as northern assays or quantitative PCR, for example.

An individual known to have bladder cancer, suspected of having bladder cancer, or at risk for having bladder cancer may be provided an effective amount of an inducer of type 1 interferon expression, including a BCG strain of the present invention comprising an expression vector of the present invention. The expression vector expresses a RV1354c protein, or functional part thereof; a cyclic GMP-AMP synthase (DncV) protein, or functional part thereof; a cyclic GMP-AMP synthase (cGAS) protein, or functional part thereof; a DNA integrity scanning (disA) protein which functions as a denylate cyclase, or functional part thereof; or a combination thereof. It is preferred that a BCG strain of the present invention comprising an expression vector of the present invention be administered into the bladder of the subject and that the expressed protein(s) enhance type 1 interferon expression in the bladder. Those at risk for bladder cancer may be those individuals having one or more genetic factors, may be of advancing age, and/or may have a family history, for example.

In particular aspects of the disclosure, an individual is given an agent for bladder cancer therapy in addition to the one or more inducers of type 1 interferon of the present invention. Such additional therapy may include intravesical chemotherapies such as mitomycin C, cyclophosphamide, or a combination thereof, for example. When combination therapy is employed with one or more inducers of type 1 interferon (such as a BCG strain expressing one or more of the following proteins: a RV1354c protein, or functional part thereof; a cyclic GMP-AMP synthase (DncV) protein, or functional part thereof; a cyclic GMP-AMP synthase (cGAS) protein, or functional part thereof; a DNA integrity scanning (disA) protein which functions as a denylate cyclase, or functional part thereof) the additional therapy may be given prior to, at the same time as, and/or subsequent to the inducer of type 1 interferon.

In some aspects, an expression vector, expression cassette, strain, pharmaceutical composition, and/or method of the invention described herein has increased safety, increased tolerability (e.g., decreased dysuria, urgency, or malaise), and/or decreased likelihood to cause infection in the bloodstream or disseminated bloodstream infection compared to non-recombinant BCG.

In one embodiment, the present invention relates to a method of treating and/or preventing cancer, including administering to a subject an expression vector, expression cassette, strain, and/or pharmaceutical composition of the invention described herein, wherein the administration results in an increased safety profile, increased tolerability (e.g., decreasing dysuria, urgency, or malaise), and/or decreased likelihood of infection in the bloodstream or disseminated bloodstream infection compared to non-recombinant BCG. In some aspects, the cancer is, for example, bladder cancer (e.g., non-muscle-invasive bladder cancer (NMIBC)), breast cancer, or a solid tumor. In other aspects, the solid tumor is, for example, a sarcoma, carcinoma, or lymphoma.

In some embodiments, the present invention relates to a method of increasing the safety, increasing the tolerability (e.g., decreasing dysuria, urgency, or malaise), and/or decreasing the likelihood to cause infection in the bloodstream or disseminated bloodstream infection compared to non-recombinant BCG, comprising administering an expression vector, expression cassette, strain, and/or pharmaceutical compositions of the invention described herein to a subject.

Pharmaceutical Preparations

Pharmaceutical compositions of the present invention include an effective amount of one or more inducers of expression of type 1 interferon such as such as a BCG strain expressing one or more of the following proteins: a RV1354c protein, or functional part thereof; a cyclic GMP-AMP synthase (DncV) protein, or functional part thereof; a cyclic GMP-AMP synthase (cGAS) protein, or functional part thereof; a DNA integrity scanning (disA) protein which functions as a denylate cyclase, or functional part thereof, dissolved or dispersed in a pharmaceutically acceptable carrier. The phrase "pharmaceutical" or "pharmacologically acceptable" refers to molecular entities and compositions that do not produce an adverse, allergic or other untoward reaction when administered to an animal, such as, for example, a human, as appropriate. The preparation of a pharmaceutical composition that comprises at least one inducer of expression of type 1 interferon or additional active ingredient will be known to those of skill in the art in light of the present disclosure, as exemplified by Remington: The Science and Practice of Pharmacy, $21^{st}$ Ed. Lippincott Williams and Wilkins, 2005, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The inducer of expression of type 1 interferon (such as a BCG strain expressing one or more of the following proteins: a RV1354c protein, or functional part thereof; a cyclic GMP-AMP synthase (DncV) protein, or functional part thereof; a cyclic GMP-AMP synthase (cGAS) protein, or functional part thereof; a DNA integrity scanning (disA) protein which functions as a denylate cyclase, or functional part thereof) may comprise different types of carriers depending on whether it is to be administered in solid, liquid or aerosol form, and whether it need to be sterile for such routes of administration as injection. In some aspects, the present invention (e.g., expression vectors, strains, or pharmaceutical compositions) can be administered intravenously, intradermally, transdermally, intrathecally, intraarterially, intraperitoneally, intranasally, intravaginally, intrarectally, intravesically (e.g., administered directly into the bladder, e.g., by injection, or by intravesical instillation), intratumorally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the foregoing as would be known to one of ordinary skill in the art (see, for example, Remington's Pharmaceutical Sciences, 18th Ed. Mack Printing Company, 1990, and Francica et al. TNFα and radio-resistant stromal cells are essential for therapeutic efficacy of cyclic dinucleotide STING agonists in non-immunogenic tumors. Cancer Immunol Res. 2018 Feb. 22. PMID: 29472271, incorporated herein by reference).

Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present disclosure, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also include various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific aspect of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in the composition include buffers, amino acids such as glycine and lysine, carbohydrates such as dextrose, mannose, galactose, fructose, lactose, sucrose, maltose, sorbitol, mannitol, etc.

In further aspects, the present invention includes the use of pharmaceutical lipid vehicle compositions that include inducer of expression of type 1 interferon, one or more lipids, and an aqueous solvent. As used herein, the term "lipid" includes any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the inducer of inducer of expression of Type 1 interferon of the present invention may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain aspects, pharmaceutical compositions may include, for example, at least about 0.1% of an active compound. In other aspects, the active compound may include between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

A. Alimentary Compositions and Formulations

In one embodiment of the present disclosure, the inducers of expression of inducer of expression of type 1 interferon of the present invention are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft- shell gelatin capsule, or they may be compressed into tablets, or they may be incorporated directly with the food of the diet.

In certain aspects, the active compounds may be incorporated with excipients and used in the form of ingestible tablets, buccal tables, troches, capsules, elixirs, suspensions, syrups, wafers, and the like (Mathiowitz E, Jacob J S, Jong Y S, Carino G P, Chickering D E, Chaturvedi P, Santos C A, Vijayaraghavan K, Montgomery S, Bassett M, Morrell C. Biologically erodable microspheres as potential oral drug delivery systems. Nature. 1997; 386:410-4. PMID: 9121559; Hwang M J, Ni X, Waldman M, Ewig C S, Hagler A T. Derivation of class II force fields. VI. Carbohydrate compounds and anomeric effects. Biopolymers. 1998; 45:435-68. PMID: 9538697; Hwang J S, Chae S Y, Lee M K, Bae Y H. Synthesis of sulfonylurea conjugated copolymer via PEO spacer and its in vitro short-term bioactivity in insulin secretion from islets of Langerhans. Biomaterials. 1998; 19:1189-95. PMID: 9720902; Hwang S J, Park H, Park K. Gastric retentive drug-delivery systems. Crit Rev Ther Drug Carrier Syst. 1998; 15:243-84. PMID: 9699081; U.S. Pat. Nos. 5,641,515; 5,580,579; and 5,792, 451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present disclosure may alternatively be incorporated with one or more excipients in the form of a mouthwash, dentifrice, buccal tablet, oral spray, or sublingual orally- administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically- effective amount to a composition that may include water, binders, abrasives, flavoring agents, foaming agents, and humectants. Alternatively, the compositions may be fashioned into a tablet or solution form that may be placed under the tongue or otherwise dissolved in the mouth.

Additional formulations which are suitable for other modes of alimentary administration include suppositories.

Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain aspects, suppositories may be formed from mixtures containing, for example, the active ingredient in the range of about 0.5% to about 10%, and preferably about 1% to about 2%.

B. Parenteral Compositions and Formulations

In further embodiments, inducer of expression of type 1 interferon of the present invention may be administered via a parenteral route. As used herein, the term "parenteral" includes routes that bypass the alimentary tract. Specifically, the pharmaceutical compositions disclosed herein may be administered, for example, intravenously, intradermally, intramuscularly, intraarterially, intrathecally, subcutaneous, or intraperitoneally. See, e.g., U.S. Pat. Nos. 6,7537,514; 6,613,308; 5,466,468; 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases, the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see, for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by FDA Office of Biologics standards.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

C. Miscellaneous Pharmaceutical Compositions and Formulations

In some aspects of the invention, the active compound inducer of expression of type 1 interferon of the present invention may be formulated for administration via various miscellaneous routes, for example, topical (i.e., transdermal) administration, mucosal administration (intranasal, vaginal, etc.) and/or inhalation. Pharmaceutical compositions for topical administration may include the active compound formulated for a medicated application such as an ointment, paste, cream or powder. Ointments include all oleaginous, adsorption, emulsion and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also include the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga M, Serizawa Y, Azechi Y, Ochiai A, Kosaka Y, Igarashi R, Mizushima Y. Microparticle resins as a potential nasal drug delivery system for insulin. J Control Release. 1998; 52:81-7. PMID: 9685938) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety). The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

Kits of the Disclosure

Any of the compositions described herein may be comprised in a kit. In a non-limiting example, an inducer of expression of type 1 interferon of the present invention (such as a BCG strain expressing one or more of the following proteins: a RV1354c protein, or functional part thereof; a cyclic GMP-AMP synthase (DncV) protein, or functional part thereof; a cyclic GMP-AMP synthase (cGAS) protein, or functional part thereof; a DNA integrity scanning (disA) protein which functions as a denylate cyclase, or functional part thereof) may be comprised in a kit.

The kits may comprise a suitably aliquoted inducer of expression of type 1 interferon of the present invention and, in some cases, one or more additional agents. The component(s) of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one components in the kit, the kit also will generally contain a second, third or other additional container into which the additional components may be separately placed. However, various combinations of components may be included in a vial. The kits of the present invention also will typically include a means for containing the inducer of expression of type 1 interferon of the present invention and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. The inducer of expression of type 1 interferon of the present invention composition(s) may be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means.

The Examples above have been included to provide guidance to one of ordinary skill in the art for practicing representative embodiments of the presently disclosed subject matter. In light of the present disclosure and the general level of skill in the art, those of skill can appreciate that the Examples above are intended to be exemplary only and that numerous changes, modifications, and alterations can be employed without departing from the scope of the presently disclosed subject matter. The Examples above are offered by way of illustration and not by way of limitation.

All references, including publications, patent applications, and patents, cited herein are hereby incorporated by reference to the same extent as if each reference were individually and specifically indicated to be incorporated by reference and were set forth in its entirety herein.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Presented below are examples discussing enhancement of trained immunity by re-engineered BCG overexpressing the PAMP molecule cyclic di-AMP, contemplated for the discussed applications. The following examples are provided to further illustrate the embodiments of the present invention but are not intended to limit the scope of the invention. While they are typical of those that might be used, other procedures, methodologies, or techniques known to those skilled in the art may alternatively be used.

EXAMPLES

Example 1

Material and Methods

Referring specifically to FIGS. 39-62, the following material and methods are provided to details the methods used to obtain the presented results.

Bacterial Strains and Culture Conditions:

*Mycobacterium bovis* (*M. bovis*) Bacillus Calmette-Guérin (BCG) Pasteur (BCG-WT Pasteur) (a generous gift from Dr. Frank Collins [FDA] and identical to BCG-Pasteur provided by the Pasteur Institute to the Trudeau Institute in 1967 as TMC No. 1011) and commercially available BCG-Tice (Onco-Tice®, Merck) were used for the generation of c-di-AMP overexpressing recombinant BCG strains. Genomic DNA from *Mycobacterium tuberculosis* (*M. tb*) strain CDC1551 was used for PCR amplification of disA (MT3692/ Rv3586). Single isolated bacterial colonies growing on 7H11 plates supplemented with oleic-albumin-dextrose-catalase (OADC) (Cat. B11886, Fisher Scientific) were picked and propagated in 7H9 Middlebrook liquid medium (Cat. B271310, Fisher Scientific) supplemented with (OADC) (Cat. B11886, Fisher Scientific), 0.5% glycerol (Cat. G55116, Sigma) and 0.05% Tween-80 (Cat. BP338, Fisher Scientific). Cloning experiments were performed using $E.\ coli$ strain DH5-α (Cat. 18258012, Fisher Scientific) and was routinely maintained in LB broth. For generation of disA overexpressing BCG, an $E.\ coli$-mycobacterial shuttle vector (pSD5. hsp60) was used to clone $M.tb$ gene MT3692 or Rv3586 under the strong mycobacterial promoter hsp60. Clones were confirmed by gene sequencing and were used for bacterial transformation by electroporation method. Recombinant strains were confirmed using colony PCR against kanamycin cassette, subjected to whole genome sequencing and qPCR analyses. Details of all bacterial strains, plasmids and constructs are listed in Table 3.

TABLE 3

| Name | Description/Source |
|---|---|
| | Bacterial strains |
| | *M. tuberculosis* strain |
| Mtb-CDC1551 | Wild-type *M. tuberculosis* |
| | *M. bovis* BCG strains |
| BCG Pasteur | *M. bovis* BCG Pasteur |
| BCG-disA-OE (Pasteur) | BCG Pasteur strain overexpressing disA (MT3692) of M.tb |
| BCG Tice | *M. bovis* BCG Tice |
| BCG-disA-OE (Tice) | BCG Tice strain overexpressing disA (MT3692) of M.tb |
| | *E. coli* strain |
| DH5-α | Competent *E. coli* (High Efficiency) |
| | Cell lines |
| | Urinary bladder carcinoma cells |
| RT4 (ATCC ® HTB-2 ™) | Human low grade urothelial cancer |
| 5637 (ATCC ® HTB-9 ™) | Human high-grade urothelial cancer |
| NBT-II (ATCC ® CRL-1655 ™) | N-butyl-N-(4-hydroxybutyl) nitrosamine induced tumor cell line in Rattus norvegicus Nara Bladder Tumor No. 2 |
| MB49 (Cat. SSC148, EMD Millipore) | DMBA [7,12-dimethylbenz[a]anthracene] induced murine urothelial carcinoma cells, |
| UPPL-1595 | Luminal cell line established from a spontaneous primary bladder tumor in an Uroplakin-Cre driven PTEN/P53 knockout genetically engineered mouse model |
| BBN 975 | Basal- cell line established from, 0.05% N-Butyl-N-(4-hydroxybutyl) nitrosamine (BBN) induced murine urothelial cancer model |
| J28 (ATCC ® HTB-1 ™) | high grade urothelial cancer |
| | Reporter cells |
| RAW-Lucia ISG (InvivoGen) | IFN Reporter Raw 264.7 murine macrophages |
| | Macrophage cell lines |
| J774A.1 (ATCC ® TIB67 ™) | Murine macrophage cell line |
| | Plasmids |
| pSD5.hsp60 | Mycobacterial expression plasmid with hsp60 promoter |
| pSD5hsp60.MT3692 | disA over-expression plasmid |
| | Confocal Microscopy Reagents |
| | Primary Antibodies |
| LC3B | NB100-2220, Novus Biologicals |
| P62/SQSTM1 | P0067, Sigma |
| | Secondary Antibodies |
| Goat anti-Rabbit IgG Alexa Fluor Plus 647 | A32733, Thermo Fisher Scientific |
| | Chemicals/Probes |
| Fluorescein 5(6)-isothiocyanate (FITC) | 46950, Sigma |
| Hoechst 33342 | 62249, Thermo Fisher Scientific |
| | Flow Cytometry Reagents |
| | Antibodies (mouse BMDM study) |
| anti-CD45 (clone 30-F11) | Biolegend |
| anti-CD124 (I clone 015F8) | Biolegend |
| anti-I-A/I-E (clone 107630) | Biolegend |
| anti-Ly6C (clone HK1.4) | Biolegend |
| anti-CD11b (clone M1/70) | Biolegend |
| anti-F4/80 (clone BM8) | Biolegend |

TABLE 3-continued

| Name | Description/Source |
|---|---|
| anti-Ly6G (clone 1A8) | Biolegend |
| anti CD206 (clone C068C2) | Biolegend |
| anti-TNF (clone MP6-XT22) | Biolegend |
| anti- IL-10 (clone JES5-16E3) | eBioscience |
| Antibodies (HMDM study) | |
| anti-CD16 (clone 3G8) | Biolegend |
| anti-CD14 (clone 63D3) | Biolegend |
| anti-HLA-DR (clone L243) | Biolegend |
| anti-CD11b (clone ICRF44) | Biolegend |
| anti-TLR4 (clone HTA125) | Biolegend |
| anti-CD206 (clone 15-2) | Biolegend |
| anti-CD163 (clone GHI/61) | Biolegend |
| anti-TNF (clone Mab11) | Biolegend |
| anti-IL-6 (clone MQ2-13A5) | Biolegend |
| Antibodies (myeloid cell panel, Syngeneic MB49 urothelial cancer model) | |
| CD45 (clone 30-F11) | Biolegend |
| CD124 (IL-4Ra) (clone I015F8) | Biolegend |
| I-a/I-e (clone M5/114.15.2) | Biolegend |
| F4/80 (clone BM8) | Biolegend |
| CD206 (clone C068C2) | Biolegend) |
| TNF (clone MP6-XT22) | Thermo Fisher |
| IL-10 (clone JES5-16E3) | Thermo Fisher |
| Antibodies (lymphoid cell panel, Syngeneic MB49 urothelial cancer model) | |
| CD45 (clone PerCP) | Biolegend |
| CD25 (clone PC61) | Biolegend |
| CD3 (clone 17A2) | Biolegend |
| CD4 (clone GK1.5) | Biolegend |
| CD8a (clone 53-6.7) | Biolegend |
| FOXP3 (clone MF-14) | Biolegend |
| Mouse IFN-γ (clone XMG1.2) | Biolegend |
| FOXP3 (clone MF-14) | Biolegend |
| Reagents/Kits | |
| Protein transport inhibitor cocktail | eBioscience, 00-4980-03 |
| Zombie Aqua ™ Fixable Viability Kit | Biolegend, 423101 |
| TruStain FcX ™ | Biolegend, 101320 |
| Fixation and Permeabilization Buffer Set | Biolegend, 421403 |
| Human TruStain FcX ™ | Biolegend, 422302 |
| True-Stain Monocyte Blocker ™ | Biolegend, 426102 |
| ELISA | |
| Mouse ELISA Kits | |
| TNF- DuoSet | DY410, R6000B, R and D Systems |
| IL-6 DuoSet | DY406, R6000B, R and D Systems |
| IFN- DuoSet | DY485, R6000B, R and D Systems |
| CCL2/JE/MCP-1 DuoSet | DY479, R6000B, R and D Systems |
| LEGEND MAX ™ Mouse IFN-β | 439407, Biolegend |
| Human ELISA Kits | |
| TNF- DuoSet | DY210, R6000B, R and D Systems |
| IL-6 DuoSet | DY206, R6000B, R and D Systems |
| IFN-β ELISA Kit | 41410-2, PBL Assay Science |
| Rat ELISA Kits | |
| IFN- Quantikine | RIF00, R and D Systems |
| TNF- Quantikine | RTA00, R and D Systems |
| IL-2 Quantikine | R2000, R and D Systems |
| Chromatin Immunoprecipitation | |
| ChIP Antibodies | |
| Histone H3K9me3 (H3K9 Trimethyl) Polyclonal Antibody | (cat. A-4036-100, epigentek) |
| Anti-Histone H3 (tri methyl K4) antibody - ChIP Grade | (cat. ab8580, abcam) |
| ChIP Reagents | |
| BSA | (Cat. A3294, Sigma-Aldrich) |
| Salmon Sperm DNA | (Cat. 15632011, ThermoFisher Scientific) |
| HEPES | (Cat. H3375, Sigma-Aldrich) |
| Formaldehyde | (Cat. 252549, Sigma-Aldrich) |
| EGTA | (Cat. 03777, Sigma-Aldrich) |
| EDTA | (Cat. E6758, Sigma-Aldrich) |

TABLE 3-continued

| Name | Description/Source |
|---|---|
| TritonX-100 | (Cat. T8787, Sigma-Aldrich) |
| SDS | (Cat. 71736, Sigma-Aldrich) |
| NaHCO3 | (Cat. 5761, Sigma-Aldrich) |
| Nuclease free water | (Cat. AM9930, ThermoFisher Scientific) |
| SYBR green dye | (Cat. 4385614, Applied Biosystems) |

Mammalian Cell Culture:

Cell lines: For cell-based in vitro infection assays J774.1 (American Type Culture Collection-ATCC® TIB67™, Manassas, VA, USA) murine macrophage cell lines were cultivated in RPMI-Glutamax (Cat. 61870-036, Fischer Scientific), supplemented with 10% heat inactivated fetal bovine serum (FBS) (Cat. 10082147, Fischer Scientific) with 1% streptomycin/penicillin at 37° C. with 5% CO2. Urothelial carcinoma cell lines 5637 (ATCC® HTB-9™), a human high grade urothelial cancer; RT4 (ATCC® HTB-2™), a human transitional cell low grade urothelial cancer; J82 (ATCC® HTB-1™), a human high grade urothelial cancer; and NBT II (ATCC® CRL-1655™), N-butyl-N-(4-hydroxybutyl) nitrosamine induced tumor cell line in Rattus norvegicus Nara Bladder Tumor No. 2, UPPL1595 (luminal cell line established from a spontaneous primary bladder tumor in an Uroplakin-Cre driven PTEN/P53 knockout genetically engineered mouse model and were generously provided by Dr. William Kim (UNC Chapel Hill)., BBN975 (basal-cell line established from , 0.05% N-Butyl-N-(4-hydroxybutyl) nitrosamine (BBN) induced murine urothelial cancer model and was generously provided by Dr. William Kim (UNC Chapel Hill), and MB49 (murine urothelial carcinoma cells, 7,12-dimethylbenz[a]anthracene (DMBA, EMD Millipore, Cat. SSC148) were maintained as monolayer in RPMI1640 medium supplemented with 10% heat inactivated fetal bovine serum (FBS) with 1% streptomycin/penicillin at 37° C. with 5% CO2. Mouse fibroblast cell line NCTC clone 929 µL cell, L-929, derivative of Strain L1 (ATCC® CCL-1™) were routinely maintained as monolayer in DMEM media supplemented with 10% heat inactivated fetal bovine serum (FBS) with 1% streptomycin/penicillin at 37° C. with 5% CO2. All cell lines were not maintained more than 10 passage cycle and Mycoplasma testing was performed periodically while cells were in culture. Reporter mouse cell line, RAW-Lucia ISG (InvivoGen, CA, USA) was cultivated in custom prepared media as per manufacturer's instructions.

Primary Cells (Macrophages and Dendritic Cells):

For generation of murine bone-marrow-derived macrophages (BMDMs) and dendritic cells (BMDCs), bone marrow (BM) cells were isolated from 4-week old wild-type (WT) C57BL/6J (Charles River laboratories, North Wilmington, Mass) and STING-KO mice (C57BL/6J-Tmem173gt/J, Jackson laboratories). Multiple vials of bone-marrow cells were preserved in cryopreservation media containing 10% DMSO (Cat. D2650; Sigma) and 90% heat inactivated FBS (Cat. 10082147, Fischer Scientific) in liquid nitrogen. For differentiation of BM cells into macrophages or DCs, random cryopreserved vials were chosen and differentiated for 6 days in BMDM-differentiation media made from DMEM containing 10% FBS, 1% MEM amino acids (Cat. 11130051, Thermo Fisher Scientific), 1% MEM non-essential amino acids (Cat. 11140050, Thermo Fisher Scientific), 1% sodium pyruvate (Cat. 11360070, Thermo Fisher Scientific), 1% MEM vitamin (Cat. 11120052, Thermo Fisher Scientific) and antibiotics (Penicillin-Streptomycin solution) supplemented with 30% sterile mouse fibroblast L929 (ATCC® CCL-1™) conditioned media. Differentiation of BM cells into DCs was carried out in low attachment 10 mm cell culture dish in presence of bone marrow-differentiation media in presence of recombinant murine Granulocyte-Macrophage Colony-Stimulating Factor (GM-CSF) (Cat. 315-03, Peprotech) for 48 h. Non-adherent cells were washed and loosely attached cells were allowed to differentiate into BMDCs for next 6 days. Cells were characterized for macrophage and DC markers using cell-surface staining and flow cytometry analyses. Human primary monocytes and human monocyte-derived macrophages (HMDMs) were used for cell-based in vitro infection assays. Peripheral blood-derived mononuclear cells (PBMCs) isolated from healthy male donors (leukopacks) aged between 18-30 were used for isolation of human monocytes (HM) or human monocyte-derived macrophages (HMDM). To separate blood constituents and isolation of buffy coat density gradient centrifugation (400×g at 18° C. for 30 min) of RPMI-1640 diluted blood over a Ficoll-Paque™ Plus reagent (Cat. 17-1440-02, GE Healthcare, Piscataway, NJ) was performed. Cells were washed several times using 1×PBS and were counted using hemocytometer. Once counted CD14+ human monocytes were isolated from PBMCs using magnetic labeling (Monocyte Isolation Kit II, Cat. 130-091-153, Miltenyi Biotec, San Diego, CA) and magnetic columns as per manufacturer's instructions. The purity of isolated CD14+ cells was confirmed using a fraction of cells stained with a fluorochrome-conjugated antibody against a monocyte marker as recommended by manufacturer and cells were analyzed using BD-LSR2 flow cytometer. Human monocytes were seeded (2.0-3.0×105 cells/ml in RPMI 1640 medium supplemented with 10% FBS and 1% streptomycin/penicillin at 37° C. with 5% $CO_2$. Monolayers of CD14+ monocytes were differentiated into M1 [GM-CSF (20 ng/ml, PeproTech, Rocky Hill, NJ) and IFN-γ (20 ng/ml, PeproTech, Rocky Hill, NJ PeproTech)] or M2 [M-CSF (20 ng/ml, PeproTech, Rocky Hill, NJ) and IL-4 (20 ng/ml, PeproTech, Rocky Hill, NJ PeproTech)] for next 7 days.

Animals:

Experimental procedures involving live animals were carried out in agreement with the protocols approved by the Institutional Animal Care and Use Committee (IACUC) at The Johns Hopkins University School of Medicine. For animal infection protocols, pathogen-free age 4-6 weeks female C57BL/6J (Charles River Laboratories, North Wilmington, Mass) and Fox Chase SCID mice (Charles River Laboratories North Wilmington, Mass.) were purchased and housed under pathogen-free conditions at an Animal Biosafety Level-3 animal facility without cross-ventilation. Fischer 344 female rats age 8 weeks (Harlan, avg. weight 160 g) were housed at an BSL2 animal facility. Animals were given free access to water and standard chow and were monitored daily for general behavior and appearance by veterinary specialists.

In Vitro Infection Assays:

For in vitro infection assays, cell lines or primary cells were seeded at required cell density in 6-well tissue culture plates or 10 mm petri dishes. For infection, log-phase wild-type and BCG-disA-OE strains were harvested by centrifugation and washed twice using DPBS to remove residual detergent and BSA then suspended in antibiotic-free RPMI 1640 media supplemented with 10% FBS. For infection assays, the bacteria were deposited at pre-calibrated multiplicity of infection (MOI). Infection was allowed for next 4 hours, followed by repeated washing of infected cells using warm DPBS to remove non-internalized bacteria. Infected cells were incubated until endpoints in presence of RPMI-1640 medium supplemented with 10% FBS and antibiotics.

Toxicity Assays:

Human urothelial cancer cell lines, RT4, 5637, and J82, were cultured at 37° C. under 5% CO2 in RPMI 1640 containing 10% FBS without antibiotics. For cell toxicity assay, 3000 cells for RT4 and 1500 cells for 5637 and J82 were seeded in a 96-well tissue-treated plate in triplicate, respectively. Twenty-four hours after seeding, cells were treated with the indicated ratio of BCG to cells for 72 hours. To measure cell viability, CellTiter-Glo Luminescent Cell Viability Assay (Promega, Madison, WI, USA) and FLUO-star OPTIMA (BMG Labtech, Ortenberg, Germany) were used according to manufacturer's protocols. Relative cell viability was calculated by dividing the viability of the indicated ratio by that of a control.

For Annexin-PI staining, 0.5 million J774.1 cell and BMDMs were plated per well in 6-well plates for physical attachment. Cells were exposed at 1:10 MOIs for 24 hours using wild-type and BCG-disA-OE strains of Tice and Pasteur to determine the BCG cytotoxicity following exposure. At the endpoint of infection or treatment cells were non-enzymatically removed using 0.02% EDTA-PBS solution. Cells were washed twice with ice-cold PBS and FITC-annexin-PI was done as per manufacturer's instruction using FITC Annexin V Apoptosis Detection Kit I (Cat. 556547, BD Biosciences). Flow cytometry was performed using a BD LSR II flow cytometer of the Flow Cytometry Core Facility at The Bloomberg School of Public Health, Johns Hopkins University). Data was processed using FlowJo software (Tree Star v10).

Quantitative Real-Time QPCR:

Gene expression profiling was carried out using total RNA isolated from cell lines or primary cells. For RNA isolation from rat bladders, pieces of whole bladder samples were excised, snap frozen in liquid nitrogen immediately after harvesting and stored in RNAlater (Cat. AM7021, Ambion) at −80° C. Total RNA isolation was carried out using RNeasy system (Cat. 74106, Qiagen). Real-time qPCR was performed using the StepOnePlus system (Applied Biosystems). For gene expression analyses in cell lines and primary cells, SYBR Fast green double stranded DNA binding dye (Cat. 4085612, Applied Biosystems) was used. Gene expression analyses in rat bladder tissues were performed using TaqMan gene expression assays. Gene-specific qPCR primers were purchased from Integrated DNA Technologies and all TaqMan gene expression assays were purchased from Thermo Fischer Scientific Amplification of RNU6a, β-actin, GAPDH were used as endogenous control for RNA samples derived from human, mouse and rat cells/tissues respectively. All experiments were performed at least in triplicate and data analyses was done using 2-ΔΔCT method. Details of NCBI gene identifiers and primer sequences are given in the Table 4.

TABLE 4

| Accession Number | Gene | Sequence (5'-3') | SEQ ID NO: |
|---|---|---|---|
| | Cloning primers used in the study | | |
| | pSD5hsp60.MT3692 (F) | GGGCATCATATGCACGCTGTGACTCGTC | SEQ ID NO: 107 |
| | pSD5hsp60.MT3692 (R) | GGGACGCGTTATTGATCGCTGATGGTCGATT | SEQ ID NO: 42 |
| | Kanamycin cassette (F) | GAGAAAACTCACCGAGGCAG | SEQ ID NO: 43 |
| | Kanamycin cassette (R) | GTATTTCGTCTCGCTCAGGC | SEQ ID NO: 44 |
| 32287254 | M.tb sigH (F) | GCGATGGTGGCTTCTCCCTCG | SEQ ID NO: 45 |
| | M.tb sigH (R) | CCATCTTGCACAGCTCGCGTAG | SEQ ID NO: 46 |
| | qPCR primers used in the study | | |
| | Mouse Primers | | |
| 11461 | Mouse.β actin (F) | TAAGGCCAACCGTGAAAAGATG | SEQ ID NO: 47 |
| | Mouse.β actin (R) | CTGGATGGCTACGTACATGGCT | SEQ ID NO: 48 |
| 21926 | Mouse.TNF-α (F) | GACCCTCACACTCAGATCATC | SEQ ID NO: 49 |
| | Mouse.TNF-α (R) | GCTGCTCCTCCACTTGGT | SEQ ID NO: 50 |
| 15977 | Mouse.IFN-β (F) | CCACAGCCCTCTCCATCAAC | SEQ ID NO: 51 |
| | Mouse.IFN-β (R) | CTCCGTCATCTCCATAGGGA | SEQ ID NO: 52 |
| 16193 | Mouse.IL6 (F) | CTGCAAGAGACTTCCATCCAG | SEQ ID NO: 53 |
| | Mouse.IL6 (R) | CAGGTCTGTTGGGAGTGG | SEQ ID NO: 54 |
| 15978 | Mouse.IFN (F) | AGCGGCTGACTGAACTCAGATTGT | SEQ ID NO: 55 |
| | Mouse.IFN (R) | GTCACAGTTTTCAGCTGTATAGGG | SEQ ID NO: 56 |
| 16176 | Mouse.IL1 (F) | GGAGAGTGTGGATCCCAA | SEQ ID NO: 57 |
| | Mouse.IL1 (R) | GTGGAGTTTGAGTCTGCAG | SEQ ID NO: 58 |
| 20296 | Mouse.MCP1 (F) | GGCTCAGCCAGATGCAGTTAAC | SEQ ID NO: 59 |
| | Mouse.MCP1 (R) | GATCCTCTTGTAGCTCTCCAGC | SEQ ID NO: 60 |
| 16160 | Mouse.IL12b (F) | GAAAGACGTTTATGTTGTAGAGG | SEQ ID NO: 61 |
| | Mouse.IL12b (R) | GACTCCATGTCTCTGGTCTG | SEQ ID NO: 62 |
| 17329 | Mouse.CXCL9 (F) | GGAGTTCGAGGAACCCTAGTG | SEQ ID NO: 63 |
| | Mouse.CXCL9 (R) | GGGATTTGTAGTGGATCGTGC | SEQ ID NO: 64 |

TABLE 4-continued

| Accession Number | Gene | Sequence (5'-3') | SEQ ID NO: |
|---|---|---|---|
| 15945 | Mouse.CXCL10 (F) | GTGGGACTCAAGGGATCCCTCTC | SEQ ID NO: 65 |
|  | Mouse.CXCL10 (R) | GCTTCCCTATGGCCCTCATTC | SEQ ID NO: 66 |
| 18126 | Mouse.NOS2 (F) | GTTCTCAGCCCAACAATACAAG | SEQ ID NO: 67 |
|  | Mouse.NOS2 (R) | GGAACATTCTGTGCTGTCCC | SEQ ID NO: 68 |
| 20299 | Mouse.CCL22 (F) | CTCTGATGCAGGTCCCTATGGTG | SEQ ID NO: 69 |
|  | Mouse.CCL22 (R) | GGCAGAGGGTGACGGATGTAG | SEQ ID NO: 70 |
| Human Primers | | | |
| 26827 | Human.RNU6A (F) | CTCGCTTCGGCAGCACATATAC | SEQ ID NO: 71 |
|  | Human.RNU6A (R) | AATATGGAACGCTTCACGAATTTG | SEQ ID NO: 72 |
| 3456 | Human.IFNβ (F) | CAACTTGCTTGGATTCCTACAAAG | SEQ ID NO: 73 |
|  | Human.IFNβ (R) | TATTCAAGCCTCCCATTCAATTG | SEQ ID NO: 74 |
| 3569 | Human.IL6 (F) | GGTACATCCTCGACGGCATCT | SEQ ID NO: 75 |
|  | Human.IL6 (R) | GTGCCTCTTTGCTGCTTTCAC | SEQ ID NO: 76 |
| Rat Primers | | | |
| 64367 | Rat.PPIB (F) | CAGGATTCATGTGCCAGGGT | SEQ ID NO: 77 |
|  | Rat.PPIB (R) | CCAAAGACCACATGCTTGCC | SEQ ID NO: 78 |
| 24481 | Rat.IFN-β (F) | GAGTCTTCACACTCCTGGC | SEQ ID NO: 79 |
|  | Rat.IFN-β (R) | GTCCTTCAGGCATGAGACAG | SEQ ID NO: 80 |
| 298210 | Rat.IFN-α (F) | GCGTTCCTGCTGTGCTTCTC | SEQ ID NO: 81 |
|  | Rat.IFN-α (R) | CCATTCAGCTGCCTCAGGAGC | SEQ ID NO: 82 |
| 25712 | Rat.IFN-γ (F) | CGTCTTGGTTTTGCAGCTCT | SEQ ID NO: 83 |
|  | Rat.IFN-γ (R) | CGTCCTTTTGCCAGTTCCTC | SEQ ID NO: 84 |
| 24599 | Rat.iNOS (F) | GGTGAGGGGACTGGACTTTTAG | SEQ ID NO: 85 |
|  | Rat.iNOS (R) | TTGTTGGGCTGGGAATAGCA | SEQ ID NO: 86 |
| 245920 | Rat.IP 10 (F) | TCCACCTCCCTTTACCCAGT | SEQ ID NO: 87 |
|  | Rat.IP 10 (R) | AGAGCTAGGAGAGCCGTCAT | SEQ ID NO: 88 |
| 24770 | Rat.MCP-1 (F) | CAGGTCTCTGTCACGCTTCTG | SEQ ID NO: 89 |
|  | Rat.MCP-1 (R) | GCCAGTGAATGAGTAGCAGCAG | SEQ ID NO: 90 |
| 25542 | Rat.MIP-1α (F) | ACAAGCGCACCCTCTGTTAC | SEQ ID NO: 91 |
|  | Rat.MIP-1α (R) | GGTCAGGAAAATGACACCCG | SEQ ID NO: 92 |
| 24494 | Rat.IL-1β (F) | GACTTCACCATGGAACCCGT | SEQ ID NO: 93 |
|  | Rat.IL-1β (R) | GGAGACTGCCCATTCTCGAC | SEQ ID NO: 94 |
| 24835 | Rat.TNF-α (F) | CGTCCCTCTCATACACTGG | SEQ ID NO: 95 |
|  | Rat.TNF-α (R) | CATGCTTTCCGTGCTCATG | SEQ ID NO: 96 |
| 59086 | Rat.TGF-β (F) | TGACGTCACTGGAGTTGTCC | SEQ ID NO: 97 |
|  | Rat.TGF-β (R) | CCTCGACGTTTGGGACTGAT | SEQ ID NO: 98 |
| 25325 | Rat.IL-10 (F) | CCTCTGGATACAGCTGCGAC | SEQ ID NO: 99 |
|  | Rat.IL-10 (R) | TGCCGGGTGGTTCAATTTTTC | SEQ ID NO: 100 |
| ChIP-PCR Primers | | | |
|  | Human.GAPDH (F) | TACTAGCGGTTTTACGGGCG | SEQ ID NO: 101 |
|  | Human.GAPDH (R) | TCGAACAGGAGGAGCAGAGAGCGA | SEQ ID NO: 102 |
|  | Human.IL-6 (F) | CGGTGAAGAATGGATGACCT | SEQ ID NO: 103 |
|  | Human.IL-6 (R) | AAACGAGACCCTTGCACAAC | SEQ ID NO: 104 |
|  | Human.TNF-α (F) | ATCAGTCAGTGGCCCAGAAGACCC | SEQ ID NO: 105 |
|  | Human.TNF-α (R) | CCACGTCCCGGATCATGCTTCAG | SEQ ID NO: 106 |

ELISA:

Sandwiched ELISA was performed for cytokine (IFN-γ, TNF-α, IL-6, IFN-β, IL-1β and MCP-1/ CCL2) measurement in culture supernatants and animal tissues from lung, spleen or urinary bladder. Tissues and culture supernatants were flash frozen in liquid nitrogen immediately after harvest and stored at −80° C. Animal tissues were homogenized using micro tissue homogenizers (Cat. 1215D61, Kimble) and filter sterilized for measurement of various cytokine protein expression levels using sandwiched ELISA as per manufacturer's recommendations. Details of all ELISA kits and accessory reagents are given in Table 4.

Multicolor Confocal Microscopy:

Multicolor laser confocal microscopy experiments were performed to determine phagocytosis, autophagy, and colocalization studies in urothelial cancer cells and primary macrophages. Cells were allowed to adhere on sterile glass cover slips placed in 6-well tissue culture plates and infections were carried at pre-calibrated MOI. Log phase bacterial cultures were labeled using FITC (Cat. F7250, Sigma). Following infection and treatment conditions, cells were fixed, permeabilized and blocked followed by overnight incubation with a primary antibody for LC3B (Cat. NB100-2220, Novus) or p62/ SQSTM1 (Cat. P0067, Sigma-Aldrich) at recommended dilutions at 4° C. Cells were washed and incubated in the dark with Alexa Flour 647 conjugated secondary antibody (Cat. A32733, Thermo Fisher Scientific) at 4° C. for 1hour. DNA staining was carried out using Hoechst 33342 (Cat. 62249, Thermo Fisher Scientific) for 5 minutes. Images were acquired using Zeiss LSM700 single-point, laser scanning confocal microscope at 63× magnification at the Microscope Facility, Johns Hopkins School of Medicine. Image processing and analyses was carried out using open source Fiji software. For LC3B or p62 quantification, perinuclear LC3B puncta (spot) was counted in a minimum 100 cells across different fields using and Imaris 9.5.0. Quantification carried out using GraphPad Prism software.

Phagocytosis Assay:

IgG-FITC conjugated latex bead phagocytosis assay kit (Item No. 500290, Cayman Chemicals, USA) was used for phagocytosis studies. HMDMs were placed on sterile glass cover slip for attachment. Infection was carried out at 5:1 (HMDM versus BCG) ratio for 3 hours followed by addition of IgG-FITC beads in warm RPMI 1640 media at 1:400 dilutions for 3 hours. Nuclear staining was carried out using Hoechst 33342 (Cat. 62249, Thermo Scientific) and cells were visualized for bead phagocytosis using Zeiss LSM700 single-point, laser scanning confocal microscope. Quantification of beads was measured by mean fluorescence intensity (M.F.I.) calculations using open source Fiji Software.

Multicolor Flow Cytometry:

The cell surface and intracellular staining was carried out on J774.1, murine BMDMs, human HMDMs and single cells derived from murine MB49 tumors and spleens. Flow cytometry panel were designed and if needed modified form murine myeloid and lymphoid cells and human myeloid cells. Details of all antibodies and the dilutions used are given in the Table 3. For in vitro infection assays, protein transport inhibitor cocktail (Cat. 00-4980-03, eBioscience) at recommended dilution, 12 hours before harvesting monolayer of cells. At the endpoint cells were harvested using a cell-detachment buffer (ice-cold PBS-10 mM EDTA solution). Single cell isolation was performed using animal tissues by harvesting tumors and spleens following necropsy. Briefly, tissues were manually disrupted before incubating in collagenase type I (Gibco) and DNase (Roche) in RMPI for 30 minutes at 37° C. Tumor and spleen cells were dissociated through a 70-μm filter and washed with PBS. RBC lysis was performed for 5 minutes using ACK lysis buffer (Cat. A1049201, Thermo Fisher Scientific) at room temperature. Cells were washed twice using ice-cold PBS and stained using Zombie Aqua™ Fixable Viability Kit (Cat. 423101, Biolegend). Cells were washed and resuspended in FACS buffer (1% BSA, 2 mM EDTA in PBS), Fc blocked (TruStain FcX™, Cat. 101320, and True-Stain Monocyte Blocker™ Cat. 426102 Biolegend) and stained with conjugated primary antibodies as per manufacturer's protocol. Intracellular staining was performed following fixation and permeabilization (Fixation and Permeabilization Buffer Set, eBioscience). Cells were washed and resuspended in flow buffer and acquired using BD LSRII with FACSDiva Software. analyses were performed using FlowJo (v10) (TreeStar).

The following antibodies were used to stain myeloid and lymphoid cells:

Mouse BMDMs: Anti-CD45 (clone 30-F11), anti-CD124 (clone I015F8), anti-I-A/I-E (clone 107630), anti-Ly6C (clone HK1.4), anti-CD11b (clone M1/70), anti-F4/80 (clone BM8), anti-Ly6G (clone 1A8), anti CD206 (clone C068C2), anti-TNF (clone MP6-XT22) all Biolegend and anti- IL-10 (clone JESS-16E3 eBiosciences).

Human HMDMs: anti CD16 (clone 3G8), anti-CD14 (clone 63D3), anti-HLA-DR (clone L243), anti-CD11b (clone ICRF44), anti-CD206 (clone 15-2), anti-CD163 (clone GHI/61), anti-TNF (clone MAb11), and anti-TNF (clone MAb11) all Biolegend.

Mouse macrophages (syngeneic MB49 model of urothelial carcinoma): CD45 (clone 30-F11, Biolegend), CD124 (IL-4Ra) (clone I015F8, Biolegend), I-a/I-e (clone M5/114.15.2, Biolegend), F4/80 (clone BM8, Biolegend), CD206 (clone C068C2, Biolegend), TNF (clone MP6-XT22, Thermo Fisher), IL-10 (clone JESS-16E3, Thermo Fisher)

Mouse T cells (syngeneic MB49 model of urothelial carcinoma): CD45 (clone PerCP, Biolegend), CD25 (clone PC61, Biolegend), CD3 (clone 17A2, Biolegend), CD4 (clone GK1.5, Biolegend), CD8a (clone 53-6.7, Biolegend), FOXP3 (clone MF-14, Biolegend), Mouse IFN-γ (clone XMG1.2, Biolegend) and FOXP3 (clone MF-14 Biolegend).

In Vitro Monocyte Trained Immunity Experiment:

In vitro training of primary human monocytes was performed as described earlier47. PBMCs were isolated from healthy donors (leukopaks). Following magnetic separation, CD14+ monocytes were seeded in 10 mm3 tissue culture dishes for 3 hours in warm RPMI 1640 media supplemented with 10% FBS at 37° C. with 5% $CO_2$. Non-adherent cells were removed by washing cells using warm PBS. Monolayer culture of human monocytes was infected with BCG-WT and BCG-disA-OE strains at 5:1 (monocyte versus BCG) MOIs for 4 hours in presence of RPMI 1640 supplemented with 10% FBS. Non-internalized bacilli were washed out using warm PBS and subsequently incubated for 24 hours. Cells were again washed using warm PBS and fresh warm RPMI 1640 media was added. For the following 5 days, cells were allowed to rest with a PBS wash and addition of fresh media every 2nd day. Cells were re-stimulated on day 6 with RPMI 1640 supplemented with 10% FBS (negative control, without training) or TLR1/2 agonist, Pam3Cys (Cat. tlrl-pms, InvivoGen). Following stimulation, for 24 h, culture supernatants were collected, filter sterilized and quickly snap-frozen (−80° C.) for cytokine measurement. Cells were harvested for chromatin immunoprecipitation (ChIP) experiments to measure epigenetic changes on gene promoters.

Chromatin immunoprecipitation (ChIP): Human monocytes were fixed with a final concentration of 1% formaldehyde for 10 minutes at room temperature. Cell fixation was stopped using 125 mM glycine (Cat no. 50046, Sigma-Aldrich, USA), followed by sonication to fragment cellular DNA to an average size between 300 to 600 bp using Qsonica Sonicator Q125 (Cat. 15338283, Thermo Fisher Scientific). Sonicated cell lysates were subjected to immunoprecipitation (IP) by overnight incubation with recommended concentration of primary antibodies [(Histone H3K9me3 (H3K9 Trimethyl) Polyclonal Antibody cat. A-4036-100, epigentek); Anti-Histone H3 (tri methyl K4) antibody—ChIP Grade (ab8580), abeam)] in presence of magnetic Dynabeads (Cat no. 10004D, Thermo Fisher Scientific, USA) at 4° C. Non-bound material was removed by sequentially washing the Dynabeads with lysis buffer, chromatin IP (ChIP) wash buffer and Tris-EDTA (TE buffer). DNA elution was done using ChIP elution buffer. Amplification of different segments of the regulatory regions of immunity genes was carried out using qPCR using specific primers. Reactions were normalized with input DNA while beads served as negative control. Details of all primary antibodies and sequence of primers have been given in Table 4.

Targeted Metabolite Analysis with LC-MS/MS:

Targeted metabolite analysis was performed with liquid-chromatography tandem mass spectrometry (LC-MS/MS) as described earlier48. Metabolites from cells or snap-frozen xenograft tumor tissue were extracted with 80% (v/v) methanol solution equilibrated at −80° C., and the metabolite-containing supernatants were dried under nitrogen gas. Dried samples were re-suspended in 50% (v/v) acetonitrile solution and 4 ml of each sample were injected and analyzed on a 5500 QTRAP triple quadrupole mass spectrometer (AB Sciex) coupled to a Prominence ultra-fast liquid chromatography (UFLC) system (Shimadzu). The instrument was operated in selected reaction monitoring (SRM) with positive and negative ion-switching mode as described. This targeted metabolomics method allows for analysis of over two hundred of metabolites from a single 25-min LC-MS acquisition with a 3-ms dwell time and these analyzed metabolites cover all major metabolic pathways. The optimized MS parameters were: ESI voltage was +5,000V in positive ion mode and −4,500V in negative ion mode; dwell time was 3 ms per SRM transition and the total cycle time was 1.57 seconds. Hydrophilic interaction chromatography (HILIC) separations were performed on a Shimadzu UFLC system using an amide column (Waters XBridge BEH Amide, 2.1×150 mm, 2.5 µm). The LC parameters were as follows: column temperature, 40° C.; flow rate, 0.30 ml/min. Solvent A, Water with 0.1% formic acid; Solvent B, Acetonitrile with 0.1% formic acid; A non-linear gradient from 99% B to 45% B in 25 minutes with 5 min of post-run time. Peak integration for each targeted metabolite in SRM transition was processed with MultiQuant software (v2.1, AB Sciex). The preprocessed data with integrated peak areas were exported from MultiQuant and re-imported into Metaboanalyst software for further data analysis including statistical and principle components analyses.

Histologic Analyses and Immunohistochemistry (IHC):

For histologic analyses, a portion of bladder was formalin fixed and paraffin embedded. Sections of 5µ in thickness on glass slides were stained with hematoxylin-eosin for classification according to the World Health Organization/International Society of Urological Pathological consensus as described earlier27. Tumor staging was performed by 2 board certified genitourinary pathologists (A.S.B., A.M.). Specimens were classified based on the percentage of involvement of abnormal tissue (1=10% involvement, 2=20% involvement, and so forth). For IHC staining, high-temperature antigen retrieval (18-23 psi/126° C.) was performed by immersing the slides in Trilogy (Cell Marque). Endogenous peroxidase activity was blocked for 5 min in using Dual Endogenous Enzyme Block (Cat. S2003, Dako). Primary Antibodies used included Ki67 (1:50, Cat. ab16667; Abcam), CD68 (1:250, Cat. MCA341R; Serotec), CD86 (1:100, Cat. bs-1035R; Bioss) and CD206 (1:10K, Cat. ab64693; Abcam). For Ki67, slides were stained with ImmPACT DAB (Vector Labs) for 3 min and counterstained with haematoxylin (Richard-Allen). Dual staining for CD68/ CD206 and CD68/ CD86 was achieved by first staining for CD68 with Impact DAB (Vector Labs) followed by secondary antigen retrieval and incubation as above with either CD86 or CD206 and visualized with ImmPACT AEC (Vector Labs). For each section, Ki67 expression was scored as a percentage of positive cells in the urothelium. Dual stains for CD68/ CD86 and CD68/ CD206 were scored based on positive clusters of cells for each marker (0=no staining, 1=rare isolated cells positive, 2=clusters of up to 10 positive cells, 3=clusters of >10 positive cells).

In Vivo Experiments:

Intravesical BCG Treatment in Carcinogen Induced NMIBC Rat Model:

The induction of urothelial cancer in rats and subsequent treatment of intravesical BCG were performed. N-methyl-N-nitrosourea (MNU) instillations were given every other week for a total of 4 instillations. Fischer 344 female rats age 7 weeks (Harlan, avg. weight 160 g) were anesthetized with 3% isoflurane. After complete anesthesia, a 20G angiocatheter was placed into the rat's urethra. MNU (1.5 mg/kg) (Spectrum) dissolved in 0.9. % sodium chloride was then instilled and the catheter removed, with continued sedation lasting for 60 minutes to prevent spontaneous micturition and allow absorption. Eighteen weeks after the first MNU instillation, intravesical treatment with PBS or $5 \times 10^6$ CFU of each BCG strain (0.3 ml via a 20G angiocatheter) was administered weekly for a total of 6 doses. Rodents were sacrificed 2 d after the last intravesical treatment, and bladders were harvested within 48 hours of the last BCG instillation for mRNA and protein expression analysis as well as histological evaluation.

BCG Infection of BALB/c Mice and CFU Enumeration:

To determine the lung bacillary burden of wild-type and BCG-disA-OE strains 6-week-old female BALB/c mice were exposed using the aerosol route in a Glasscol inhalation exposure system (Glasscol). The inoculum implanted in the lungs at day 1 (n=3 mice per group) in female BALB/c mice was determined by plating the whole lung homogenate on 7H11 selective plates containing carbenicillin (50 mg/ml), Trimethoprim (20 mg/ml), Polymyxin B (25 mg/ml) and Cycloheximide (10 mg/ml). Following infection, mice lungs were harvested (n=5 animals/group), homogenized in their entirety in sterile PBS and plated on 7H11 selective plates at different dilutions. The 7H11 selective plates were incubated at 37° C. and single colonies were enumerated at week 3 and 4. Single colonies were expressed at log CFU per organ.

SCID Mice Time to Death Study:

The virulence testing of BCG-WT and BCG-disA-OE strains was done in severely compromised immunodeficient mice aerosol infection model as described previously. The inoculum implanted in the lungs at day 1 (n=3 animals per group) was determined by plating the whole lung homogenate on 7H11 selective plates. For time to death analyses (n=10 animals per group) infected animal were monitored until their death.

Syngeneic MB49 Model of Urothelial Cancer:

MB49 tumor cells are urothelial carcinoma line derived from an adult C57BL/6 mouse by exposure of primary bladder epithelial cell explant to 7,12-dimethylbenz[a]anthracene (DMBA) for 24 hours followed by a long-term culture79. Before implantation, MB49 cells were cultured as monolayers in RPMI 1640 media supplemented with 10% FBS and 1% streptomycin/penicillin at 37° C. with 5% CO2. Cells were harvested using Trypsinization and cell viability was determined using Trypan blue dye. Live MB49 cells were resuspended in sterile PBS and adjusted at $1 \times 10^5$ live cells per 100 µl. Female C57BL/6J mice, age 4-6 weeks (Charles River Laboratories) were subcutaneously injected with $1 \times 10^5$ MB49 cells in the right flank of hind leg. Tumor growth was monitored every 2nd day to observe the increase the tumor burden at the time of treatment initiation. Once palpable tumor developed (7 to 9 days, average volume ~30 mm3), $1 \times 10^6$ bacilli of BCG-WT or BCG-disA-OE in a total 50 µl PBS was injected intratumorally (FIG. 41). A total of 4 intratumoral injections of BCG was given every 3rd day. Tumors were measured by electronic caliper, and tumor volume was calculated using the following equation: tumor volume=length×width×height×0.5326. Mice were killed at specified time, and tumors and spleens were collected after necropsy for single cell preparation.

Example 2

Figure 39A:
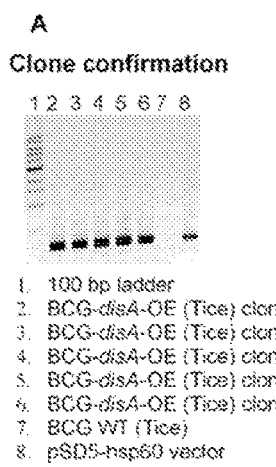
FIGS. 39A-39C shows confirmation of *M.tb*-disA overexpression phenotype of BCG-disA-OE and induction of IRF signaling.
Figure 39B:
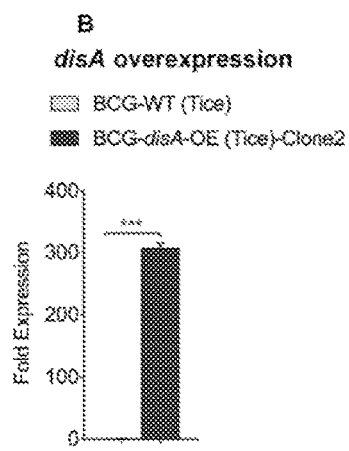
Figure 39C:
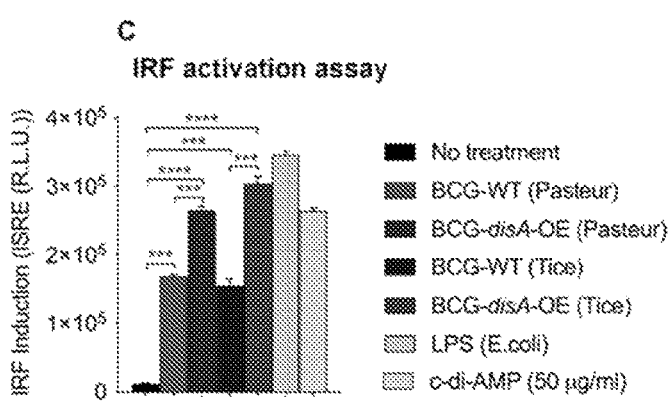

BCG-DISA-OE Elicits Greater Pro-Inflammatory Cytokine Responses in Macrophages than BCG-WT BCG-disA-OE is a genetically-engineered BCG strain in which an endogenous diadenylate cyclase gene, disA, is fused to a strong promoter, leading to a 300-fold overexpression of disA and a 15-fold increase in production of cyclic di-AMP (FIG. 39). Compared with BCG-WT, BCG-disA-OE significantly increased STING pathway activation in macrophages as measured by IRF3 induction (FIG. 39). To control for the fact that numerous BCG strains are used worldwide and variabilities in their clinical efficacies have been described, two versions of BCG-disA-OE and a corresponding BCG-WT were generated: one using BCG-Tice and one using BCG-Pasteur. No significant differences between the Tice and Pasteur versions were detected.

Figure 40A:
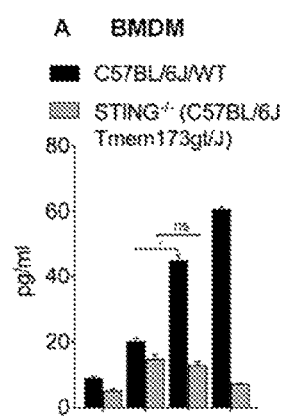
FIGS. 40A-40C show BCG strains overexpressing c-di-AMP as strong inducers of type I interferon in STING-dependent manner.
Figure 40B:
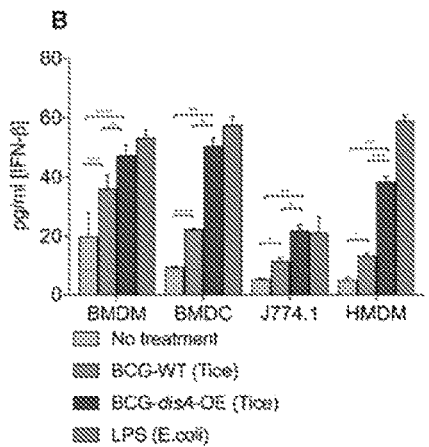
Figure 40C:
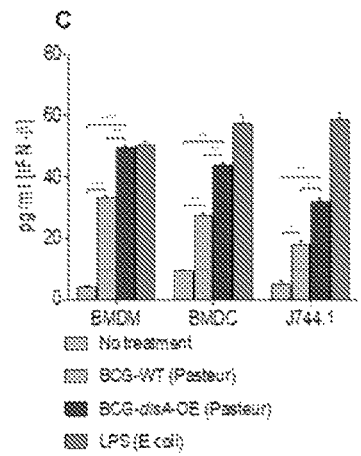
Figure 41A:
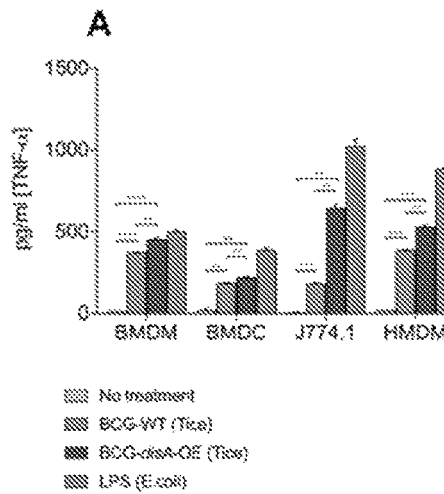
FIGS. 41A-41D show BCG strains overexpressing c-di-AMP are strong inducers of proinflammatory cytokines, TNF-α, and IL-6. (A-B) Quantitative measurement of TNF-α in culture supernatants of wild-type C57BL/6-derived BMDMs, BMDCs, J774.1 macrophages and human monocyte-derived macrophages (HMDMs).
Figure 41B:
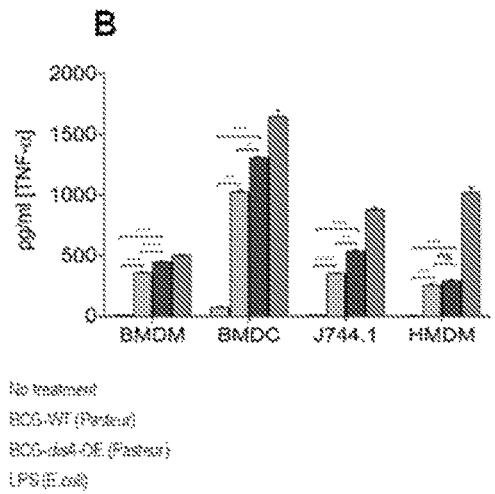
Figure 41C:
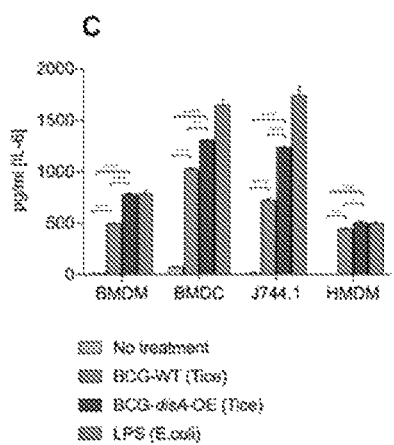
Figure 41D:
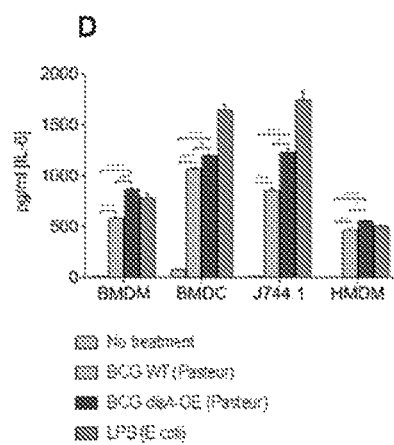
Figure 42:
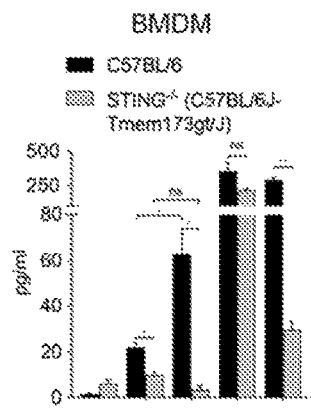
FIG. 42 shows BCG overexpressing c-di-AMP strongly induces proinflammatory cytokine TNF-α in STING-dependent manner. Quantitative measurement of TNF-α in culture supernatants of wild-type C57BL/6-derived BMDMs and STING-KO BMDM (C57BL/6J-Tmem173gt/J) 24 h after BCG-disA-OE (Tice) infection. Macrophage to BCG infection ratio=1:20. Data represent mean±SEM (n=3 replicates). Student's t-test (two-tailed) *P<0.05, P<0.01, *P<0.001, ****P<0.0001

To characterize the trained immunity-inducing potential of BCG-disA-OE versus BCG-WT, their capacity to induce cytokine expression in human monocyte-derived macrophages (HMDMs), primary murine bone marrow-derived macrophages (BMDM), and dendritic cells (BMDC) as well as a macrophage cell line (J774.1) were evaluated. Consistent induction of IRF3, IFN-β, TNF-α and IL-6 in all myeloid cell types were found in response to BCG-disA-OE that was significantly higher than that seen with BCG-WT-exposed cells (FIG. 40 and FIG. 43), and in human MDM and murine BMDM this difference was observed even in when cells were IFN-γ primed (FIG. 43). These differences were strictly STING-dependent as confirmed using BMDM from STING$^{-/-}$ mice (FIG. 40). Since STING activation leads to upregulation of NF-κB via the TBK1-IRF3 pathway, it was found that expression of both TNF-α and IL-6 in the same panel of cells paralleled that of IFN-β and was significantly higher following exposure to BCG-disA-OE compared with BCG-WT (FIGS. 41 and 43). Cyclic dinucleotides including cyclic di-AMP are known to be potent inducers of several chemokines (CXCL9, CXCL10 [IP-10], CXCL22, and MCP-1) as well as iNOS; consistent with this, IFN-γ-primed BMDMs showed a more robust induction of these chemokines and iNOS when challenged with BCG-disA-OE strain than with BCG-WT (FIG. 41). The cellular toxicity was also assessed using annexin-PI staining and found that whereas late apoptotic cell death remained at baseline with BCG-disA-OE exposure in both BMDM and J774.1 macrophages, BCG-WT exposure elicited significantly higher levels of apoptotic cell death (FIG. 44) in the BMDM cells. These observations demonstrate that BCG-disA-OE elicits pro-inflammatory cytokine expression more potently than BCG-WT in primary human MDM as well as murine primary macrophages and macrophage cell lines.

Example 3

Pro-Inflammatory Polarization of Macrophages is Greater with BCG-DISA-OE than with BCG-WT Trained immunity is associated with polarization of macrophages towards inflammatory phenotypes with a concomitant shift away from anti-inflammatory states. To investigate macrophage polarization, flow cytometry was used to monitor phenotypic shifts of both murine and human primary macrophages following a 24 h exposure to BCG-disA-OE or BCG-WT. First, the MHC class II-expressing CD45$^+$ CD11b$^+$F4/80$^+$ murine BMDM population were focused on, following in vitro BCG exposure using the gating scheme. As may be seen in FIG. 50 and FIG. 48, a significantly greater expansion of TNF-α-expressing CD11b$^+$ F4/80$^+$ (M1) murine BMDMs was observed following exposure to BCG-disA-OE than with BCG-WT. Next cells expressing the M2 surface receptors CD206$^+$ and CD124$^+$ among CD45$^+$ CD11b$^+$ F4/80$^+$ macrophages were gated on and a greater reduction of this population with BCG-disA-OE than with to BCG-WT was observed (FIG. 50 and FIG. 49). Within this immunosuppressive cell population, there was a higher proportion of IL-10-expressing CD206$^+$ CD124$^+$ cells in BCG-WT-exposed macrophages, while IL-10-expressing cells were significantly reduced in response to BCG-disA-OE exposure (FIG. 50 and FIG. 49). These results demonstrate that compared with BCG-WT, BCG-disA-OE exposure elicits more extensive macrophage reprogramming with expansion of pro-inflammatory M1 macrophages displaying increased antigen presentation (MHC class II expression) and TNF-α expression and contraction of immunosuppressive M2 macrophages expressing IL-10.

Myeloid-derived suppressor cells (MDSCs) are a heterogeneous population of immature myeloid cells known to foster immunosuppression. Accordingly, the induction of monocytic-myeloid derived suppressor cells, M-MDSCs, was investigated (CD45$^+$ Ly6C$^{hi}$ Ly6G$^-$CD11b$^+$ F4/80$^-$) using primary murine BMDMs using the gating scheme shown. Following BCG-WT exposure a significant expansion of M-MDSCs was observed, while in contrast this same population showed minimal expansion following BCG-disA-OE exposure (FIG. 50). Moreover, the M-MDSCs elicited by BCG-WT exhibited higher IL-10 expression, whereas IL-10-expressing M-MDSCs were virtually absent after BCG-disA-OE exposure (FIG. 50). These observations suggest that BCG-WT contributes to an expansion of M-MDSCs which have immunosuppressive properties; however, forced overexpression of the pro-inflammatory PAMP cyclic di-AMP by BCG prevents M-MDSC expansion.

The macrophage activation phenotypes in HMDMs isolated from several independent healthy human donors was next characterized. Both the BCG-WT and BCG-disA-OE strains elicited increases in the population of classical macrophages (CD11b$^+$ CD14$^+$ CD16$^-$), but these inductions were comparatively higher in response to BCG-disA-OE (FIG. 51 and FIG. 52). classically activated antigen-presenting macrophages (CD14$^+$ CD16$^-$ HLA-DR$^+$) and their ability to produce TNF-α or IL-6 were examined and it was found a significantly increased proportion of TNF-α and IL6- producing HLA-DR$^+$ cells following exposure to BCG-disA-OE compared to BCG-WT (FIG. 52 and FIG. 53). The M2 surface markers, CD206$^+$ and CD163$^+$, were also investigated on transitional or intermediate macrophages (CD11b$^+$ CD14$^+$ CD16$^+$) and it was found a consistently greater decrease in them following BCG-disA-OE exposure than with BCG-WT (FIG. 51, FIG. 53). The fraction of these intermediate macrophages expressing M2 surface markers and IL-10 was also significantly lower in response to exposure to BCG-disA-OE than with BCG-WT (FIG. 53). In summary, using both mouse and human primary macrophage ex vivo models, it was found that, compared with BCG-WT, BCG-disA-OE promotes greater macrophage activation towards an M1 phenotype (inflammatory), and concomitantly reduces the emergence of cells with immunosuppressive abilities, including M-MDSCs.

Example 4

Macrophages Exposed to BCG-DISA-OE are More Phagocytic than Those with BCG-WT

Cyclic dinucleotides have been reported to recruit inflammatory macrophages which display high phagocytic potential. Consistent with these observations it was we confirmed that HMDMs transfected with cyclic di-AMP showed increased phagocytosis and exhibited elongated dendrites compared to mock-transfected populations. It was then evaluated the phagocytic properties of HMDMs following exposure to the different BCG strains and found significantly greater phagocytosis of IgG-opsonized FITC-latex beads by macrophages exposed to BCG-disA-OE compared to BCG-WT (FIG. 54). In keeping with the previously established role of STING pathway activation in augmenting autophagy, it was found that a majority of intracellular BCG-disA-OE bacilli were co-localized with LC3B in IFN-γ-activated primary BMDMs, while autophagy induction in BCG-WT was significantly lower. It was also found a significantly greater co-localization of BCG-disA-OE bacilli with the autophagy adapter protein p62 compared to that observed with BCG-WT. These results reveal BCG-disA-OE increases the levels of phagocytosis and autophagic processing within macrophages to a greater degree than BCG-WT, a phenomenon associated with enhanced peptide antigen presentation to MHC class-II molecules.

Example 5

BCG-DISA-OE Reprograms Macrophages Epigenetically and Potentiates Trained Immunity to a Greater Degree than BCG-WT In light of recent data showing BCG to be a potent inducer of trained immunity through epigenetic modifications of key pro-inflammatory genes, it was hypothesized that the addition of cyclic di-AMP overexpression to standard BCG might potentiate epigenetic modifications in primary human monocytes. Having already established that BCG-disA-OE is a more potent inducer of macrophage TNF-α and IL-6 secretion than BCG-WT, it was confirmed this in primary human monocytes from a group of 6 healthy human subjects. The ability of traditional BCG to elicit trained immunity has been correlated with changes in epigenetic marks that increase pro-inflammatory gene expression. Thus, it was asked if the enhanced induction of TNF-α and IL-6 expression elicited by BCG-disA-OE compared with BCG-WT is epigenetically mediated. To this end, it was evaluated the promoter regions of the TNF-α and IL-6 genes for durable, antigen-independent epigenetic changes using an assay in which human monocytes exposed to BCG strains for 24 h were rested for five days prior to challenge with a heterologous antigen, the TLR1/2 agonist Pam3CSK4 on day 6 (FIG. 56). Using chromatin immunoprecipitation-polymerase chain reaction (ChIP-PCR) assays the activating histone methylation mark H3K4me3 present in the TNF-α and IL-6 promoters was quantified. It was observed that exposure to BCG-disA-OE led to greater enrichment of this mark than BCG-WT even without the heterologous second stimulation (i.e., adding RPMI media alone at day 6). Upon re-stimulation with Pam3CSK4 at day 6, the abundance of the activating epigenetic mark was further increased by both BCG strains, but BCG-disA-OE-pretreatment yielded notably more enrichment than BCG-WT (FIG. 56). Similarly, it was investigated the chromatin repression mark H3K9me3 at the same two promoters and found that, while both BCG strains led to reduced levels of H3K9me3 (which were further accentuated by addition of Pam3CSK4), the degree of reduction mediated by BCG-disA-OE was consistently greater than that mediated by BCG-WT, both upon initial exposure and after rest and re-stimulation (FIG. 56). Simultaneous measurement of TNF-α and IL-6 in BCG-trained culture supernatant following non-specific stimulation by Pam3CSK4 revealed that BCG-disA-OE-trained macrophages produced significantly higher levels of these pro-inflammatory cytokines than did those trained with BCG-WT. These results indicate that an augmented BCG which overexpresses the PAMP molecule cyclic di-AMP leads to significantly more robust epigenetic changes classically associated with trained immunity.

Example 6

BCG-DISA-OE Reprograms the Macrophage Immunometabolic State Towards Pro-inflammatory Signatures to a Greater Degree than BCG-WT BCG-training has been reported to stimulate glycolysis as well as the tricarboxylic acid cycle through glutamine replenishment with accumulation of fumarate. To address whether the addition of cyclic di-AMP overexpression alters the BCG-mediated metabolomic shifts, LC-MS was used to characterize key metabolites in primary human and murine macrophages exposed to the two BCG strains. HMDMs or BMDMs showed increased catabolic signatures (elevated intracellular glucose and lactate) to a greater degree following a 24 h exposure to BCG-disA-OE than with BCG-WT. Also, the TCA cycle metabolites itaconate and fumarate were also more elevated with BCG-disA-OE than with BCG-WT. These observations suggest greater catabolism of carbon substrates for ATP generation consistent with a pro-inflammatory bioenergetic profile in macrophages infected with BCG-disA-OE than with BCG-WT.

Excess tryptophan catabolism to kynurenine by tryptophan dehydrogenase and indoleamine 2,3-dioxygenase (IDO) has been strongly associated with immunosuppression, and IDO inhibitors have shown potential as immune activators in a variety of infectious and oncologic diseases. Kynurenine levels were dramatically lower in macrophages following BCG-disA-OE exposure than those seen with BCG-WT, and as would be expected tryptophan levels were elevated by BCG-disA-OE while BCG-WT led to tryptophan levels comparable to the baseline seen with heat-killed BCG controls. Citrulline levels were also higher while putrescine levels were lower with BCG-disA-OE than BCG-WT suggesting that nitric oxide synthase-mediated conversion of arginine to NO (pro-inflammatory) and citrulline was more strongly induced by BCG-disA-OE. Finally, it was of interest that itaconate, an isocitrate lyase inhibitor made by macrophages that has been shown to have antibacterial activity, was more potently induced by BCG-disA-OE than BCG-WT. Thus, compared with BCG-WT, BCG-disA-OE elicited a greater pro-inflammatory metabolomic signature with reduced kynurenine accumulation and increases in glycolytic metabolites, NOS products, and itaconate production.

Example 7

Functional Efficacy In Vivo: BCG-DISA-OE Demonstrates Superior Immunotherapeutic Outcomes in Relevant Animal Models of Trained Immunity In addition to being used as a TB vaccine, BCG has served as a first-line immunotherapy for the treatment of non-muscle invasive bladder cancer (NMIBC) since the mid- 1970s. Recent studies have indicated that BCG exerts its antitumor effects via a trained immunity mechanism. Having demonstrated that augmenting BCG with excess cyclic di-AMP release leads to improved trained immunity parameters across a battery of in vitro assays, it was sought to determine if these effects could be demonstrated in vivo.

First, BCG-disA-OE versus BCG-WT was tested in a carcinogen-induced model of NMIBC in which intravesical therapies can be introduced into the bladder as they are in humans with non-invasive urothelial cancer. The rat N-methyl-N-nitrosourea (MNU) model of bladder cancer (BC) is schematized in FIG. 57 In this model urothelial dysplasia develops at week 14 after the first intravesical instillation of MNU and by week 24 rats display a different forms of urothelial cancer severity including carcinoma-in-situ (CIS), papillary Ta (superficial), or higher-grade T1-T2 urothelial carcinoma with histopathologic and immunophenotypic features similar to those observed in human bladder cancer. Following carcinogen-mediated tumor induction with 4 cycles of MNU (wk 0, wk 2, wk 4, wk6), groups of rats were treated with 6 weekly doses of intravesical BCG-disA-OE, BCG-WT, or no treatment from week 18-23. Upon sacrifice at wk 24 the rat urinary bladders were divided into halves for (i) RT-PCR analysis, and (ii) histologic analysis including tumor staging by a blinded genitourinary pathologist. Transcriptional analysis of the whole excised bladders at week 24 showed that compared with BCG-WT, BCG-disA-OE elicited significantly increased levels of IFN-β, IFN-γ, TNF-α, IL-1β, CXCL10, MCP-1, MIP-1α, and iNOS transcription while mRNA levels of the immunosuppressive cytokines IL-10 and TGF-β were reduced by both BCG strains (FIG. 57). These patterns of cytokine expression were confirmed at the protein level using ELISA for TNF-α IL-2, and IFN-γ and noted that intravesical BCG-disA-OE, strongly increased the levels of IFN-γ in rat spleens while BCG-WT did not. Correspondingly, it was found a significant decrease in highest pathology grade, tumor involvement index and highest tumor stage (FIG. 57) in rats treated with BCG-disA-OE in comparison to untreated. By tumor involvement index BCG-disA-OE was statistically significantly superior to no treatment ($p<0.001$) and to BCG-WT ($p=0.05$), whereas BCG-WT showed only a trend towards improvement over no treatment. Importantly, the highest tumor stage observed in BCG-disA-OE-treated rats was CIS, whereas it was T1 in those receiving BCG-WT, and T2 in untreated rats, and 53.3% of BCG-disA-OE-treated rats were cancer free ($p=0.009$) compared with 31.2% of BCG-WT and 0% of the untreated rats (FIG. 57) Immunohistochemical analyses revealed a significant reduction in Ki67 staining in BCG-disA-OE-treated MNU rat bladders when compared to untreated ($p=0.01$) and BCG-WT ($p=0.05$) suggesting reduced tumor proliferation. CD68 staining of rat bladder showed significantly higher levels of macrophage recruitment with a trend toward elevation of the pro-inflammatory M1-like CD86+ macrophages and a significant reduction in CD206+ M2-like macrophages that are associated with tumor promotion in the BCG-disA-OE-treated rats compared with untreated controls. These observations indicate that the enhanced induction of type I IFN and other proinflammatory signatures in bladders of tumor-bearing rats treated with BCG-disA-OE correlated with the enhanced antitumor activity of the recombinant BCG strain.

The functional efficacy of BCG-disA-OE was also tested in a murine heterotopic, syngeneic bladder cancer model using MB49 urothelial cancer cells. Following flank engraftment with MB49 tumor cells, mice received four intratumoral treatments over 9 days as shown in FIG. 61. In this model BCG-disA-OE also showed more robust immunotherapeutic efficacy than BCG-WT as measured by tumor volume and weight after intratumoral injection of BCG-disA-OE when compared with BCG-WT (FIG. 61). Histopathology demonstrated extensive necrosis and congestion in MB49 tumors treated with BCG-disA-OE when compared to BCG-WT and untreated. There were no significant changes in body weights of mice receiving BCG, however splenic weight was significantly increased by both BCG strains. We further characterized the impact of the treatments on macrophage polarization and recruitment of activated T cells in the tumor microenvironment (TME). As shown in FIG. 61, compared with BCG-WT, BCG-disA-OE significantly reduced the abundance of immunosuppressive M2 macrophages when compared to untreated and BCG-WT and significantly ($p=0.01$) increased proinflammatory M1 macrophages. Similarly, BCG-disA-OE recruited significantly more IFN-γ-producing CD4+ T cells when compared to BCG-WT, and both BCG strains increased IFN-γ-producing CD8+ T cells. While both BCG strains recruited more CD4+ and CD8+ cells to the tumors, BCG-disA-OE uniquely recruited more CD8+ T cells to the spleens of treated animals. BCG-disA-OE also significantly reduced tumor-associated T-regulatory (Treg) cells to a greater degree than BCG-WT in both tumor and spleen. In keeping with our earlier findings in primary cells, we also found that compared with BCG-WT, BCG-disA-OE elicited more potent cytokine responses and autophagy in human urothelial cancer cells representing various tumor stages. These results indicate that in this murine model of urothelial cancer, BCG-disA-OE has superior antitumor efficacy than BCG-WT, and its efficacy correlates with shift in polarization of macrophages to M1, increased activation of both CD4+ and CD8+ T cells, and a reduction of local intratumoral and systemic Treg cell populations.

Example 8

Safety: BCG-DISA-OE is Less Pathogenic than BCG-WT in Two Mouse Models

To address concerns that the enhanced pro-inflammatory immune responses elicited by BCG-disA-OE might lead to adverse effects, safety in two separate mouse models was evaluated. An immunocompetent BALB/c mouse model of aerosol exposure was used and measured the lung bacillary burden after four weeks when adaptive immune responses are maximal (FIG. 58). While the day 1 implantation of the two BCG strains was equivalent, we observed that BCG-disA-OE proliferated in murine lungs to a significantly lower degree than BCG-WT by a margin of 0.43 login colony forming units (FIG. 58). As previously observed in cell-based models, pro-inflammatory cytokine levels in both lungs and spleens were significantly higher in BCG-disA-OE-exposed mice than those receiving BCG-WT (FIG. 60). the two strains in immunocompromised SCID mice which do not survive infection with BCG were also tested. Again, using a low dose aerosol exposure model (FIG. 59), it was observed a statistically significant survival prolongation with BCG-disA-OE compared to BCG-WT (FIG. 59). Thus, despite eliciting more profound inflammatory signatures in numerous model systems, BCG-disA-OE is less pathogenic than BCG-WT in these two murine model systems.

Example 9

Discussion

Numerous recombinant BCG strains have been generated and tested over the years. These studies were generally conducted with the goal of improving either TB protective efficacy or bladder cancer immunotherapy, but in certain cases the goal has been prevention of other infectious diseases. A common strategy has been to overexpress an antigen to elicit disease-specific immunity or a cytokine gene to boost local host responses. While many modified BCGs have shown efficacy in pre-clinical models, few have progressed to human clinical trials. To date only BCGΔureC::hly (VPM1002), a BCG designed to enhance phagosome permeability and exposure of BCG antigens to cytosolic MHC class I antigen processing, has advanced to late stage clinical trials for tuberculosis. This is the first to specifically re-engineer BCG with the specific goal of improving trained immunity by overexpressing the PAMP molecular cyclic-di-AMP to increase STING pathway engagement.

To determine if trained immunity parameters may be increased, BCG-disA-OE versus BCG-WT were tested in a battery of in vitro assays. Cytokine release profiles, macrophage polarization, autophagy, phagocytosis, epigenetic modifications, and metabolic remodeling in human and murine primary cells were evaluated. In each assay system, BCG-disA-OE was a more potent potentiator of pro-inflammatory responses than BCG-WT. the cyclic-di-AMP expressing BCG was further tested in a functional in vivo assay of trained immunity, namely bladder cancer immunotherapy. In two separate models of urothelial cancer, BCG-disA-OE has greater immunotherapeutic efficacy than did BCG-WT indicating that our in vitro results were predictive of functional efficacy in a relevant animal model. Interestingly, despite eliciting a significantly more potent pro-inflammatory responses in our in vitro assay systems, BCG-disA-OE did not produce excess pathogenicity in two animal models of BCG infection or BCGosis.

It was also observed that BCG-WT did not uniformly elicit pro-inflammatory responses. For example, it was observed that treatment of murine macrophages with BCG-WT in fact induced a higher percentage of M-MDSCs (anti-inflammatory) compared with untreated controls (FIG. 50), and similarly BCG-WT led to elevated levels of the anti-inflammatory metabolite kynurenine. These findings of certain anti-inflammatory consequences of BCG-WT may correlate with the observation that in countries which routinely use BCG for TB prevention, vaccines display reduced levels of asthma and atopic dermatitis. In contrast, this expansion of M-MDSCs in macrophages by BCG-WT was reversed by cyclic di-AMP overexpression which is in keeping with recent studies showing that STING pathway activation reduces the induction of MDSCs in certain cancers.

Trained immunity changes elicited by BCG may underlie the immunotherapeutic effects of BCG in cancer prevention. Therefore, another goal of this study was to evaluate whether the salutary effects of BCG-disA-OE as a NMIBC immunotherapy is mediated through engagement of STING pathway and modulates BCG-mediated trained immunity. In a rat model of NMIBC, it was found that whereas invasive tumors developed in untreated tumor-bearing rats (highest tumor grade of T2) as well as BCG-WT-treated animals (highest tumor grade of T1), invasive bladder cancer was completely absent in rats treated with BCG-disA-OE. Similarly, in the MB49 mouse model of bladder cancer, BCG-disA-OE was superior to BCG-WT in reducing tumor growth with associated increase in tumor necrosis, and these effects were accompanied by significantly higher recruitment of M1 macrophages, IFN-γ-producing CD4 cells, and reduced accumulation of Treg cells in the tumors. Elevated levels of pro-inflammatory cytokines and chemokines were observed in bladders from tumor-bearing animals treated with BCG-disA-OE compared to BCG-WT. Since non-immune cells have also been shown to possess immunological memory, the possibility that this cytokine response may have originated from myeloid cells in the TME and/or the tumor cells themselves was considered. Indeed, it was found that compared with BCG-WT, BCG-disA-OE elicited more potent cytokine responses in both primary macrophages and human urothelial cancer cells representing various tumor stages. This appeared to be a downstream consequence of STING activation since we found dramatically reduced expression in BMDMs from STING$^{-/-}$ mice. In addition, robust induction of several chemokines as has been observed in other studies with stimulation using exogenous STING agonists was found.

Although the invention has been described with reference to the above examples, it will be understood that modifications and variations are encompassed within the spirit and scope of the invention. Accordingly, the invention is limited only by the following claims.

Although the invention has been described with reference to the above examples, it will be understood that modifications and variations are encompassed within the spirit and scope of the invention. Accordingly, the invention is limited only by the following claims.

---

What is claimed is:

1. A method of inhibiting the expansion of myeloid-derived suppressor cells (MDSCs), reducing M2 macrophages activation, and reducing levels of tumor-associated Treg cells in a tumor and inducing M1 macrophages activation and T effector cells level in a tumor comprising
administering to a subject having a tumor an effective amount of a pharmaceutical composition comprising a strain of mycobacteria comprising a vector, the vector comprising (i) a nucleic acid sequence encoding a protein that makes a STING agonist, wherein the protein that makes the STING agonist is a DNA integrity scanning (DisA) protein wherein the STING agonist is a 3'-5' c-di-AMP (also known as c-di-AMP), and wherein the protein that makes the STING agonist lacks an EAL domain, and (ii) a panCD nucleic acid encoding a PanC protein and a nucleic acid sequence encoding a PanD protein,
wherein the strain of Mycobacteria is a panthothenate-auxotroph *Mycobacterium bovis Bacillus* Calmette Guerin (BCG) thereby inhibiting the expansion of MDSCs, reducing M2 macrophages activation, and reducing levels of tumor-associated Treg cells and inducing M1 macrophages activation and T effector cells level in the tumor.

2. The method of claim 1, wherein inhibiting the expansion of MDSCs, reducing M2 macrophages activation, and reducing levels of tumor-associated Treg cells in the tumor is as compared to the expansion of MDSCs, M2 macrophages activation, and levels of Treg cells in a tumor of a referenced subject not administered a pharmaceutical composition comprising the strain of Mycobacteria comprising the vector expressing a protein that makes a STING agonist.

3. The method of claim 1, wherein inducing M1 macrophages activation and T effector cells level in a tumor is as compared to the M1 macrophages activation and T effector cells level in a tumor of a referenced subject not administered a pharmaceutical composition comprising the strain of Mycobacteria comprising the vector expressing a protein that makes a STING agonist.

4. The method of claim 1, wherein the tumor is a cancer selected from the group consisting of epithelial cancers, breast cancer, non-muscle invasive bladder cancer, melanoma, and a combination thereof.

5. The method of claim 4, wherein the tumor is a non-muscle invasive bladder cancer and is a BCG-unresponsive non-muscle invasive bladder cancer (BCG-unresponsive NMIBC) and the pharmaceutical composition is administered by intravesical instillation.

6. The method of claim 4, wherein the tumor is non-muscle invasive bladder cancer and is a BCG-naïve non-muscle invasive bladder cancer (BCG-naïve NMIBC) and the pharmaceutical composition is administered by intravesical instillation.

7. The method of claim 4, wherein the tumor is an epithelial cancer is selected from the group consisting of colon cancer, uterine cancer, cervical cancer, vaginal cancer, esophageal cancer, nasopharyngeal cancer, endobronchial cancer, and a combination thereof and the pharmaceutical composition is administered to a luminal surface of the epithelial cancer.

8. The method of claim 1, wherein the tumor is a solid tumor and the pharmaceutical composition is administered by intratumoral, intravenous, intradermal, transdermal, intravesical, topical, intramuscular or subcutaneous injection.

9. The method of claim 1, further comprising the step of administering a checkpoint inhibitor.

10. The method of claim 9, wherein the checkpoint inhibitor is selected from the group consisting of ipilimumab (anti-CTLA-4 antibody), nivolumab (anti-PD-1 antibody), pembrolizumab (anti-PD-1 antibody), cemiplimab (anti-PD-1 antibody), atezolizumab (anti-PD-L1 antibody), avelumab (anti-PD-L1 antibody), durvalumab (anti-PD-L1 antibody) and a combination thereof.

11. The method of claim 1, wherein the T effector cells are CD4+ T cells.

12. The method of claim 1, wherein the T effector cells are CD8+ T cells.

13. A method of inhibiting the expansion of myeloid-derived suppressor cells (MDSCs), reducing M2 macrophages activation, and reducing levels of tumor-associated Treg cells in a tumor and inducing M1 macrophages activation, and T effector cells level in a bladder cancer comprising administering to a subject having bladder cancer an effective amount of a pharmaceutical composition comprising a strain of Mycobacteria comprising a vector comprising (i) a nucleic acid sequence encoding a protein that makes a STING agonist, wherein the protein that makes the STING agonist is a DNA integrity scanning (DisA) protein, wherein the STING agonist is a 3'-5' c-di-AMP (also known as c-di-AMP), and wherein the protein that makes the STING agonist lacks an EAL domain, and (ii) a panCD nucleic acid encoding a PanC protein and a nucleic acid sequence encoding a PanD protein, wherein the strain of Mycobacteria is a panthothenate-auxotroph *Mycobacterium bovis Bacillus* Calmette Guerin (BCG), thereby inhibiting the expansion of MDSCs, reducing M2 macrophages activation, and reducing levels of tumor-associated Treg cells and inducing M1 macrophages activation and T effector cells level in the bladder cancer.

14. The method of claim 1, wherein the nucleic acid sequence encoding the protein that makes a STING agonist is operably linked to a promoter derived from *Mycobacterium leprae*.

15. The strain of claim 14, wherein the promoter is a Phsp60 or a Phsp65 promoter, derived from *Mycobacterium leprae* Hsp65 5'UTR.

16. The method of claim 1, wherein the strain of Mycobacteria overexpresses a STING agonist as compared to a Mycobacteria strain that does not comprise the vector.

17. The method of claim 1, wherein the vector has a nucleic acid sequence comprising SEQ ID NO:31.

* * * * *